(12) United States Patent
Wagner et al.

(10) Patent No.: US 11,203,601 B2
(45) Date of Patent: Dec. 21, 2021

(54) TRICYCLIC COMPOUNDS AS GLYCOGEN SYNTHASE KINASE 3 (GSK3) INHIBITORS AND USES THEREOF

(71) Applicants: The Broad Institute, Inc., Cambridge, MA (US); Biogen MA Inc., Cambridge, MA (US)

(72) Inventors: Florence Fevrier Wagner, Ashland, MA (US); Michel Weiwer, Cambridge, MA (US); Arthur J. Campbell, Cambridge, MA (US); Joshua R. Sacher, Somerville, MA (US); Edward Holson, Newton, MA (US); Brian Stuart Lucas, Arlington, MA (US); TeYu Chen, Charlestown, MA (US)

(73) Assignees: The Broad Institute, Inc., Cambridge, MA (US); Biogen MA Inc., Cambridge, MA (US)

( * ) Notice: Subject to any disclaimer, the term of this patent is extended or adjusted under 35 U.S.C. 154(b) by 0 days.

(21) Appl. No.: 16/603,112

(22) PCT Filed: Apr. 5, 2018

(86) PCT No.: PCT/US2018/026339
§ 371 (c)(1),
(2) Date: Oct. 4, 2019

(87) PCT Pub. No.: WO2018/187630
PCT Pub. Date: Oct. 11, 2018

(65) Prior Publication Data
US 2020/0109154 A1 Apr. 9, 2020

Related U.S. Application Data

(60) Provisional application No. 62/481,981, filed on Apr. 5, 2017.

(51) Int. Cl.
*C07D 513/04* (2006.01)
*C07D 498/04* (2006.01)
*C07D 513/20* (2006.01)
*A61K 45/06* (2006.01)

(52) U.S. Cl.
CPC ......... *C07D 513/04* (2013.01); *C07D 498/04* (2013.01); *C07D 513/20* (2013.01); *A61K 45/06* (2013.01)

(58) Field of Classification Search
CPC ..... C07D 13/04; C07D 513/20; C07D 498/04
See application file for complete search history.

(56) References Cited

U.S. PATENT DOCUMENTS

| 4,270,537 | A | 6/1981 | Romaine |
| 4,596,556 | A | 6/1986 | Morrow et al. |
| 4,790,824 | A | 12/1988 | Morrow et al. |
| 4,886,499 | A | 12/1989 | Cirelli et al. |
| 4,940,460 | A | 7/1990 | Casey et al. |
| 4,941,880 | A | 7/1990 | Burns |
| 5,015,235 | A | 5/1991 | Crossman |
| 5,064,413 | A | 11/1991 | McKinnon et al. |
| 5,141,496 | A | 8/1992 | Dalto et al. |
| 5,190,521 | A | 3/1993 | Hubbard et al. |
| 5,312,335 | A | 5/1994 | McKinnon et al. |
| 5,328,483 | A | 7/1994 | Jacoby |

(Continued)

FOREIGN PATENT DOCUMENTS

DE 2722416 A1 11/1978
JP 2005-501800 A 1/2005
(Continued)

OTHER PUBLICATIONS

Lee. Journal of Combinatorial Chemistry, 2010, 12, 95-99 (Year: 2010).*
Forde. Cellular and Molecular Life Sciences, 2007, 64, 1930-1944 (Year: 2007).*
Lei. SAGE: Hindawi Access to Research, 2011, 1-9 (Year: 2011).*
U.S. Appl. No. 14/052,661, filed Oct. 11, 2013, Wagner et al.
U.S. Appl. No. 14/799,281, filed Jul. 14, 2015, Wagner et al.
U.S. Appl. No. 16/198,589, filed Nov. 21, 2018, Wagner et al.
U.S. Appl. No. 15/260,262, filed Sep. 8, 2016, Scolnick et al.
U.S. Appl. No. 16/525,494, filed Jul. 29, 2019, Scolnick et al.
U.S. Appl. No. 16/785,344, filed Feb. 7, 2020, Scolnick et al.

(Continued)

*Primary Examiner* — Noble E Jarrell
(74) *Attorney, Agent, or Firm* — Wolf, Greenfield & Sacks, P.C.

(57) ABSTRACT

The present disclosure provides compounds of Formula (I), and salts, solvates, hydrates, polymorphs, co-crystals, tautomers, stereoisomers, isotopically labeled derivatives, and prodrugs thereof. The provided compounds may be useful for inhibiting kinases, e.g., glycogen synthase kinase 3 (GSK3). The provided compounds may be able to selectively inhibit GSK3a, as compared to GSK3β and/or other kinases. The present disclosure further provides pharmaceutical compositions, kits, and methods of use, each of which involve the compounds. The compounds, pharmaceutical compositions, and kits may be useful for treating diseases associated with aberrant activity of GSK3a (e.g., Fragile X syndrome, attention deficit hyperactivity disorder (ADHD), childhood seizure, intellectual disability, diabetes, acute myeloid leukemia (AML), autism, and psychiatric disorder).

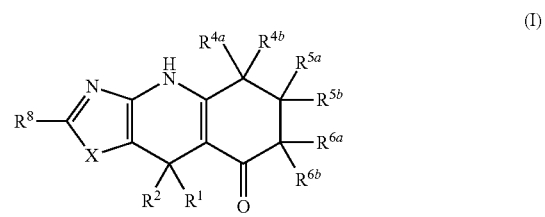

41 Claims, 6 Drawing Sheets

(56) References Cited

U.S. PATENT DOCUMENTS

| | | | |
|---|---|---|---|
| 5,334,114 A | 8/1994 | Ando et al. | |
| 5,339,163 A | 8/1994 | Homma et al. | |
| 5,383,851 A | 1/1995 | McKinnon et al. | |
| 5,417,662 A | 5/1995 | Hjertman et al. | |
| 5,466,220 A | 11/1995 | Brenneman | |
| 5,480,381 A | 1/1996 | Weston | |
| 5,503,627 A | 4/1996 | McKinnon et al. | |
| 5,520,639 A | 5/1996 | Peterson et al. | |
| 5,527,288 A | 6/1996 | Gross et al. | |
| 5,569,189 A | 10/1996 | Parsons | |
| 5,599,302 A | 2/1997 | Lilley et al. | |
| 5,649,912 A | 7/1997 | Peterson | |
| 5,704,911 A | 1/1998 | Parsons | |
| 5,750,528 A | 5/1998 | Brown et al. | |
| 5,893,397 A | 4/1999 | Peterson et al. | |
| 5,993,412 A | 11/1999 | Deily et al. | |
| 6,977,262 B2 | 12/2005 | Kohara et al. | |
| 7,067,507 B2 * | 6/2006 | Pulley | A61P 43/00 514/183 |
| 8,778,986 B1 | 7/2014 | Tan et al. | |
| 9,096,594 B2 | 8/2015 | Wagner et al. | |
| 10,137,122 B2 | 11/2018 | Wagner et al. | |
| 2008/0051394 A1 | 2/2008 | Schiemann et al. | |
| 2009/0181986 A1 | 7/2009 | Abelman et al. | |
| 2011/0008468 A1 | 1/2011 | Haggarty et al. | |
| 2014/0107141 A1 | 4/2014 | Wagner et al. | |
| 2015/0307516 A1 | 10/2015 | Lee et al. | |
| 2015/0313890 A1 | 11/2015 | Wagner et al. | |
| 2016/0375006 A1 | 12/2016 | Scolnick et al. | |
| 2019/0175584 A1 | 6/2019 | Wagner et al. | |

FOREIGN PATENT DOCUMENTS

| | | |
|---|---|---|
| JP | 2009-501778 A | 1/2009 |
| WO | WO 94/24131 A1 | 10/1994 |
| WO | WO 00/32606 A1 | 6/2000 |
| WO | WO 02/062795 A2 | 8/2002 |
| WO | WO 2007/012972 A2 | 2/2007 |
| WO | WO 2008/016123 A1 | 2/2008 |
| WO | WO 2010/133794 A1 | 11/2010 |
| WO | WO 2013/007663 A1 | 1/2013 |
| WO | WO 2014/003098 A1 | 1/2014 |
| WO | WO 2014/059383 A1 | 4/2014 |
| WO | WO 2015/087996 A1 | 6/2015 |
| WO | WO 2016/037026 A1 | 3/2016 |

OTHER PUBLICATIONS

PCT/US2013/064716, Nov. 19, 2013, International Search Report and Written Opinion.
PCT/US2013/064716, Apr. 23, 2015, International Preliminary Report on Patentability.
PCT/US2018/26339, May 31, 2018, Invitation to Pay Additional Fees.
PCT/US2018/26339, Jul. 20, 2018, International Search Report and Written Opinion.
PCT/US2018/26339, Oct. 17, 2019, International Preliminary Report on Patentability.
International Search Report and Written Opinion for PCT/US2013/064716, dated Nov. 19, 2013.
International Preliminary Report on Patentability for PCT/US2013/064716, dated Apr. 23, 2015.
Invitation to Pay Additional Fees for PCT/US2018/26339, dated May 31, 2018.
International Search Report and Written Opinion for PCT/US2018/26339, dated Jul. 20, 2018.
International Preliminary Report on Patentability for PCT/US2018/26339, dated Oct. 17, 2019.
[No Author Listed] American Psychiatric Association: Diagnostic and Statistical Manual of Mental Disorders, Fifth Edition. Arlington, VA, American Psychiatric Association, 2013. pp. 33-41, 809-816.
Achab et al., A short route to functionalized imidazo[4,5-c]carbazoles. Synthesis of the first example of the imidazo[4,5-c]β-carboline ring system. Tetrahedron Letters. Dec. 10, 2001;42(50):8825-28.
An et al., Discovery of Potent and Highly Selective Inhibitors of GSK3b. Received on Apr. 16, 2012. Released in excerpt form on May 7, 2013. [Last Update: May 13, 2014]. Full report published on Jul. 17, 2014. In: Probe Reports from the NIH Molecular Libraries Program [Internet]. Bethesda (MD): National Center for Biotechnology Information (US); 2010-. Available from: https://www.ncbi.nlm.nih.gov/books/NBK133436/.
Banerji et al., The intersection of genetic and chemical genomic screens identifies GSK-3α as a target in human acute myeloid leukemia. J Clin Invest. Mar. 1, 2012;122(3):935-47. doi: 10.1172/JCI46465. Epub Feb. 13, 2012.
Bang et al., GSK-3α promotes oncogenic KRAS function in pancreatic cancer via TAK1-TAB stabilization and regulation of noncanonical NF-κB. Cancer Discov. Jun. 2013;3(6):690-703. doi: 10.1158/2159-8290.CD-12-0541. Epub Apr. 1, 2013.
Barnes et al., Convergence of Hippocampal Pathophysiology in Syngap+/− and Fmr1 −/γMice. J Neurosci. Nov. 11, 2015;35(45):15073-81. doi: 10.1523/JNEUROSCI.1087-15.2015.
Beaulieu et al., The Akt-GSK-3 signaling cascade in the actions of dopamine. Trends Pharmacol Sci. Apr. 2007;28(4):166-72. Epub Mar. 8, 2007. Review.
Beurel et al., Inhibition of glycogen synthase kinase-3 is necessary for the rapid antidepressant effect of ketamine in mice. Mol Psychiatry. Nov. 2011;16(11):1068-70. doi: 10.1038/mp.2011.47. Epub Apr. 19, 2011.
Biechele et al., Assaying beta-catenin/TCF transcription with beta-catenin/TCF transcription-based reporter constructs. Methods Mol Biol. 2008;468:99-110. doi: 10.1007/978-1-59745-249-6_8.
Chalecka-Franaszek et al., Lithium activates the serine/threonine kinase Akt-1 and suppresses glutamate-induced inhibition of Akt-1 activity in neurons. Proc Natl Acad Sci U S A. Jul. 20, 1999;96(15):8745-50.
Chang et al., Synthesis and application of functionally diverse 2,6,9-trisubstituted purine libraries as CDK inhibitors. Chem Biol. Jun. 1999;6(6):361-75.
Cheong et al., Phosphatase and tensin homologue phosphorylation in the C-terminal regulatory domain is frequently observed in acute myeloid leukaemia and associated with poor clinical outcome. Br J Haematol. Aug. 2003;122(3):454-6.
Cozza et al., Identification of novel protein kinase CK1 delta (CK1delta) inhibitors through structure-based virtual screening. *Bioorg Med Chem Lett.* Oct. 15, 2008;18(20):5672-5. doi: 10.1016/j.bmcl.2008.08.072. Epub Aug. 26, 2008.
Dahlhoff et al., AKT/GSK-3beta/beta-catenin signalling within hippocampus and amygdala reflects genetically determined differences in posttraumatic stress disorder like symptoms. Neuroscience. Sep. 1, 2010;169(3):1216-26. doi: 10.1016/j.neuroscience.2010.05.066.
De Sarno et al., Regulation of Akt and glycogen synthase kinase-3 beta phosphorylation by sodium valproate and lithium. Neuropharmacology. Dec. 2002;43(7):1158-64.
Dirzin et al., Structure-Activity studies for a novel series of tricyclic dihydropyrimidines as K(ATP) channel openers (KCOs). Bioorg Med Chem Lett. Jun. 3, 2002;12(11):1481-4.
Doble et al., Functional redundancy of GSK-3alpha and GSK-3beta in Wnt/beta-catenin signaling shown by using an allelic series of embryonic stem cell lines. Dev Cell. Jun. 2007;12(6):957-71.
Emamian et al., Convergent evidence for impaired AKT1-GSK3beta signaling in schizophrenia. Nat Genet. Feb. 2004;36(2):131-7. Epub Jan. 25, 2004.
Emamian, AKT/GSK3 signaling pathway and schizophrenia. Front Mol Neurosci. Mar. 15, 2012;5:33. doi: 10.3389/fnmol.2012.00033. eCollection 2012.
Forde et al., Glycogen synthase kinase 3: a key regulator of cellular fate. Cell Mol Life Sci. Aug. 2007;64(15):1930-44. Review.
Franklin et al., Glycogen synthase kinase-3 inhibitors reverse deficits in long-term potentiation and cognition in fragile X mice. Biol Psychiatry. Feb. 1, 2014;75(3):198-206. doi: 10.1016/j.biopsych.2013.08.003. Epub Sep. 13, 2013.

(56) References Cited

OTHER PUBLICATIONS

Georgievska et al., AZD1080, a novel GSK3 inhibitor, rescues synaptic plasticity deficits in rodent brain and exhibits peripheral target engagement in humans. J Neurochem. May 2013;125(3):446-56. doi: 10.1111/jnc.12203.
Gould et al., Targeting glycogen synthase kinase-3 in the CNS: implications for the development of new treatments for mood disorders. Curr Drug Targets. Nov. 2006;7(11):1399-409. Review.
Hahn et al., Proteomic and genetic approaches identify Syk as an AML target. Cancer Cell. Oct. 6, 2009;16(4):281-94. doi: 10.1016/j.ccr.2009.08.018.
Harris, Intellectual Disability: A Guide for Families and Professionals. Oxford University Press, 2010. pp. 51-53, 65.
Hooper et al., The GSK3 hypothesis of Alzheimer's disease. J Neurochem. Mar. 2008;104(6):1433-9. Epub Dec. 18, 2007. Review.
Jones et al., Animal models of schizophrenia. Br J Pharmacol. Oct. 2011;164(4):1162-94. doi: 10.1111/j.1476-5381.2011.01386.x. Review.
Kaidanovich-Beilin et al., Abnormalities in brain structure and behavior in GSK-3alpha mutant mice. Mol Brain. Nov. 19, 2009;2:35. doi: 10.1186/1756-6606-2-35.
Kelleher et al., The autistic neuron: troubled translation? Cell. Oct. 31, 2008;135(3):401-6. doi: 10.1016/j.cell.2008.10.017.
Koh et al., Inhibition of glycogen synthase kinase-3 suppresses the onset of symptoms and disease progression of G93A-SOD1 mouse model of ALS. Exp Neurol. Jun. 2007;205(2):336-46. Epub Mar. 12, 2007.
Kozlovsky et al., Reduced GSK-3beta mRNA levels in postmortem dorsolateral prefrontal cortex of schizophrenic patients. J Neural Transm. Dec. 2004;111(12):1583-92. Epub Jun. 30, 2004.
Leclerc et al., Indirubins inhibit glycogen synthase kinase-3 beta and CDK5/p25, two protein kinases involved in abnormal tau phosphorylation in Alzheimer's disease. A property common to most cyclin-dependent kinase inhibitors? J Biol Chem. Jan. 5, 2001;276(1):251-60.
Lee et al., Developing therapeutic approaches to tau, selected kinases, and related neuronal protein targets. Cold Spring Harb Perspect Med. Sep. 2011;1(1):a006437. doi: 10.1101/cshperspect.a006437. Review.
Lei et al., GSK-3 in Neurodegenerative Diseases. Int J Alzheimers Dis. 2011;2011:189246, 9 pages, doi: 10.4061/2011/189246. Epub May 4, 2011.
Leost et al., Paullones are potent inhibitors of glycogen synthase kinase-3beta and cyclin-dependent kinase 5/p25. Eur J Biochem. Oct. 2000;267(19):5983-94.
Lo Monte et al., Identification of glycogen synthase kinase-3 inhibitors with a selective sting for glycogen synthase kinase-3α. J Med Chem. May 10, 2012;55(9):4407-24. doi: 10.1021/jm300309a. Epub May 1, 2012.
MacAulay et al., Glycogen synthase kinase 3alpha-specific regulation of murine hepatic glycogen metabolism. Cell Metab. Oct. 2007;6(4):329-37.
Manisastry et al., Early temporal-specific responses and differential sensitivity to lithium and Wnt-3A exposure during heart development. Dev Dyn. Aug. 2006;235(8):2160-74.
Manoukian et al., Role of glycogen synthase kinase-3 in cancer: regulation by Wnts and other signaling pathways. Adv Cancer Res. 2002;84:203-29. Review.
Mao et al., Disrupted in schizophrenia 1 regulates neuronal progenitor proliferation via modulation of GSK3beta/beta-catenin signaling. Cell. Mar. 20, 2009;136(6):1017-31. doi:10.1016/j.cell.2008.12.044.
Matsuda et al., Distinct roles of GSK-3alpha and GSK-3beta phosphorylation in the heart under pressure overload. Proc Natl Acad Sci U S A. Dec. 30, 2008;105(52):20900-5. doi: 10.1073/pnas.0808315106. Epub Dec. 23, 2008.
Meijer et al., GSK-3-selective inhibitors derived from Tyrian purple indirubins. Chem Biol. Dec. 2003;10(12):1255-66.
Meijer et al., Inhibition of cyclin-dependent kinases, GSK-3beta and CK1 by hymenialdisine, a marine sponge constituent. Chem Biol. Jan. 2000;7(1):51-63.

Mines et al., GSK3 influences social preference and anxiety-related behaviors during social interaction in a mouse model of fragile X syndrome and autism. PLoS One. Mar. 16, 2010;5(3):e9706, 12 pages, doi: 10.1371/journal.pone.0009706.
Mukai et al., Molecular substrates of altered axonal growth and brain connectivity in a mouse model of schizophrenia. Neuron. May 6, 2015;86(3):680-95. doi: 10.1016/j.neuron.2015.04.003.
Neumann et al., Evaluation of Improved Glycogen Synthase Kinase-3α Inhibitors in Models of Acute Myeloid Leukemia. J Med Chem. Nov. 25, 2015;58(22):8907-19. doi: 10.1021/acs.jmedchem.5b01200.
Norton et al. Association analysis of AKT1 and schizophrenia in a UK case control sample. Schizophr Res. Jul. 2007;93(1-3):58-65. Epub Mar. 26, 2007.
Pan et al., AKT kinase activity is required for lithium to modulate mood-related behaviors in mice. Neuropsychopharmacology. Jun. 2011;36(7):1397-411. doi: 10.1038/npp.2011.24. Epub Mar. 9, 2011.
Phiel et al., GSK-3alpha regulates production of Alzheimer's disease amyloid-beta peptides. Nature. May 22, 2003;423(6938):435-9.
Piazza et al., Glycogen Synthase Kinase-3 regulates multiple myeloma cell growth and bortezomib-induced cell death. BMC Cancer. Oct. 4, 2010;10:526. doi: 10.1186/1471-2407-10-526.
Polter et al., Deficiency in the inhibitory serine-phosphorylation of glycogen synthase kinase-3 increases sensitivity to mood disturbances. Neuropsychopharmacology. Jul. 2010;35(8):1761-74. doi: 10.1038/npp.2010.43. Epub Mar. 31, 2010.
Polychronopoulos et al., Structural basis for the synthesis of indirubins as potent and selective inhibitors of glycogen synthase kinase-3 and cyclin-dependent kinases. J Med Chem. Feb. 12, 2004;47(4):935-46.
Portis et al., The role of glycogen synthase kinase-3 signaling in neurodevelopment and fragile X syndrome. Int J Physiol Pathophysiol Pharmacol. 2012;4(3):140-8. Epub Sep. 20, 2012.
Quiroga et al., An efficient synthesis of pyrazolo[3,4-b]pyridine-4-spiroindolinones by a three-component reaction of 5-aminopyrazoles, isatin, and cyclic β-diketones. Tetrahedron Letters. 2011;52(21):2664-6.
Quiroga et al., Regioselective synthesis of 4,7,8,9-tetrahydro-2H-pyrazolo[3,4-b]quinolin-5(6H)-ones. Mechanism and structural analysis. Tetrahedron. 2001;57(32):6947-53.
Robinson. Protein -RNA interaction links fragile X syndrome and Alzheimer disease. PLoS Biology. 2007;(5)e84.
Rowe et al., GSK-3 is a viable potential target for therapeutic intervention in bipolar disorder. Neurosci Biobehav Rev. 2007;31(6):920-31. Epub Mar. 15, 2007.
Ryves et al., Lithium inhibits glycogen synthase kinase-3 by competition for magnesium. Biochem Biophys Res Commun. Jan. 26, 2001;280(3):720-5.
Song et al., Central role of glycogen synthase kinase-3beta in endoplasmic reticulum stress-induced caspase-3 activation. J Biol Chem. Nov. 22, 2002;277(47):44701-8. Epub Sep. 12, 2002.
Stegmater et al., Gene expression-based high-throughput screening(GE-HTS) and application to leukemia differentiation. Nat Genet. Mar. 2004;36(3):257-63. Epub Feb. 8, 2004.
Thiselton et al., AKT1 is associated with schizophrenia across multiple symptom dimensions in the Irish study of high density schizophrenia families. Biol Psychiatry. Mar. 1, 2008;63(5):449-57. Epub Sep. 6, 2007.
Wada, GSK-3 inhibitors and insulin receptor signaling in health, disease, and therapeutics. Front Biosci (Landmark Ed). Jan. 1, 2009;14:1558-70. Review.
Wagman et al., Discovery and development of GSK3 inhibitors for the treatment of type 2 diabetes. Curr Pharm Des. 2004;10(10):1105-37. Review.
Wagner et al., Inhibitors of Glycogen Synthase Kinase 3 with Exquisite Kinome-Wide Selectivity and Their Functional Effects. ACS Chem Biol. Jul. 15, 2016;11(7):1952-63. doi: 10.1021/acschembio.6b00306. Epub May 13, 2016.
Walpita et al., A human islet cell culture system for high-throughput screening. J Biomol Screen. Apr. 2012;17(4):509-18. doi: 10.1177/1087057711430253.

(56) References Cited

OTHER PUBLICATIONS

Wang et al., Changes of tau profiles in brains of the hamsters infected with scrapie strains 263 K or 139 A possibly associated with the alteration of phosphate kinases. BMC Infect Dis. Apr. 1, 2010;10:86, 10 pages. doi: 10.1186/1471-2334-10-86.

Wang et al., Downregulation of Mcl-1 through GSK-3β activation contributes to arsenic trioxide-induced apoptosis in acute myeloid leukemia cells. Leukemia. Feb. 2013;27(2):315-24. doi: 10.1038/leu.2012.180. Epub Jul. 3, 2012.

Wang et al., Glycogen synthase kinase 3 in MLL leukaemia maintenance and targeted therapy. Nature. Oct. 30, 2008;455(7217):1205-9. doi: 10.1038/nature07284. Epub Sep. 17, 2008.

Wang et al., GSK-3 promotes conditional association of CREB and its coactivators with MEIS1 to facilitate HOX-mediated transcription and oncogenesis. Cancer Cell. Jun. 15, 2010;17(6):597-608. doi: 10.1016/j.ccr.2010.04.024.

Wang et al., The Wnt/beta-catenin pathway is required for the development of leukemia stem cells in AML. Science. Mar. 26, 2010;327(5973):1650-3. doi: 10.1126/science.1186624.

Wexler et al., Lithium regulates adult hippocampal progenitor development through canonical Wnt pathway activation. Mol Psychiatry. Mar. 2008;13(3):285-92. Epub Oct. 30, 2007.

Woodgett, Physiological roles of glycogen synthase kinase-3: potential as a therapeutic target for diabetes and other disorders. Curr Drug Targets Immune Endocr Metabol Disord. Dec. 2003;3(4):281-90. Review.

Zhao et al., A high-throughput screen for Wnt/β-catenin signaling pathway modulators in human iPSC-derived neural progenitors. J Biomol Screen. Oct. 2012;17(9):1252-63. Epub Aug. 24, 2012.

Zhou et al., Forebrain overexpression of CK1delta leads to downregulation of dopamine receptors and altered locomotor activity reminiscent of ADHD. Proc Natl Acad Sci U S A. Mar. 2, 2010;107(9):4401-6. doi: 10.1073/pnas.0915173107. Epub Feb. 9, 2010.

Extended European Search Report for Application No. 18781394.4, dated Nov. 19, 2020.

Foucourt et al., Design and synthesis of thiazolo[5,4-f]quinazolines as DYRK1A inhibitors, part I. Molecules. Sep. 29, 2014;19(10):15546-71. doi: 10.3390/molecules191015546.

Mayeku et al., Thalictramine, a new alkaloid from Thalictrum rhyncocarpum (Dill & Rich) and its anti-bacterial activity. Journal of Chemical and Pharmaceutical Research. Dec. 31, 2014; 6(11):1-5.

EP 18781394.4, No. 19, 2020, Extened European Search Report.

Beaulieu et al., Lithium antagonizes dopamine-dependent behaviors mediated by an AKT/glycogen synthase kinase 3 signaling cascade. Proc Natl Acad Sci U S A. Apr. 6, 2004;101(14):5099-104. doi: 10.1073/pnas.0307921101. Epub Mar. 24, 2004.

Hinze et al., Synthetic Lethality of Wnt Pathway Activation and Asparaginase in Drug-Resistant Acute Leukemias. Cancer Cell. Apr. 15, 2019;35(4):664-676.e7. doi: 10.1016/j.ccell.2019.03.004.

Li et al., Lithium chloride suppresses colorectal cancer cell survival and proliferation through ROS/GSK-3β/NF-κB signaling pathway. Oxid Med Cell Longev. 2014;2014:241864. doi: 10.1155/2014/241864. Epub Jun. 5, 2014.

Min et al., Elevated glycogen synthase kinase-3 activity in Fragile X mice: key metabolic regulator with evidence for treatment potential. Neuropharmacology. Feb. 2009;56(2):463-72. doi: 10.1016/j.neuropharm.2008.09.017. Epub Oct. 14, 2008.

\* cited by examiner

FIG. 4

TRICYCLIC COMPOUNDS AS GLYCOGEN SYNTHASE KINASE 3 (GSK3) INHIBITORS AND USES THEREOF

RELATED APPLICATIONS

The present application is a national stage filing under 35 U.S.C. § 371 of international PCT application, PCT/US2018/026339, filed Apr. 5, 2018, which claims priority under 35 U.S.C. § 119(e) to U.S. provisional patent application, U.S. Ser. No. 62/481,981, filed Apr. 5, 2017, each of which is incorporated herein by reference.

BACKGROUND

The search for new therapeutic agents has been greatly aided in recent years by a better understanding of the structure of enzymes and other biomolecules associated with diseases. One important class of enzymes that has been the subject of extensive study is protein kinases.

Protein kinases constitute a large family of structurally related enzymes that are responsible for the control of a variety of signal transduction processes within the cell. Protein kinases are thought to have evolved from a common ancestral gene due to the conservation of their structure and catalytic function. Almost all kinases contain a similar 250-300 amino acid catalytic domain. The kinases may be categorized into families by the substrates they phosphorylate (e.g., protein-tyrosine, protein-serine/threonine, lipids, etc.).

In general, protein kinases mediate intracellular signaling by effecting a phosphoryl transfer from a nucleoside triphosphate to a protein acceptor that is involved in a signaling pathway. These phosphorylation events act as molecular on/off switches that can modulate or regulate the target protein biological function. These phosphorylation events are ultimately triggered in response to a variety of extracellular and other stimuli. Examples of such stimuli include environmental and chemical stress signals (e.g., osmotic shock, heat shock, ultraviolet radiation, bacterial endotoxin, and $H_2O_2$), cytokines (e.g., interleukin-1 (IL-I) and tumor necrosis factor α (TNF-α)), and growth factors (e.g., granulocyte macrophage-colony-stimulating factor (GM-CSF), and fibroblast growth factor (FGF)). An extracellular stimulus may affect one or more cellular responses related to cell growth, migration, differentiation, secretion of hormones, activation of transcription factors, muscle contraction, glucose metabolism, control of protein synthesis, and regulation of the cell cycle.

Many diseases are associated with abnormal cellular responses triggered by protein kinase-mediated events as described above. These diseases include autoimmune diseases, inflammatory diseases, bone diseases, metabolic diseases, neurological, neuropsychiatric and neurodegenerative diseases, cancer, cardiovascular diseases, allergies and asthma, Alzheimer's disease, metabolic disorders (e.g., diabetes), and hormone-related diseases. Accordingly, there remains a need to find protein kinase inhibitors, particularly GSK3 inhibitors, useful as therapeutic agents.

SUMMARY OF THE INVENTION

The present disclosure provides compounds (e.g., compounds of Formula (I), and salts (e.g., pharmaceutically acceptable salts), solvates, hydrates, polymorphs, co-crystals, tautomers, stereoisomers, isotopically labeled derivatives, and prodrugs thereof). The provided compounds may be useful for inhibiting kinases, e.g., glycogen synthase kinase 3 (GSK3 or GSK-3). The present disclosure further provides pharmaceutical compositions of the compounds, kits of the compounds, and methods of using the compounds. The compounds, pharmaceutical compositions, and kits may be useful for treating a disease, such as a disease associated with aberrant activity of a kinase (e.g., GSK3). In certain embodiments, the compounds, pharmaceutical compositions, and kits are useful for treating a disease associated with aberrant activity of glycogen synthase kinase 3α (GSK3α, GSK-3α, or GSK-3alpha) (e.g., Fragile X syndrome, attention deficit hyperactivity disorder (ADHD), childhood seizure, intellectual disability, diabetes, acute myeloid leukemia (AML), autism, or psychiatric disorder). In certain embodiments, the compounds, pharmaceutical compositions, and kits are useful in treating a disease associated with aberrant activity of glycogen synthase kinase 3β (GSK3β, GSK-3β, or GSK-3beta) (e.g., mood disorder, PTSD, psychiatric disorder, diabetes, or neurodegenerative disease). The compounds, pharmaceutical compositions, and kits may also be useful for preventing the diseases described herein.

In one some embodiments, the present disclosure provides compounds of Formula (I):

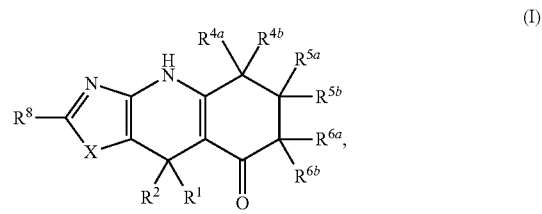

(I)

and salts, solvates, hydrates, polymorphs, co-crystals, tautomers, stereoisomers, isotopically labeled derivatives, and prodrugs thereof, wherein X, $R^1$, $R^2$, $R^{4a}$, $R^{4b}$, $R^{5a}$, $R^{5b}$, $R^{6a}$, $R^{6b}$, and $R^8$ are as defined herein.

Exemplary compounds of Formula (I) include compounds of formula:

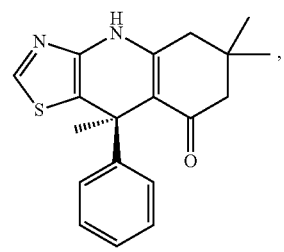

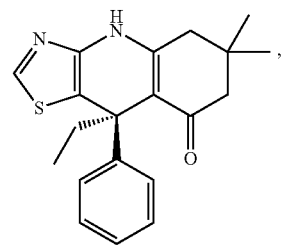

(1 or 1-E2)

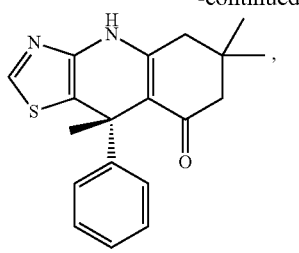
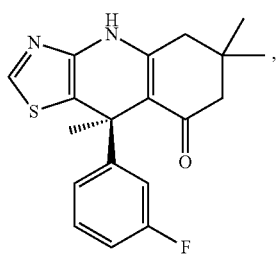
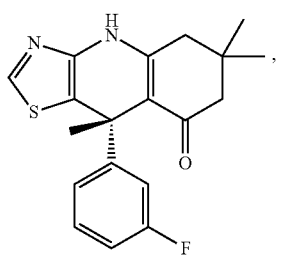
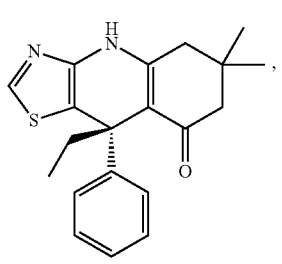
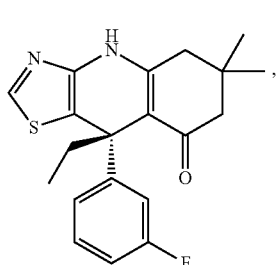
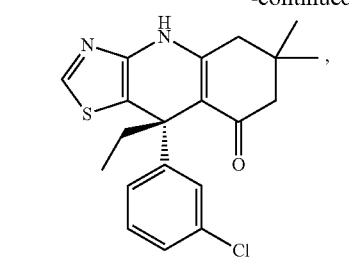
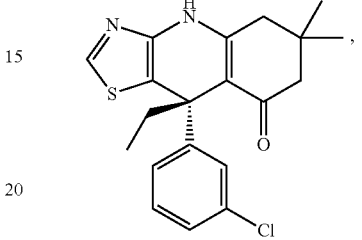
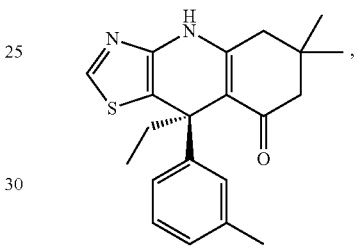
(1-E1)
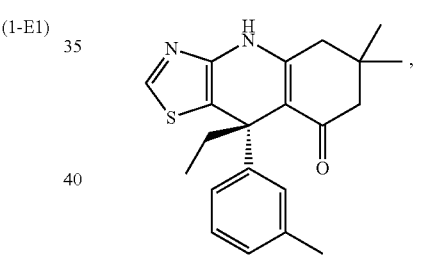
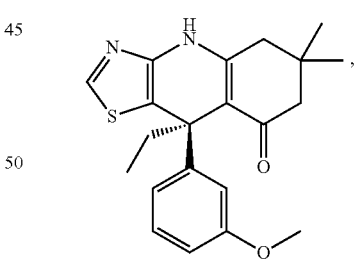
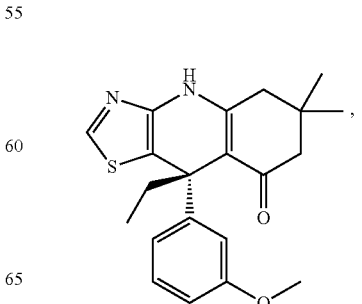

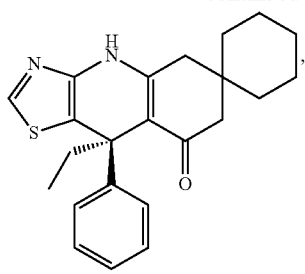
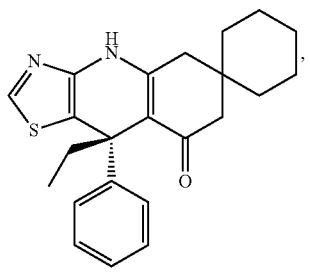
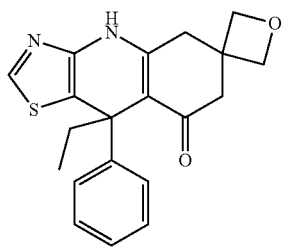
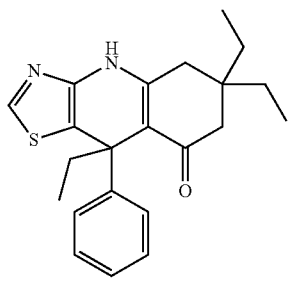
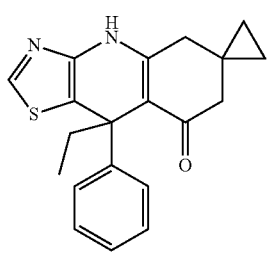
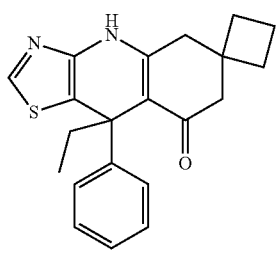
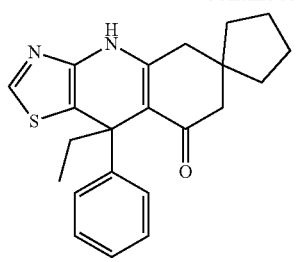
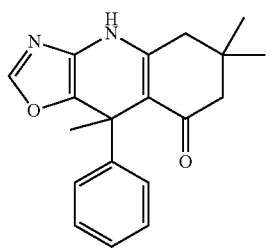
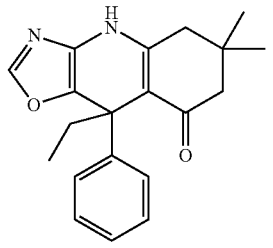
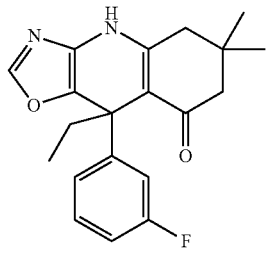
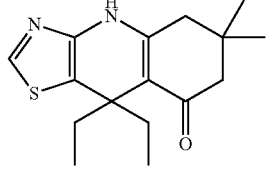

-continued
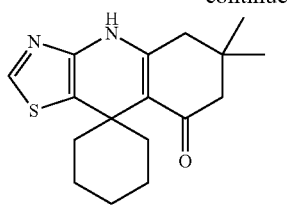
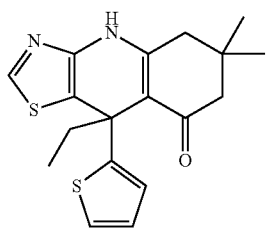
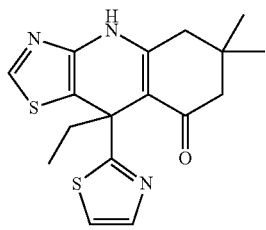
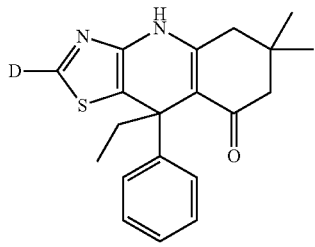
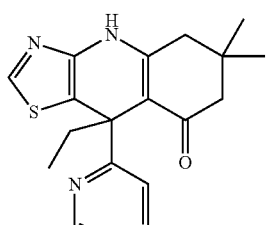
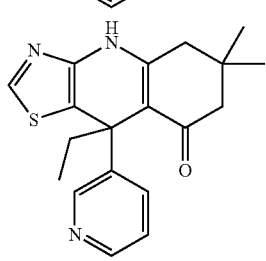
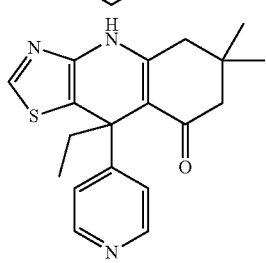
-continued
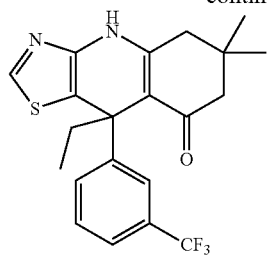
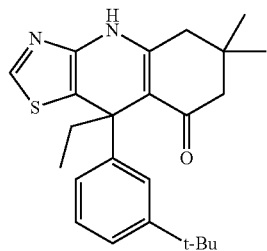
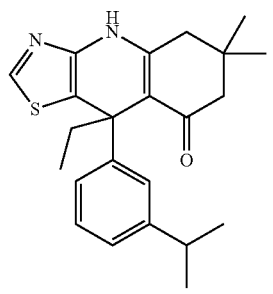
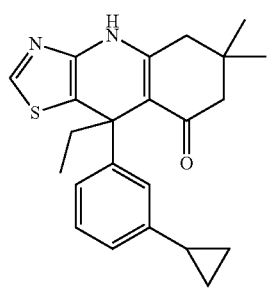
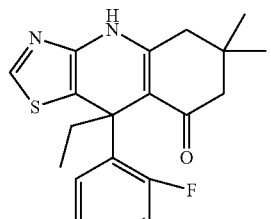
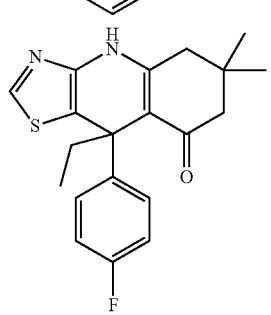

-continued
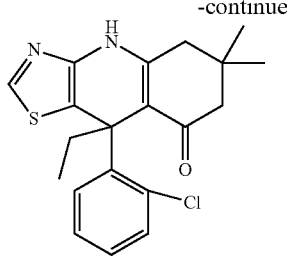
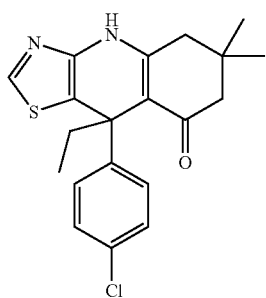
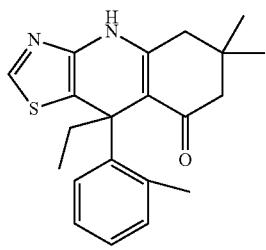
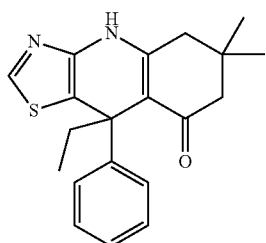
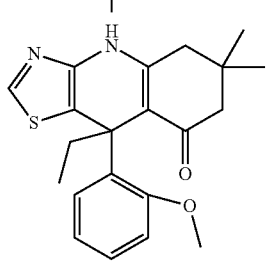
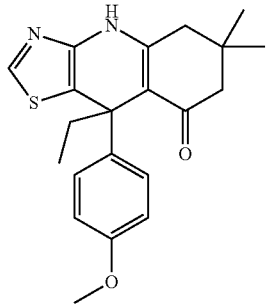
-continued
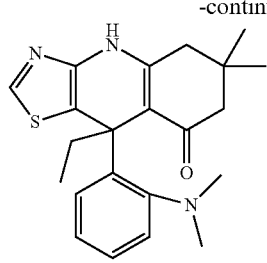
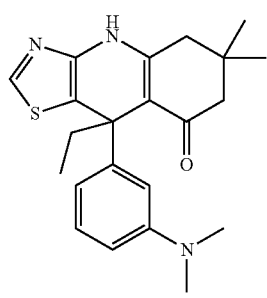
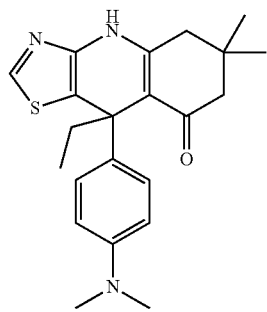
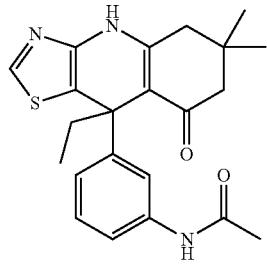
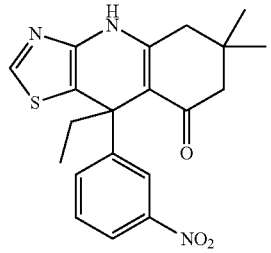
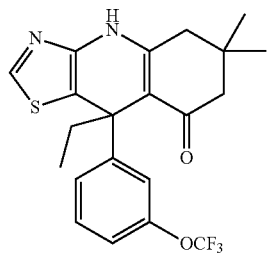

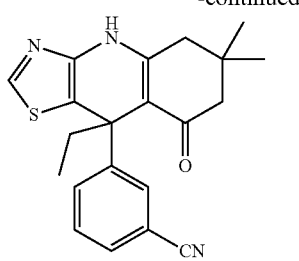
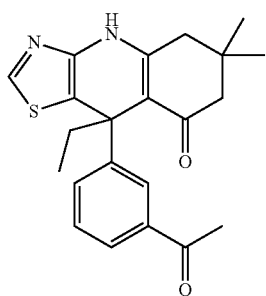
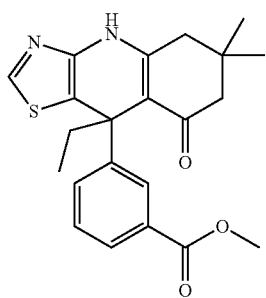
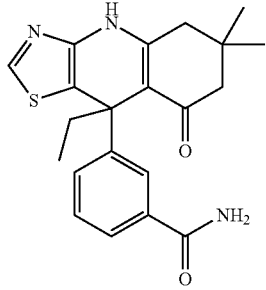
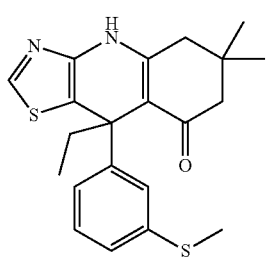
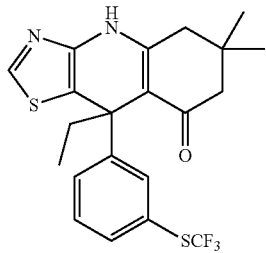
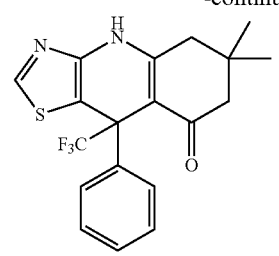
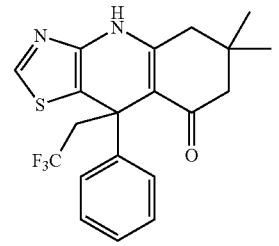
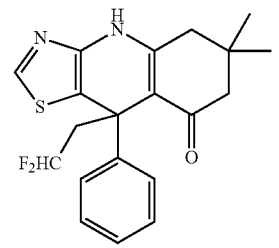
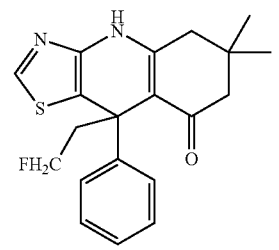
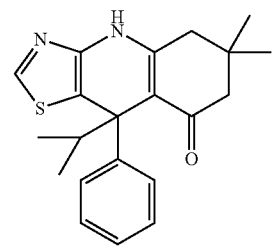
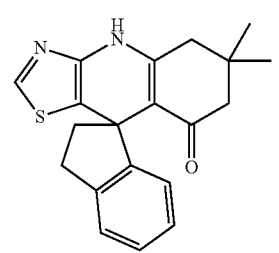

-continued
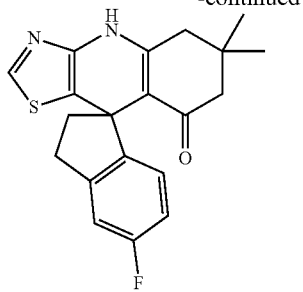
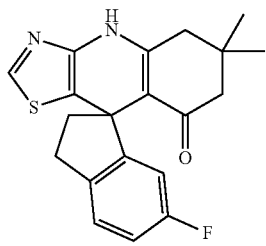
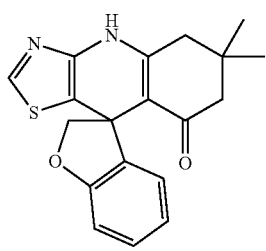
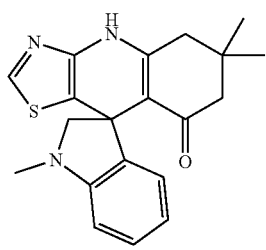
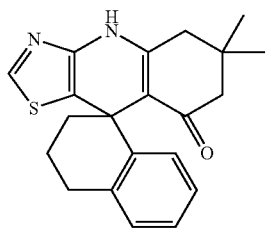
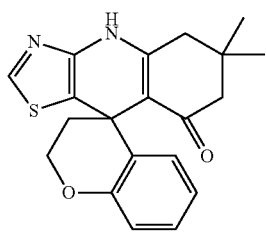
and salts, solvates, hydrates, polymorphs, co-crystals, tautomers, stereoisomers, isotopically labeled derivatives, and prodrugs thereof.
Exemplary compounds of Formula (I) further include compounds of the formulae:
(1-rac)
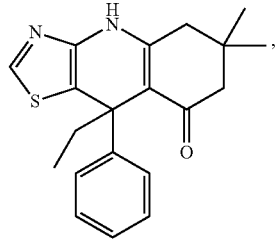
2
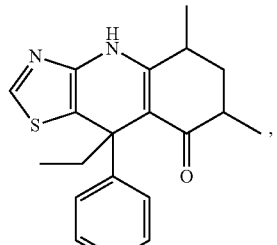
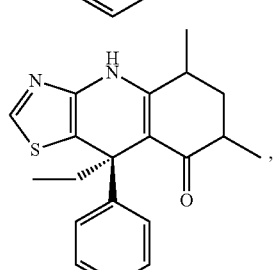
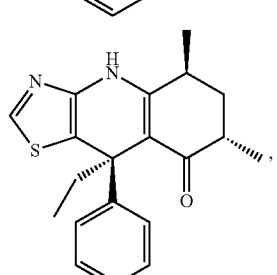
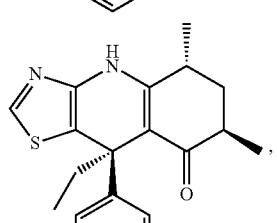
3
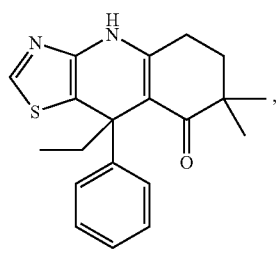

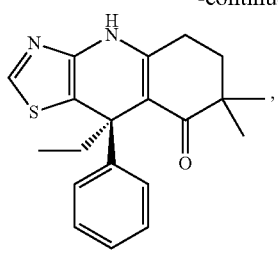
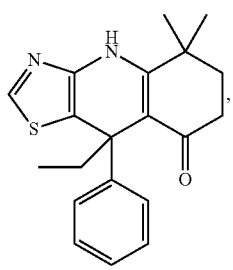
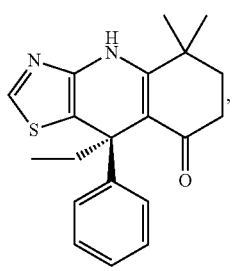
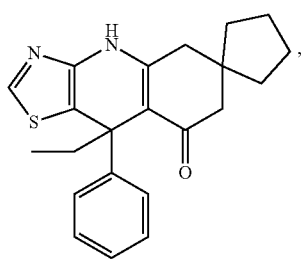
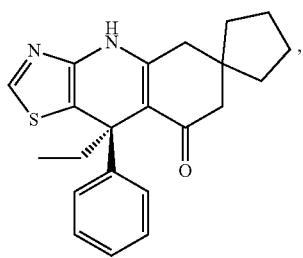
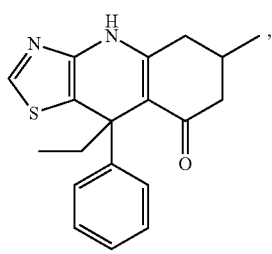
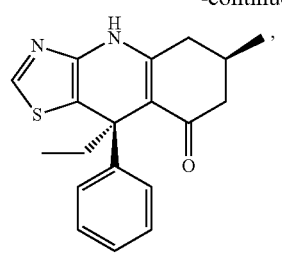
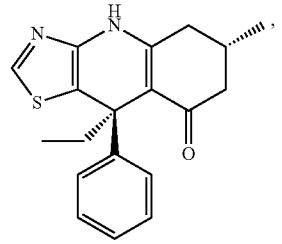
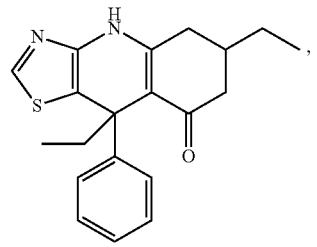
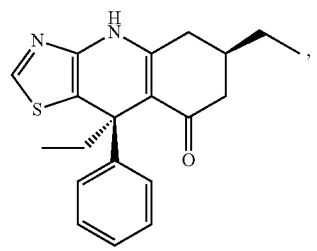
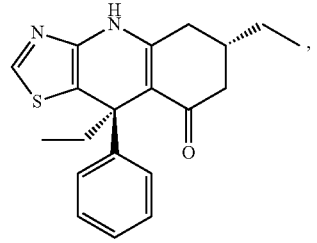
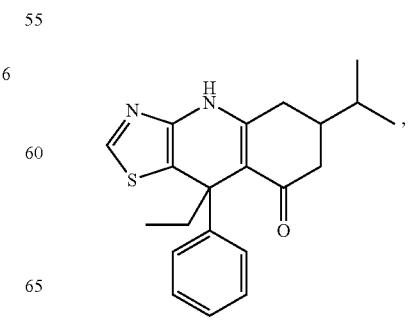

-continued
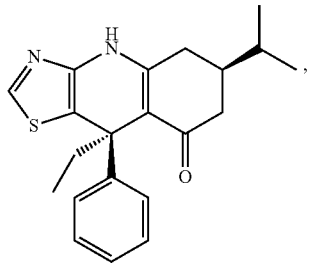
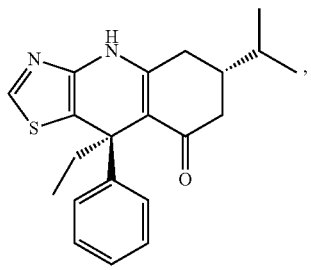
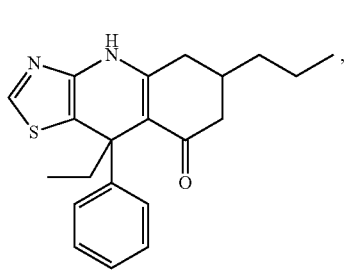
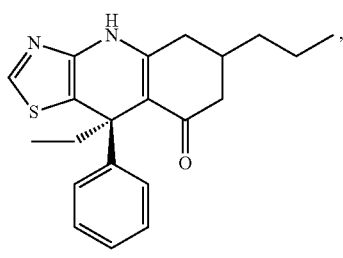
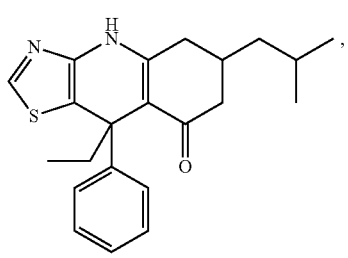
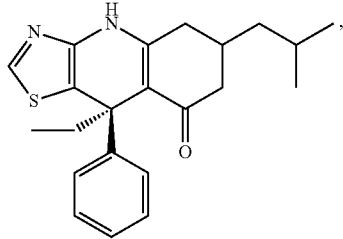
-continued
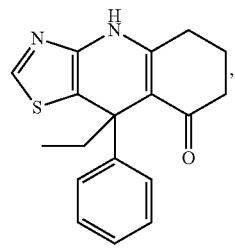
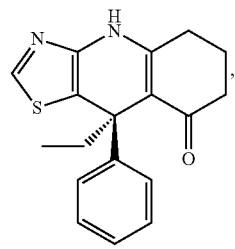
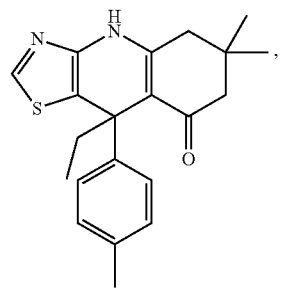
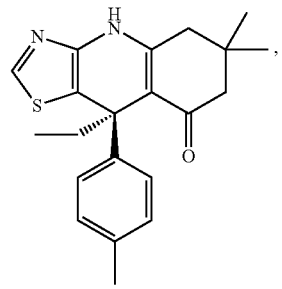
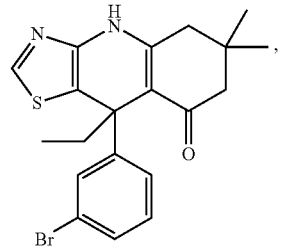
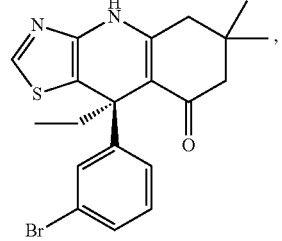

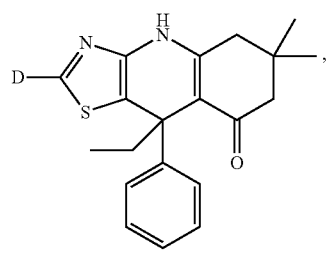
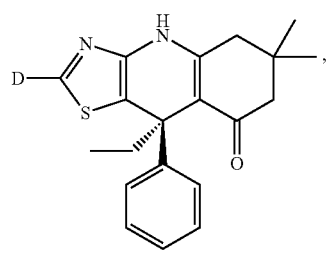
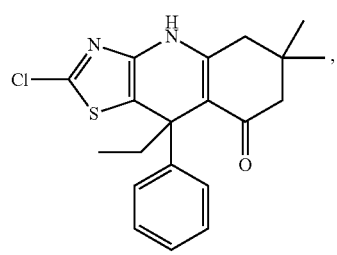
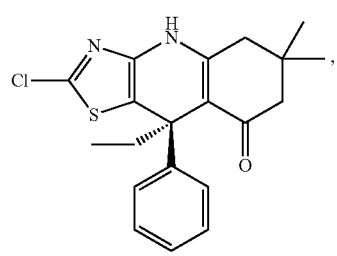
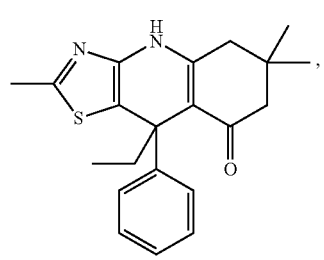
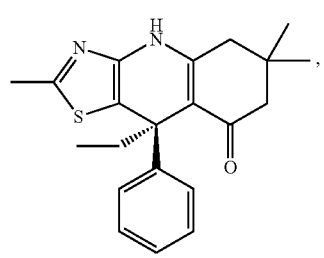
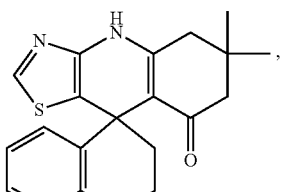
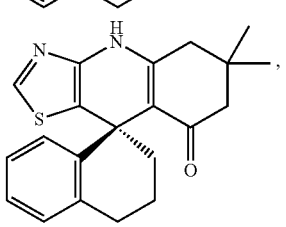
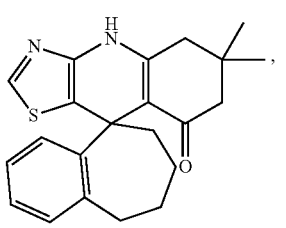
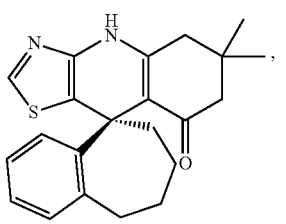
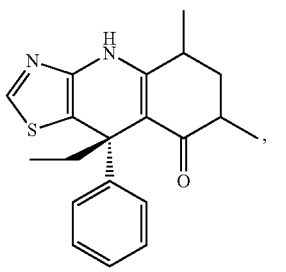
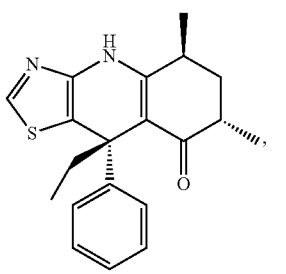
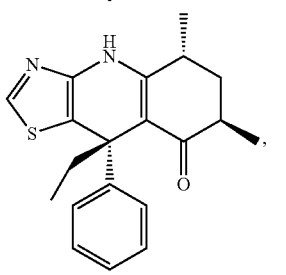

-continued
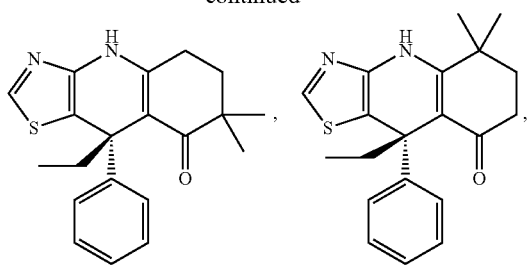
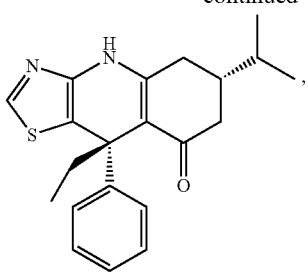
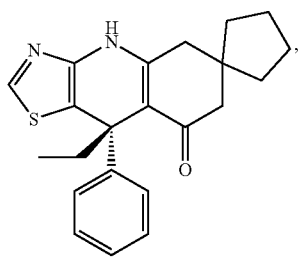
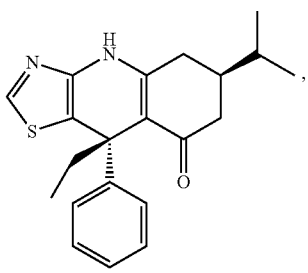
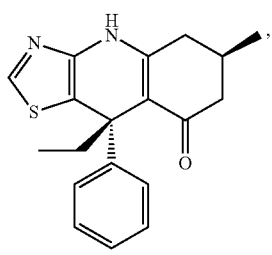
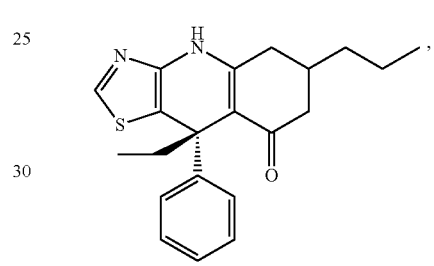
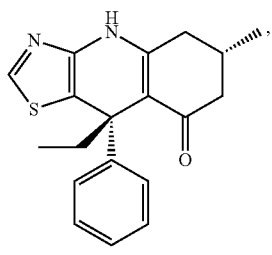
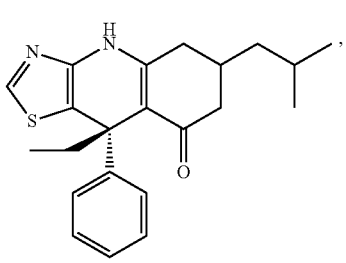
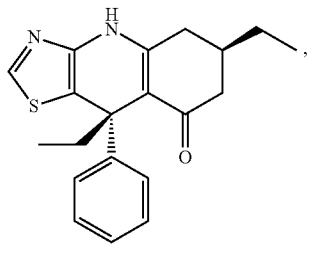
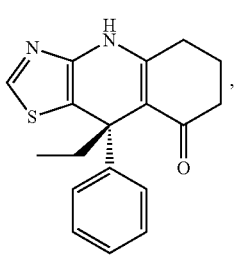
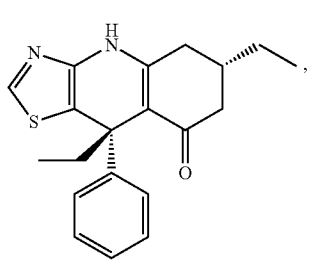
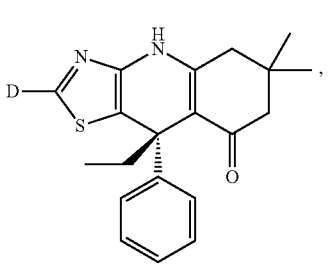

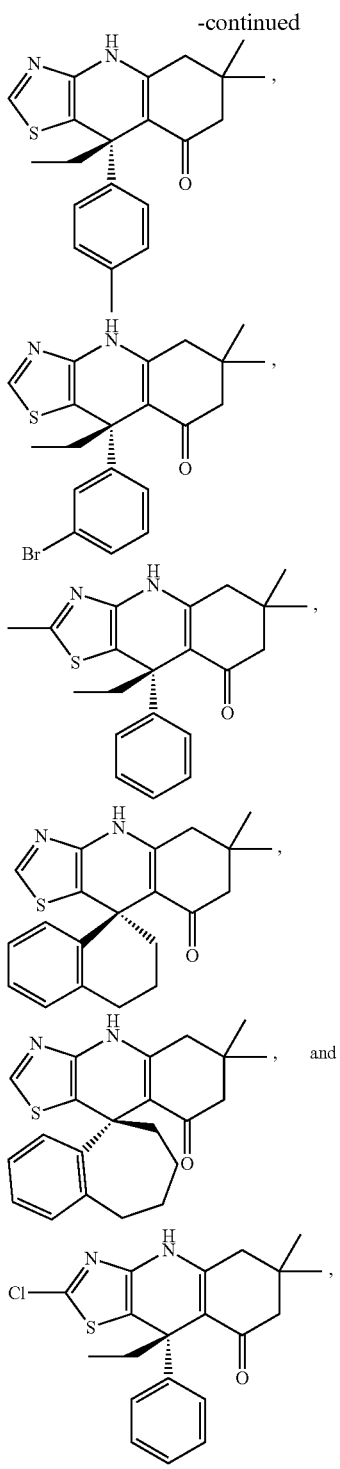

and salts, solvates, hydrates, polymorphs, co-crystals, tautomers, stereoisomers, isotopically labeled derivatives, and prodrugs thereof.

The provided compounds may be able to selectively inhibit GSK3, as compared to other kinases. The provided compounds may also be able to selectively inhibit GSK3α, as compared to GSK3β and/or other kinases. In certain embodiments, a compound described herein is selective for GSK3α when compared with GSK3β by at least 3-fold. The selective kinase inhibitors described herein may be advantageous over non-selective kinase inhibitors because the selective kinase inhibitors may be able to reduce off-target effects. In some embodiments, a compound described herein further shows improved potency, efficacy, safety, absorption, distribution, metabolism, excretion, liberation, and/or stability, as compared to other kinase inhibitors (e.g., non-selective kinase inhibitors, such as non-selective GSK3 inhibitors). In certain embodiments, a compound described herein shows increased brain penetration, as compared to other kinase inhibitors (e.g., non-selective kinase inhibitors, such as non-selective GSK3 inhibitors, or selective kinase inhibitors, such as selective GSK3 inhibitors). In certain embodiments, a compound described herein shows increased metabolic stability (e.g., microsomal stability), as compared to other kinase inhibitors (e.g., non-selective kinase inhibitors, such as non-selective GSK3 inhibitors; or selective kinase inhibitors, such as selective GSK3 inhibitors).

In another aspect, provided herein are pharmaceutical compositions comprising a compound described herein and optionally a pharmaceutically acceptable excipient.

In another aspect, provided herein are methods of inhibiting the activity of GSK3 in a subject in need thereof, the method comprising administering to the subject an effective amount of a compound or pharmaceutical composition described herein, wherein the effective amount is effective for inhibiting the activity of the GSK3.

In another aspect, provided herein are methods of inhibiting the activity of GSK3 in a cell or tissue, the method comprising contacting the cell or tissue with an effective amount of a compound or pharmaceutical composition described herein, wherein the effective amount is effective for inhibiting the activity of the GSK3.

In certain embodiments, the GSK3 is GSK3α. In certain embodiments, the GSK3 is GSK3β.

In another aspect, provided herein are methods of treating a disease in a subject in need thereof, the method comprising administering to the subject an effective amount of a compound or pharmaceutical composition described herein, wherein the effective amount is effective for treating the disease.

In another aspect, provided herein are methods of preventing a disease in a subject in need thereof, the method comprising administering to the subject an effective amount of a compound or pharmaceutical composition described herein, wherein the effective amount is effective for preventing the disease.

In certain embodiments, the disease is a disease associated with aberrant activity of a kinase (e.g., GSK3). In certain embodiments, the disease is a disease associated with aberrant activity of GSK3α (e.g., Fragile X syndrome, attention deficit hyperactivity disorder (ADHD), childhood seizure, intellectual disability, diabetes (e.g., Type I diabetes or Type II diabetes), acute myeloid leukemia (AML) (e.g., acute promyelocytic leukemia (APML)), autism, or psychiatric disorder (e.g., schizophrenia)). In certain embodiments, the disease is a disease associated with aberrant activity of GSK3β (e.g., mood disorder (e.g., major depressive disorder, clinical depression, major depression, or bipolar disorder), PTSD, psychiatric disorder (e.g., schizophrenia), diabetes (Type I diabetes or Type II diabetes), or neurodegenerative disease (e.g., Alzheimer's disease, frontotemporal dementia, or amyotrophic lateral sclerosis (ALS)).

In another aspect, provided herein are methods of probing the role of kinase signaling, e.g., GSK3 signaling, e.g., in the pathophysiology of various disorders, e.g., bipolar disorder and other psychiatric disorders, the methods comprising contacting a kinase with a compound described herein.

In certain embodiments, compounds described herein are useful as a tool to probe stem cell induction. In another aspect, provided herein are methods of probing stem cell induction, the methods comprising contacting a stem cell with a compound described herein.

In certain embodiments, provided compounds are useful as probe compounds for modulating neurogenesis in a subject. In another aspect, provided herein are methods of probing neurogenesis in a subject, the methods comprising administering to the subject a compound described herein.

In another aspect, provided herein are uses of the compounds and uses of the pharmaceutical compositions.

This application refers to various issued patent, published patent applications, journal articles, and other publications, all of which are incorporated herein by reference.

Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC), supercritical fluid chromatography (SFC), and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, NY, 1962); and Wilen, *Tables of Resolving Agents and Optical Resolutions* p. 268 (E. L. Eliel, Ed., Univ. of Notre Dame Press, Notre Dame, Ind. 1972). The present disclosure additionally encompasses compounds described herein as individual isomers substantially free of other isomers, and alternatively, as mixtures of various isomers.

In a formula, the bond ∼∼∼ is a single bond, the dashed line --- is a single bond or absent, and the bond === or ≠ is a single or double bond.

Unless otherwise provided, a formula depicted herein includes compounds that do not include isotopically enriched atoms and also compounds that include isotopically enriched atoms. Compounds that include isotopically enriched atoms may be useful as, for example, analytical tools, and/or probes in biological assays.

The term "aliphatic" includes both saturated and unsaturated, nonaromatic, straight chain (i.e., unbranched), branched, acyclic, and cyclic (i.e., carbocyclic) hydrocarbons. In some embodiments, an aliphatic group is optionally substituted with one or more functional groups (e.g., halo, such as fluorine). As will be appreciated by one of ordinary skill in the art, "aliphatic" is intended herein to include alkyl, alkenyl, alkynyl, cycloalkyl, cycloalkenyl, and cycloalkynyl moieties.

When a range of values ("range") is listed, it is intended to encompass each value and sub-range within the range. A range is inclusive of the values at the two ends of the range unless otherwise provided. For example, "an integer between 1 and 4" refers to 1, 2, 3, and 4. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$ $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

"Alkyl" refers to a radical of a straight-chain or branched saturated hydrocarbon group having from 1 to 20 carbon atoms ("$C_{1-20}$ alkyl"). In some embodiments, an alkyl group has 1 to 12 carbon atoms ("$C_{1-12}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ is alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently optionally substituted, e.g., unsubstituted (an "unsubstituted alkyl") or substituted (a "substituted alkyl") with one or more substituents. In certain embodiments, the alkyl group is unsubstituted $C_{1-12}$ alkyl (e.g., —$CH_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu or s-Bu), unsubstituted isobutyl (i-Bu)). In certain embodiments, the alkyl group is substituted $C_{1-12}$alkyl (such as substituted $C_{1-6}$ alkyl, e.g., —$CH_2F$, —$CHF_2$, —$CF_3$, —$CH_2CH_2F$, —$CH_2CHF_2$, —$CH_2CF_3$, or benzyl (Bn)). The attachment point of alkyl may be a single bond (e.g., as in —$CH_3$), double bond (e.g., as in =$CH_2$), or triple bond (e.g., as in ≡CH). The moieties =$CH_2$ and ≡CH are also alkyl.

In some embodiments, an alkyl group is substituted with one or more halogens. "Perhaloalkyl" is a substituted alkyl group as defined herein wherein all of the hydrogen atoms are independently replaced by a halogen, e.g., fluoro, bromo, chloro, or iodo. In some embodiments, the alkyl moiety has 1 to 8 carbon atoms ("$C_{1-8}$ perhaloalkyl"). In some embodiments, the alkyl moiety has 1 to 6 carbon atoms ("$C_{1-6}$ perhaloalkyl"). In some embodiments, the alkyl moiety has 1 to 4 carbon atoms ("$C_{1-4}$ perhaloalkyl"). In some embodiments, the alkyl moiety has 1 to 3 carbon atoms ("$C_{1-3}$ perhaloalkyl"). In some embodiments, the alkyl moiety has 1 to 2 carbon atoms ("$C_{1-2}$ perhaloalkyl"). In some embodiments, all of the hydrogen atoms are replaced with fluoro. In some embodiments, all of the hydrogen atoms are replaced with chloro. Examples of perhaloalkyl groups include —$CF_3$, —$CF_2CF_3$, —$CF_2CF_2CF_3$, —$CCl_3$, —$CFCl_2$, —$CF_2Cl$, and the like.

"Alkenyl" refers to a radical of a straight-chain or branched hydrocarbon group having from 2 to 20 carbon atoms, one or more (e.g., two, three, or four, as valency permits) carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, e.g., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl. In an alkenyl group, a C=C double bond for which the stereochemistry is not specified (e.g., —CH=CHCH₃,

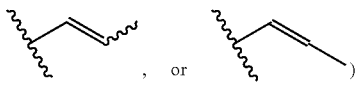

, or

)

or may be in the (E)- or (Z)-configuration.

"Alkynyl" refers to a radical of a straight-chain or branched hydrocarbon group having from 2 to 20 carbon atoms, one or more (e.g., two, three, or four, as valency permits) carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, e.g., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

"Carbocyclyl" or "carbocyclic" refers to a radical of a non-aromatic cyclic hydrocarbon group having from 3 to 13 ring carbon atoms ("$C_{3-13}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 7 ring carbon atoms ("$C_{3-7}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl"). Carbocyclyl can be saturated, and saturated carbocyclyl is referred to as "cycloalkyl." In some embodiments, carbocyclyl is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted C$_{3-10}$ cycloalkyl. In certain embodiments, the cycloalkyl group is substituted C$_{3-10}$ cycloalkyl. Carbocyclyl can be partially unsaturated. Carbocyclyl may include zero, one, or more (e.g., two, three, or four, as valency permits) C=C double bonds in all the rings of the carbocyclic ring system that are not aromatic or heteroaromatic. Carbocyclyl including one or more (e.g., two or three, as valency permits) C=C double bonds in the carbocyclic ring is referred to as "cycloalkenyl." Carbocyclyl including one or more (e.g., two or three, as valency permits) C≡C triple bonds in the carbocyclic ring is referred to as "cycloalkynyl." Carbocyclyl includes aryl. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently optionally substituted, e.g., unsubstituted (an "unsubstituted carbocyclyl") or substituted (a "substituted carbocyclyl") with one or more substituents. In certain embodiments, the carbocyclyl group is unsubstituted C$_{3-10}$ carbocyclyl. In certain embodiments, the carbocyclyl group is a substituted C$_{3-10}$ carbocyclyl. In certain embodiments, the carbocyclyl is substituted or unsubstituted, 3- to 7-membered, and monocyclic. In certain embodiments, the carbocyclyl is substituted or unsubstituted, 5- to 13-membered, and bicyclic.

In some embodiments, "carbocyclyl" is a monocyclic, saturated carbocyclyl group having from 3 to 10 ring carbon atoms ("C$_{3-10}$ cycloalkyl"). In some embodiments, a cycloalkyl group has 3 to 8 ring carbon atoms ("C$_{3-8}$ cycloalkyl"). In some embodiments, a cycloalkyl group has 3 to 6 ring carbon atoms ("C$_{3-6}$ cycloalkyl"). In some embodiments, a cycloalkyl group has 5 to 6 ring carbon atoms ("C$_{5-6}$ cycloalkyl"). In some embodiments, a cycloalkyl group has 5 to 10 ring carbon atoms ("C$_{5-10}$ cycloalkyl"). Examples of C$_{5-6}$ cycloalkyl groups include cyclopentyl (C$_5$) and cyclohexyl (C$_5$). Examples of C$_{3-6}$ cycloalkyl groups include the aforementioned C$_{5-6}$ cycloalkyl groups as well as cyclopropyl (C$_3$) and cyclobutyl (C$_4$). Examples of C$_{3-8}$ cycloalkyl groups include the aforementioned C$_{3-6}$ cycloalkyl groups as well as cycloheptyl (C$_7$) and cyclooctyl (C$_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted C$_{3-10}$ cycloalkyl. In certain embodiments, the cycloalkyl group is substituted C$_{3-10}$ cycloalkyl.

"Heterocyclyl" or "heterocyclic" refers to a radical of a 3- to 13-membered non-aromatic ring system having ring carbon atoms and 1 to 4 ring heteroatoms, wherein each heteroatom is independently selected from nitrogen, oxygen, and sulfur ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged, or spiro ring system such as a bicyclic system ("bicyclic heterocyclyl"). A heterocyclyl group can be saturated or can be partially unsaturated. Heterocyclyl may include zero, one, or more (e.g., two, three, or four, as valency permits) double bonds in all the rings of the heterocyclic ring system that are not aromatic or heteroaromatic. Partially unsaturated heterocyclyl groups includes heteroaryl. Heterocyclyl bicyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently optionally substituted, e.g., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl. In certain embodiments, the heterocyclyl is substituted or unsubstituted, 3- to 7-membered, and monocyclic. In certain embodiments, the heterocyclyl is substituted or unsubstituted, 5- to 13-membered, and bicyclic.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include azirdinyl, oxiranyl, or thiiranyl. Exemplary 4-membered heterocyclyl groups containing one heteroatom include azetidinyl, oxetanyl and thietanyl. Exemplary 5-membered heterocyclyl groups containing one heteroatom include tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include dioxolanyl, oxasulfuranyl, disulfuranyl, and oxazolidin-2-one. Exemplary 5-membered heterocyclyl groups containing three heteroatoms include triazolinyl, oxadiazolinyl, and thiadiazolinyl. Exemplary 6-membered heterocyclyl groups containing one heteroatom include piperidinyl, tetrahydropyranyl, dihydropyridinyl, and thianyl. Exemplary 6-membered heterocyclyl groups containing two heteroatoms include piperazinyl, morpholinyl, dithianyl, and dioxanyl. Exemplary 6-membered heterocyclyl groups containing two heteroatoms include triazinanyl. Exemplary 7-membered heterocyclyl groups containing one heteroatom include azepanyl, oxepanyl and thiepanyl. Exemplary 8-membered heterocyclyl groups containing one heteroatom include azocanyl, oxecanyl, and thiocanyl. Exemplary 5-membered heterocyclyl groups fused to a C$_6$ aryl ring (also referred to herein as a 5,6-bicyclic heterocyclic ring) include indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, e.g., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Heteroaryl" refers to a radical of a 5-10 membered monocyclic or bicyclic 4n+2 aromatic ring system (e.g., having 6 or 10 π electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, e.g., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, e.g., unsubstituted ("unsubstituted heteroaryl") or substituted ("substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include pyrrolyl, furanyl and thiophenyl. Exemplary 5-membered heteroaryl groups containing two heteroatoms include imidazolyl, pyrazolyl, oxazolyl, isoxazolyl, thiazolyl, and isothiazolyl. Exemplary 5-membered heteroaryl groups containing three heteroatoms include triazolyl, oxadiazolyl, and thiadiazolyl. Exemplary 5-membered heteroaryl groups containing four heteroatoms include tetrazolyl. Exemplary 6-membered heteroaryl groups containing one heteroatom include pyridinyl. Exemplary 6-membered heteroaryl groups containing two heteroatoms include pyridazinyl, pyrimidinyl, and pyrazinyl. Exemplary 6-membered heteroaryl groups containing three or four heteroatoms include triazinyl and tetrazinyl, respectively. Exemplary 7-membered heteroaryl groups containing one heteroatom include azepinyl, oxepinyl, and thiepinyl. Exemplary 5,6-bicyclic heteroaryl groups include indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include naphthyridinyl, pteridinyl, quinolinyl, isoquinolinyl, cinnolinyl, quinoxalinyl, phthalazinyl, and quinazolinyl.

"Partially unsaturated" refers to a group that includes at least one double or triple bond. The term "partially unsaturated" is intended to encompass rings having multiple sites of unsaturation, but is not intended to include aromatic groups (e.g., aryl or heteroaryl groups) as herein defined. Likewise, "saturated" refers to a group that does not contain a double or triple bond, i.e., contains all single bonds.

In some embodiments, aliphatic, alkyl, alkenyl, alkynyl, carbocyclyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present disclosure contemplates any and all such combinations in order to arrive at a stable compound. For purposes of this disclosure, heteroatoms such as nitrogen may have hydrogen substituents and/or any suitable substituent as described herein which satisfy the valencies of the heteroatoms and results in the formation of a stable moiety.

Exemplary carbon atom substituents include halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(Rb)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)(R$^{aa}$)$_2$, —P(=O)(OR$^{cc}$)$_2$, —OP(=O)(R$^{aa}$)$_2$, —OP(=O)(OR$^{cc}$)$_2$, —P(=O)(N(R$^{bb}$)$_2$)$_2$, —OP(=O)N(R$^{bb}$)$_2$)$_2$, —NR$^{bb}$P(=O)(R$^{aa}$)$_2$, —NR$^{bb}$P(=O)(OR$^{cc}$)$_2$, —NR$^{bb}$P(O)(N(R$^{bb}$)$_2$)$_2$, —P(R$^{cc}$)$_2$, —P(OR$^{cc}$)$_2$, —P(R$^{cc}$)$_3$$^+$X$^-$, —P(OR$^{cc}$)$_3$$^+$X$^-$, —P(R$^{cc}$)$_4$, —P(OR$^{cc}$)$_4$, —OP(R$^{cc}$)$_2$, —OP(R$^{cc}$)$_3$$^+$X$^-$, —OP(OR$^{cc}$)$_2$, —OP(OR$^{cc}$)$_3$$^+$X$^-$, —OP(R$^{cc}$)$_4$, —OP(OR$^{cc}$)$_4$, —B(R$^{cc}$)$_2$, —B(OR$^{cc}$), —BR(OR$^{cc}$), C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(R$^{aa}$)$_2$, —P(=O)(OR$^{cc}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)(OR$^{ee}$)$_2$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S; wherein X$^-$ is a counterion;

each instance of R$^{ee}$ is, independently, selected from C$_{1-6}$ alkyl, C$_{1-6}$ perhaloalkyl, C$_{2-6}$ alkenyl, C$_{2-6}$ alkynyl, heteroC$_{1-6}$ alkyl, heteroC$_{2-6}$alkenyl, heteroC$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl and 5-10 membered heteroaryl, or two R$^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)+X$-$, —NH$_3$$^+$X$^-$, —N(OC$_{1-6}$ alkyl)(C$_{1-6}$ alkyl), —N(OH)(C$_{1-6}$ alkyl), —NH (OH), —SH, —SC$_{1-6}$ alkyl, —SS(C$_{1-6}$ alkyl), —C(=O) (C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N (C$_{1-6}$ alkyl)$_2$, —OC(=O)NH(C$_{1-6}$ alkyl), —NHC(=O) (C$_{1-6}$ alkyl), —N(C$_{1-6}$ alkyl)C(=O)(C$_{1-6}$ alkyl), —NHCO$_2$ (C$_{1-6}$ alkyl), —NHC(=O)N(C$_{1-6}$ alkyl)$_2$, —NHC(=O)NH (C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$C$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$ —C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)(OC$_{1-6}$ alkyl)$_2$,—P(=O)(C$_{1-6}$ alkyl)$_2$, —OP(=O)(C$_{1-6}$ alkyl)$_2$, —OP(=O)(C$_{1-6}$ alkyl)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$ alkenyl, heteroC$_{2-6}$alkynyl, C$_{3-10}$ carbocyclyl, C$_{6-10}$ aryl, 3-10 membered heterocyclyl, 5-10 membered heteroaryl; or two geminal R$^{gg}$ substituents can be joined to form =O or =S; wherein X$^-$ is a counterion.

In certain embodiments, the carbon atom substituents are independently halogen, substituted (e.g., substituted with one or more halogen) or unsubstituted C$_{1-6}$ alkyl, —OR$^{aa}$, —SR$^{aa}$, —N(R$^{bb}$)$_2$, —CN, —SCN, —NO$_2$, —C(=O)R$^{aa}$, —CO$_2$R$^{aa}$, —C(=O)N(R$^{bb}$)$_2$, —OC(=O)R$^{aa}$, —OCO$_2$R$^{aa}$, —OC(=O)N(R$^{bb}$)$_2$, —NR$^{bb}$C(=O)R$^{aa}$, —NR$^{bb}$CO$_2$R$^{aa}$, or —NR$^{bb}$C(=O)N(R$^{bb}$)$_2$. In certain embodiments, the carbon atom substituents are independently halogen, substituted (e.g., substituted with one or more halogen) or unsubstituted C$_{1-6}$ alkyl, —OR$^{aa}$, —SR$^{aa}$, —N(R$^{bb}$)$_2$, —CN, —SCN, —NO$_2$, —C(=O)R$^{aa}$, —CO$_2$R$^{aa}$, —C(=O)N(R$^{bb}$)$_2$, —OC(=O)R$^{aa}$, —OCO$_2$R$^{aa}$, —OC(=O)N(R$^{bb}$)$_2$, —NR$^{bb}$(=O)R$^{aa}$, —NR$^{bb}$O$_2$R$^{aa}$, or —NR$^{bb}$C(=O)N(R$^{bb}$)$_2$, wherein R$^{aa}$ is hydrogen, substituted (e.g., substituted with one or more halogen) or unsubstituted C$_{1-6}$ alkyl, an oxygen protecting group when attached to an oxygen atom, or a sulfur protecting group (e.g., acetamidomethyl, t-Bu, 3-nitro-2-pyridine sulfenyl, 2-pyridine-sulfenyl, or triphenylmethyl) when attached to a sulfur atom; and each R$^{bb}$ is independently hydrogen, substituted (e.g., substituted with one or more halogen) or unsubstituted C$_{1-6}$ alkyl, or a nitrogen protecting group. In certain embodiments, the carbon atom substituents are independently halogen, substituted (e.g., substituted with one or more halogen) or unsubstituted C$_{1-6}$ alkyl, —OR$^{aa}$, —SR$^{aa}$, —N(R$^{bb}$)$_2$, —CN, —SCN, or —NO$_2$. In certain embodiments, the carbon atom substituents are independently halogen, substituted (e.g., substituted with one or more halogen moieties) or unsubstituted C$_{1-6}$ alkyl, —OR$^{aa}$, —SR$^{aa}$, —N(R$^{bb}$)$_2$, —CN, —SCN, or —NO$_2$, wherein R$^{aa}$ is hydrogen, substituted (e.g., substituted with one or more halogen) or unsubstituted C$_{1-6}$ alkyl, an oxygen protecting group when attached to an oxygen atom, or a sulfur protecting group (e.g., acetamidomethyl, t-Bu, 3-nitro-2-pyridine sulfenyl, 2-pyridine-sulfenyl, or triphenylmethyl) when attached to a sulfur atom; and each R$^{bb}$ is independently hydrogen, substituted (e.g., substituted with one or more halogen) or unsubstituted C$_{1-6}$ alkyl, or a nitrogen protecting group.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., F$^-$, Cl$^-$, Br$^-$, I$^-$), NO$_3^-$, ClO$_4^-$, OH$^-$, H$_2$PO$_4^-$, HCO$_3^-$, HSO$_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), BF$_4^-$, PF$_4^-$, PF$_6^-$, AsF$_6^-$, SbF$_6^-$, B[3,5-(CF$_3$)$_2$C$_6$H$_3$]$_4^-$, B(C$_6$F$_5$)$_4^-$, BPh$_4^-$, Al(OC(CF$_3$)$_3$)$_4^-$, and carborane anions (e.g., CB$_{11}$H$_{12}^-$ or (HCB$_{11}$Me$_5$Br$_6$)$^-$). Exemplary counterions which may be multivalent include CO$_3^{2-}$, HPO$_4^{2-}$, PO$_4^{3-}$, B$_4$O$_7^{2-}$, SO$_4^{2-}$, S$_2$O$_3^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

"Halo" or "halogen" refers to fluorine (fluoro, —F), chlorine (chloro, —Cl), bromine (bromo, —Br), or iodine (iodo, —I).

Nitrogen atoms can be substituted or unsubstituted as valency permits, and include primary, secondary, tertiary, and quaternary nitrogen atoms. Exemplary nitrogen atom substituents include hydrogen. —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(OR$^{cc}$)$_2$, —P(=O)(R$^{aa}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

In certain embodiments, the nitrogen atom substituents are independently substituted (e.g., substituted with one or more halogen) or unsubstituted C$_{1-6}$ alkyl, —C(=O)R$^{aa}$, —CO$_2$R$^{aa}$, —C(=O)N(R$^{bb}$)$_2$, or a nitrogen protecting group. In certain embodiments, the nitrogen atom substituents are independently substituted (e.g., substituted with one or more halogen) or unsubstituted C$_{1-6}$ alkyl, —C(=O)R$^{aa}$, —CO$_2$R$^{aa}$, —C(=O)N(R$^{bb}$)$_2$, or a nitrogen protecting group, wherein R$^{aa}$ is hydrogen, substituted (e.g., substituted with one or more halogen) or unsubstituted C$_{1-6}$ alkyl, or an oxygen protecting group when attached to an oxygen atom, and each R$^{bb}$ is independently hydrogen, substituted (e.g., substituted with one or more halogen) or unsubstituted C$_{1-6}$ alkyl, or a nitrogen protecting group. In certain embodiments, the nitrogen atom substituents are independently substituted (e.g., substituted with one or more halogen) or unsubstituted C$_{1-6}$ alkyl or a nitrogen protecting group.

In certain embodiments, the substituent present on a nitrogen atom is a nitrogen protecting group (also referred to as an amino protecting group). Nitrogen protecting groups include —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$, and R$^{dd}$ are as defined herein. Nitrogen protecting groups are well known in the art and include those described in detail in *Protecting*

*Groups in Organic Synthesis*, T. W. Greene and P. G. M. Wuts, 3rd edition, John Wiley & Sons, 1999, incorporated herein by reference.

Amide nitrogen protecting groups (e.g., —C(=O)R$^{aa}$) include formamide, acetamide, chloroacetamide, trichloroacetamide, trifluoroacetamide, phenylacetamide, 3-phenylpropanamide, picolinamide, 3-pyridylcarboxamide. N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine, o-nitrobenzamide, and o-(benzoyloxymethyl)benzamide.

Carbamate nitrogen protecting groups (e.g., —C(=O)OR$^{aa}$) include methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(NN-dicyclohexylcarboxamido)ethyl carbamate, i-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Sulfonamide nitrogen protecting groups (e.g., —S(=O)$_2$R$^{aa}$) include p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, a nitrogen protecting group is Bn, Boc, Cbz, Fmoc, trifluoroacetyl, triphenylmethyl, acetyl, or Ts.

In certain embodiments, the oxygen atom substituents are independently substituted (e.g., substituted with one or more halogen) or unsubstituted $C_{1-6}$ alkyl, —C(=O)R$^{aa}$, —CO$_2$R$^{aa}$, —C(=O)N(R$^{bb}$)$_2$, or an oxygen protecting group. In certain embodiments, the oxygen atom substituents are independently substituted (e.g., substituted with one or more halogen) or unsubstituted $C_{1-6}$ alkyl, $-C(=O)R^{aa}$, $-CO_2R^{aa}$, $-C(=O)N(R^{bb})_2$, or an oxygen protecting group, wherein $R^{aa}$ is hydrogen, substituted (e.g., substituted with one or more halogen) or unsubstituted $C_{1-6}$ alkyl, or an oxygen protecting group when attached to an oxygen atom; and each $R^{bb}$ is independently hydrogen, substituted (e.g., substituted with one or more halogen) or unsubstituted $C_{1-6}$ alkyl, or a nitrogen protecting group. In certain embodiments, the oxygen atom substituents are independently substituted (e.g., substituted with one or more halogen) or unsubstituted $C_{1-6}$ alkyl or an oxygen protecting group.

In certain embodiments, the substituent present on an oxygen atom is an oxygen protecting group (also referred to herein as an "hydroxyl protecting group"). Oxygen protecting groups include $-R^{aa}$, $-N(R^{bb})_2$, $-C(=O)SR^{aa}$, $-C(=O)R^{aa}$, $-CO_2R^{aa}$, $-C(=O)N(R^{bb})_2$, $-C(=NR^{bb})R^{aa}$, $-C(=NR^{bb})OR^{aa}$, $-C(=NR^{bb})N(R^{bb})_2$, $-S(=O)R^{aa}$, $-SO_2R^{aa}$, $-Si(R^{aa})_3$, $-P(R^{cc})_2$, $-P(R^{cc})_3{}^+X^-$, $-P(OR^{cc})_2$, $-P(OR^{cc})_3{}^+X^-$, $-P(=O)(R^{aa})_2$, $-P(=O)(OR^{cc})_2$, and $-P(=O)(N(R^{bb})_2)_2$, wherein X-, $R^{aa}$, $R^{bb}$, and $R^{cc}$ are as defined herein. Oxygen protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference.

Exemplary oxygen protecting groups include methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-naphthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, an oxygen protecting group is silyl, TBDPS, TBDMS, TIPS, TES, TMS, MOM, THP, t-Bu, Bn, allyl, acetyl, pivaloyl, or benzoyl.

In certain embodiments, the sulfur atom substituents are independently substituted (e.g., substituted with one or more halogen) or unsubstituted $C_{1-6}$ alkyl, $-C(=O)R^{aa}$, $-CO_2R^{aa}$, $-C(=O)N(R^{bb})_2$, or a sulfur protecting group. In certain embodiments, the sulfur atom substituents are independently substituted (e.g., substituted with one or more halogen) or unsubstituted $C_{1-6}$ alkyl, $-C(=O)R^{aa}$, $-CO_2R^{aa}$, $-C(=O)N(R^{bb})_2$, or a sulfur protecting group, wherein $R^{aa}$ is hydrogen, substituted (e.g., substituted with one or more halogen) or unsubstituted $C_{1-6}$ alkyl, or an oxygen protecting group when attached to an oxygen atom; and each $R^{bb}$ is independently hydrogen, substituted (e.g., substituted with one or more halogen) or unsubstituted $C_{1-6}$ alkyl, or a nitrogen protecting group. In certain embodiments, the sulfur atom substituents are independently substituted (e.g., substituted with one or more halogen) or unsubstituted $C_{1-6}$ alkyl or a sulfur protecting group.

In certain embodiments, the substituent present on a sulfur atom is a sulfur protecting group (also referred to as a "thiol protecting group"). Sulfur protecting groups include $-R^{aa}$, $-N(R^{bb})_2$, $-C(=O)SR^{aa}$, $-C(=O)R^{aa}$, $-CO_2R^{aa}$, $-C(=O)N(R^{bb})_2$, $-C(=NR^{bb})R^{aa}$, $-C(=NR^{bb})OR^{aa}$, $-C(=NR^{bb})N(R^{bb})_2$, $-S(=O)R^{aa}$, $-SO_2R^{aa}$, $-Si(R^{aa})_3$, $-P(R^{cc})_2$, $-P(R^{cc})_3{}^+X^-$, $-P(OR^{cc})_2$, $-P(OR^{cc})_3{}^+X^-$, $-P(=O)(R^{aa})_2$, $-P(=O)(OR^{cc})_2$, and $-P(=O)(N(R^{bb})_2)_2$, wherein $R^{aa}$, $R^{bb}$, and $R^{cc}$ are as defined herein. Sulfur protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference. In certain embodiments, a sulfur protecting group is acetamidomethyl, t-Bu, 3-nitro-2-pyridine sulfenyl, 2-pyridine-sulfenyl, or triphenylmethyl.

The "molecular weight" of —R, wherein —R is any monovalent moiety, is calculated by subtracting the atomic weight of a hydrogen atom from the molecular weight of the molecule R—H. The "molecular weight" of -L-, wherein -L- is any divalent moiety, is calculated by subtracting the combined atomic weight of two hydrogen atoms from the molecular weight of the molecule H-L-H.

In certain embodiments, the molecular weight of a substituent is lower than 200, lower than 150, lower than 100, lower than 50, or lower than 25 g/mol. In certain embodiments, a substituent consists of carbon, hydrogen, fluorine, chlorine, bromine, iodine, oxygen, sulfur, nitrogen, and/or silicon atoms. In certain embodiments, a substituent consists of carbon, hydrogen, fluorine, chlorine, bromine, and/or iodine atoms. In certain embodiments, a substituent consists of carbon, hydrogen, and/or fluorine atoms. In certain embodiments, a substituent does not comprise one or more, two or more, or three or more hydrogen bond donors. In certain embodiments, a substituent does not comprise one or more, two or more, or three or more hydrogen bond acceptors.

These and other exemplary substituents are described in more detail in the Detailed Description, Examples, and claims. The present disclosure is not intended to be limited in any manner by the above exemplary listing of substituents.

"Pharmaceutically acceptable salt" refers to those salts which are, within the scope of sound medical judgment, suitable for use in contact with the tissues of humans and other animals without undue toxicity, irritation, allergic response, and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences* (1977) 66:1-19. Pharmaceutically acceptable salts of the compounds describe herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid, or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, quaternary salts.

A "subject" to which administration is contemplated includes humans (e.g., a male or female of any age group, e.g., a pediatric subject (e.g., infant, child, adolescent) or adult subject (e.g., young adult, middle-aged adult or senior adult)) and/or other non-human animals, for example mammals (e.g., primates (e.g., cynomolgus monkeys, rhesus monkeys); commercially relevant mammals such as cattle, pigs, horses, sheep, goats, cats, and/or dogs), birds (e.g., commercially relevant birds such as chickens, ducks, geese, and/or turkeys), reptiles, amphibians, and fish. In certain embodiments, the non-human animal is a mammal. The non-human animal may be a male or female at any stage of development. A non-human animal may be a transgenic animal.

"Condition," "disease," and "disorder" are used interchangeably herein.

"Treat," "treating" and "treatment" encompasses an action that occurs while a subject is suffering from a condition which reduces the severity of the condition or retards or slows the progression of the condition ("therapeutic treatment"). "Treat," "treating" and "treatment" also encompasses an action that occurs before a subject begins to suffer from the condition and which inhibits or reduces the severity of the condition ("prophylactic treatment").

An "effective amount" of a compound refers to an amount sufficient to elicit the desired biological response, e.g., treat the condition. As will be appreciated by those of ordinary skill in this art, the effective amount of a compound described herein may vary depending on such factors as the desired biological endpoint, the pharmacokinetics of the compound, the condition being treated, the mode of administration, and the age and health of the subject. An effective amount encompasses therapeutic and prophylactic treatment.

A "therapeutically effective amount" of a compound is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms or causes of the condition, or enhances the therapeutic efficacy of another therapeutic agent.

A "prophylactically effective amount" of a compound is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

The term "kinase" represents transferase class enzymes that are able to transfer a phosphate group from a donor molecule to an acceptor molecule, e.g., an amino acid residue of a protein or a lipid molecule. Examples of kinases include Abl, ACK, Akt1/PKBα, Akt2/PKBβ, Akt3/PKBγ, ALK1, ALK2, Alk4, AMPKα1/β1/γ1, AMPKα1/β1/γ2, AMPKα1/β1/γ3, AMPKα1/β2/γ1, AMPKα2/β1/γ1, AMPKα2/β2/γ2, Abl2, ARKS, Ask1, Aurora A, Aurora B, Aurora C, Ax1, BARK1, Blk, Bmx, B-Raf, Brk, BrSK1, BrSK2, Btk, CaMK1α, CaMK1β, CaMK1γ, CaMK1δ, CAMK2α, CaMK2β, CAMK2δ, CAMK2γ, CAMK4, CAMKK1, CAMKK2, CDK1, CDK2, CDK3, CDK4, CDK5, CDK6, CDK7, CDK9, CDK1/cyclin B, CDK2/cyclin A, CDK2/cyclin E, CDK3/cyclin E, CDK5/p25, CDK5/p35, CDK6/cyclinD3, CDK7/cyclin H/MAT1, CDK9/cyclin T1, CHK1, CHK2, CK1α, CK1γ, CK1δ, CK1ε, CK1β1, CK1γ1, CK1γ2, CK1γ3, CK2α1, CK2α2, cKit, c-RAF, CLK1, CLK2, CLK3, COT, Csk, DAPK1, DAPK2, DAPK3, DCAMLK2, DDR2, DMPK, DRAK1, DYRK1A, DYRK2, DYRK3, eEF2K, EGFR, EPHA1, EPHA2, EPHA3, EPHA4, EPHA5, EPHA6, EPHA7, EPHA8, EphB1, EphB2, EphB3, EphB4, ErbB4, Erk1, Erk2, FAK, Fer, Fes, FGFR1, Flt2, Flt4, FLT3 D835Y, FGFR2, FGFR3, FGFR4, Fgr, Flt1, Flt3, Fms, FRK, FynA, GCK, GPRK5, GRK2, GRK4, GRK6, GRK7, GSK3α, GSK3β, Hck, HER2, HER4, HIPK1, HIPK2, HIPK3, HIPK4, IGF1R, IKKβ, IKKα, IKKε, IR, InsR, IRR, IRAK1, IRAK2, IRAK4, Itk, JAK2, JAK3, JNK1, JNK2, JNK3, KDR, KHS1, Kit, Lck, LIMK1, LKB1, LOK, LRRK2, Lyn A, Lyn B, MAPK1, MAPK2, MAPK12, MAPKAP-K2, MAPKAP-K3, MAPKAPK2, MAPKAPK3, MAPKAPK5, MARK1, MARK2, MARK3, MARK4, MELK, MEK1, MEK2, MEKK2, MEKK3, Mer, Met, MET M1250T, MINK, MKK4, MKK6, MKK7β, MLCK, MLK1, MLK3, MNK1, MNK2, MRCKα, MRCKβ, MSK1, MSK2, MSSK1, STK23, STK4, STK3, STK24, MST1, MST2, MST3, MST4, MUSK, mTOR, MYO3β, MYT1, NDR1, NEK11, NEK2, NEK3, NEK6, NEK7, NEK9, NLK, NUAK2, p38α, p38β, p38δ, p38γ, p70S6K, S6K, SRK, PAK1/CDC42, PAK2, PAK3, PAK4, PAK5, PAK6, PAR-1Bα, PASK, PBK, PDGFRα, PDGFRβ, PDK1, PEK, PHKG2, PI3Kα, PI3Kβ, PI3Kγ, PI3Kδ, Pim1, Pim2, PKAcα, PKAcβ, PKAcγ, PKA(b), PKA, PKBα, PKBβ, PKBγ, PKCα, PKCβ1, PKCβ2, PKCβ11, PKCδ, PKCε, PKCγ, PKCμ, PKCη, PKCι, PKCθ, PKCξ, PKD1, PKD2, PKD3, PKG1α, PKG1B, PKN1, PKN2, PKR, PLK1, PLK2, PLK3, PLK4, Polo, PRAK, PRK2, PrKX, PTK5, PYK2, QIK, Raf1, Ret, RIPK2, RIPK5, ROCK1, ROCK2, RON, ROS, Rse, RSK1, RSK2, RSK3, RSK4, SAPK2a, SAPK2b, SAPK3, SAPK4, SGK1, SGK2, SGK3, SIK, MLCK, SLK, Snk, Src, SRPK1, SRPK2, STK33, SYK, TAK1-TAB, TAK1, TBK1, TAO1, TAO2, TAO3, TBK1, TEC, TESK1, TGFβR1, TGFβR2, Tie2, TLK2, TrkA, TrkB, TrkC, TSSK1, TSSK2, TTK, TXK, TYK2, TYRO3, ULK1, ULK2, WEE1, WNK2, WNK3, Yes1, YSK1, ZAK, ZAP70, ZC3, and ZIPK.

The term "mutant" refers to a sequence (e.g., a protein sequence or a nucleic acid sequence) having at least one mutation. The term "mutation," as used herein, refers to a substitution of a residue within a sequence, e.g., a nucleic acid or amino acid sequence, with another residue, or a deletion or insertion of one or more residues within a sequence.

The term "variant" refers to variations of the nucleic acid or amino acid sequences of the biomolecule of interest. Encompassed within the term "variant" are nucleotide and amino acid substitutions, additions, or deletions. Also, encompassed within the term "variant" are chemically modified natural and synthetic biomolecules. For example, variant may refer to polypeptides that differ from a reference polypeptide. Generally, the differences between the polypeptide that differs in amino acid sequence from reference polypeptide, and the reference polypeptide are limited so that the amino acid sequences of the reference and the variant are closely similar overall and, in some regions, identical. A variant and reference polypeptide may differ in amino acid sequence by one or more substitutions, deletions, additions, fusions and truncations that may be conservative or non-conservative and may be present in any combination. For example, variants may be those in which several, for instance from 50 to 30, from 30 to 20, from 20 to 10, from 10 to 5, from 5 to 3, from 3 to 2, from 2 to 1 or 1 amino acids are inserted, substituted, or deleted, in any combination. Additionally, a variant may be a fragment of a polypeptide that differs from a reference polypeptide sequence by being shorter than the reference sequence, such as by a terminal or internal deletion. A variant of a polypeptide also includes a polypeptide which retains essentially the same biological function or activity as such polypeptide, e.g., precursor proteins which can be activated by cleavage of the precursor portion to produce an active mature polypeptide. These variants may be allelic variations characterized by differences in the nucleotide sequences of the structural gene coding for the protein, or may involve differential splicing or post-translational modification. Variants also include a related protein having substantially the same biological activity, but obtained from a different species. The skilled artisan can produce variants having single or multiple amino acid substitutions, deletions, additions, or replacements. These variants may include, inter alia: (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more amino acids are deleted from the peptide or protein, or (iii) one in which one or more amino acids are added to the polypeptide or protein, or (iv) one in which one or more of the amino acid residues include a substituent group, or (v) one in which the mature polypeptide is fused with another compound, such as a compound to increase the half-life of the polypeptide (for example, polyethylene glycol), or (vi) one in which the additional amino acids are fused to the mature polypeptide such as a leader or secretory sequence or a sequence which is employed for purification of the mature polypeptide or a precursor protein sequence. A variant of the polypeptide may also be a naturally occurring variant such as a naturally occurring allelic variant, or it may be a variant that is not known to occur naturally.

BRIEF DESCRIPTION OF THE DRAWINGS

FIG. 4 shows a plate map of additional GSK3α and GSK3β biochemical assay of Example 5.

DETAILED DESCRIPTION OF CERTAIN EMBODIMENTS

Figure 1:
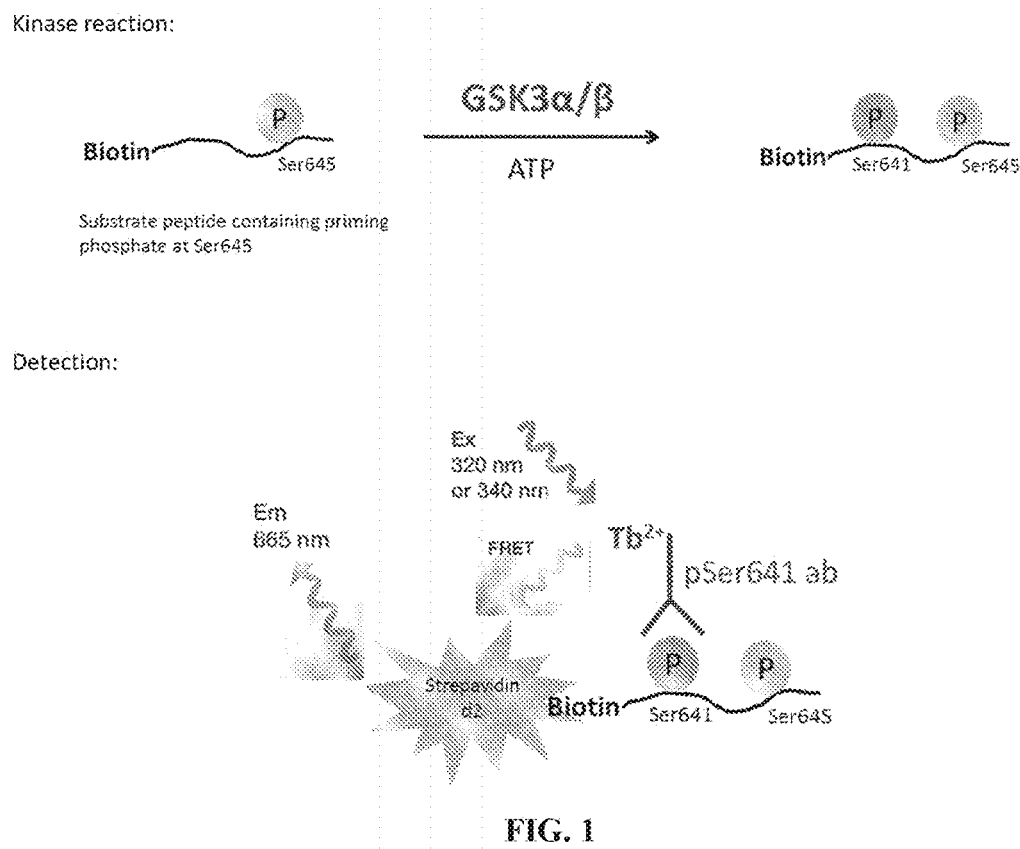
FIG. 1 shows the GSK3α and GSK3β biochemical assay (TR-FRET assay) overview.

The present disclosure provides compounds (e.g., compounds of Formula (I), and salts, solvates, hydrates, polymorphs, co-crystals, tautomers, stereoisomers, isotopically labeled derivatives, and prodrugs thereof). The compounds may be useful for inhibiting kinases, e.g., GSK3. The provided compounds may be able to selectively inhibit GSK3α, as compared to GSK3β and/or other kinases. The present disclosure further provides pharmaceutical compositions of the compounds, kits of the compounds, and methods of using the compounds. The compounds, pharmaceutical compositions, and kits described herein may be useful for treating a disease, such as a disease associated with aberrant activity of GSK3. In certain embodiments, the compounds, pharmaceutical compositions, and kits are useful for treating a disease associated with aberrant activity of GSK3α (e.g., Fragile X syndrome, attention deficit hyperactivity disorder (ADHD, childhood seizure, intellectual disability, diabetes, acute myeloid leukemia (AML), autism, or psychiatric disorder). In certain embodiments, the compounds, pharmaceutical compositions, and kits are useful in treating a disease associated with aberrant activity of GSK3β (e.g., mood disorder, PTSD, psychiatric disorder, diabetes, or neurodegenerative disease). The compounds, pharmaceutical compositions, and kits described herein may also be useful for preventing the diseases described herein.

Compounds

In one aspect, the present disclosure provides compounds of Formula (I):

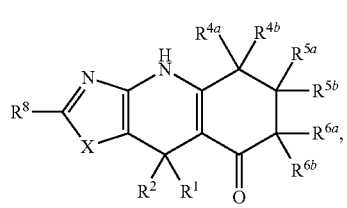

and salts, solvates, hydrates, polymorphs, co-crystals, tautomers, stereoisomers, isotopically labeled derivatives, and prodrugs thereof, wherein:

X is —O— or —S—;

$R^1$ is substituted or unsubstituted $C_{1-12}$ alkyl, substituted or unsubstituted $C_{2-12}$ alkenyl, substituted or unsubstituted $C_{2-12}$ alkynyl, substituted or unsubstituted, 3- to 13-membered, monocyclic or bicyclic carbocyclyl, substituted or unsubstituted, 3- to 13-membered, monocyclic or bicyclic heterocyclyl, substituted or unsubstituted, 6- to 10-membered, monocyclic or bicyclic aryl, or substituted or unsubstituted, 5- to 11-membered, monocyclic or bicyclic heteroaryl;

$R^2$ is substituted or unsubstituted $C_{1-6}$ alkyl, substituted or unsubstituted $C_{2-6}$ alkenyl, substituted or unsubstituted $C_{2-6}$ alkynyl, substituted or unsubstituted, 3- to 7-membered, monocyclic carbocyclyl, or substituted or unsubstituted phenyl;

or $R^1$ and $R^2$ are joined to form substituted or unsubstituted, 3- to 13-membered, monocyclic or bicyclic carbocyclyl, or substituted or unsubstituted, 3- to 13-membered, monocyclic or bicyclic heterocyclyl;

each one of $R^{4a}$ and $R^{4b}$ is independently hydrogen, halogen, —CN, —OR$^A$, —SR$^A$, —N(R$^A$)$_2$, substituted or unsubstituted $C_{1-6}$ alkyl, substituted or unsubstituted $C_{2-6}$ alkenyl, or substituted or unsubstituted $C_{2-6}$ alkynyl; or $R^{4a}$ and $R^{4b}$ are joined to form substituted or unsubstituted $C_{1-6}$ alkenyl, substituted or unsubstituted, 3- to 7-membered, monocyclic carbocyclyl, or substituted or unsubstituted, 3- to 7-membered, monocyclic heterocyclyl;

each one of $R^{5a}$ and $R^{5b}$ is independently hydrogen, halogen, —CN, —OR$^A$, —SR$^A$, —N(R$^A$)$_2$, substituted or unsubstituted $C_{1-6}$ alkyl, substituted or unsubstituted $C_{2-6}$ alkenyl, or substituted or unsubstituted $C_{2-6}$ alkynyl; or $R^{5a}$ and $R^{5b}$ are joined to form substituted or unsubstituted $C_{1-6}$ alkenyl, substituted or unsubstituted, 3- to 7-membered, monocyclic carbocyclyl, or substituted or unsubstituted, 3- to 7-membered, monocyclic heterocyclyl;

each one of $R^{6a}$ and $R^{6b}$ is independently hydrogen, halogen, halogen, —CN, —OR$^A$, —SR$^A$, —N(R$^A$)$_2$, substituted or unsubstituted $C_{1-6}$ alkyl, substituted or unsubstituted $C_{2-6}$ alkenyl, or substituted or unsubstituted $C_{2-6}$ alkynyl; or $R^{6a}$ and $R^{6b}$ are joined to form substituted or unsubstituted $C_{1-6}$ alkenyl, substituted or unsubstituted, 3- to 7-membered, monocyclic carbocyclyl, or substituted or unsubstituted, 3- to 7-membered, monocyclic heterocyclyl;

$R^8$ is hydrogen, halogen, —CN, —OR$^A$, —SR$^A$, —N(R$^A$)$_2$, substituted or unsubstituted $C_{1-6}$ alkyl, substituted or unsubstituted $C_{2-6}$ alkenyl, or substituted or unsubstituted $C_{2-6}$ alkynyl, or substituted or unsubstituted, 3- to 5-membered, monocyclic carbocyclyl;

each $R^A$ is independently hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted, 3- to 7-membered, monocyclic carbocyclyl, substituted or unsubstituted, 3- to 7-membered, monocyclic heterocyclyl, substituted or unsubstituted phenyl, substituted or unsubstituted, 5- or 6-membered, monocyclic heteroaryl, an oxygen protecting group when attached to an oxygen atom, a sulfur protecting group when attached to a sulfur atom, or a nitrogen protecting group when attached to a nitrogen atom; or two $R^A$ attached to the same nitrogen atom are joined to form substituted or unsubstituted, 3- to 7-membered, monocyclic heterocyclyl, or substituted or unsubstituted, 5- or 6-membered, monocyclic heteroaryl;

each instance of the heterocyclyl comprises in the heterocyclic ring system one, two, three, or four heteroatoms independently selected from the group consisting of oxygen, nitrogen, and sulfur, as valency permits; and each instance of the heteroaryl comprises in the heteroaryl ring system one, two, three, or four heteroatoms independently selected from the group consisting of oxygen, nitrogen, and sulfur, as valency permits.

Formula (I) include the moiety X. In certain embodiments, X is —O—. In certain embodiments, X is —S—.

Formula (I) also includes the substituent $R^1$. In some embodiments, $R^1$ is substituted or unsubstituted $C_{1-12}$ alkyl. In certain embodiments, $R^1$ is substituted or unsubstituted $C_{1-6}$ alkyl. In certain embodiments, $R^1$ is substituted or unsubstituted $C_{1-4}$ alkyl. In certain embodiments, $R^1$ is substituted or unsubstituted $C_{5-12}$ alkyl. In certain embodiments, $R^1$ is Me. In certain embodiments, $R^1$ is Et. In certain embodiments, $R^1$ is Pr or Bu. In certain embodiments, $R^1$ is substituted methyl (e.g., fluorinated methyl, e.g., —CH$_2$F, —CHF$_2$, or —CF$_3$). In certain embodiments, $R^1$ is substituted ethyl (e.g., fluorinated ethyl, e.g., —CH$_2$CH$_2$F, —CH$_2$CHF$_2$, or —CH$_2$CF$_3$). In certain embodiments, $R^1$ is substituted propyl or substituted butyl (e.g., fluorinated propyl or fluorinated butyl).

In certain embodiments, $R^1$ is substituted or unsubstituted $C_{2-12}$ alkenyl. In certain embodiments, $R^1$ is substituted or unsubstituted $C_{2-6}$ alkenyl. In certain embodiments, $R^1$ is substituted or unsubstituted $C_{2-4}$ alkenyl. In certain embodiments, $R^1$ is substituted or unsubstituted $C_{5-12}$ alkenyl. In certain embodiments, $R^1$ is substituted or unsubstituted vinyl or substituted or unsubstituted allyl.

In certain embodiments, $R^1$ is substituted or unsubstituted $C_{2-12}$ alkynyl. In certain embodiments, $R^1$ is substituted or unsubstituted $C_{2-6}$ alkynyl. In certain embodiments, $R^1$ is substituted or unsubstituted $C_{2-4}$ alkynyl. In certain embodiments, $R^1$ is substituted or unsubstituted $C_{5-12}$ alkynyl. In certain embodiments, $R^1$ is substituted or unsubstituted ethynyl.

In certain embodiments, $R^1$ is substituted or unsubstituted, 3- to 13-membered, monocyclic or bicyclic carbocyclyl. In certain embodiments, $R^1$ is substituted or unsubstituted, 3- to 7-membered, monocyclic carbocyclyl. In certain embodiments, $R^1$ is substituted or unsubstituted cyclopropyl. In certain embodiments, $R^1$ is substituted or unsubstituted cyclobutyl, substituted or unsubstituted cyclopentyl, or substituted or unsubstituted cyclohexyl. In certain embodiments, $R^1$ is substituted or unsubstituted, 5- to 13-membered, bicyclic carbocyclyl. In certain embodiments, $R^1$ is substituted or unsubstituted, 5- to 13-membered, bicyclic carbocyclyl that is fused, spiro, or bridged.

In certain embodiments, $R^1$ is substituted or unsubstituted, 3- to 13-membered, monocyclic or bicyclic heterocyclyl. In certain embodiments, $R^1$ is substituted or unsubstituted, 3- to 7-membered, monocyclic heterocyclyl. In certain embodiments, $R^1$ is substituted or unsubstituted oxetanyl, substituted or unsubstituted azetidinyl, substituted or unsubstituted tetrahydrofuranyl, substituted or unsubstituted pyrrolidinyl, substituted or unsubstituted tetrahydropyranyl, substituted or unsubstituted piperidinyl, substituted or unsubstituted morpholinyl, or substituted or unsubstituted piperazinyl. In certain embodiments, $R^1$ is substituted or unsubstituted, 5- to 13-membered, bicyclic heterocyclyl. In certain embodiments, $R^1$ is substituted or unsubstituted, 5- to 13-membered, bicyclic heterocyclyl that is fused, spiro, or bridged.

In certain embodiments, $R^1$ is substituted or unsubstituted, 6- to 10-membered, monocyclic or bicyclic aryl. In certain embodiments, $R^1$ is substituted or unsubstituted phenyl. In certain embodiments, $R^1$ is Ph. In certain embodiments, $R^1$ is substituted phenyl. In certain embodiments, $R^1$ is of the formula:

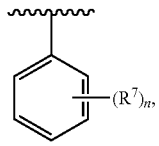

wherein each instance of $R^7$ is independently as described herein, and n is as described herein. In certain embodiments, $R^1$ is of the formula:

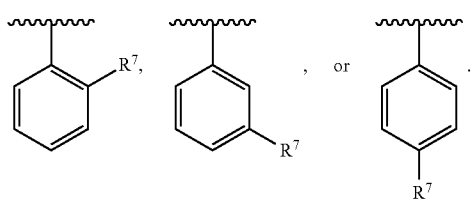

In certain embodiments, $R^1$ is of the formula:

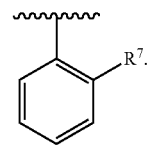

In certain embodiments, $R^1$ is of the formula:

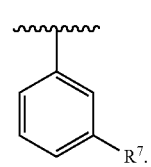

In certain embodiments, $R^1$ is of the formula:

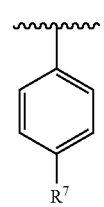

In certain embodiments, $R^1$ is of the formula:

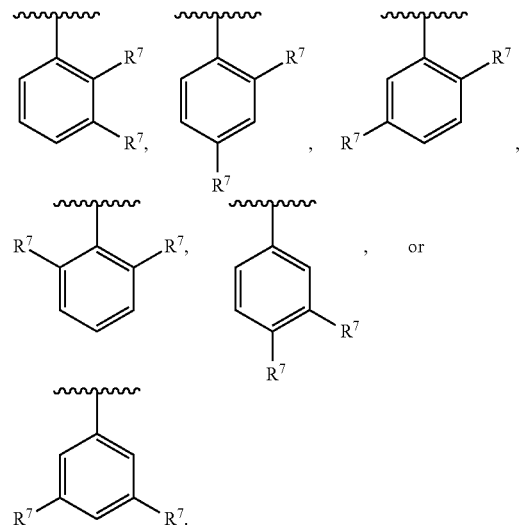

In certain embodiments, $R^1$ is of the formula:

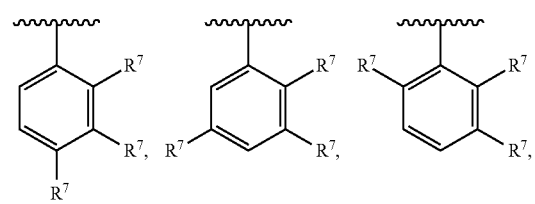

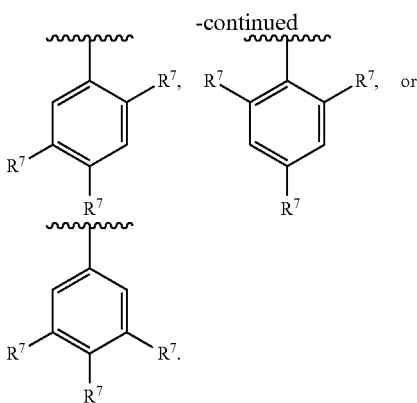

In certain embodiments, the carbon atom to which $R^1$ is directly attached is of the S configuration. In certain embodiments, the carbon atom to which $R^1$ is directly attached is of the R configuration.

Each instance of $R^7$ is independently hydrogen, halogen, substituted or unsubstituted $C_{1-12}$ alkyl, substituted or unsubstituted $C_{2-12}$ alkenyl, substituted or unsubstituted $C_{2-12}$ alkynyl, substituted or unsubstituted, 3- to 13-membered, monocyclic or bicyclic carbocyclyl, substituted or unsubstituted, 3- to 13-membered, monocyclic or bicyclic heterocyclyl, substituted or unsubstituted, 6- to 10-membered, monocyclic or bicyclic aryl, substituted or unsubstituted, 5- to 11-membered, monocyclic or bicyclic heteroaryl, —$OR^A$, —$N(R^A)_2$, —$SR^A$, —CN, —SCN, —C(=O)$R^A$, —C(=O)O$R^A$, —C(=O)N($R^A$)$_2$, —C(=N$R^A$)$R^A$, —C(=N$R^A$)O$R^A$, —C(=N$R^A$)N($R^A$), —NO$_2$, —N$_3$, —N$R^A$C(=O)$R^A$, —N$R^A$C(=O)O$R^A$, —N$R^A$C(=O)N($R^A$)$_2$, —N$R^A$C(=N$R^A$)$R^A$, —N$R^A$C(=N$R^A$)O$R^A$, —N$R^A$C(=N$R^A$)N($R^A$)$_2$, —OC(=O)$R^A$, —OC(=O)O$R^A$, —OC(=O)N($R^A$)$_2$, —OC(=N$R^A$)$R^A$, —OC(=N$R^A$)O$R^A$, —OC(=N$R^A$)N($R^A$)$_2$, —N$R^A$S(=O)$_2$$R^A$, —N$R^A$S(=O)$_2$O$R^A$, —N$R^A$S(=O)$_2$N($R^A$)$_2$, —OS(=O)$_2$$R^A$, —OS(=O)$_2$O$R^A$, —OS(=O)$_2$N($R^A$)$_2$, —S(=O)$_2$$R^A$, —S(=O)$_2$O$R^A$, or —S(=O)$_2$N($R^A$)$_2$, or two $R^7$ groups are joined to form substituted or unsubstituted, 3- to 7-membered, monocyclic carbocyclyl, substituted or unsubstituted, 3- to 7-membered, monocyclic heterocyclyl, substituted or unsubstituted phenyl, or substituted or unsubstituted, 5- or 6-membered, monocyclic heteroaryl.

When Formula (I) includes two or more $R^7$ groups, any two $R^7$ groups may be the same or different from each other. In certain embodiments, each instance of $R^7$ is independently halogen, substituted or unsubstituted $C_{1-12}$ alkyl, substituted or unsubstituted $C_{2-12}$ alkenyl, substituted or unsubstituted $C_{2-12}$ alkynyl, substituted or unsubstituted, 3- to 13-membered, monocyclic or bicyclic carbocyclyl, substituted or unsubstituted, 3- to 13-membered, monocyclic or bicyclic heterocyclyl, substituted or unsubstituted, 6- to 11-membered, monocyclic or bicyclic aryl, substituted or unsubstituted, 5- to 11-membered, monocyclic or bicyclic heteroaryl, —$OR^A$, —$N(R^A)_2$, —$SR^A$, —CN, —SCN, —C(=O)$R^A$, —C(=O)O$R^A$, —C(=O)N($R^A$)$_2$, —C(=N$R^A$)$R^A$, —C(=N$R^A$)O$R^A$, (=N$R^A$)N($R^A$)$_2$, —NO$_2$, —N$_3$, —N$R^A$C(=O)$R^A$, —N$R^A$C(=O)O$R^A$, —N$R^A$C(=O)N($R^A$)$_2$, —N$R^A$C(=N$R^A$)$R^A$, —N$R^A$C(=N$R^A$)O$R^A$, —N$R^A$C(=N$R^A$)N($R^A$)$_2$, —OC(=O)$R^A$, —OC(=O)O$R^A$, —OC(=O)N($R^A$)$_2$, —OC(=N$R^A$)$R^A$, —OC(=N$R^A$)O$R^A$, —OC(=N$R^A$)N($R^A$), —N$R^A$S(=O)$_2$$R^A$, —N$R^A$S(=O)$_2$O$R^A$, —N$R^A$S(=O)$_2$N($R^A$)$_2$, —OS(=O)$_2$$R^A$, —OS(=O)$_2$O$R^A$, —OS(=O)$_2$N($R^A$)$_2$, —S(=O)$_2$$R^A$, —S(=O)$_2$O$R^A$, or —S(=O)$_2$N($R^A$)$_2$; or two $R^7$ groups on the same carbon atom are joined to form substituted or unsubstituted $C_{1-6}$ alkenyl.

In some embodiments, at least one $R^7$ is hydrogen. In some embodiments, each $R^7$ is hydrogen. In some embodiments, no $R^7$ is hydrogen. In some embodiments, at least one $R^7$ is halogen. In some embodiments, at least one $R^7$ is F. In some embodiments, at least one $R^7$ is Cl. In some embodiments, at least one $R^7$ is Br or I. In some embodiments, at least one $R^7$ is substituted or unsubstituted $C_{1-12}$ alkyl. In certain embodiments, at least one $R^7$ is substituted or unsubstituted $C_{1-6}$ alkyl. In certain embodiments, at least one $R^7$ is substituted or unsubstituted $C_{1-4}$ alkyl. In certain embodiments, at least one $R^7$ is substituted or unsubstituted $C_{5-12}$ alkyl. In certain embodiments, at least one $R^7$ is Me. In certain embodiments, at least one $R^7$ is Et. In certain embodiments, at least one $R^7$ is Pr or Bu. In certain embodiments, at least one $R^7$ is substituted methyl (e.g., fluorinated methyl, e.g., —CH$_2$F, —CHF$_2$, or —CF$_3$). In certain embodiments, at least one $R^7$ is substituted ethyl (e.g., fluorinated ethyl, e.g., —CH$_2$CH$_2$F, —CH$_2$CHF$_2$, or —CH$_2$CF$_3$). In certain embodiments, at least one $R^7$ is substituted propyl or substituted butyl (e.g., fluorinated propyl or fluorinated butyl).

In certain embodiments, at least one $R^7$ is substituted or unsubstituted $C_{2-12}$ alkenyl. In certain embodiments, at least one $R^7$ is substituted or unsubstituted $C_{2-6}$ alkenyl. In certain embodiments, at least one $R^7$ is substituted or unsubstituted $C_{2-4}$ alkenyl. In certain embodiments, at least one $R^7$ is substituted or unsubstituted $C_{5-12}$ alkenyl. In certain embodiments, at least one $R^7$ is substituted or unsubstituted vinyl or substituted or unsubstituted allyl.

In certain embodiments, at least one $R^7$ is substituted or unsubstituted $C_{2-12}$ alkynyl. In certain embodiments, at least one $R^7$ is substituted or unsubstituted $C_{2-6}$ alkynyl. In certain embodiments, at least one $R^7$ is substituted or unsubstituted $C_{2-4}$ alkynyl. In certain embodiments, at least one $R^7$ is substituted or unsubstituted $C_{5-12}$ alkynyl. In certain embodiments, at least one $R^7$ is substituted or unsubstituted ethynyl.

In certain embodiments, at least one $R^7$ is substituted or unsubstituted, 3- to 13-membered, monocyclic or bicyclic carbocyclyl. In certain embodiments, at least one $R^7$ is substituted or unsubstituted, 3- to 7-membered, monocyclic carbocyclyl. In certain embodiments, at least one $R^7$ is substituted or unsubstituted cyclopropyl. In certain embodiments, at least one $R^7$ is substituted or unsubstituted cyclobutyl, substituted or unsubstituted cyclopentyl, or substituted or unsubstituted cyclohexyl. In certain embodiments, at least one $R^7$ is substituted or unsubstituted, 5- to 13-membered, bicyclic carbocyclyl. In certain embodiments, at least one $R^7$ is substituted or unsubstituted, 5- to 13-membered, bicyclic carbocyclyl that is fused, spiro, or bridged.

In certain embodiments, at least one $R^7$ is substituted or unsubstituted, 3- to 13-membered, monocyclic or bicyclic heterocyclyl. In certain embodiments, at least one $R^7$ is substituted or unsubstituted, 3- to 7-membered, monocyclic heterocyclyl. In certain embodiments, at least one $R^7$ is substituted or unsubstituted oxetanyl, substituted or unsubstituted azetidinyl, substituted or unsubstituted tetrahydrofuranyl, substituted or unsubstituted pyrrolidinyl, substituted or unsubstituted tetrahydropyranyl, substituted or unsubstituted piperidinyl, substituted or unsubstituted morpholinyl, or substituted or unsubstituted piperazinyl. In certain embodiments, at least one $R^7$ is substituted or unsubstituted, 5- to 13-membered, bicyclic heterocyclyl. In certain embodiments, at least one $R^7$ is substituted or unsubstituted, 5- to 13-membered, bicyclic heterocyclyl that is fused, spiro, or bridged.

In certain embodiments, at least one $R^7$ is substituted or unsubstituted, 6- to 10-membered, monocyclic or bicyclic aryl. In certain embodiments, at least one $R^7$ is substituted or unsubstituted phenyl. In certain embodiments, at least one $R^7$ is Ph. In certain embodiments, at least one $R^7$ is substituted phenyl. In certain embodiments, at least one $R^7$ is substituted or unsubstituted, 7- to 11-membered, bicyclic aryl. In certain embodiments, at least one $R^7$ is substituted or unsubstituted phenyl fused with substituted or unsubstituted, 3- to 7-membered, monocyclic carbocyclyl. In certain embodiments, at least one $R^7$ is substituted or unsubstituted phenyl fused with substituted or unsubstituted, 3- to 7-membered, monocyclic heterocyclyl. In certain embodiments, at least one $R^7$ is substituted or unsubstituted naphthyl. In certain embodiments, at least one $R^7$ is substituted or unsubstituted phenyl fused with substituted or unsubstituted, 5- or 6-membered, monocyclic heteroaryl.

In certain embodiments, at least one $R^7$ is substituted or unsubstituted, 5- to 11-membered, monocyclic or bicyclic heteroaryl. In certain embodiments, at least one $R^7$ is substituted or unsubstituted, 5-membered, monocyclic heteroaryl. In certain embodiments, at least one $R^7$ is substituted or unsubstituted pyrrolyl or substituted or unsubstituted furanyl. In certain embodiments, at least one $R^7$ is substituted or unsubstituted thienyl. In certain embodiments, at least one $R^7$ is substituted or unsubstituted thiazolyl. In certain embodiments, at least one $R^7$ is substituted or unsubstituted imidazolyl, substituted or unsubstituted pyrazolyl, substituted or unsubstituted oxazolyl, substituted or unsubstituted isoxazolyl, substituted or unsubstituted isothiazolyl, substituted or unsubstituted triazolyl, substituted or unsubstituted oxadiazolyl, substituted or unsubstituted thiadiazolyl, or substituted or unsubstituted tetrazolyl. In certain embodiments, at least one $R^7$ is substituted or unsubstituted, 6-membered, monocyclic heteroaryl. In certain embodiments, at least one $R^7$ is substituted or unsubstituted pyridinyl. In certain embodiments, at least one $R^7$ is substituted or unsubstituted pyridazinyl, substituted or unsubstituted pyrimidinyl, substituted or unsubstituted pyrazinyl, substituted or unsubstituted triazinyl, or substituted or unsubstituted tetrazinyl. In certain embodiments, at least one $R^7$ is substituted or unsubstituted, 6- to 11-membered, bicyclic heteroaryl. In certain embodiments, at least one $R^7$ is substituted or unsubstituted, 5- or 6-membered, monocyclic heteroaryl fused with substituted or unsubstituted, 3- to 7-membered, monocyclic carbocyclyl, or with substituted or unsubstituted, 3- to 7-membered, monocyclic heterocyclyl. In certain embodiments, at least one $R^7$ is substituted or unsubstituted, 5- or 6-membered, monocyclic heteroaryl fused with substituted or unsubstituted phenyl. In certain embodiments, at least one $R^7$ is substituted or unsubstituted, 5- or 6-membered, monocyclic heteroaryl fused with another substituted or unsubstituted, 5- or 6-membered, monocyclic heteroaryl.

In certain embodiments, at least one $R^7$ is —$OR^A$ (e.g., —OH, —O(substituted or unsubstituted $C_{1-6}$ alkyl) (e.g., —OMe, —$OCF_3$, —OEt, —OPr, —OBu, or —OBn), or —O(substituted or unsubstituted phenyl) (e.g., —OPh)). In certain embodiments, at least one $R^7$ is —OMe. In certain embodiments, at least one $R^7$ is —$SR^A$ (e.g., —SH, —S(substituted or unsubstituted $C_{1-6}$ alkyl) (e.g., —SMe, —$SCF_3$, —SEt, —SPr, —SBu, or —SBn), or —S(substituted or unsubstituted phenyl) (e.g., —SPh)). In certain embodiments, at least one $R^7$ is —$N(R^A)_2$ (e.g., —$NH_2$, —NH (substituted or unsubstituted $C_{1-6}$ alkyl) (e.g., —NHMe), or —N(substituted or unsubstituted $C_{1-6}$ alkyl)-(substituted or unsubstituted $C_{1-6}$ alkyl) (e.g., —$NMe_2$)). In certain embodiments, at least one $R^7$ is —CN or —SCN. In certain embodiments, at least one $R^7$ is —$NO_2$. In certain embodiments, at least one $R^7$ is —C(=$NR^A$)$R^A$, —C(=$NR^A$)$OR^A$, or —C(=$NR^A$)N($R^A$)$_2$. In certain embodiments, at least one $R^7$ is —C(=O)$R^A$ (e.g., —C(=O)(substituted or unsubstituted alkyl) (e.g., —C(=O)Me) or —C(=O)(substituted or unsubstituted phenyl)). In certain embodiments, at least one $R^7$ is —C(=O)$OR^A$ (e.g., —C(=O)OH, —C(=O)O(substituted or unsubstituted alkyl) (e.g., —C(=O)OMe), or —C(=O)O(substituted or unsubstituted phenyl)). In certain embodiments, at least one $R^7$ is —C(=O)N($R^A$)$_2$ (e.g., —C(=O)$NH_2$, —C(=O)NH(substituted or unsubstituted alkyl) (e.g., —C(=O)NHMe), —C(=O)NH(substituted or unsubstituted phenyl), —C(=O)N(substituted or unsubstituted alkyl)-(substituted or unsubstituted alkyl), or —C(=O)N(substituted or unsubstituted phenyl)-(substituted or unsubstituted alkyl)). In certain embodiments, at least one $R^7$ is —$NR^A$C(=O)$R^A$ (e.g., —NHC(=O)(substituted or unsubstituted $C_{1-6}$ alkyl) (e.g., —NHC(=O)Me) or —NHC(=O)(substituted or unsubstituted phenyl)). In certain embodiments, at least one $R^7$ is —$NR^A$C(=O)$OR^A$. In certain embodiments, at least one $R^7$ is —$NR^A$C(=O)N($R^A$)$_2$ (e.g., —NHC(=O)$NH_2$, —NHC(=O)NH(substituted or unsubstituted $C_{1-6}$ alkyl) (e.g., —NHC(=O)NHMe)). In certain embodiments, at least one $R^7$ is —OC(=O)$R^A$ (e.g., —OC(=O)(substituted or unsubstituted alkyl) or —OC(=O)(substituted or unsubstituted phenyl)), —OC(=O)$OR^A$ (e.g., —OC(=O)O(substituted or unsubstituted alkyl) or —OC(=O)O(substituted or unsubstituted phenyl)), or —OC(=O)N($R^A$)$_2$ (e.g., —OC(=O)$NH_2$, —OC(=O)NH (substituted or unsubstituted alkyl), —OC(=O)NH(substituted or unsubstituted phenyl), —OC(=O)N(substituted or unsubstituted alkyl)-(substituted or unsubstituted alkyl), or —OC(=O)N(substituted or unsubstituted phenyl)-(substituted or unsubstituted alkyl)). In certain embodiments, at least one $R^7$ is —OC(=$NR^A$)$R^A$, —OC(=$NR^A$)$OR^A$, or —OC(=$NR^A$)N($R^A$)$_2$. In certain embodiments, at least one $R^7$ is —$NR^A$S(O)$_2R^A$, —$NR^A$S(=O)$_2OR^A$, —$NR^A$S(=O)$_2$N($R^A$)$_2$, —OS(=O)$_2R^A$, —OS(=O)$_2OR^A$, or —OS(=O)$_2$N($R^A$)$_2$. In certain embodiments, at least one $R^7$ is —S(=O)$_2R^A$, —S(=O)$_2OR^A$, or —S(=O)$_2$N($R^A$)$_2$.

In certain embodiments, two $R^7$ groups are joined to form substituted or unsubstituted, 3- to 7-membered, monocyclic carbocyclyl. In certain embodiments, two $R^7$ groups are joined to form substituted or unsubstituted, 3- to 7-membered, monocyclic heterocyclyl. In certain embodiments, two $R^7$ groups are joined to form substituted or unsubstituted phenyl. In certain embodiments, two $R^7$ groups are joined to form substituted or unsubstituted, 5- or 6-membered, monocyclic heteroaryl.

In certain embodiments, when an instance of $R^7$ is directly attached to a nitrogen atom, the instance of $R^7$ is hydrogen, substituted or unsubstituted $C_{1-12}$ alkyl, substituted or unsubstituted $C_{2-12}$ alkenyl, substituted or unsubstituted $C_{2-12}$ alkynyl, substituted or unsubstituted, 3- to 13-membered, monocyclic or bicyclic carbocyclyl, substituted or unsubstituted, 3- to 13-membered, monocyclic or bicyclic heterocyclyl, substituted or unsubstituted, 6- to 10-membered, monocyclic or bicyclic aryl, substituted or unsubstituted, 5- to 11-membered, monocyclic or bicyclic heteroaryl, —C(=O)$R^A$, —C(=O)$OR^A$, —C(=O)N($R^A$)$_2$, —C(=$NR^A$)$R^A$, —C(=$NR^A$)$OR^A$, —(=$NR^A$)N($R^A$)$_2$. In certain embodiments, when an instance of $R^7$ is directly attached to a nitrogen atom, the instance of $R^7$ is hydrogen.

In certain embodiments, when an instance of $R^7$ is directly attached to a nitrogen atom, the instance of $R^7$ is not hydrogen. In certain embodiments, when an instance of $R^7$ is directly attached to a nitrogen atom, the instance of $R^7$ is substituted or unsubstituted $C_{1-12}$ alkyl (e.g., unsubstituted $C_{1-12}$ alkyl, e.g., Me). In certain embodiments, when an instance of $R^7$ is directly attached to a nitrogen atom, the instance of $R^7$ is hydrogen or substituted or unsubstituted $C_{1-12}$ alkyl (e.g., unsubstituted $C_{1-12}$ alkyl, e.g., Me).

In certain embodiments, each instance of $R^7$ is independently hydrogen, halogen, substituted or unsubstituted $C_{1-6}$ alkyl (e.g., unsubstituted $C_{1-6}$ alkyl), or —O-(substituted or unsubstituted $C_{1-6}$ alkyl) (e.g., —O-(unsubstituted $C_{1-6}$ alkyl)).

In certain embodiments, the molecular weight of each $R^7$ is lower than 300, lower than 200, lower than 100, or lower than 50 g/mol.

The variable n is 0, 1, 2, 3, 4, or 5. In certain embodiments, n is 0. In certain embodiments, n is 1. In certain embodiments, n is 2, 3, or 4. In certain embodiments, n is 5.

Formula (I) may include one or more $R^A$ groups. When Formula (I) includes two or more $R^A$ groups, any two $R^A$ groups may be the same or different from each other. In some embodiments, at least one $R^A$ is hydrogen. In some embodiments, each $R^A$ is hydrogen. In some embodiments, at least one $R^A$ is not hydrogen. In some embodiments, each $R^A$ is not hydrogen. In some embodiments, at least one $R^A$ is substituted or unsubstituted $C_{1-6}$ alkyl. In certain embodiments, at least one $R^A$ is substituted or unsubstituted $C_{1-4}$ alkyl. In certain embodiments, at least one $R^A$ is substituted or unsubstituted $C_{1-6}$ alkyl. In certain embodiments, at least one $R^A$ is Me. In certain embodiments, at least one $R^A$ is Et. In certain embodiments, at least one $R^A$ is Pr or Bu. In certain embodiments, at least one $R^A$ is substituted methyl (e.g., fluorinated methyl). In certain embodiments, at least one $R^A$ is —CH$_2$F, —CHF$_2$, or —CF$_3$. In certain embodiments, at least one $R^A$ is substituted ethyl (e.g., fluorinated ethyl). In certain embodiments, at least one $R^A$ is —CH$_2$CH$_2$F, —CH$_2$CHF$_2$, or —CH$_2$CF$_3$. In certain embodiments, at least one $R^A$ is substituted propyl or substituted butyl (e.g., fluorinated propyl or fluorinated butyl).

In certain embodiments, at least one $R^A$ is substituted or unsubstituted $C_{2-6}$ alkenyl. In certain embodiments, at least one $R^A$ is substituted or unsubstituted $C_{2-4}$ alkenyl. In certain embodiments, at least one $R^A$ is substituted or unsubstituted $C_{5-6}$ alkenyl. In certain embodiments, at least one $R^A$ is substituted or unsubstituted vinyl or substituted or unsubstituted allyl.

In certain embodiments, at least one $R^A$ is substituted or unsubstituted $C_{2-6}$ alkynyl. In certain embodiments, at least one $R^A$ is substituted or unsubstituted $C_{2-4}$ alkynyl. In certain embodiments, at least one $R^A$ is substituted or unsubstituted $C_{5-6}$ alkynyl. In certain embodiments, at least one $R^A$ is substituted or unsubstituted ethynyl.

In certain embodiments, at least one $R^A$ is substituted or unsubstituted, 3- to 7-membered, monocyclic carbocyclyl. In certain embodiments, at least one $R^A$ is substituted or unsubstituted cyclopropyl. In certain embodiments, at least one $R^A$ is substituted or unsubstituted cyclobutyl, substituted or unsubstituted cyclopentyl, or substituted or unsubstituted cyclohexyl. In certain embodiments, at least one $R^A$ is substituted or unsubstituted, 3- to 7-membered, monocyclic heterocyclyl. In certain embodiments, at least one $R^A$ is substituted or unsubstituted phenyl. In certain embodiments, at least one $R^A$ is substituted or unsubstituted, 5- or 6-membered, monocyclic heteroaryl. In certain embodiments, at least one $R^A$ is a nitrogen protecting group (e.g., Bn, Boc, Cbz, Fmoc, trifluoroacetyl, triphenylmethyl, acetyl, or Ts) when attached to a nitrogen atom. In certain embodiments, at least one $R^A$ is an oxygen protecting group (e.g., silyl, TBDPS, TBDMS, TIPS, TES, TMS, MOM, THP, t-Bu, Bn, allyl, acetyl, pivaloyl, or benzoyl) when attached to an oxygen atom. In certain embodiments, at least one $R^A$ is a sulfur protecting group (e.g., acetamidomethyl, t-Bu, 3-nitro-2-pyridine sulfenyl, 2-pyridine-sulfenyl, or triphenylmethyl) when attached to a sulfur atom. In certain embodiments, two $R^A$ groups attached to the same nitrogen atom are joined to form substituted or unsubstituted, 3- to 7-membered, monocyclic heterocyclyl. In certain embodiments, two $R^A$ groups attached to the same nitrogen atom are joined to form substituted or unsubstituted, 5- or 6-membered, monocyclic heteroaryl.

In certain embodiments. $R^1$ is substituted or unsubstituted, 7- to 11-membered, bicyclic aryl. In certain embodiments, $R^1$ is substituted or unsubstituted phenyl fused with substituted or unsubstituted, 3- to 7-membered, monocyclic carbocyclyl. In certain embodiments, $R^1$ is substituted or unsubstituted phenyl fused with substituted or unsubstituted, 3- to 7-membered, monocyclic heterocyclyl. In certain embodiments, $R^1$ is substituted or unsubstituted naphthyl. In certain embodiments, $R^1$ is substituted or unsubstituted phenyl fused with substituted or unsubstituted, 5- or 6-membered, monocyclic heteroaryl.

In certain embodiments, $R^1$ is substituted or unsubstituted, 5- to 11-membered, monocyclic or bicyclic heteroaryl. In certain embodiments, $R^1$ is substituted or unsubstituted, 5-membered, monocyclic heteroaryl. In certain embodiments, $R^1$ is substituted or unsubstituted pyrrolyl or substituted or unsubstituted furanyl. In certain embodiments, $R^1$ is substituted or unsubstituted thienyl. In certain embodiments, $R^1$ is substituted or unsubstituted thiazolyl. In certain embodiments, $R^1$ is substituted or unsubstituted imidazolyl, substituted or unsubstituted pyrazolyl, substituted or unsubstituted oxazolyl, substituted or unsubstituted isoxazolyl, substituted or unsubstituted isothiazolyl, substituted or unsubstituted triazolyl, substituted or unsubstituted oxadiazolyl, substituted or unsubstituted thiadiazolyl, or substituted or unsubstituted tetrazolyl. In certain embodiments, $R^1$ is substituted or unsubstituted, 6-membered, monocyclic heteroaryl. In certain embodiments, $R^1$ is substituted or unsubstituted pyridinyl. In certain embodiments, $R^1$ is substituted or unsubstituted pyridazinyl, substituted or unsubstituted pyrimidinyl, substituted or unsubstituted pyrazinyl, substituted or unsubstituted triazinyl, or substituted or unsubstituted tetrazinyl. In certain embodiments, $R^1$ is substituted or unsubstituted, 6- to 11-membered, bicyclic heteroaryl. In certain embodiments, $R^1$ is substituted or unsubstituted, 5- or 6-membered, monocyclic heteroaryl fused with substituted or unsubstituted, 3- to 7-membered, monocyclic carbocyclyl, or with substituted or unsubstituted, 3- to 7-membered, monocyclic heterocyclyl. In certain embodiments, $R^1$ is substituted or unsubstituted, 5- or 6-membered, monocyclic heteroaryl fused with substituted or unsubstituted phenyl. In certain embodiments, $R^1$ is substituted or unsubstituted, 5- or 6-membered, monocyclic heteroaryl fused with another substituted or unsubstituted, 5- or 6-membered, monocyclic heteroaryl.

In certain embodiments, $R^1$ is substituted or unsubstituted pyridinyl, substituted or unsubstituted thienyl, or substituted or unsubstituted thiazolyl.

In certain embodiments. $R^1$ is of the formula:

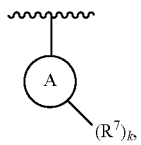

wherein:

Ring A

is substituted or unsubstituted, 5- to 6-membered, monocyclic heteroaryl;
each instance of $R^7$ is independently as described herein; and
k is 0, 1, 2, 3, or 4, as valency permits.

In certain embodiments, k is 0. In certain embodiments, k is 1. In certain embodiments, k is 2 or 3. In certain embodiments, k is 4.

In certain embodiments, the molecular weight of $R^1$ is lower than 400, lower than 300, lower than 200, or lower than 100 g/mol.

Formula (I) also includes the substituent $R^2$. In some embodiments, $R^2$ is substituted or unsubstituted $C_{1-6}$ alkyl. In certain embodiments, $R^2$ is substituted or unsubstituted $C_{1-4}$ alkyl. In certain embodiments, $R^2$ is substituted or unsubstituted $C_{5-6}$ alkyl. In certain embodiments, $R^2$ is Me. In certain embodiments, $R^2$ is Et. In certain embodiments, $R^2$ is Pr (e.g., n-Pr or i-Pr). In certain embodiments, $R^2$ is Bu (e.g., n-Bu, i-Bu, s-Bu, or t-Bu). In certain embodiments, $R^2$ is substituted methyl (e.g., fluorinated methyl). In certain embodiments, $R^2$ is —$CH_2F$, —$CHF_2$, or —$CF_3$. In certain embodiments, $R^2$ is substituted ethyl (e.g., fluorinated ethyl). In certain embodiments, $R^2$ is —$CH_2CH_2F$, —$CH_2CHF_2$, or —$CH_2CF_3$. In certain embodiments, $R^2$ is substituted propyl or substituted butyl (e.g., fluorinated propyl or fluorinated butyl).

In certain embodiments, $R^2$ is substituted or unsubstituted $C_{2-6}$ alkenyl. In certain embodiments, $R^2$ is substituted or unsubstituted $C_{2-4}$ alkenyl. In certain embodiments, $R^2$ is substituted or unsubstituted $C_{5-6}$ alkenyl. In certain embodiments, $R^2$ is substituted or unsubstituted vinyl or substituted or unsubstituted allyl.

In certain embodiments, $R^2$ is substituted or unsubstituted $C_{2-6}$ alkynyl. In certain embodiments, $R^2$ is substituted or unsubstituted $C_{2-4}$ alkynyl. In certain embodiments, $R^2$ is substituted or unsubstituted $C_{5-6}$ alkynyl. In certain embodiments, $R^2$ is substituted or unsubstituted ethynyl.

In certain embodiments, $R^2$ is substituted or unsubstituted, 3- to 7-membered, monocyclic carbocyclyl. In certain embodiments, $R^2$ is substituted or unsubstituted cyclopropyl. In certain embodiments, $R^2$ is substituted or unsubstituted cyclobutyl, substituted or unsubstituted cyclopentyl, or substituted or unsubstituted cyclohexyl.

In certain embodiments, $R^2$ is substituted or unsubstituted phenyl. In certain embodiments, $R^2$ is Ph. In certain embodiments, $R^2$ is substituted phenyl. In certain embodiments, $R^2$ is of the formula:

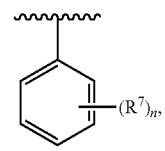

wherein each instance of $R^7$ is independently as described herein; and n is as described herein. In certain embodiments, $R^2$ is of the formula:

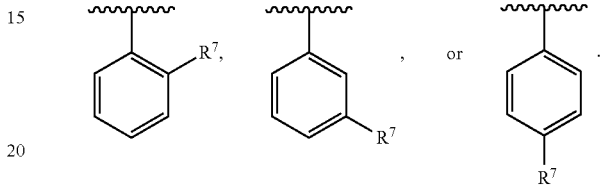

In certain embodiments, $R^2$ is of the formula:

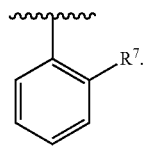

In certain embodiments, $R^2$ is of the formula:

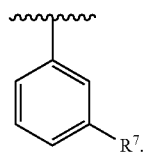

In certain embodiments, $R^2$ is of the formula:

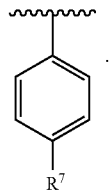

In certain embodiments, $R^2$ is of the formula:

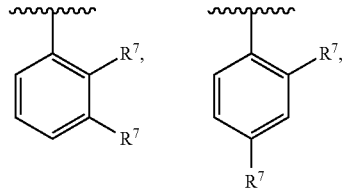

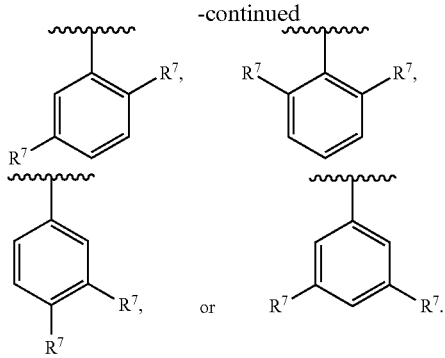

In certain embodiments, the molecular weight of $R^2$ is lower than 150, lower than 100, or lower than 50 g/mol. In certain embodiments, $R^2$ consists of carbon, hydrogen, fluorine, and/or chlorine atoms. In certain embodiments, $R^2$ consists of carbon, hydrogen, and/or fluorine atoms.

In certain embodiments, $R^1$ and $R^2$ are joined to form substituted or unsubstituted, 3- to 13-membered, monocyclic or bicyclic carbocyclyl. In certain embodiments, $R^1$ and $R^2$ are joined to form substituted or unsubstituted, 3- to 7-membered (e.g., 4- or 5-membered), monocyclic carbocyclyl. In certain embodiments, $R^1$ and $R^2$ are joined to form substituted or unsubstituted cyclopropyl, substituted or unsubstituted cyclobutyl, or substituted or unsubstituted cyclopentyl. In certain embodiments, $R^1$ and $R^2$ are joined to form substituted or unsubstituted cyclohexyl. In certain embodiments, $R^1$ and $R^2$ are joined to form substituted or unsubstituted cycloheptyl.

In certain embodiments, $R^1$ and $R^2$ are joined to form substituted or unsubstituted, 5- to 13-membered, bicyclic carbocyclyl. In certain embodiments, $R^1$ and $R^2$ are joined to form substituted or unsubstituted, 5- to 13-membered, bicyclic carbocyclyl that is fused, spiro, or bridged. In certain embodiments, $R^1$ and $R^2$ are joined to form substituted or unsubstituted, 3- to 7-membered, monocyclic carbocyclyl fused or forming a spiro linkage with substituted or unsubstituted, 3- to 7-membered, monocyclic heterocyclyl, or with another, substituted or unsubstituted, 3- to 7-membered, monocyclic carbocyclyl.

In certain embodiments, $R^1$ and $R^2$ are joined to form substituted or unsubstituted, 3- to 7-membered, monocyclic carbocyclyl fused with substituted or unsubstituted phenyl. In certain embodiments, $R^1$ and $R^2$ are joined to form

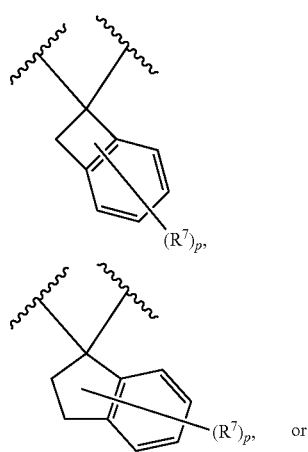

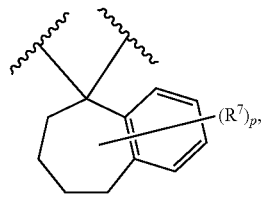

wherein each instance of $R^7$ is as described herein and may independently be directly attached to any one of the atoms in the carbocyclyl-phenyl fused ring system, and p is 0, 1, 2, 3, 4, 5, 6, 7, 8, 9, or 10, as valency permits. In certain embodiments, $R^1$ and $R^2$ are joined to form wherein each instance of $R^7$ is as described herein and may independently be directly attached to any one of the atoms in the carbocyclyl-phenyl fused ring system, and p is 0 or an integer between 1 and 12, as valency permits. In certain embodiments, p is 0. In certain embodiments, p is 1. In certain embodiments, p is 2, 3, 4, 5, or 6. In certain embodiments, p is 2, 3, 4, 5, 6, 7, or 8. In certain embodiments, p is 2, 3, 4, 5, 6, 7, 8, 9, or 10. In certain embodiments, p is an integer between 2 and 12.

In certain embodiments, $R^1$ and $R^2$ are joined to form substituted or unsubstituted, 3- to 7-membered, monocyclic carbocyclyl fused with substituted or unsubstituted, 5- or 6-membered, monocyclic heteroaryl.

In certain embodiments, $R^1$ and $R^2$ are joined to form substituted or unsubstituted, 3- to 13-membered, monocyclic or bicyclic heterocyclyl. In certain embodiments, $R^1$ and $R^2$ are joined to form substituted or unsubstituted, 3- to 7-membered (e.g., 4- or 5-membered), monocyclic heterocyclyl. In certain embodiments, $R^1$ and $R^2$ are joined to form substituted or unsubstituted oxetanyl, substituted or unsubstituted azetidinyl, substituted or unsubstituted tetrahydrofuranyl, substituted or unsubstituted pyrrolidinyl, substituted or unsubstituted tetrahydropyranyl, substituted or unsubstituted piperidinyl, substituted or unsubstituted morpholinyl, or substituted or unsubstituted piperazinyl.

In certain embodiments, $R^1$ and $R^2$ are joined to form substituted or unsubstituted, 5- to 13-membered, bicyclic heterocyclyl. In certain embodiments, $R^1$ and $R^2$ are joined to form substituted or unsubstituted, 5- to 13-membered, bicyclic heterocyclyl that is fused, spiro, or bridged. In certain embodiments, $R^1$ and $R^2$ are joined to form substituted or unsubstituted, 3- to 7-membered, monocyclic heterocyclyl fused or forming a spiro linkage with substituted or unsubstituted, 3- to 7-membered, monocyclic carbocyclyl or with another, substituted or unsubstituted, 3- to 7-membered, monocyclic heterocyclyl.

In certain embodiments, $R^1$ and $R^2$ are joined to form substituted or unsubstituted, 3- to 7-membered, monocyclic heterocyclyl fused with substituted or unsubstituted phenyl. In certain embodiments, $R^1$ and $R^2$ are joined to form

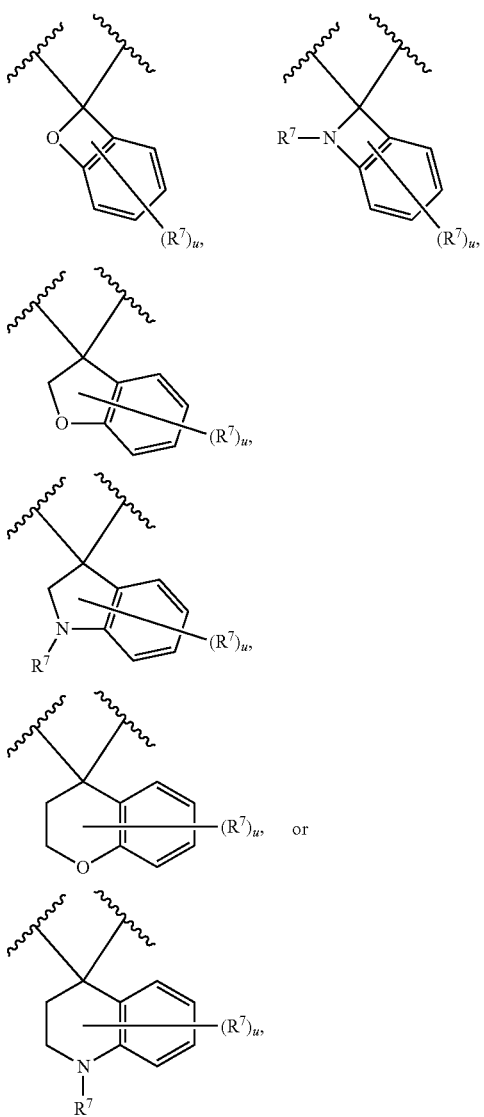

wherein each instance of $R^7$ is as described herein and may independently be directly attached to any one of the atoms in the heterocyclyl-phenyl fused ring system, and u is 0, 1, 2, 3, 4, 5, 6, 7, or 8, as valency permits. In certain embodiments, u is 0. In certain embodiments, u is 1. In certain embodiments, u is 2, 3, or 4. In certain embodiments, u is 2, 3, 4, 5, or 6. In certain embodiments, u is 2, 3, 4, 5, 6, 7, or 8.

In certain embodiments, $R^1$ and $R^2$ are joined to form substituted or unsubstituted, 3- to 7-membered, monocyclic heterocyclyl fused with substituted or unsubstituted, 5- or 6-membered, monocyclic heteroaryl.

In certain embodiments,

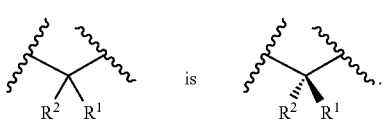

In certain embodiments,

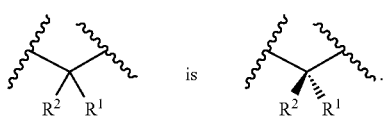

In certain embodiments, the compound is of the formula:

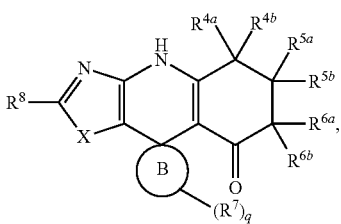

or a salt, solvate, hydrate, polymorph, co-crystal, tautomer, stereoisomer, isotopically labeled derivative, or prodrug thereof, wherein

each instance of $R^7$, and q are as described herein.

Ring B is substituted or unsubstituted, 3- to 7-membered, monocyclic carbocyclyl, or substituted or unsubstituted, 3- to 7-membered, monocyclic heterocyclyl. The variable q is 0, 1, 2, 3, 4, 5, 6, 7, 8, 9, 10, 11, or 12, as valency permits. In certain embodiments, q is 0. In certain embodiments, q is 1. In certain embodiments, q is 2, 3, 4, 5, 6, 7, 8, 9, 10, 11, or 12, as valency permits.

In certain embodiments, the compound is of the formula:

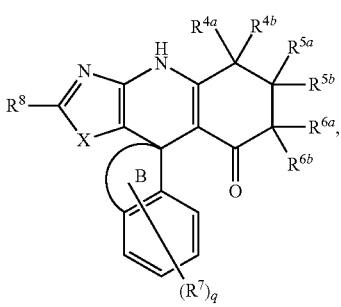

or a salt, solvate, hydrate, polymorph, co-crystal, tautomer, stereoisomer, isotopically labeled derivative, or prodrug thereof, wherein

each instance of $R^7$, and q are as described herein, and each instance of $R^7$ may independently be directly attached to any one of the atoms in the Ring B-phenyl fused ring system.

In certain embodiments, the compound is of the formula:

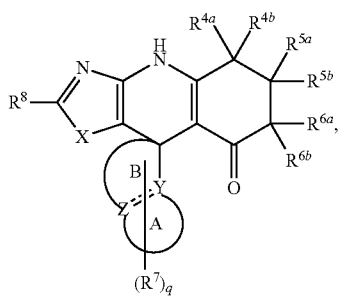

or a salt, solvate, hydrate, polymorph, co-crystal, tautomer, stereoisomer, isotopically labeled derivative, or prodrug thereof, wherein:

each instance of $R^7$, and q are as described herein, and each instance of $R^7$ may independently be directly attached to any one of the atoms in the Ring A-Ring B fused ring system;
Y is C or N;
Z is C or N; and
--- is a single or double bond, as valency permits.

Formula (I) includes substituent $R^{4a}$. In certain embodiments, $R^{4a}$ is hydrogen. In certain embodiments, $R^{4a}$ is halogen. In certain embodiments, $R^{4a}$ is F. In certain embodiments, $R^{4a}$ is Cl. In certain embodiments, $R^{4a}$ is Br or I. In certain embodiments, $R^{4a}$ is —CN. In certain embodiments, $R^{4a}$ is —$OR^A$ or —$SR^A$. In certain embodiments, $R^{4a}$ is —$OR^A$ or —$SR^A$, wherein each $R^A$ is not hydrogen. In certain embodiments, $R^{4a}$ is —$OR^A$ or —$SR^A$, wherein $R^A$ is substituted or unsubstituted $C_{1-6}$ alkyl. In certain embodiments, $R^{4a}$ is —$N(R^A)_2$. In certain embodiments, $R^{4a}$ is —$N(R^A)_2$, wherein each $R^A$ is not hydrogen. In certain embodiments, $R^{4a}$ is —$N(R^A)_2$, wherein each $R^A$ is independently substituted or unsubstituted $C_{1-6}$ alkyl.

In certain embodiments, $R^{4a}$ is substituted or unsubstituted $C_{1-6}$ alkyl. In certain embodiments, $R^{4a}$ is substituted or unsubstituted $C_{1-4}$ alkyl. In certain embodiments, $R^{4a}$ is Me. In certain embodiments, $R^{4a}$ is Et. In certain embodiments, $R^{4a}$ is Pr or Bu. In certain embodiments, $R^{4a}$ is substituted methyl (e.g., fluorinated methyl, e.g., —$CH_2F$, —$CHF_2$, or —$CF_3$). In certain embodiments, $R^{4a}$ is substituted ethyl (e.g., fluorinated ethyl, e.g., —$CH_2CH_2F$, —$CH_2CHF_2$, or —$CH_2CF_3$). In certain embodiments, $R^{4a}$ is substituted propyl or substituted butyl (e.g., fluorinated propyl or fluorinated butyl).

In certain embodiments, $R^{4a}$ is substituted or unsubstituted $C_{2-6}$ alkenyl. In certain embodiments, $R^{4a}$ is substituted or unsubstituted $C_{2-4}$ alkenyl. In certain embodiments, $R^{4a}$ is substituted or unsubstituted vinyl or substituted or unsubstituted allyl.

In certain embodiments, $R^{4a}$ is substituted or unsubstituted $C_{2-6}$ alkynyl. In certain embodiments, $R^{4a}$ is substituted or unsubstituted $C_{2-4}$ alkynyl. In certain embodiments, $R^{4a}$ is substituted or unsubstituted ethynyl.

In certain embodiments, the molecular weight of $R^{4a}$ is lower than 100, lower than 70, or lower than 50 g/mol. In certain embodiments, $R^{4a}$ consists of carbon, hydrogen, fluorine, chlorine, and/or oxygen atoms.

Formula (I) includes substituent $R^{4b}$. In certain embodiments, $R^{4b}$ is hydrogen. In certain embodiments, $R^{4b}$ is halogen. In certain embodiments, $R^{4b}$ is F. In certain embodiments, $R^{4b}$ is Cl. In certain embodiments, $R^{4b}$ is Br or I. In certain embodiments, $R^{4b}$ is —CN. In certain embodiments, $R^{4b}$ is —$OR^A$ or —$SR^A$. In certain embodiments, $R^{4b}$ is —$OR^A$ or —$SR^A$, wherein each $R^A$ is not hydrogen. In certain embodiments, $R^{4b}$ is —$OR^A$ or —$SR^A$, wherein $R^A$ is substituted or unsubstituted $C_{1-6}$ alkyl. In certain embodiments, $R^{4b}$ is —$N(R^A)_2$. In certain embodiments, $R^{4b}$ is —$N(R^A)_2$, wherein each $R^A$ is not hydrogen. In certain embodiments, $R^{4b}$ is —$N(R^A)_2$, wherein each $R^A$ is independently substituted or unsubstituted $C_{1-6}$ alkyl.

In certain embodiments, $R^{4b}$ is substituted or unsubstituted $C_{1-6}$ alkyl. In certain embodiments, $R^{4b}$ is substituted or unsubstituted $C_{1-4}$ alkyl. In certain embodiments, $R^{4b}$ is Me. In certain embodiments, $R^{4b}$ is Et. In certain embodiments, $R^{4b}$ is Pr or Bu. In certain embodiments, $R^{4b}$ is substituted methyl (e.g., fluorinated methyl, e.g., —$CH_2F$, —$CHF_2$, or —$CF_3$). In certain embodiments, $R^{4b}$ is substituted ethyl (e.g., fluorinated ethyl, e.g., —$CH_2CH_2F$, —$CH_2CHF_2$, or —$CH_2CF_3$). In certain embodiments, $R^{4b}$ is substituted propyl or substituted butyl (e.g., fluorinated propyl or fluorinated butyl).

In certain embodiments, $R^{4b}$ is substituted or unsubstituted $C_{2-6}$ alkenyl. In certain embodiments, $R^{4b}$ is substituted or unsubstituted $C_{2-4}$ alkenyl. In certain embodiments, $R^{4b}$ is substituted or unsubstituted vinyl or substituted or unsubstituted allyl.

In certain embodiments, $R^{4b}$ is substituted or unsubstituted $C_{2-6}$ alkynyl. In certain embodiments, $R^{4b}$ is substituted or unsubstituted $C_{2-4}$ alkynyl. In certain embodiments, $R^{4b}$ is substituted or unsubstituted ethynyl.

In certain embodiments, the molecular weight of $R^{4b}$ is lower than 100, lower than 70, or lower than 50 g/mol. In certain embodiments, $R^{4b}$ consists of carbon, hydrogen, fluorine, chlorine, and/or oxygen atoms.

In certain embodiments, each of $R^{4a}$ and $R^{4b}$ is hydrogen. In certain embodiments, $R^{4a}$ is substituted or unsubstituted $C_{1-6}$ alkyl (e.g., unsubstituted $C_{1-4}$ alkyl, e.g., Me), and $R^{4b}$ is hydrogen. In certain embodiments, each of $R^{4a}$ and $R^{4b}$ is independently substituted or unsubstituted $C_{1-6}$ alkyl (e.g., unsubstituted $C_{1-4}$ alkyl, e.g., Me).

In certain embodiments, $R^{4a}$ and $R^{4b}$ are joined to form substituted or unsubstituted $C_{1-6}$ alkenyl (e.g., =CH—($C_{0-5}$ alkyl), which is substituted or unsubstituted). In certain embodiments, $R^{4a}$ and $R^{4b}$ are joined to form substituted or unsubstituted, 3- to 7-membered, monocyclic carbocyclyl. In certain embodiments, $R^{4a}$ and $R^{4b}$ are joined to form substituted or unsubstituted cyclopropyl, substituted or unsubstituted cyclobutyl, substituted or unsubstituted cyclopentyl, or substituted or unsubstituted cyclohexyl.

In certain embodiments, $R^{4a}$ and $R^{4b}$ are joined to form substituted or unsubstituted, 3- to 7-membered, monocyclic heterocyclyl. In certain embodiments, $R^{4a}$ and $R^{4b}$ are joined to form substituted or unsubstituted oxetanyl, substituted or unsubstituted tetrahydrofuranyl, or substituted or unsubstituted tetrahydropyranyl. In certain embodiments, $R^{4a}$ and $R^{4b}$ are joined to form substituted or unsubstituted azetidinyl, substituted or unsubstituted pyrrolidinyl, substituted or unsubstituted piperidinyl, substituted or unsubstituted morpholinyl, or substituted or unsubstituted piperazinyl. In certain embodiment

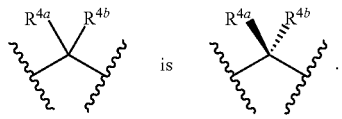

In certain embodiments,

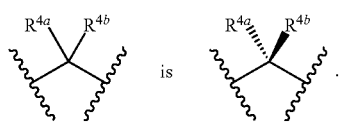

Formula (I) includes substituent $R^{5a}$. In certain embodiments, $R^{5a}$ is hydrogen. In certain embodiments, $R^{5a}$ is halogen. In certain embodiments, $R^{5a}$ is F. In certain embodiments, $R^{5a}$ is Cl. In certain embodiments, $R^{5a}$ is Br or I. In certain embodiments, $R^{5a}$ is —CN. In certain embodiments, $R^{5a}$ is —$OR^A$ or —$SR^A$. In certain embodiments, $R^{5a}$ is —$OR^A$ or —$SR^A$, wherein each $R^A$ is not hydrogen. In certain embodiments, $R^{5a}$ is —$OR^A$ or —$SR^A$, wherein $R^A$ is substituted or unsubstituted $C_{1-6}$ alkyl. In certain embodiments, $R^{5a}$ is —$N(R^A)_2$. In certain embodiments, $R^{5a}$ is —$N(R^A)_2$, wherein each $R^A$ is not hydrogen. In certain embodiments, $R^{5a}$ is —$N(R^A)_2$, wherein each $R^A$ is independently substituted or unsubstituted $C_{1-6}$ alkyl.

In certain embodiments, $R^{5a}$ is substituted or unsubstituted $C_{1-6}$ alkyl. In certain embodiments, $R^{5a}$ is substituted or unsubstituted $C_{1-4}$ alkyl. In certain embodiments, $R^{5a}$ is substituted or unsubstituted $C_{1-3}$ alkyl. In certain embodiments, $R^{5a}$ is Me. In certain embodiments, $R^{5a}$ is Et. In certain embodiments, $R^{5a}$ is Pr or Bu. In certain embodiments, $R^{5a}$ is substituted methyl (e.g., fluorinated methyl, e.g., —$CH_2F$, —$CHF_2$, or —$CF_3$). In certain embodiments, $R^{5a}$ is substituted ethyl (e.g., fluorinated ethyl, e.g., —$CH_2CH_2F$, —$CH_2CHF_2$, or —$CH_2CF_3$). In certain embodiments, $R^{5a}$ is substituted propyl or substituted butyl (e.g., fluorinated propyl or fluorinated butyl).

In certain embodiments, $R^{5a}$ is substituted or unsubstituted $C_{2-6}$ alkenyl. In certain embodiments, $R^{5a}$ is substituted or unsubstituted $C_{2-4}$ alkenyl. In certain embodiments, $R^{5a}$ is substituted or unsubstituted vinyl or substituted or unsubstituted allyl.

In certain embodiments, $R^{5a}$ is substituted or unsubstituted $C_{2-6}$ alkynyl. In certain embodiments, $R^{5a}$ is substituted or unsubstituted $C_{2-4}$ alkynyl. In certain embodiments, $R^{5a}$ is substituted or unsubstituted ethynyl.

In certain embodiments, the molecular weight of $R^{5a}$ is lower than 100, lower than 70, or lower than 50 g/mol. In certain embodiments, $R^{5a}$ consists of carbon, hydrogen, fluorine, chlorine, and/or oxygen atoms.

Formula (I) includes substituent $R^{5b}$. In certain embodiments, $R^{5b}$ is hydrogen. In certain embodiments, $R^{5b}$ is halogen. In certain embodiments, $R^{5b}$ is F. In certain embodiments, $R^{5b}$ is Cl. In certain embodiments, $R^{5b}$ is Br or I. In certain embodiments, $R^{5b}$ is —CN. In certain embodiments, $R^{5b}$ is —$OR^A$ or —$SR^A$. In certain embodiments, $R^{5b}$ is —$OR^A$ or —$SR^A$, wherein each $R^A$ is not hydrogen. In certain embodiments, $R^{5b}$ is —$OR^A$ or —$SR^A$, wherein $R^A$ is substituted or unsubstituted $C_{1-6}$ alkyl. In certain embodiments, $R^{5b}$ is —$N(R^A)_2$. In certain embodiments, $R^{5b}$ is —$N(R^A)_2$, wherein each $R^A$ is not hydrogen. In certain embodiments, $R^{5b}$ is —$N(R^A)_2$, wherein each $R^A$ is independently substituted or unsubstituted $C_{1-6}$ alkyl.

In certain embodiments, $R^{5b}$ is substituted or unsubstituted $C_{1-6}$ alkyl. In certain embodiments, $R^{5b}$ is substituted or unsubstituted $C_{1-4}$ alkyl. In certain embodiments, $R^{5b}$ is Me. In certain embodiments, $R^{5b}$ is Et. In certain embodiments, $R^{5b}$ is Pr or Bu. In certain embodiments, $R^{5b}$ is substituted methyl (e.g., fluorinated methyl, e.g., —$CH_2F$, —$CHF_2$, or —$CF_3$). In certain embodiments, $R^{5b}$ is substituted ethyl (e.g., fluorinated ethyl, e.g., —$CH_2CH_2F$, —$CH_2CHF_2$, or —$CH_2CF_3$). In certain embodiments, $R^{5b}$ is substituted propyl or substituted butyl (e.g., fluorinated propyl or fluorinated butyl).

In certain embodiments, $R^{5b}$ is substituted or unsubstituted $C_{2-6}$ alkenyl. In certain embodiments, $R^{5b}$ is substituted or unsubstituted $C_{2-4}$ alkenyl. In certain embodiments, $R^{5b}$ is substituted or unsubstituted vinyl or substituted or unsubstituted allyl.

In certain embodiments, $R^{5b}$ is substituted or unsubstituted $C_{2-6}$ alkynyl. In certain embodiments, $R^{5b}$ is substituted or unsubstituted $C_{2-4}$ alkynyl. In certain embodiments, $R^{5b}$ is substituted or unsubstituted ethynyl.

In certain embodiments, the molecular weight of $R^{5b}$ is lower than 100, lower than 70, or lower than 50 g/mol. In certain embodiments, $R^{5b}$ consists of carbon, hydrogen, fluorine, chlorine, and/or oxygen atoms.

In certain embodiments, each of $R^{5a}$ and $R^{5b}$ is hydrogen. In certain embodiments, $R^{5a}$ is substituted or unsubstituted $C_{1-6}$ alkyl (e.g., unsubstituted $C_{1-4}$ alkyl, e.g., Me), and $R^{5b}$ is hydrogen. In certain embodiments, each of $R^{5a}$ and $R^{5b}$ is independently substituted or unsubstituted $C_{1-6}$ alkyl. In certain embodiments, each of $R^{5a}$ and $R^{5b}$ is Me. In certain embodiments, each of $R^{5a}$ and $R^{5b}$ is Et.

In certain embodiments, $R^{5a}$ and $R^{5b}$ are joined to form substituted or unsubstituted $C_{1-6}$ alkenyl (e.g., =CH—($C_{0-5}$ alkyl), which is substituted or unsubstituted). In certain embodiments, $R^{5a}$ and $R^{5b}$ are joined to form substituted or unsubstituted, 3- to 7-membered, monocyclic carbocyclyl. In certain embodiments, $R^{5a}$ and $R^{5b}$ are joined to form substituted or unsubstituted cyclopropyl, substituted or unsubstituted cyclobutyl, substituted or unsubstituted cyclopentyl, or substituted or unsubstituted cyclohexyl.

In certain embodiments, $R^{5a}$ and $R^{5b}$ are joined to form substituted or unsubstituted, 3- to 7-membered, monocyclic heterocyclyl. In certain embodiments, $R^{5a}$ and $R^{5b}$ are joined to form substituted or unsubstituted oxetanyl, substituted or unsubstituted tetrahydrofuranyl, or substituted or unsubstituted tetrahydropyranyl. In certain embodiments, $R^{5a}$ and $R^{5b}$ are joined to form substituted or unsubstituted azetidinyl, substituted or unsubstituted pyrrolidinyl, substituted or unsubstituted piperidinyl, substituted or unsubstituted morpholinyl, or substituted or unsubstituted piperazinyl. In certain embodiments,

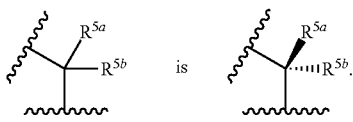

In certain embodiments,

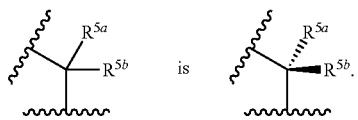

Formula (I) includes substituent $R^{6a}$. In certain embodiments, $R^{6a}$ is hydrogen. In certain embodiments, $R^{6a}$ is halogen. In certain embodiments, $R^{6a}$ is F. In certain embodiments, $R^{6a}$ is Cl. In certain embodiments, $R^{6a}$ is Br or I. In certain embodiments, $R^{6a}$ is —CN. In certain embodiments, $R^{6a}$ is —$OR^A$ or —$SR^A$. In certain embodiments, $R^{6a}$ is —$OR^A$ or —$SR^A$, wherein each $R^A$ is not hydrogen. In certain embodiments, $R^{6a}$ is —$OR^A$ or —$SR^A$, wherein $R^A$ is substituted or unsubstituted $C_{1-6}$ alkyl. In certain embodiments, $R^{6a}$ is —$N(R^A)_2$. In certain embodiments, $R^{6a}$ is —$N(R^A)_2$, wherein each $R^A$ is not hydrogen. In certain embodiments, $R^{6a}$ is —$N(R^A)_2$, wherein each $R^A$ is independently substituted or unsubstituted $C_{1-6}$ alkyl.

In certain embodiments, $R^{6a}$ is substituted or unsubstituted $C_{1-6}$ alkyl. In certain embodiments, $R^{6a}$ is substituted or unsubstituted $C_{1-4}$ alkyl. In certain embodiments, $R^{6a}$ is Me. In certain embodiments, $R^{6a}$ is Et. In certain embodiments, $R^{6a}$ is Pr or Bu. In certain embodiments, $R^{6a}$ is substituted methyl (e.g., fluorinated methyl, e.g., —$CH_2F$, —$CHF_2$, or —$CF_3$). In certain embodiments, $R^{6a}$ is substituted ethyl (e.g., fluorinated ethyl, e.g., —$CH_2CH_2F$, —$CH_2CHF_2$, or —$CH_2CF_3$). In certain embodiments, $R^{6a}$ is substituted propyl or substituted butyl (e.g., fluorinated propyl or fluorinated butyl).

In certain embodiments, $R^{6a}$ is substituted or unsubstituted $C_{2-6}$ alkenyl. In certain embodiments, $R^{6a}$ is substituted or unsubstituted $C_{2-4}$ alkenyl. In certain embodiments, $R^{6a}$ is substituted or unsubstituted vinyl or substituted or unsubstituted allyl.

In certain embodiments, $R^{6a}$ is substituted or unsubstituted $C_{2-6}$ alkynyl. In certain embodiments, $R^{6a}$ is substituted or unsubstituted $C_{2-4}$ alkynyl. In certain embodiments, $R^{6a}$ is substituted or unsubstituted ethynyl.

In certain embodiments, the molecular weight of $R^{6a}$ is lower than 100, lower than 70, or lower than 50 g/mol. In certain embodiments, $R^{6a}$ consists of carbon, hydrogen, fluorine, chlorine, and/or oxygen atoms.

Formula (I) includes substituent $R^{6b}$. In certain embodiments, $R^{6b}$ is hydrogen. In certain embodiments, $R^{6b}$ is halogen. In certain embodiments, $R^{6b}$ is F. In certain embodiments, $R^{6b}$ is Cl. In certain embodiments, $R^{6b}$ is Br or I. In certain embodiments, $R^{6b}$ is —CN. In certain embodiments, $R^{6b}$ is —$OR^A$ or —$SR^A$. In certain embodiments, $R^{6b}$ is —$OR^A$ or —$SR^A$, wherein each $R^A$ is not hydrogen. In certain embodiments, $R^{6b}$ is —$OR^A$ or —$SR^A$, wherein $R^A$ is substituted or unsubstituted $C_{1-6}$ alkyl. In certain embodiments, $R^{6b}$ is —$N(R^A)_2$. In certain embodiments, $R^{6b}$ is —$N(R^A)_2$, wherein each $R^A$ is not hydrogen. In certain embodiments, $R^{6b}$ is —$N(R^A)_2$, wherein each $R^A$ is independently substituted or unsubstituted $C_{1-6}$ alkyl.

In certain embodiments, $R^{6b}$ is substituted or unsubstituted $C_{1-6}$ alkyl. In certain embodiments, $R^{6b}$ is substituted or unsubstituted $C_{1-4}$ alkyl. In certain embodiments, $R^{6b}$ is Me. In certain embodiments, $R^{6b}$ is Et. In certain embodiments, $R^{6b}$ is Pr or Bu. In certain embodiments, $R^{6b}$ is substituted methyl (e.g., fluorinated methyl, e.g., —$CH_2F$, —$CHF_2$, or —$CF_3$). In certain embodiments, $R^{6b}$ is substituted ethyl (e.g., fluorinated ethyl, e.g., —$CH_2CH_2F$, —$CH_2CHF_2$, or —$CH_2CF_3$). In certain embodiments, $R^{6b}$ is substituted propyl or substituted butyl (e.g., fluorinated propyl or fluorinated butyl).

In certain embodiments, $R^{6b}$ is substituted or unsubstituted $C_{2-6}$ alkenyl. In certain embodiments, $R^{6b}$ is substituted or unsubstituted $C_{2-4}$ alkenyl. In certain embodiments, $R^{6b}$ is substituted or unsubstituted vinyl or substituted or unsubstituted allyl.

In certain embodiments, $R^{6b}$ is substituted or unsubstituted $C_{2-6}$ alkynyl. In certain embodiments, $R^{6b}$ is substituted or unsubstituted $C_{2-4}$ alkynyl. In certain embodiments, $R^{6b}$ is substituted or unsubstituted ethynyl.

In certain embodiments, the molecular weight of $R^{6b}$ is lower than 100, lower than 70, or lower than 50 g/mol. In certain embodiments, $R^{6b}$ consists of carbon, hydrogen, fluorine, chlorine, and/or oxygen atoms.

In certain embodiments, each of $R^{6a}$ and $R^{6b}$ is hydrogen. In certain embodiments, $R^{6a}$ is substituted or unsubstituted $C_{1-6}$ alkyl (e.g., unsubstituted $C_{1-4}$ alkyl, e.g., Me), and $R^{6b}$ is hydrogen. In certain embodiments, each of $R^{6a}$ and $R^{6b}$ is independently substituted or unsubstituted $C_{1-6}$ alkyl (e.g., unsubstituted $C_{1-4}$ alkyl, e.g., Me).

In certain embodiments, $R^{6a}$ and $R^{6b}$ are joined to form substituted or unsubstituted $C_{1-6}$ alkenyl (e.g., =CH—($C_{0-5}$ alkyl), which is substituted or unsubstituted). In certain embodiments, $R^{6a}$ and $R^{6b}$ are joined to form substituted or unsubstituted, 3- to 7-membered, monocyclic carbocyclyl. In certain embodiments, $R^{6a}$ and $R^{6b}$ are joined to form substituted or unsubstituted cyclopropyl, substituted or unsubstituted cyclobutyl, substituted or unsubstituted cyclopentyl, or substituted or unsubstituted cyclohexyl.

In certain embodiments, $R^{6a}$ and $R^{6b}$ are joined to form substituted or unsubstituted, 3- to 7-membered, monocyclic heterocyclyl. In certain embodiments, $R^{6a}$ and $R^{6b}$ are joined to form substituted or unsubstituted oxetanyl, substituted or unsubstituted tetrahydrofuranyl, or substituted or unsubstituted tetrahydropyranyl. In certain embodiments, $R^{6a}$ and $R^{6b}$ are joined to form substituted or unsubstituted azetidinyl, substituted or unsubstituted pyrrolidinyl, substituted or unsubstituted piperidinyl, substituted or unsubstituted morpholinyl, or substituted or unsubstituted piperazinyl. In certain embodiments,

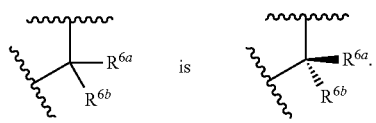

In certain embodiments,

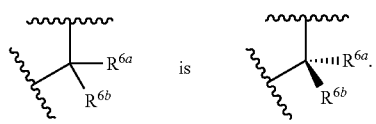

In certain embodiments, each of $R^{4a}$, $R^{4b}$, $R^{6a}$, and $R^{6b}$ is hydrogen, and each of $R^{5a}$ and $R^{5b}$ is substituted or unsubstituted $C_{1-6}$ alkyl. In certain embodiments, each of $R^{4a}$, $R^{4b}$, $R^{6a}$, and $R^{6b}$ is hydrogen, and each of $R^{5a}$ and $R^{5b}$ is Me. In certain embodiments, each of $R^{4a}$, $R^{4b}$, $R^{6a}$, and $R^{6b}$ is hydrogen, and each of $R^{5a}$ and $R^{5b}$ is Et. In certain embodiments, each of $R^{4a}$, $R^{4b}$, $R^{6a}$, and $R^{6b}$ is hydrogen, and $R^{5a}$ and $R^{5b}$ are joined to form substituted or unsubstituted, 3- to 7-membered, monocyclic carbocyclyl (e.g., substituted or unsubstituted cyclopropyl, substituted or unsubstituted cyclobutyl, substituted or unsubstituted cyclopentyl, or substituted or unsubstituted cyclohexyl). In certain embodiments, each of $R^{4a}$, $R^{4b}$, $R^{6a}$, and $R^{6b}$ is hydrogen, and $R^{5a}$ and $R^{5b}$ are joined to form substituted or unsubstituted, 3- to 7-membered, monocyclic heterocyclyl (e.g., substituted or unsubstituted oxetanyl, substituted or unsubstituted tetrahydrofuranyl, substituted or unsubstituted tetrahydropyranyl, substituted or unsubstituted azetidinyl, substituted or unsubstituted pyrrolidinyl, substituted or unsubstituted piperidinyl, substituted or unsubstituted morpholinyl, or substituted or unsubstituted piperazinyl). In certain embodiments, each of five of $R^{4a}$, $R^{4b}$, $R^{5a}$, $R^{5b}$, $R^{6a}$, and $R^{6b}$ is hydrogen, and the remaining $R^{4a}$, $R^{4b}$, $R^{5a}$, $R^{5b}$, $R^{6a}$, or $R^{6b}$ is substituted or unsubstituted $C_{1-6}$ alkyl (e.g., substituted or unsubstituted $C_{1-4}$ alkyl, e.g., unsubstituted $C_{1-4}$ alkyl). In certain embodiments, each of four of $R^{4a}$, $R^{4b}$, $R^{5a}$, $R^{5b}$, $R^{6a}$, and $R^{6b}$ is hydrogen, and the remaining two of $R^{4a}$, $R^{4b}$, $R^{5a}$, $R^{6a}$, and $R^{6b}$ are independently substituted or unsubstituted $C_{1-3}$ alkyl (e.g., substituted or unsubstituted methyl, e.g., Me), or, if directedly attached to the same carbon atom, are joined to form substituted or unsubstituted, 3- to 7-membered, monocyclic carbocyclyl, or substituted or unsubstituted, 3- to 7-membered, monocyclic heterocyclyl.

Formula (I) also includes substituent $R^8$. In certain embodiments, $R^8$ is hydrogen. In certain embodiments, $R^8$ is hydrogen that is not enriched with deuterium beyond (above) the natural abundance. In certain embodiments, $R^8$ is hydrogen that is enriched with deuterium beyond the natural abundance. In certain embodiments, $R^8$ is hydrogen that is enriched with deuterium beyond the natural abundance, wherein the abundance of deuterium of $R^8$ is at least 80%, at least 90%, at least 95%, at least 97%, at least 99%, or at least 99.5%. In certain embodiments, $R^8$ is halogen. In certain embodiments, $R^8$ is F. In certain embodiments, $R^8$ is Cl. In certain embodiments, $R^8$ is Br or 1. In certain embodiments, $R^8$ is —CN. In certain embodiments, $R^8$ is —$OR^A$ or —$SR^A$. In certain embodiments, $R^8$ is —$OR^A$ or —$SR^A$, wherein each $R^A$ is not hydrogen. In certain embodiments, $R^8$ is —$OR^A$ or —$SR^A$, wherein $R^A$ is substituted or unsubstituted $C_{1-6}$ alkyl. In certain embodiments, $R^8$ is —$N(R^A)_2$. In certain embodiments, $R^8$ is —$N(R^A)_2$, wherein each $R^A$ is not hydrogen. In certain embodiments, $R^8$ is —$N(R^A)_2$, wherein each $R^A$ is independently substituted or unsubstituted $C_{1-6}$ alkyl.

In certain embodiments, $R^8$ is substituted or unsubstituted $C_{1-6}$ alkyl. In certain embodiments, $R^8$ is substituted or unsubstituted $C_{1-6}$ alkyl. In certain embodiments, $R^8$ is Me. In certain embodiments, $R^8$ is Et. In certain embodiments, $R^8$ is Pr or Bu. In certain embodiments, $R^8$ is substituted methyl (e.g., fluorinated methyl, e.g., —$CH_2F$, —$CHF_2$, or —$CF_3$). In certain embodiments, $R^8$ is substituted ethyl (e.g., fluorinated ethyl, e.g., —$CH_2CH_2F$, —$CH_2CHF_2$, or —$CH_2CF_3$). In certain embodiments, $R^8$ is substituted propyl or substituted butyl (e.g., fluorinated propyl or fluorinated butyl).

In certain embodiments, $R^8$ is substituted or unsubstituted $C_{2-6}$ alkenyl. In certain embodiments, $R^8$ is substituted or unsubstituted $C_{2-4}$ alkenyl. In certain embodiments, $R^8$ is substituted or unsubstituted vinyl or substituted or unsubstituted allyl.

In certain embodiments, $R^8$ is substituted or unsubstituted $C_{2-6}$ alkynyl. In certain embodiments, $R^8$ is substituted or unsubstituted $C_{2-4}$ alkynyl. In certain embodiments, $R^8$ is substituted or unsubstituted ethynyl.

In certain embodiments, $R^8$ is substituted or unsubstituted, 3- to 5-membered, monocyclic carbocyclyl. In certain embodiments, $R^8$ is substituted or unsubstituted cyclopropyl. In certain embodiments, $R^8$ is unsubstituted cyclopropyl. In certain embodiments, $R^8$ is substituted or unsubstituted cyclobutyl or substituted or unsubstituted cyclopentyl.

In certain embodiments, the molecular weight of $R^8$ is lower than 100, lower than 70, lower than 50, or lower than 25 g/mol. In certain embodiments, $R^8$ consists of carbon, hydrogen, fluorine, and/or chlorine atoms. In certain embodiments, $R^8$ consists of carbon, hydrogen, and/or fluorine atoms.

In Formula (I), each instance of the heterocyclyl independently comprises in the heterocyclic ring system one, two, three, or four heteroatoms independently selected from the group consisting of oxygen, nitrogen, and sulfur, as valency permits. In Formula (I), each instance of the heterocyclyl comprises in the heterocyclic ring system one, two, or three heteroatoms independently selected from the group consisting of oxygen and sulfur, as valency permits. In Formula (I), each instance of the heteroaryl independently comprises in the heteroaryl ring system one, two, three, or four heteroatoms independently selected from the group consisting of oxygen, nitrogen, and sulfur, as valency permits. In Formula (I), each instance of the heteroaryl comprises in the heteroaryl ring system one, two, or three heteroatoms independently selected from the group consisting of oxygen and sulfur, as valency permits.

In certain embodiments, the compound is of the formula:

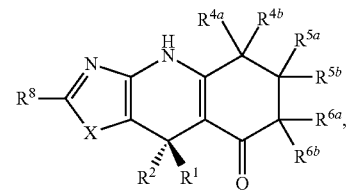

or a salt, solvate, hydrate, polymorph, co-crystal, tautomer, stereoisomer, isotopically labeled derivative, or prodrug thereof.

In certain embodiments, the compound is of the formula:

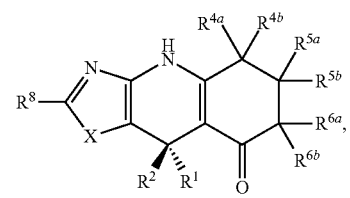

or a salt, solvate, hydrate, polymorph, co-crystal, tautomer, stereoisomer, isotopically labeled derivative, or prodrug thereof.

In certain embodiments, the compound is of the formula:

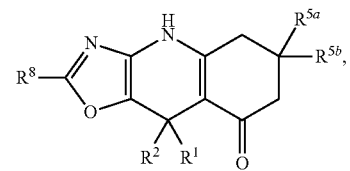

or a salt, solvate, hydrate, polymorph, co-crystal, tautomer, stereoisomer, isotopically labeled derivative, or prodrug thereof, wherein $R^8$ is hydrogen optionally enriched with deuterium beyond the natural abundance.

In certain embodiments, the compound is of the formula:

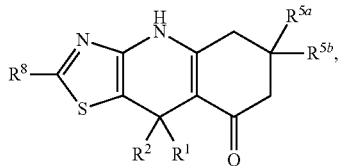

or a salt, solvate, hydrate, polymorph, co-crystal, tautomer, stereoisomer, isotopically labeled derivative, or prodrug thereof, wherein $R^8$ is hydrogen optionally enriched with deuterium beyond the natural abundance.

In certain embodiments, the compound is of the formula:

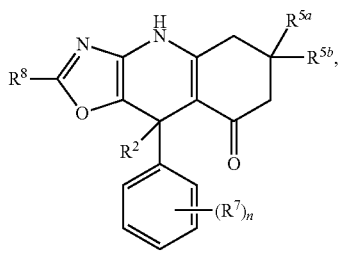

or a salt, solvate, hydrate, polymorph, co-crystal, tautomer, stereoisomer, isotopically labeled derivative, or prodrug thereof, wherein $R^8$ is hydrogen optionally enriched with deuterium beyond the natural abundance.

In certain embodiments, the compound is of the formula:

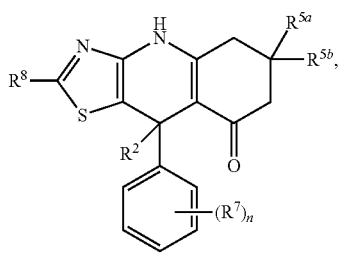

or a salt, solvate, hydrate, polymorph, co-crystal, tautomer, stereoisomer, isotopically labeled derivative, or prodrug thereof, wherein $R^8$ is hydrogen optionally enriched with deuterium beyond the natural abundance.

In certain embodiments, the compound is of the formula:

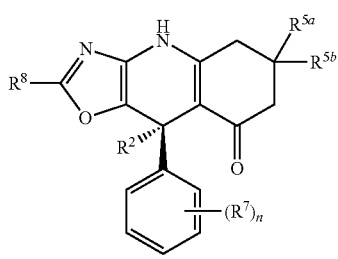 or

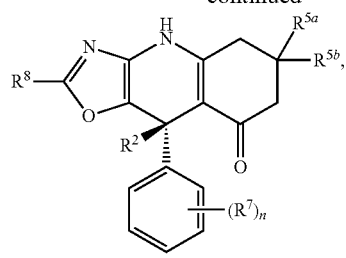

or a salt, solvate, hydrate, polymorph, co-crystal, tautomer, stereoisomer, isotopically labeled derivative, or prodrug thereof, wherein $R^8$ is hydrogen optionally enriched with deuterium beyond the natural abundance.

In certain embodiments, the compound is of the formula:

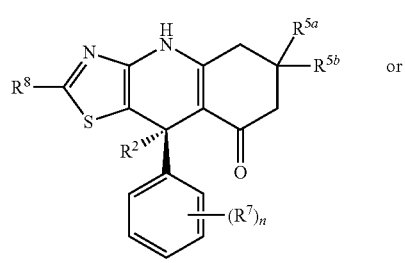 or

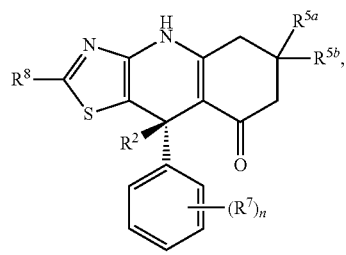

or a salt, solvate, hydrate, polymorph, co-crystal, tautomer, stereoisomer, isotopically labeled derivative, or prodrug thereof, wherein $R^8$ is hydrogen optionally enriched with deuterium beyond the natural abundance.

In certain embodiments, the compound is of the formula:

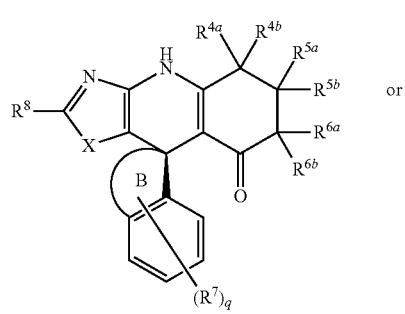 or

-continued

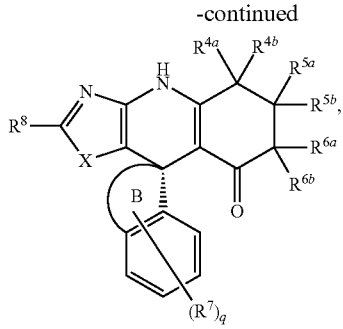

or a salt, solvate, hydrate, polymorph, co-crystal, tautomer, stereoisomer, isotopically labeled derivative, or prodrug thereof.

In certain embodiments, the compound is of the formula:

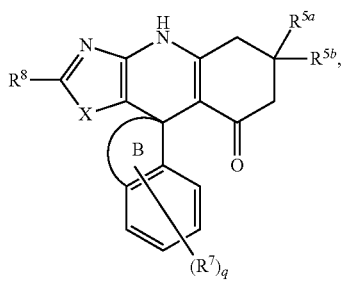

or a salt, solvate, hydrate, polymorph, co-crystal, tautomer, stereoisomer, isotopically labeled derivative, or prodrug thereof, wherein R⁸ is hydrogen optionally enriched with deuterium beyond the natural abundance.

In certain embodiments, the compound is of the formula:

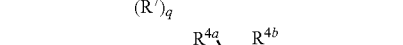

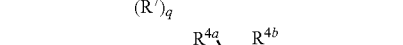

or a salt, solvate, hydrate, polymorph, co-crystal, tautomer, stereoisomer, isotopically labeled derivative, or prodrug thereof.

In certain embodiments, the compound is of the formula:

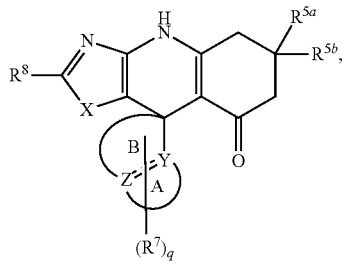

or a salt, solvate, hydrate, polymorph, co-crystal, tautomer, stereoisomer, isotopically labeled derivative, or prodrug thereof, wherein R⁸ is hydrogen optionally enriched with deuterium beyond the natural abundance.

Exemplary compounds of Formula (I) include a compound of formula:

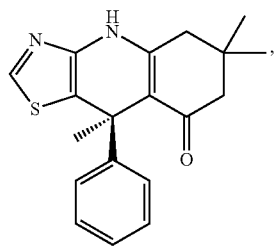 [SMILES: CC1(C)CC(=O)C2=C(C1)Nc1ncsc1[C@]2(C)c1ccccc1]

and salts, solvates, hydrates, polymorphs, co-crystals, tautomers, stereoisomers, isotopically labeled derivatives, and prodrugs thereof.

Exemplary compounds of Formula (I) further include a compound of formula:

(1 or 1-E2)

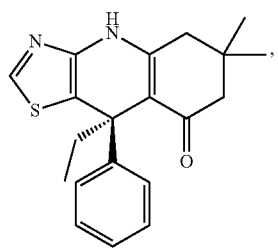

and salts, solvates, hydrates, polymorphs, co-crystals, tautomers, stereoisomers, isotopically labeled derivatives, and prodrugs thereof.

Exemplary compounds of Formula (I) further include a compound of formula:

(1-rac)

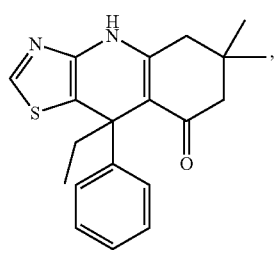

and salts, solvates, hydrates, polymorphs, co-crystals, tautomers, stereoisomers, isotopically labeled derivatives, and prodrugs thereof.
Exemplary compounds of Formula (I) further include compound of any one of formulae:
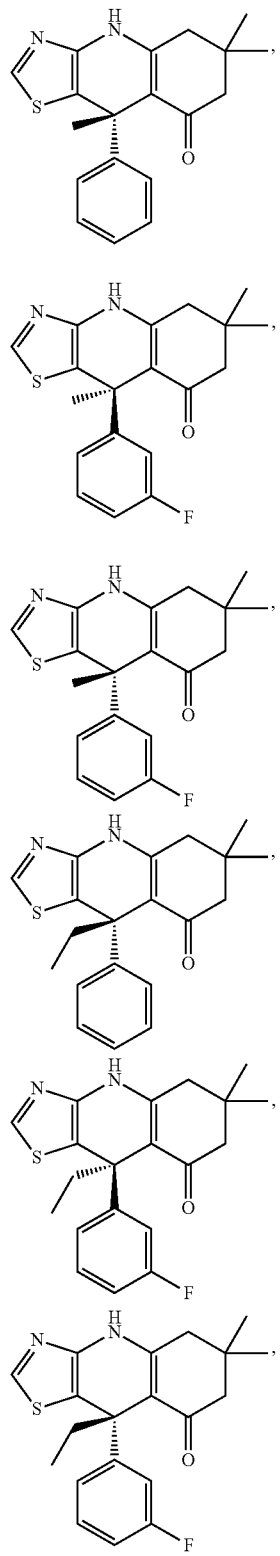
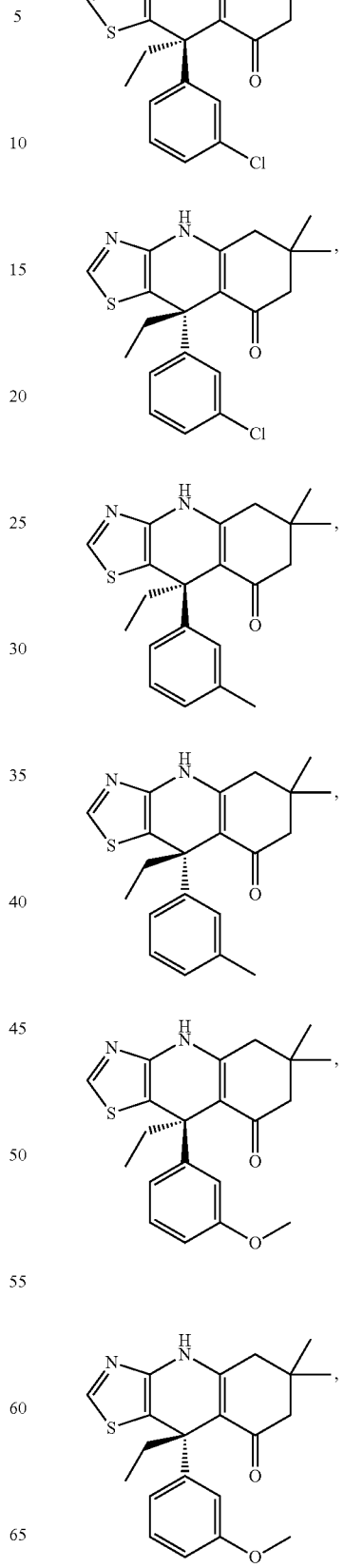

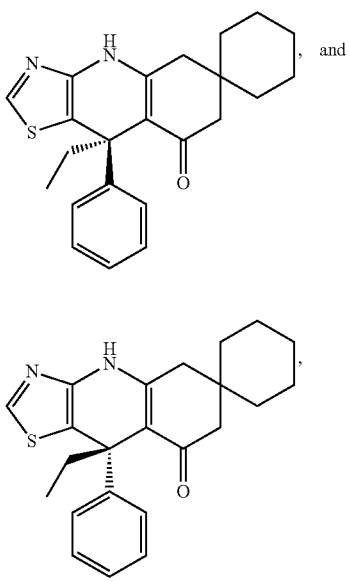 [SMILES: CC[C@@]1(c2ccccc2)C2=C(CC3(CCCCC3)CC2=O)Nc2ncsc21 ; CC[C@]1(c2ccccc2)C2=C(CC3(CCCCC3)CC2=O)Nc2ncsc21]
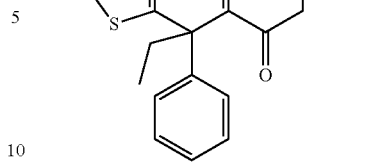
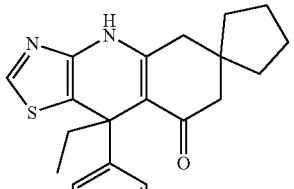
and salts, solvates, hydrates, polymorphs, co-crystals, tautomers, stereoisomers, isotopically labeled derivatives, and prodrugs thereof.
Exemplary compounds of Formula (I) further include compound of any one of formulae:
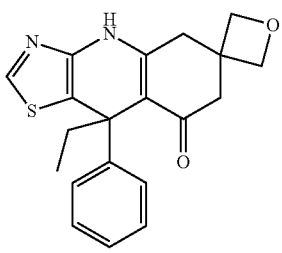
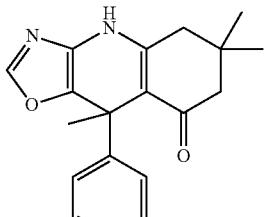
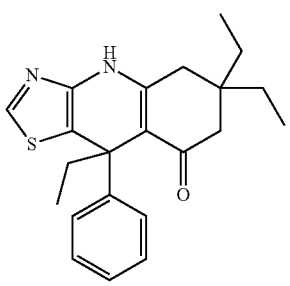
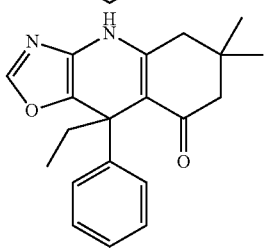
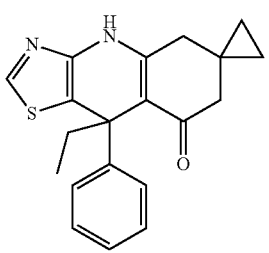
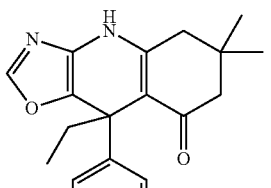
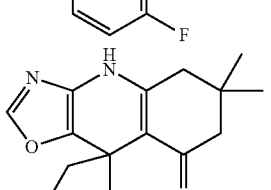
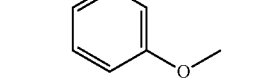
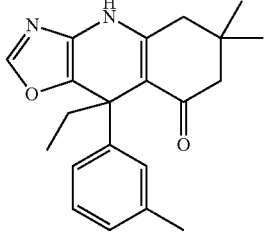
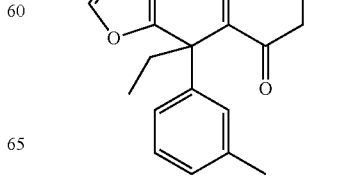

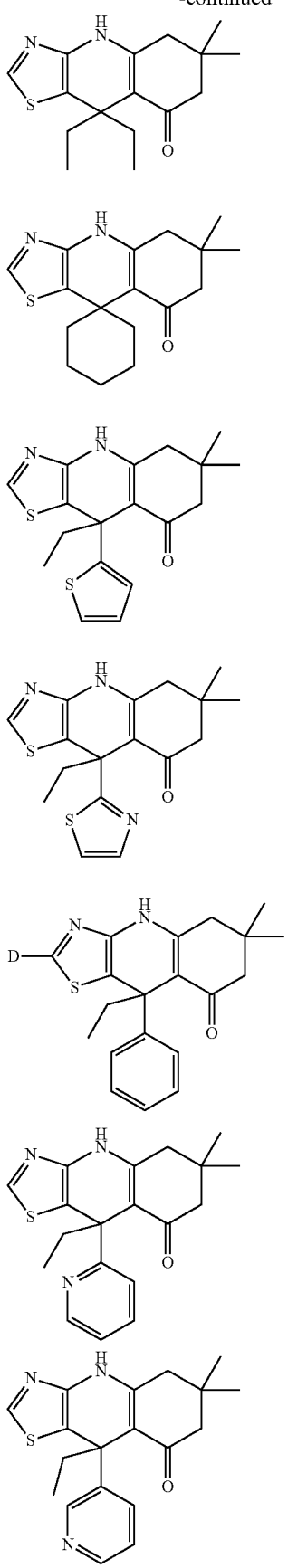
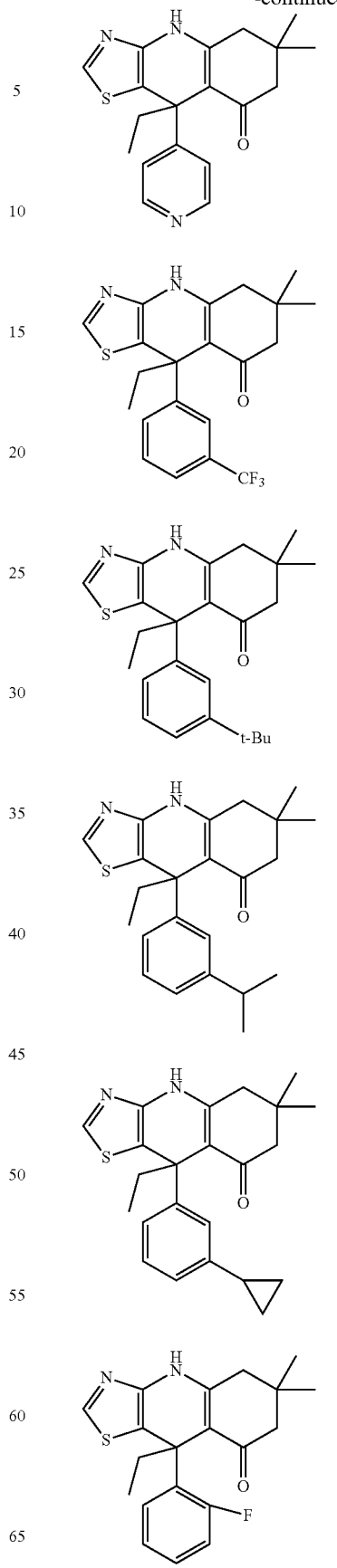

79
-continued
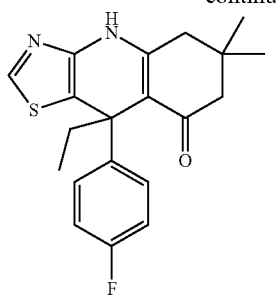
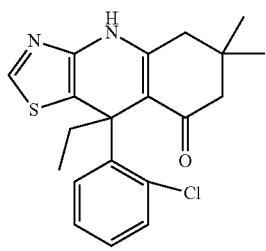
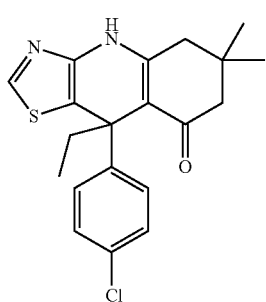
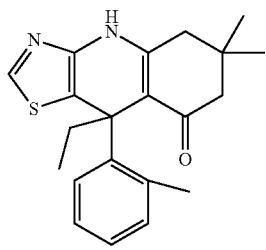
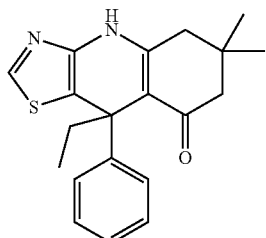
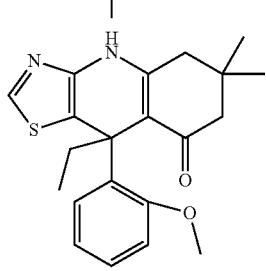
80
-continued
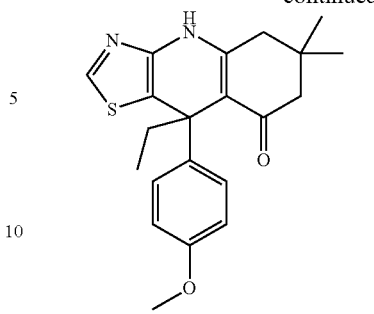
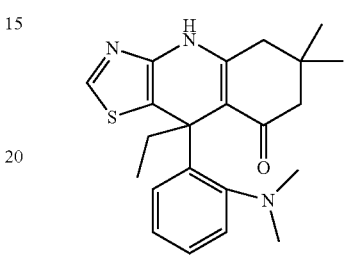
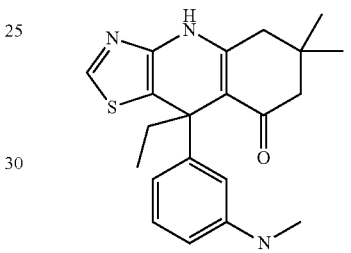
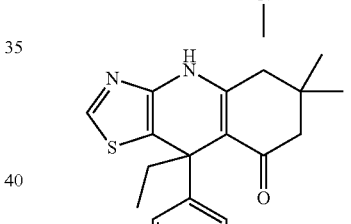
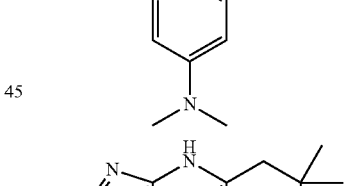
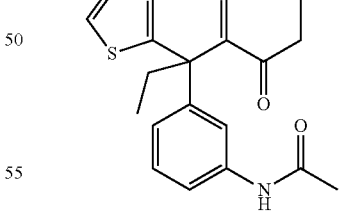
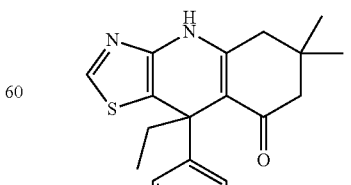

-continued
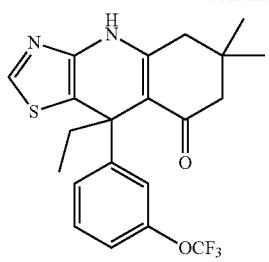
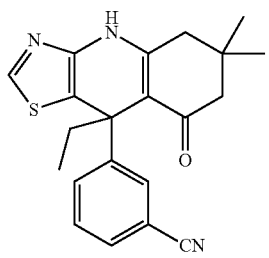
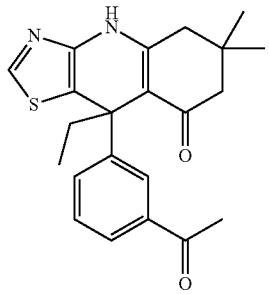
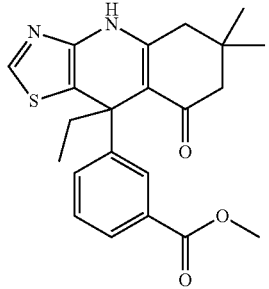
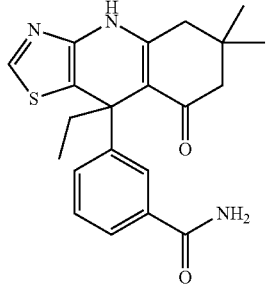
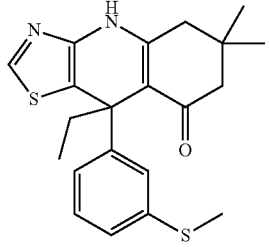
-continued
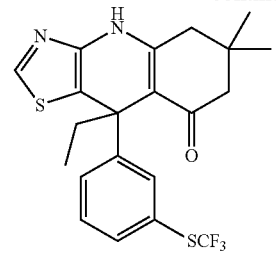
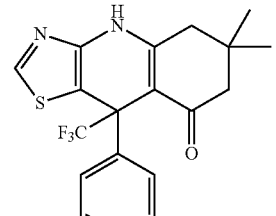
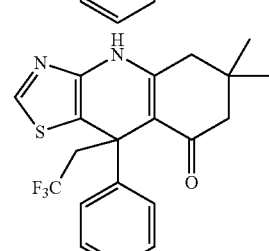
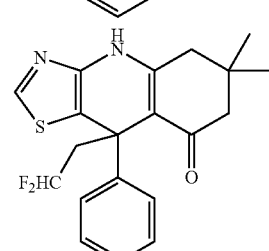
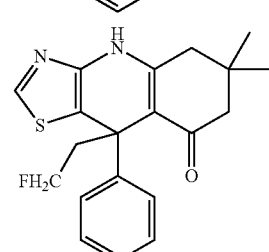
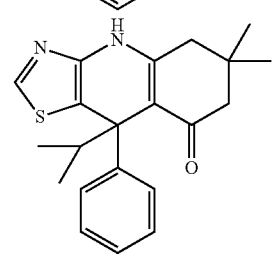
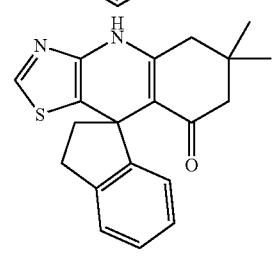

-continued
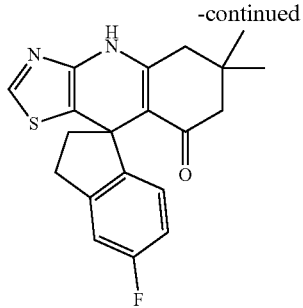
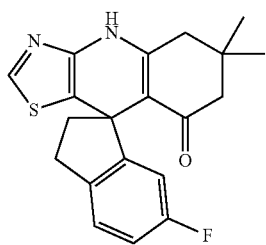
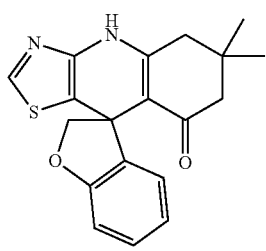
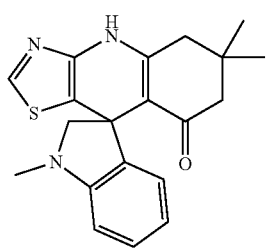
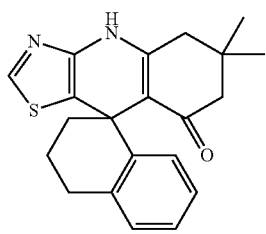
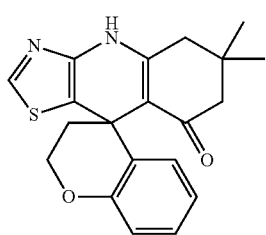
and salts, solvates, hydrates, polymorphs, co-crystals, tautomers, stereoisomers, isotopically labeled derivatives, and prodrugs thereof.
Exemplary compounds of Formula (I) further include a compound of formula:
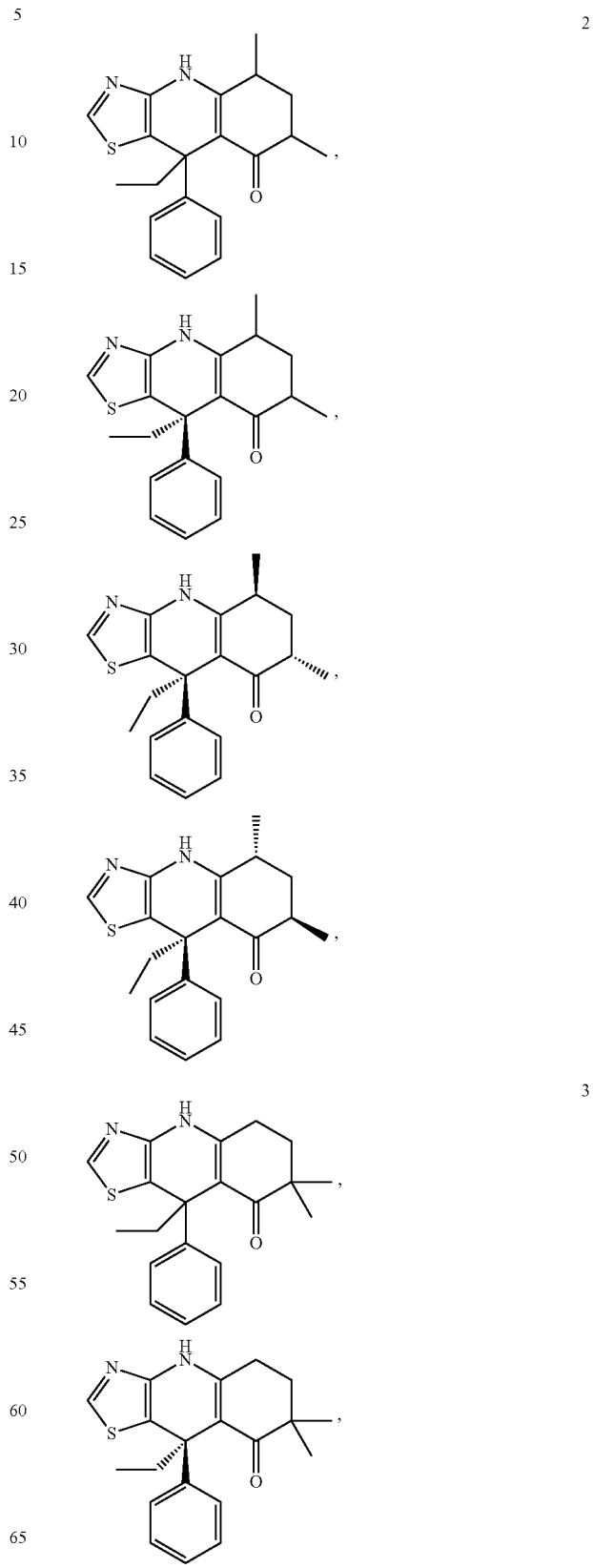

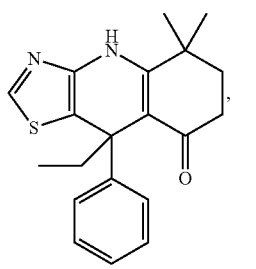,
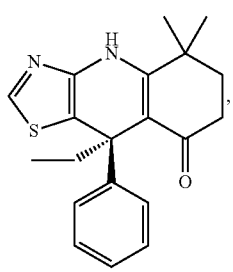,
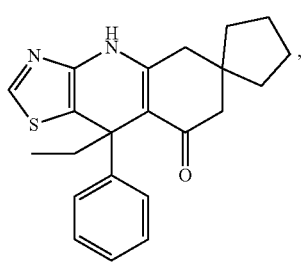,
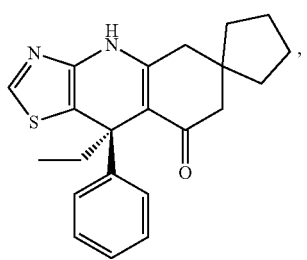,
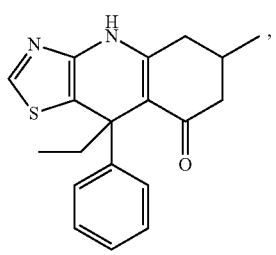,
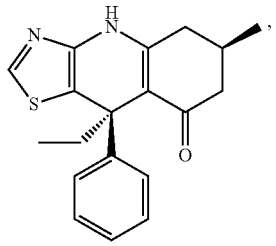,
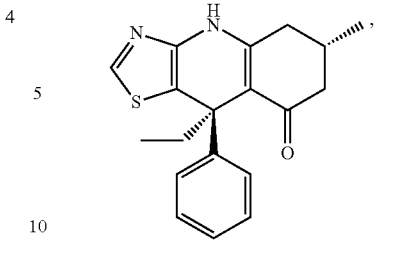,
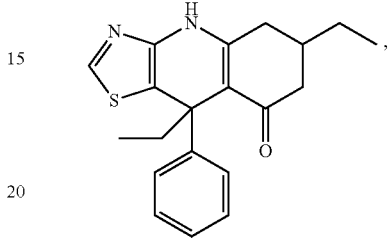,
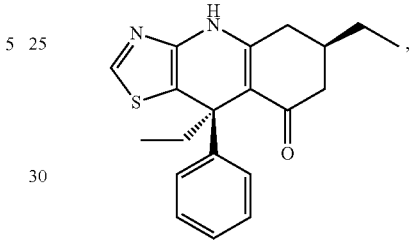,
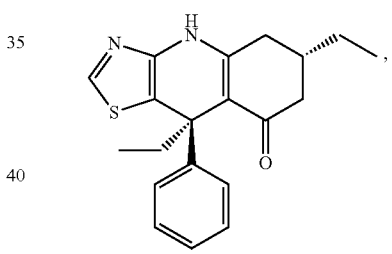,
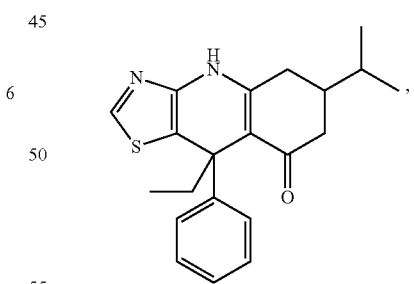,
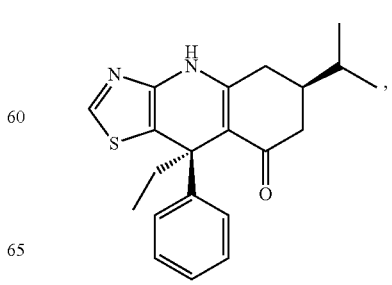, 87
-continued
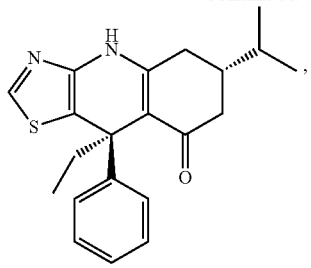
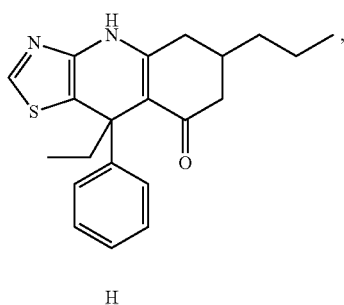
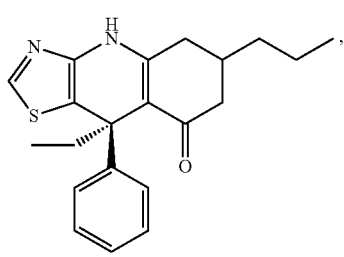
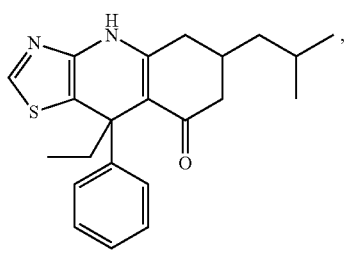
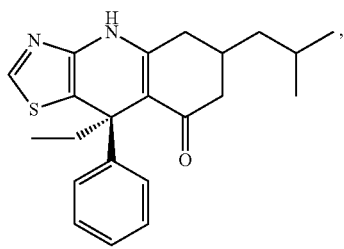
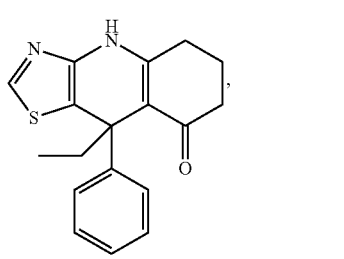
88
-continued
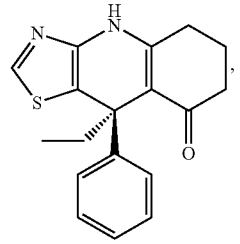
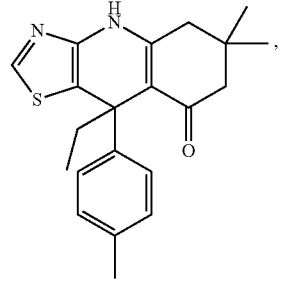
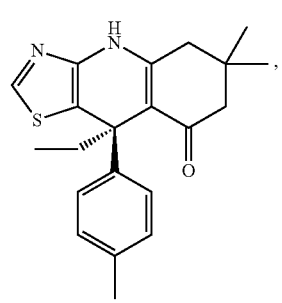
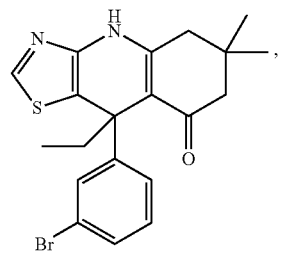
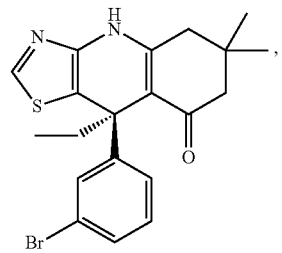
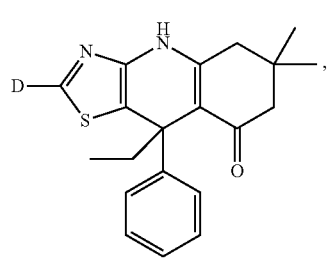

-continued

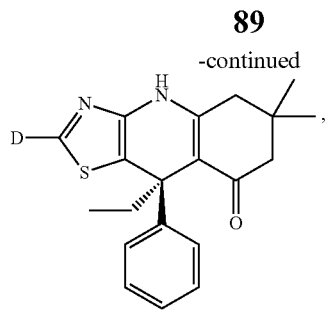

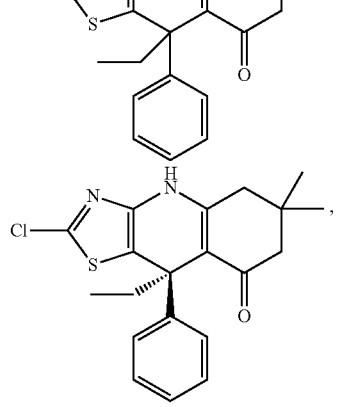

and salts, solvates, hydrates, polymorphs, co-crystals, tautomers, stereoisomers, isotopically labeled derivatives, and prodrugs thereof.

Exemplary compounds of Formula (I) further include a compound of formula:

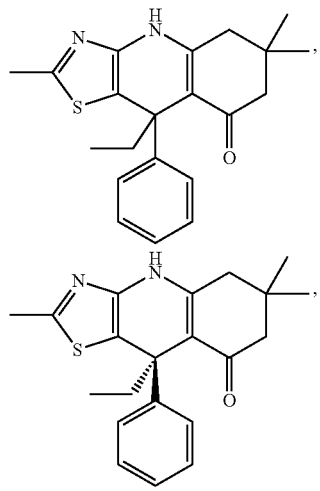

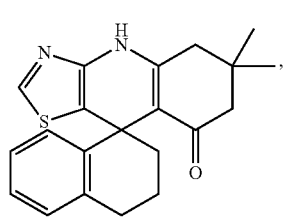

-continued

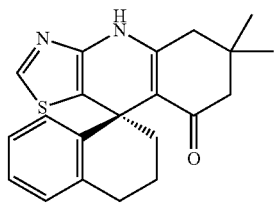

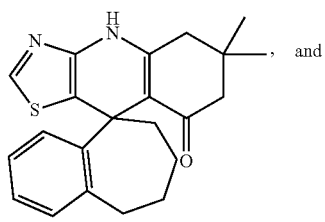

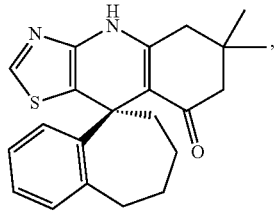

and salts, solvates, hydrates, polymorphs, co-crystals, tautomers, stereoisomers, isotopically labeled derivatives, and prodrugs thereof.

Exemplary compounds of Formula (I) further include a compound of formula:

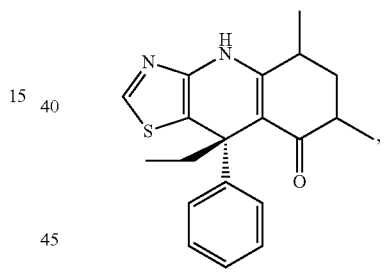

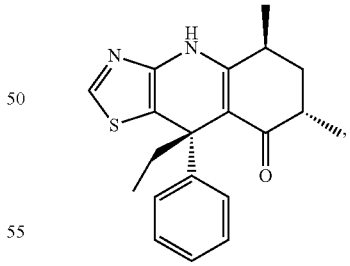

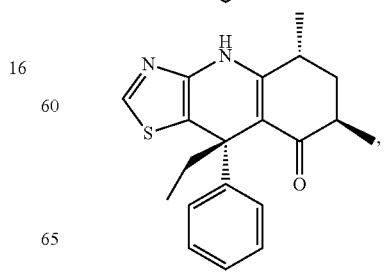

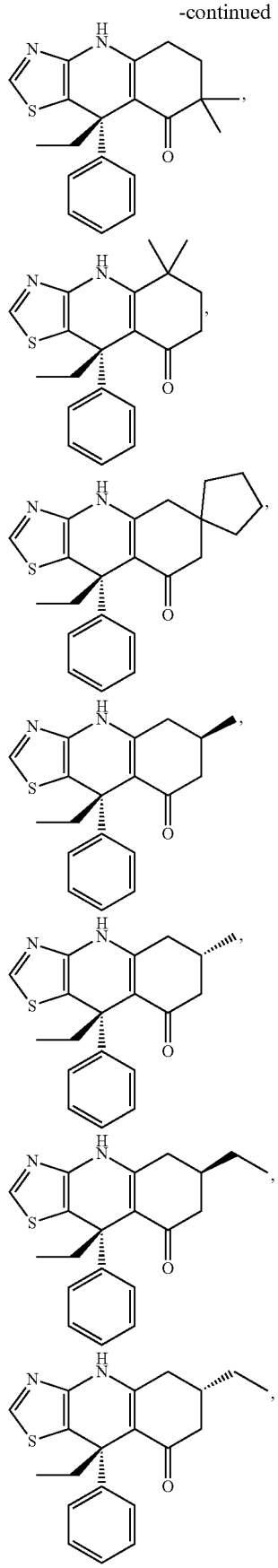
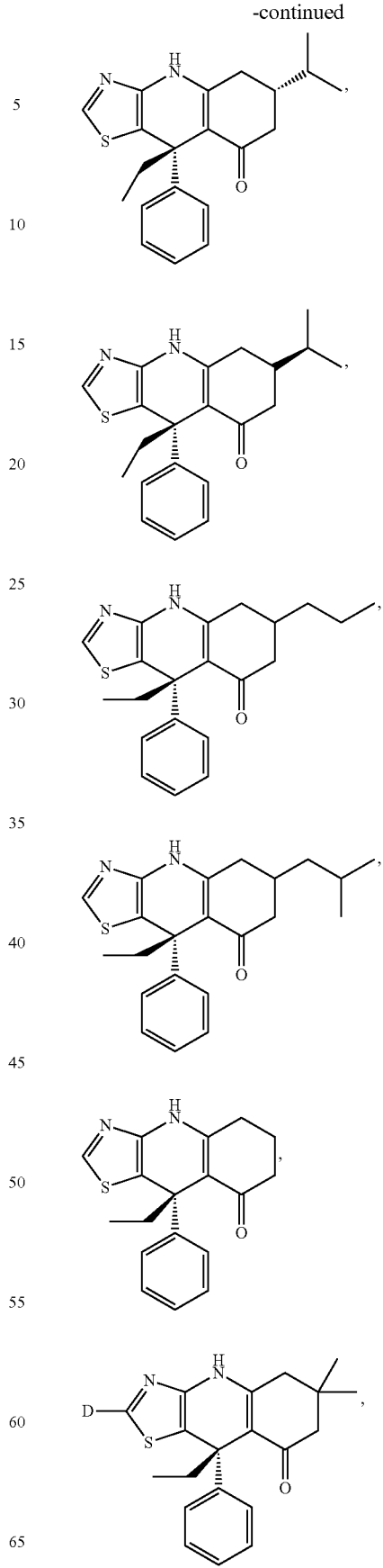

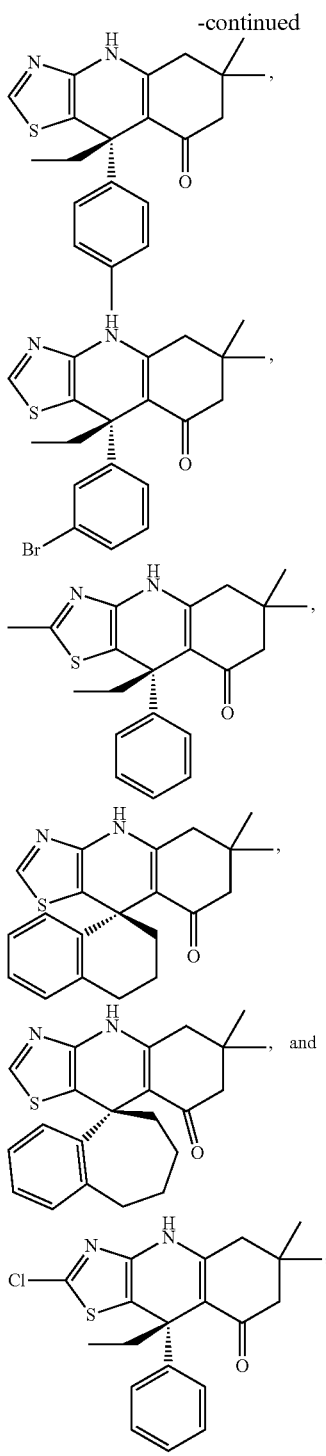

and salts, solvates, hydrates, polymorphs, co-crystals, tautomers, stereoisomers, isotopically labeled derivatives, and prodrugs thereof.

In certain embodiments, a provided compound (a compound described herein) is a compound of Formula (I), or a salt, solvate, hydrate, polymorph, co-crystal, tautomer, stereoisomer, isotopically labeled derivative, or prodrug thereof. In certain embodiments, a provided compound is a compound of Formula (I), or a pharmaceutically acceptable salt, solvate, hydrate, polymorph, co-crystal, tautomer, stereoisomer, isotopically labeled derivative, or prodrug thereof. In certain embodiments, a provided compound is a compound of Formula (I), or a salt, solvate, or hydrate thereof. In certain embodiments, a provided compound is a compound of Formula (I), or a pharmaceutically acceptable salt, solvate, or hydrate thereof. In certain embodiments, a provided compound is a compound of Formula (I), or a salt thereof. In certain embodiments, a provided compound is a compound of Formula (I), or a pharmaceutically acceptable salt thereof. In certain embodiments, a provided compound is a mixture (e.g., a racemic mixture) of enantiomers and/or diastereomers. In certain embodiments, a provided compound is a mixture of enantiomers and/or diastereomers, wherein the molar content of the combined amount of the enantiomers and diastereomers where

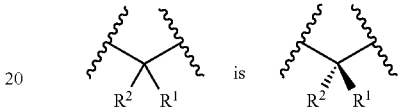

in the mixture is at least 80%, at least 90%, at least 95%, at least 97%, at least 99, or at least 99.5%. In certain embodiments, a provided compound is a mixture of enantiomers and/or diastereomers, wherein the molar content of the combined amount of the enantiomers and diastereomers where

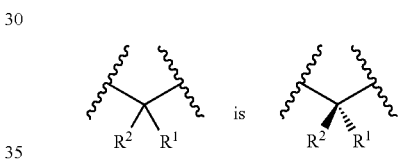

in the mixture is at least 80%, at least 90%, at least 95%, at least 97%, at least 99%, or at least 99.5%. In certain embodiments, a provided compound is a mixture of enantiomers and/or diastereomers, wherein the molar content of one enantiomer or diastereomer in the mixture is at least 80%, at least 90%, at least 95%, at least 97%, at least 99%, or at least 99.5%.

In certain embodiments, the molecular weight of a provide compound that is not in the form of a salt, solvate, hydrate, co-crystal, or prodrug is lower than 2,000, lower than 1,500, lower than 1,000, lower than 800, lower than 600, or lower than 400 g/mol. In certain embodiments, the molecular weight of a provide compound that is not in the form of a salt, solvate, hydrate, co-crystal, or prodrug is lower than 800 g/mol. In certain embodiments, the molecular weight of a provide compound that is not in the form of a salt, solvate, hydrate, co-crystal, or prodrug is lower than 600 g/mol.

In certain embodiments, a provided compound inhibits a kinase, or a mutant or variant thereof. In certain embodiments, a provided compound inhibits GSK3. In certain embodiments, a provided compound inhibits a kinase (e.g., GSK3), e.g., as measured in an assay described herein. In certain embodiments, a provided compound inhibits the kinase (e.g., GSK3) at an $IC_{50}$ less than or equal to 30 μM. In certain embodiments, a provided compound inhibits the kinase at an $IC_{50}$ less than or equal to 10 μM. In certain embodiments, a provided compound inhibits the kinase at an $IC_{50}$ less than or equal to 3 μM. In certain embodiments, a provided compound inhibits the kinase at an $IC_{50}$ less than or equal to 1 μM. In certain embodiments, a provided compound inhibits the kinase at an IC$_{50}$ less than or equal to 0.3 μM. In certain embodiments, a provided compound inhibits the kinase at an IC$_{50}$ less than or equal to 0.1 μM. In certain embodiments, a provided compound (GSK3-selective inhibitor) is selective for GSK3 when compared with other kinases. In certain embodiments, a provided compound is selective for GSK3α and/or GSK3β when compared with other kinases. In certain embodiments, a provided compound is selective for GSK3α when compared with other kinases (e.g., GSK3β). In certain embodiments, a provided compound (GSK3α-selective inhibitor) is selective for GSK3α when compared with GSK3β (e.g., selectively inhibiting the activity of GSK3α as compared to GSK3β). In certain embodiments, a provided compound is selective for GSK3α when compared with GSK3β by at least 2-fold, at least 3-fold, at least 4-fold, at least 5-fold, at least 7-fold, at least 10-fold, at least 20-fold, at least 50-fold, at least 100-fold, at least 300-fold, or at least 1,000-fold (e.g., in an in vitro assay or an assay described herein (e.g., an Caliper assay or TR-FRET assay)). For example, a provided compound is selective for GSK3α when compared with GSK3β by 3-fold when the IC$_{50}$ of the provided compound in inhibiting GSK3α equals to one third of the IC$_{50}$ of the provided compound in inhibiting GSK3β. In certain embodiments, a provided compound is selective for GSK3α when compared with GSK3β by at least 3-fold (three times). In certain embodiments, a provided compound is selective for GSK3α when compared with GSK3β by at least 4-fold (four times). In certain embodiments, a provided compound is selective for GSK3α when compared with GSK3β by at least 5-fold (five times). In certain embodiments, a provided compound is selective for GSK3α when compared with GSK3β by at least 7-fold (seven times).

In certain embodiments, a GSK3α selective inhibitor is advantageous over a pan GSK3 inhibitor (non-selective GSK3 inhibitor). In certain embodiments, a non-selective GSK3 inhibitor shows less than 2-fold, less than 3-fold, less than 4-fold, less than 5-fold, less than 7-fold, less than 10-fold, less than 20-fold, less than 50-fold, or less than 100-fold selectivity for GSK3α when compared with another kinase (e.g., GSK3β) and/or for GSK3β when compared with another kinase (e.g., GSK3α). In certain embodiments, a non-selective GSK3 inhibitor shows less than 3-fold selectivity for GSK3α when compared with another kinase (e.g., GSK3β) and/or for GSK3β when compared with another kinase (e.g., GSK3α). In certain embodiments, a non-selective GSK3 inhibitor shows less than 4-fold selectivity for GSK3α when compared with another kinase (e.g., GSK3β) and/or for GSK3β when compared with another kinase (e.g., GSK3α). In certain embodiments, a non-selective GSK3 inhibitor shows less than 5-fold selectivity for GSK3α when compared with another kinase (e.g., GSK3β) and/or for GSK3β when compared with another kinase (e.g., GSK3α).

Methods of Preparing the Compounds

In another aspect, provided are methods of preparing the compounds described herein. In certain embodiments, the methods of preparing include (a) reacting a compound of Formula (A):

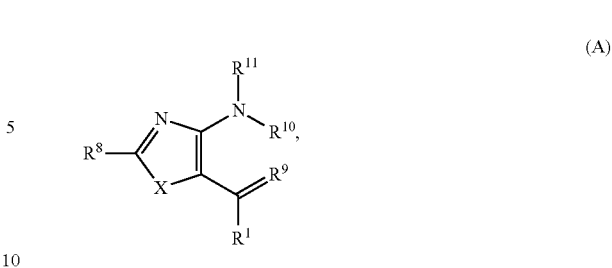

or a salt thereof, with a compound of Formula (B):

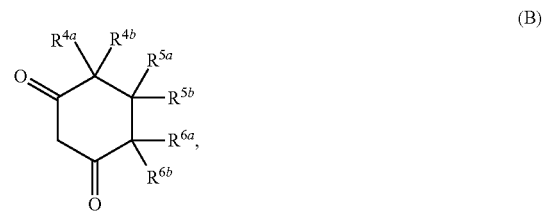

or a salt thereof, wherein:
$R^9$ is substituted or unsubstituted $C_{1-6}$ alkyl;
$R^{10}$ is hydrogen or a nitrogen protecting group; and
$R^{11}$ is hydrogen or a nitrogen protecting group;
wherein when at least one of $R^{10}$ and $R^{11}$ is a nitrogen protecting group, the step of reacting (a) is performed under a condition that deprotects all the nitrogen protecting groups.

In certain embodiments, $R^9$ is substituted or unsubstituted $C_{1-4}$ alkyl. In certain embodiments, $R^9$ is =CH$_2$. In certain embodiments, $R^9$ is =CHCH$_3$. In certain embodiments, $R^9$ is =CHCH$_2$F, =CHCHF$_2$, or =CHCF$_3$.

In certain embodiments, $R^{10}$ is hydrogen. In certain embodiments, $R^{10}$ is a nitrogen protecting group (e.g., Bn, Boc, Cbz, Fmoc, trifluoroacetyl, triphenylmethyl, acetyl, or Ts). In certain embodiments, $R^{10}$ is Boc.

In certain embodiments, $R^{11}$ is hydrogen. In certain embodiments, $R^{11}$ is a nitrogen protecting group (e.g., Bn, Boc, Cbz, Fmoc, trifluoroacetyl, triphenylmethyl, acetyl, or Ts). In certain embodiments, $R^{11}$ is Boc.

In certain embodiments, $R^{10}$ is hydrogen; and $R^{11}$ is a nitrogen protecting group (e.g., Bn, Boc, Cbz, Fmoc, trifluoroacetyl, triphenylmethyl, acetyl, or Ts). In certain embodiments, $R^{10}$ is hydrogen; and $R^{11}$ is Boc.

In certain embodiments, the step of reacting (a) is performed under an acidic condition. In certain embodiments, the acidic condition comprises the presence of an organic or inorganic acid (e.g., an organic or inorganic acid for which the pK$_a$ at 25° C. is between −10 and 5, between −6 and 2, or between −3 and 1), optionally in excess amount. In certain embodiments, the acidic condition comprises the presence of p-toluenesulfonic acid (PTSA) or trifluoroacetic acid (TFA), optionally in excess amount. In certain embodiments, the step of reacting (a) is performed at a temperature of at least 25° C., at least 40° C., at least 70° C., at least 100° C., or at least 150° C. In certain embodiments, the step of reacting (a) is performed at a temperature of at least 150° C. In certain embodiments, the step of reacting (a) is performed at a temperature of not more than 40° C., not more than 70° C., not more than 100° C., not more than 150° C., not more than 160° C., or not more than 170° C. In certain embodiments, the step of reacting (a) is performed at a temperature of not more than 160° C. In certain embodiments, the step of reacting (a) is performed substantially free (e.g., at least 90%, at least 95%, or at least 99% free by weight) of a solvent. In certain embodiments, the step of reacting (a) is performed under microwave irradiation. In certain embodiments, the step of reacting is performed under a combination of the conditions described herein. In certain embodiments, the condition that deprotects the nitrogen protecting group comprises one or more conditions described herein. In certain embodiments, the condition that deprotects all the nitrogen protecting groups comprises an acidic condition.

In certain embodiments, the methods of preparing a compound described herein, wherein $R^8$ is hydrogen enriched with deuterium beyond the natural abundance, further comprise:

(b) reacting a compound of Formula (C):

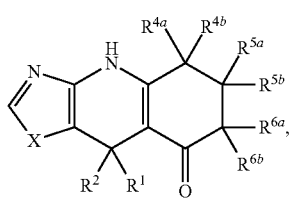

(C)

or a salt thereof, with an alkyllithium or phenyllithium; and (c) reacting the product of step (b) with a deuterium source.

In another aspect, provided are methods of preparing the compounds described herein, wherein $R^8$ is hydrogen enriched with deuterium beyond the natural abundance, the methods comprise:

(b) reacting a compound of Formula (C):

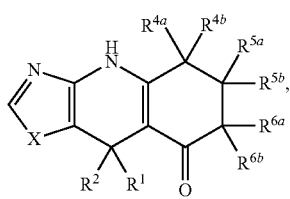

(C)

or a salt thereof, with an alkyllithium or phenyllithium; and (c) reacting the product of step (b) with a deuterium source.

In certain embodiments, the alkyllithium or phenyllithium is methyllithium, ethyllithium, isopropyllithium, n-butyllithium, sec-butyllithium, or tert-butyllithium. In certain embodiments, the alkyllithium or phenyllithium is n-butyllithium. In certain embodiments, the alkyllithium or phenyllithium is phenyllithium. In certain embodiments, step (b) is performed at a temperature of at least −100° C., at least −80° C., at least −70° C., or at least −40° C. In certain embodiments, step (b) is performed at a temperature of not more than −80° C., not more than −70° C., not more than −40° C., or not more than −20° C. In certain embodiments, step (b) is performed at about −78° C. In certain embodiments, step (b) is performed in a solvent. In certain embodiments, the solvent is Et$_2$O, methyl tert-butyl ether, THF, 2-methyl-THF, or cyclopentyl methyl ether. In certain embodiments, the solvent is THF. In certain embodiments, the solvent is pentane, hexane, or heptane. In certain embodiments, the solvent is toluene.

In certain embodiments, the deuterium source is D$_2$O, deuterium bromide, deuterium chloride, CH$_3$OD, methanol-d$_4$, CH$_3$CH$_2$OD, ethanol-d$_6$, or isopropanol-d$_8$. In certain embodiments, the deuterium source is methanol-d$_4$. In certain embodiments, step (c) is performed at a temperature of at least −100° C., at least −80° C., at least −70° C., at least −40° C., at least −20° C., at least 0° C., at least 20° C., or at least 25° C. In certain embodiments, step (c) is performed at a temperature of not more than −80° C., not more than −70° C., not more than −40° C., not more than −20° C., not more than 0° C., not more than 20° C., not more than 25° C., or not more than 40° C. In certain embodiments, step (c) is performed at about −78° C. In certain embodiments, step (c) is performed at a variable temperature starting at about −78° C. and ending at about 20° C. In certain embodiments, steps (b) and (c) are performed in one pot.

Pharmaceutical Compositions and Administration

The present disclosure also provides pharmaceutical compositions comprising a compound described herein and optionally a pharmaceutically acceptable excipient. The pharmaceutical compositions described herein may be useful in treating a disease, such as a disease associated with aberrant activity of a kinase (e.g., GSK3). In certain embodiments, the pharmaceutical compositions may be useful for treating a disease associated with aberrant activity of GSK3α (e.g., Fragile X syndrome, attention deficit hyperactivity disorder (ADHD, childhood seizure, intellectual disability, diabetes, acute myeloid leukemia (AML), autism, or psychiatric disorder). In certain embodiments, the pharmaceutical compositions may be useful for treating a disease associated with aberrant activity of GSK3β (e.g., mood disorder, PTSD, psychiatric disorder, diabetes, or neurodegenerative disease). The pharmaceutical compositions may also be useful in preventing the diseases described herein. The pharmaceutical compositions may also be useful in inhibiting the activity of a kinase (e.g., GSK3). In certain embodiments, the pharmaceutical compositions are useful in inhibiting the activity of GSK3α (e.g., selectively inhibiting the activity of GSK3α, as compared to GSK3β).

In certain embodiments, a compound described herein is provided in an effective amount in the pharmaceutical composition. In certain embodiments, the effective amount is a therapeutically effective amount. In certain embodiments, the effective amount is an amount effective for inhibiting a kinase (e.g., GSK3). In certain embodiments, the effective amount is an amount effective for inhibiting GSK3α. In certain embodiments, the effective amount is an amount effective for treating a disease associated with aberrant activity of a kinase (e.g., GSK3). In certain embodiments, the effective amount is an amount effective for treating a disease associated with aberrant activity of GSK3α.

In certain embodiments, the effective amount is a prophylactically effective amount. In certain embodiments, the effective amount is an amount effective for preventing a disease associated with aberrant activity of a kinase (e.g., GSK3). In certain embodiments, the effective amount is an amount effective for preventing a disease associated with aberrant activity of GSK3α.

Pharmaceutically acceptable excipients include any and all solvents, diluents, or other liquid vehicles, dispersions, suspension aids, surface active agents, isotonic agents, thickening or emulsifying agents, preservatives, solid binders, lubricants, and the like, as suited to the particular dosage form desired. General considerations in formulation and/or manufacture of pharmaceutical compositions agents can be found, for example, in *Remington's Pharmaceutical Sci-*

*ences*, Sixteenth Edition, E. W. Martin (Mack Publishing Co., Easton, Pa., 1980), and *Remington: The Science and Practice of Pharmacy*, 21st Edition (Lippincott Williams & Wilkins, 2005).

Pharmaceutical compositions described herein can be prepared by any method known in the art of pharmacology. In general, such preparatory methods include the steps of bringing a compound described herein (the "active ingredient") into association with a carrier and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. A "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition of the present disclosure will vary, depending upon the identity, size, and/or condition of the subject treated and further depending upon the route by which the composition is to be administered. By way of example, the composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween 20), polyoxyethylene sorbitan monostearate (Tween 60), polyoxyethylene sorbitan monooleate (Tween 80), sorbitan monopalmitate (Span 40), sorbitan monostearate (Span 60), sorbitan tristearate (Span 65), glyceryl monooleate, sorbitan monooleate (Span 80)), polyoxyethylene esters (e.g., polyoxyethylene monostearate (Myrj 45), polyoxyethylene hydrogenated castor oil, polyethoxylated castor oil, polyoxymethylene stearate, and Solutol), sucrose fatty acid esters, polyethylene glycol fatty acid esters (e.g., Cremophor™), polyoxyethylene ethers, (e.g., polyoxyethylene lauryl ether (Brij 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F68, Poloxamer 188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, alcohol preservatives, acidic preservatives, and other preservatives.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the compounds described herein are mixed with solubilizing agents such as Cremophor™, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are typically suppositories which can be prepared by mixing the compounds described herein with suitable non-irritating excipients or carriers such as cocoa butter, polyethylene glycol or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may comprise buffering agents.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type can be employed as fillers in soft and hard-filled gelatin capsules using such excipients as lactose or milk sugar as well as high molecular weight polyethylene glycols and the like.

The active ingredient can be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets, and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes.

Dosage forms for topical and/or transdermal administration of a provided compound may include ointments, pastes, creams, lotions, gels, powders, solutions, sprays, inhalants and/or patches. Generally, the active ingredient is admixed under sterile conditions with a pharmaceutically acceptable carrier and/or any desired preservatives and/or buffers as can be required. Additionally, the present disclosure encompasses the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions can be administered by devices which limit the effective penetration length of a needle into the skin, such as those described in PCT publication WO 99/34850 and functional equivalents thereof. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate vaccine in powder form through the outer layers of the skin to the dermis are suitable. Alternatively or additionally, conventional syringes can be used in the classical mantoux method of intradermal administration.

Formulations suitable for topical administration include liquid and/or semi liquid preparations such as liniments, lotions, oil in water and/or water in oil emulsions such as creams, ointments and/or pastes, and/or solutions and/or suspensions. Topically-administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A provided pharmaceutical composition can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers or from about 1 to about 6 nanometers. Such compositions are conveniently in the form of dry powders for administration using a device comprising a dry powder reservoir to which a stream of propellant can be directed to disperse the powder and/or using a self propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) and as much as 100% (w/w) of the active ingredient, and may comprise one or more of the additional ingredients described herein. A provided pharmaceutical composition can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A provided pharmaceutical composition can be prepared, packaged, and/or sold in a formulation for ophthalmic administration. Such formulations may, for example, be in the form of eye drops including, for example, a 0.1/1.0% (w/w) solution and/or suspension of the active ingredient in an aqueous or oily liquid carrier. Such drops may further comprise buffering agents, salts, and/or one or more other of the additional ingredients described herein. Other ophthalmically-administrable formulations which are useful include those which comprise the active ingredient in microcrystalline form and/or in a liposomal preparation. Ear drops and/or eye drops are contemplated as being within the scope of this disclosure.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form for ease of administration and uniformity of dosage. It will be understood, however, that the total daily usage of provided compositions will be decided by the attending physician within the scope of sound medical judgment. The specific therapeutically effective dose level for any particular subject or organism will depend upon a variety of factors including the disease, disorder, or condition being treated and the severity of the disorder; the activity of the specific active ingredient employed; the specific composition employed; the age, body weight, general health, sex and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general the most appropriate route of administration will depend upon a variety of factors including the nature of the agent (e.g., its stability in the environment of the gastrointestinal tract), and/or the condition of the subject (e.g., whether the subject is able to tolerate oral administration).

The exact amount of a compound required to achieve an effective amount will vary from subject to subject, depending, for example, on species, age, and general condition of a subject, severity of the side effects or disorder, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations). An effective amount may be included in a single dose (e.g., single oral dose) or multiple doses (e.g., multiple oral doses). In certain embodiments, when multiple doses are administered to a subject or applied to a tissue or cell, any two doses of the multiple doses include different or substantially the same amounts of a compound described herein. In certain embodiments, when multiple doses are administered to a subject or applied to a tissue or cell, the frequency of administering the multiple doses to the subject or applying the multiple doses to the tissue or cell is three doses a day, two doses a day, one dose a day, one dose every other day, one dose every third day, one dose every week, one dose every two weeks, one dose every three weeks, or one dose every four weeks. In certain embodiments, the frequency of administering the multiple doses to the subject or applying the multiple doses to the tissue or cell is one dose per day. In certain embodiments, the frequency of administering the multiple doses to the subject or applying the multiple doses to the tissue or cell is two doses per day. In certain embodiments, the frequency of administering the multiple doses to the subject or applying the multiple doses to the tissue or cell is three doses per day. In certain embodiments, when multiple doses are administered to a subject or applied to a tissue or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, tissue, or cell. In certain embodiments, the duration between the first dose and last dose of the multiple doses is three months, six months, or one year. In certain embodiments, the duration between the first dose and last dose of the multiple doses is the lifetime of the subject, tissue, or cell. In certain embodiments, a dose (e.g., a single dose, or any dose of multiple doses) described herein includes independently between 0.1 µg and 1 µg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of a compound described herein. In certain embodiments, a dose described herein includes independently between 1 mg and 3 mg, inclusive, of a compound described herein. In certain embodiments, a dose described herein includes independently between 3 mg and 10 mg, inclusive, of a compound described herein. In certain embodiments, a dose described herein includes independently between 10 mg and 30 mg, inclusive, of a compound described herein. In certain embodiments, a dose described herein includes independently between 30 mg and 100 mg, inclusive, of a compound described herein.

In certain embodiments, an effective amount of a compound for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In certain embodiments, a compound described herein may be administered at dosage levels sufficient to deliver from about 0.001 mg/kg to about 1000 mg/kg, from about 0.01 mg/kg to about mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg, of subject body weight per day, one or more times a day, to obtain the desired therapeutic effect.

In some embodiments, a compound described herein is administered one or more times per day, for multiple days. In some embodiments, the dosing regimen is continued for days, weeks, months, or years.

Dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult. In certain embodiments, a dose described herein is a dose to an adult human whose body weight is approximately 70 kg.

A compound or pharmaceutical composition can be administered in combination with one or more additional pharmaceutical agents (e.g., therapeutically active agents). The compounds or pharmaceutical compositions can be administered in combination with additional therapeutically active agents that improve their efficacy, potency, and/or bioavailability, reduce and/or modify their metabolism, inhibit their excretion, and/or modify their distribution within the body. The therapy employed may achieve a desired effect for the same disorder, and/or it may achieve different effects.

The compound or pharmaceutical composition can be administered concurrently with, prior to, or subsequent to, one or more additional therapeutically active agents. In general, each agent will be administered at a dose and/or on a time schedule determined for that agent. The additional therapeutically active agent utilized in this combination can be administered together in a single composition or administered separately in different compositions. The particular combination to employ in a regimen will take into account compatibility of a provided compound with the additional therapeutically active agent and/or the desired therapeutic effect to be achieved. In general, it is expected that additional therapeutically active agents utilized in combination be utilized at levels that do not exceed the levels at which they are utilized individually. In some embodiments, the levels utilized in combination will be lower than those utilized individually.

Exemplary additional therapeutically active agents include antimicrobial agents, antifungal agents, antiparasitic agents, anti-inflammatory agents, and a pain-relieving agent Therapeutically active agents include small organic molecules such as drug compounds (e.g., compounds approved by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells.

In certain embodiments, a provided compound is combined with an additional therapeutically active agent (e.g., lithium and/or ketamine) for use in treating bipolar disorder and/or depression (e.g., lithium-resistant depression). Lithium has long been the therapy of choice for bipolar disorder and manic syndromes though the exact mechanism of action has been difficult to discern (J. A. Quiroz, T. D. Gould and H. K. Manji, Mol. Interv., 2004, 4, 259). Lithium is known to affect the function of a variety of enzymes, an effect attributed to lithium competing for essential magnesium binding sites (W. J. Ryves and A. J. Harwood, *Biochem. Biophys. Res. Commun.*, 2001, 280, 720). Therapeutically efficacious doses of $Li^+$ (0.6-1.2 mM plasma levels) do approach its GSK3 $IC_{50}$ ($IC_{50}$=2 mM) (Annual Reports in Medicinal Chemistry, 2005, Volume 40, page 137).

In certain embodiments, a provided compound is combined with an additional therapeutically active agent (e.g., all-trans retinoic acid) for use in treating leukemia (e.g., AML (e.g., APML)). In certain embodiments, a combination of a provided compound and an additional therapeutically active agent shows synergistic effect in treating a neurological disease, psychiatric disorder (e.g., bipolar disorder or depression (e.g., lithium-resistant depression)), metabolic disorder (e.g., diabetes), and/or cancer (e.g., AML).

Also encompassed by the invention are kits (e.g., pharmaceutical packs). In certain embodiments, the kit described herein comprises a compound or pharmaceutical composition described herein, and instructions for using the compound or pharmaceutical composition. The compound or pharmaceutical composition may be included in a first container (e.g., a vial, ampule, bottle, syringe, dispenser package, tube, inhaler, and/or other suitable container). In some embodiments, the kit further includes a second container comprising an excipient (e.g., an excipient for dilution or suspension of the compound or pharmaceutical composition). In some embodiments, the compound or pharmaceutical composition provided in the first container and the excipient provided in the second container are combined to form one unit dosage form.

In certain embodiments, the kits are useful in treating a disease (e.g., disease associated with aberrant activity of a kinase (e.g., GSK3)). In certain embodiments, the kits are useful in treating a disease associated with aberrant activity of GSK3α (e.g., Fragile X syndrome, attention deficit hyperactivity disorder (ADHD, childhood seizure, intellectual disability, diabetes, acute myeloid leukemia (AML), autism, or psychiatric disorder). In certain embodiments, the kits are useful in treating a disease associated with aberrant activity of GSK3β (e.g., mood disorder, PTSD, psychiatric disorder, diabetes, or neurodegenerative disease). In certain embodiments, the kits are useful in preventing a disease described herein. The kits may also be useful in inhibiting the activity of a kinase (e.g., GSK3). In certain embodiments, the kits are useful in inhibiting the activity of GSK3α (e.g., selectively inhibiting the activity of GSK3α, as compared to GSK3β).

In certain embodiments, the instructions are for administering the compound or pharmaceutical composition to a subject in need of treatment or prevention of a disease described herein). In certain embodiments, the instructions are for contacting a cell or tissue with the compound or pharmaceutical composition. The kits may also include information as required by a regulatory agency such as the U.S. Food and Drug Administration (FDA). In certain embodiments, the information included in the kits is prescribing information. The kits may include one or more additional agents described herein (e.g., additional pharmaceutical agents) as a separate composition.

Methods of Use and Treatment

In another aspect, provided herein are methods of inhibiting the activity of GSK3 in a subject in need thereof, the method comprising administering to the subject an effective amount of a compound or pharmaceutical composition described herein, wherein the effective amount is effective for inhibiting the activity of the GSK3.

In another aspect, provided herein are methods of inhibiting the activity of GSK3 in a cell or tissue, the method comprising contacting the cell or tissue with an effective amount of a compound or pharmaceutical composition described herein, wherein the effective amount is effective for inhibiting the activity of the GSK3.

In certain embodiments, the subject described herein is an animal. In certain embodiments, the subject is a non-human animal. In certain embodiments, the subject is a non-human mammal. In certain embodiments, the subject is a human. In certain embodiments, the subject is a domesticated animal, such as a dog, cat, cow, pig, horse, sheep, or goat. In certain embodiments, the subject is a companion animal, such as a dog or cat. In certain embodiments, the subject is a livestock animal, such as a cow, pig, horse, sheep, or goat. In certain embodiments, the subject is a zoo animal. In another embodiment, the subject is a research animal, such as a rodent, dog, or non-human primate. In certain embodiments, the subject is a non-human transgenic animal, such as a transgenic mouse or transgenic pig.

In certain embodiments, the cell or tissue is in vitro. In certain embodiments, the cell or tissue is in vivo.

In certain embodiments, the GSK3 is GSK3α. In certain embodiments, the GSK3 is GSK3β.

In certain embodiments, the effective amount is at least three times (three folds), at least four times (four folds), at least five times (five folds), at least seven times (seven folds), at least ten times (ten folds), at least thirty times (thirty folds), at least one hundred times (one hundred folds), or at least one thousand times (one thousand folds) more effective in inhibiting the activity of GSK3 than another kinase. In certain embodiments, the effective amount is at least three times (three folds) more effective in inhibiting the activity of GSK3α than GSK3β. In certain embodiments, the effective amount is at least four times (four folds) more effective in inhibiting the activity of GSK3α than GSK3β. In certain embodiments, the effective amount is at least five times (five folds) more effective in inhibiting the activity of GSK3α than GSK3β. In certain embodiments, the effective amount is at least seven times (seven folds) more effective in inhibiting the activity of GSK3α than GSK3β.

In another aspect, provided herein are methods of treating a disease in a subject in need thereof, the method comprising administering to the subject an effective amount of a compound or pharmaceutical composition described herein, wherein the effective amount is effective for treating the disease.

In another aspect, provided herein are methods of preventing a disease in a subject in need thereof, the method comprising administering to the subject an effective amount of a compound or pharmaceutical composition described herein, wherein the effective amount is effective for preventing the disease.

In certain embodiments, the disease is a disease associated with aberrant activity of a kinase (e.g., GSK3). In certain embodiments, the disease is a disease associated with aberrant activity of GSK3α (e.g., Fragile X syndrome, attention deficit hyperactivity disorder (ADHD), childhood seizure, intellectual disability, diabetes (e.g., Type I diabetes or Type II diabetes), acute myeloid leukemia (AML) (e.g., acute promyelocytic leukemia), autism, or psychiatric disorder (e.g., schizophrenia)). In certain embodiments, the disease is a disease associated with aberrant activity of GSK3β (e.g., mood disorder (e.g., major depressive disorder, clinical depression, major depression, or bipolar disorder), PTSD, psychiatric disorder (e.g., schizophrenia), diabetes (Type I diabetes or Type II diabetes), or neurodegenerative disease (e.g., Alzheimer's disease, frontotemporal dementia, or amyotrophic lateral sclerosis (ALS)). In certain embodiments, the effective amount is further effective for inhibiting the activity of a kinase (e.g., GSK3). In certain embodiments, the effective amount is further effective for inhibiting the activity of GSK3α. In certain embodiments, the effective amount is further effective for inhibiting the activity of GSK3β.

In certain embodiments, the disease is Fragile X syndrome. In certain embodiments, the disease is ADHD. In certain embodiments, the disease is childhood seizure. In certain embodiments, the disease is intellectual disability. In certain embodiments, the disease is diabetes. In certain embodiments, the disease is Type I diabetes. In certain embodiments, the disease is Type II diabetes. In certain embodiments, the disease is AML. In certain embodiments, the disease is acute promyelocytic leukemia. In certain embodiments, the disease is autism. In certain embodiments, the disease is a psychiatric disorder. In certain embodiments, the disease is schizophrenia.

In certain embodiments, the disease is a mood disorder. In certain embodiments, the disease is major depressive disorder, clinical depression, or major depression. In certain embodiments, the disease is bipolar disorder. In certain embodiments, the disease is a neurological disease or neurodegenerative disease. In certain embodiments, the disease is Alzheimer's disease. In certain embodiments, the disease is frontotemporal dementia. In certain embodiments, the disease is ALS.

GSK3 inhibitors have been reported in U.S. patent application publications, US 2014/0107141 and US 2016/0375006, and in U.S. provisional patent application, U.S. Ser. No. 62/417,110, filed Nov. 3, 2016, each of which is incorporated herein by reference. The serine/threonine kinase glycogen synthase kinase-3 (GSK3) is a known master regulator for several cellular pathways that include insulin signaling and glycogen synthesis, neurotrophic factor signaling, Wnt signaling, neurotransmitter signaling and microtubule dynamics (Forde, et al. Cell Mol Life Sci, 2007, 64(15):1930-44, Phiel, et al. Nature, 2003, 423(6938):435-9; Beaulieu, et al. Trends Pharmacol Sci, 2007, 28(4): 166-72). Consequently, this enzyme has a critical role in metabolism, transcription, development, cell survival, and neuronal functions and has been implicated in multiple human disorders including neurological diseases (e.g., Alzheimer's disease), psychiatric disorders (e.g., bipolar disorder), noninsulin-dependent diabetes mellitus, cardiac hypertrophy, and cancer (Gould, T D, et al. Curr Drug Targets, 2006, 7(11): 1399-409; Matsuda, et al. Proc Natl Acad Sci USA, 2008, 105(52):20900-5; Biechele, et al. Methods Mol Biol, 2008, 468:99-110; Woodgett, Curr Drug Targets Immune Endocr Metabol Disord, 2003, 3(4):281-90; Manoukian, et al. Adv Cancer Res, 2002, 84:203-29). For example, acute myeloid leukemia (AML) is a cancer characterized by multiple cellular derangements, including a block in myeloid cell differentiation. And while current therapy for the majority of patients with AML utilizes high-dose cytotoxic chemotherapy, the most successfully treated subtype of AML, acute promyelocytic leukemia, combines all-trans-retinoic acid differentiation therapy with low-dose cytotoxic therapy (Ades L, Guerci A, Raffoux E, Sanz M, Chevallier P, Lapusan S, Recher C, Thomas X, Rayon C, Castaigne S, Tournilhac O, de Botton S, Ifrah N, Cahn J Y, Solary E, Gardin C, Fegeux N, Bordessoule D, Ferrant A, Meyer-Monard S, Vey N, Dombret H, Degos L, Chevret S, Fenaux P. Very long-term outcome of acute promyelocytic leukemia after treatment with all-trans retinoic acid and chemotherapy: the European APL Group experience. *Blood.* 115: 1690-1696). To identify new targets of AML differentiation, two independent small-molecule library screens and an shRNA screen were performed. Glycogen synthase kinase-3α (GSK3α) emerged as a target at the intersection of these three screens (Banerji V, Frumm S M, Ross K N, Li L S, Schinzel A C, Hahn C K, Kakoza R M, Chow K T, Ross L, Alexe G, Tolliday N, Inguilizian H, Galinsky I, Stone R M, DeAngelo D J, Roti G, Aster J C, Hahn W C, Kung A L, Stegmaier K. The intersection of genetic and chemical genomic screens identifies GSK-3alpha as a target in human acute myeloid leukemia. *J Clin Invest.* 2012; 122:935-947). It was demonstrated that alpha-specific loss of GSK3 induces differentiation in AML by multiple measurements, including morphological changes, expression of cell surface marker consistent with myeloid maturation and induction of a gene expression program consistent with myeloid maturation. GSK3α-specific suppression also leads to impaired growth and proliferation in vitro, induction of apoptosis, loss of colony formation in methylcellulose, and anti-AML activity in vivo. Importantly, selective inhibition of GSK3α in AML does not lead to the stabilization of β-catenin. The stabilization of 3-catenin is undesirable in AML therapy because β-catenin promotes the AML stem cell population (Wang Y, Krivtsov A V, Sinha A U, North T E, Goessling W, Feng Z, Zon L I, Armstrong S A. The Wnt/beta-catenin pathway is required for the development of leukemia stem cells in AML. *Science.* 2010; 327:1650-1653). While much of the literature has focused on the role of pan GSK3 inhibition in AML, there have been data that support a role for selective GSK3α inhibitors in this disease (Wang Z, Smith K S, Murphy M, Piloto O, Somervaille T C, Cleary M L. Glycogen synthase kinase 3 in MLL leukaemia maintenance and targeted therapy. *Nature.* 2008, 455:1205-1209; Wang Z, Iwasaki M, Ficara F, Lin C, Matheny C, Wong S H, Smith K S, Cleary M L. GSK-3 promotes conditional association of CREB and its coactivators with MEIS1 to facilitate HOX-mediated transcription and oncogenesis. *Cancer Cell.* 2010; 17:597-608). Moreover, a growing literature suggests a broader role for perturbing GSK3α in cancer (Piazza F, Manni S, Tubi L Q, Montini B, Pavan L, Colpo A, Gnoato M, Cabrelle A, Adami F, Zambello R, Trentin L, Gurrieri C, Semenzato G. Glycogen Synthase Kinase-3 regulates multiple myeloma cell growth and bortezomib-induced cell death. *BMC Cancer.* 2010; 10:526; Bang D, Wilson W, Ryan M, Yeh J J, Baldwin A S. GSK-3alpha promotes oncogenic KRAS function in pancreatic cancer via TAK1-TAB stabilization and regulation of noncanonical NF-kappaB. *Cancer discovery.* 2013; 3:690-703).

Lithium has been shown to inhibit GSK3 kinase activity directly, via competition with magnesium, and indirectly, by increasing inhibitory phosphorylation of GSK3 (Beaulieu et al., 2004, 2008; Chalecka-Franaszek and Chuang, 1999; De Sarno et al., 2002; Klein and Melton, 1996). Furthermore, GSK3α null or GSK3β haploinsufficient mice phenocopy lithium's effect of attenuating aberrant behaviors (Beaulieu et al., 2004; Kaidanovich-Beilin et al., 2009; O'Brien et al., 2004). Conversely, mice overexpressing GSK3β or carrying mutations preventing inhibitory phosphorylation of GSK3α (Ser21) and GSK3β (Ser9) exhibit behaviors modeling psychiatric symptoms, as do mice with targeted disruption of AKT1, which phosphorylates and inactivates GSK3α (Ser21) and GSK3β (Ser9) (Emamian et al., 2004; Lai et al., 2006; Polter et al., 2010; Prickaerts et al., 2006).

Pan et al. showed that GSK3 inhibitors are efficacious in lithium insensitive models (Pan et al., *Neuropsychopharmacology,* 2011, 36(7): 1397-411). Therefore, GSK3 inhibitors may be efficacious in lithium resistant bipolar patients.

AKT/GSK3 signaling has been implicated in the pathophysiology of neuropsychiatric disorders through biochemical and genetic association studies of patients (Emamian et al., 2004; Tan et al., 2008; Thiselton et al., 2008). In addition to lithium, antidepressants, antipsychotics, and other mood stabilizers also modulate GSK3 activity (Beaulieu et al., 2009), further supporting its involvement in psychiatric illness. Various pharmacological probes of GSK3 have been used to implicate GSK3 kinase activity in the regulation of behavior in vivo (Beaulieu et al., 2007a; Gould et al., 2004).

In Beurel et al. (*Mol. Psych.,* 2011), removing GSK3 inhibition demonstrated insensitivity to the model of antidepressant treatment by ketamine. In addition, recently, inhibiting GSK3 has shown to be effective in models of fragile X syndrome (Franklin et al., *Biol. Psychiatry.* 2013 Sep. 13, Glycogen Synthase Kinase-3 Inhibitors Reverse Deficits in Long-term Potentiation and Cognition in Fragile X Mice). Thus, inhibiting GSK3 may lead to multiple indication of treating mental illnesses and mood disorders.

Significant evidence exists for a critical role for GSK3 signaling in the regulation of neurogenesis, neurodevelopment, and in neuroplasticity. GSK3 function is modulated by both mood stabilizers that treat bipolar disorder patients and antipsychotics for treating schizophrenia. Aberrant GSK3 signaling has further been implicated in the etiology of neuropsychiatric disorders which demonstrates a role for the inhibition of GSK3 by the schizophrenia-associated gene DISC 1 (Mao Y, et al. Cell 2009, 136(6): 1017-1031). Accordingly, small molecules that inhibit GSK3 signaling are useful as valuable tool compounds for probing the role of Wnt/GSK3 signaling in the pathophysiology of bipolar disorder and other neuropsychiatric disorders and also as therapeutics for modulating human neurogenesis.

Doble et al. discloses that
  GSK-3α and GSK-3β are equally capable of maintaining low levels of β-catenin, and that only upon inactivation of three of the four alleles, or complete loss of all four, is there any discernable impact on Wnt signaling proteins and β-catenin levels. This is of clinical relevance in conditions in which elevated GSK-3 activity is deleterious, such as Alzheimer's disease . . . .

Moreover, Hooper et al. (*J. Neurochem.*, 2008, 104(6): 1433-9) discloses that

In various cell culture, invertebrate and mammalian models of [Alzheimer's disease (AD)] increasing GSK3 activity leads to the hyperphosphorylation of tau, increased Aβ generation and deficits in learning and memory accompanied with neurodegeneration. Most importantly inhibiting GSK3 activity reverses some of the pathological effects of over-expression of mutated APP and tau in the best available models of AD . . . .

Our 'GSK3 hypothesis of AD' integrates and extends the well established 'amyloid cascade hypothesis of AD' incorporating the known key molecular events and linking these with outcomes such as memory impairment and inflammation. If correct, then this hypothesis strongly implicates GSK3 inhibitors as a novel treatment strategy for AD.

Furthermore, Lei et al. (*International Journal of Alzheimer's Disease*, Volume 2011, Article ID 189246) discloses that "The inhibition of GSK-3 may be a potential target for [Alzheimer's disease (AD)], since it has regulatory effects on both [β-amyloid (Aβ)] and tau. Similarly, GSK-3 inhibition could interact with α-synuclein to affect the pathogenesis of [Parkinson's disease (PD)]." Furthermore, Koh et al. (*Exp. Neurol.*, 2007, 205(2):336-46) discloses that "GSK-3 plays an important role in the pathogenic mechanisms of [amyotrophic lateral sclerosis (ALS)] and that inhibition of GSK-3 could be a potential therapeutic candidate for ALS." Furthermore, Wang et al. (*BMC Infectious Diseases*, 2010, 10:86) discloses that "Alteration of tau, p-tau (Ser396, Ser404, and Ser202/Thr205), GSK33 and CDK5 were either intermediate or consequent events in [transmissible spongiform encephalopathy (TSE)] pathogenesis and proposed the potential linkage of these bioactive proteins with the pathogenesis of prion diseases."

It has been reported that GSK3 inhibitors may be useful in treating post-traumatic stress disorder (PTSD). See, e.g., Dahlhoff et al., Neuroscience, 2010, 169(3):1216-26.

In certain embodiments, the compounds described herein are useful as probe compounds for investigating the role of kinase signaling, e.g., GSK3 signaling, in the pathophysiology of a disease described herein. In another aspect, provided herein are methods of probing the role of kinase signaling, e.g., GSK3 signaling, e.g., in the pathophysiology of various disorders, e.g., bipolar disorder and other psychiatric disorders, the methods comprising contacting a kinase with a compound described herein. In certain embodiments, the methods of probing the role of kinase signaling further comprise determining a biomarker prior and/or subsequent to contacting the kinase with the compound.

In certain embodiments, a provided compound is useful as a tool to probe stem cell induction. In another aspect, provided herein are methods of probing stem cell induction, the methods comprising contacting a stem cell with a compound described herein. In certain embodiments, the methods of probing stem cell induction further comprise determining a biomarker prior and/or subsequent to contacting the stem cell with the compound.

In certain embodiments, a provided compound is useful as a tool to probe the GSK/Wnt molecular pathways both in in vitro studies with human and rodent neural progenitors, and/or in vivo. Wnt/GSK3 signaling has been shown to play an important role in regulating mammalian neurogenesis and neurodevelopment (Chen, et al. J Neurochem. 2000, 75(4): 1729-34; Wexler, et al. Mol Psychiatry. 2008, 13(3):285-92). In certain embodiments, the compounds are useful as a tool to probe the effect of decreasing tau phosphorylation. Aberrant tau phosphorlyation, including at GSK3 sites, has been implicated in the pathophysiology of a number of human neurodegenerative disorders, including Alzheimer's disease and the primary tauopathies (e.g., progressive supranuclear palsy and other frontotemporal dementias). (Lee, et al. Cold Spring Harb Perspect Med. 2011, 1(1):a006437; Hooper, et al. J Neurochem. 2008, 104(6): 1433-9) Thus decreasing tau phosphorylation with a selective GSK3 inhibitor can provide insight into the underlying disease mechanisms and may provide a method of reversing disease symptoms.

In certain embodiments, the compounds described herein are useful as a tool to assess whether there are differences in the response of induced pluripotent stem cell (iPSC)-derived neural progenitor cells (iPSC-NPCs) from patients with neuropsychiatric disorders to GSK3 modulators than those without such disorders. For examples, a panel of iPSC models developed from patients with bipolar disorder, schizophrenia, and/or Fragile X syndrome may be used; evidence exists that such disorders are related to dysregulation of GSK3 signaling.

In certain embodiments, the compounds described herein are useful as a tool to probe whether selective GSK3 inhibition can rescue deficits caused by genetic variation in human/mouse DISC 1, including in assays of in vivo neurogenesis in embryonic and adult mice. The role of DISC 1/GSK3 signaling in the pathophysiology of neuropsychiatric disorders (Mao, et al. Cell. 2009, 136(6):1017-1031) is an area of ongoing study.

In another aspect, provided herein are methods of probing neurogenesis in a subject, the methods comprising administering to the subject a compound described herein. In certain embodiments, the methods of probing neurogenesis in a subject further comprise determining a biomarker prior and/or subsequent to administering to the subject the compound. In certain embodiments, the subject is a subject diagnosed with a neurodegenerative disease.

In certain embodiments, the compounds described herein modulate post-natal and/or adult neurogenesis, providing a therapeutic avenue for multiple neuropsychiatric and neurodegenerative disorders including bipolar disorder, major depression, traumatic brain injury, Alzheimer's disease, Parkinson's disease, and Huntington's disease.

The term "neurological disease" refers to a condition having as a component a central or peripheral nervous system malfunction. A neurological disease may cause a disturbance in the structure or function of the nervous system resulting from developmental and functional abnormalities, disease, genetic defects, injury or toxin. These disorders may affect the central nervous system (e.g., the brain, brainstem and cerebellum), the peripheral nervous system (e.g., the cranial nerves, spinal nerves, and sympathetic and parasympathetic nervous systems) and/or the autonomic nervous system (e.g., the part of the nervous system that regulates involuntary action and that is divided into the sympathetic and parasympathetic nervous systems). Accordingly, a neurodegenerative disease is an example for a neurological disease.

The term "neurodegenerative disease" refers to a condition characterized by loss of neuronal cells or neuronal cell supporting cells causing cognitive and/or motoric dysfunction and/or disabilities. Accordingly, the term refers to any disease or disorder that might be reversed, deterred, managed, treated, improved, or eliminated with agents that stimulate the generation of new neurons. Examples of neurodegenerative diseases include: (i) chronic neurodegenerative diseases such as familial and sporadic amyotrophic lateral sclerosis (FALS and ALS, respectively), familial and sporadic Parkinson's disease, Huntington's disease, familial and sporadic Alzheimer's disease, Fragile X syndrome, multiple sclerosis, olivopontocerebellar atrophy, multiple system atrophy, progressive supranuclear palsy, diffuse Lewy body disease, corticodentatonigral degeneration, progressive familial myoclonic epilepsy, strionigral degeneration, torsion dystonia, familial tremor, Down's syndrome, Gilles de la Tourette syndrome, Hallervorden-Spatz disease, dementia pugilistica, AIDS dementia, age related dementia, age associated memory impairment, and amyloidosis-related neurodegenerative diseases such as those caused by the prion protein (PrP) which is associated with transmissible spongiform encephalopathy (Creutzfeldt-Jakob disease, Gerstmann-Straussler-Scheinker syndrome, scrapic, and kuru), and those caused by excess cystatin C accumulation (hereditary cystatin C angiopathy); and (ii) acute neurodegenerative disorders such as traumatic brain injury (e.g., surgery-related brain injury), cerebral edema, peripheral nerve damage, spinal cord injury, Leigh's disease, Guillain-Barre syndrome, lysosomal storage disorders such as lipofuscinosis, Alper's disease, vertigo as result of CNS degeneration; pathologies arising with chronic alcohol or drug abuse including, for example, the degeneration of neurons in locus coeruleus and cerebellum; pathologies arising with aging including degeneration of cerebellar neurons and cortical neurons leading to cognitive and motor impairments; and pathologies arising with chronic amphetamine abuse including degeneration of basal ganglia neurons leading to motor impairments; pathological changes resulting from focal trauma such as stroke, focal ischemia, vascular insufficiency, hypoxic-ischemic encephalopathy, hyperglycemia, hypoglycemia or direct trauma; pathologies arising as a negative side-effect of therapeutic drugs and treatments (e.g., degeneration of cingulate and entorhinal cortex neurons in response to anticonvulsant doses of antagonists of the NMDA class of glutamate receptor) and Wernicke-Korsakoff's related dementia. Neurodegenerative diseases affecting sensory neurons include Friedreich's ataxia and retinal neuronal degeneration. Other neurodegenerative diseases include nerve injury or trauma associated with spinal cord injury. Neurodegenerative diseases of limbic and cortical systems include cerebral amyloidosis, Pick's atrophy, and Rett syndrome. The foregoing examples are not meant to be comprehensive but serve merely as an illustration of the term "neurodegenerative disorder".

Alzheimer's disease is a degenerative brain disorder characterized by cognitive and noncognitive psychiatric symptoms. Psychiatric symptoms are common in Alzheimer's disease, with psychosis (hallucinations and delusions) present in approximately fifty percent of affected patients. Similar to schizophrenia, positive psychotic symptoms are common in Alzheimer's disease. Delusions typically occur more frequently than hallucinations. Alzheimer's patients may also exhibit negative symptoms, such as disengagement, apathy, diminished emotional responsiveness, loss of volition, and decreased initiative. Indeed, antipsychotic compounds that are used to relieve psychosis of schizophrenia are also useful in alleviating psychosis in Alzheimer's patients. The term "dementia" refers to the loss of cognitive and intellectual functions without impairment of perception or consciousness. Dementia is typically characterized by disorientation, impaired memory, judgment, and intellect, and a shallow labile affect.

Fragile X Syndrome, or Martin-Bell Syndrome, is a genetic syndrome, which results in a spectrum of characteristic physical, intellectual, emotional and behavioral features which range from severe to mild in manifestation. The syndrome is associated with the expansion of a single trinucleotide gene sequence (CGG) on the X chromosome, and results in a failure to express the FMRP protein that is required for normal neural development. There are four generally accepted forms of Fragile X Syndrome which relate to the length of the repeated CGG sequence in the FMR1 gene; Normal (29-31 CGG repeats), Premutation (55-200 CGG repeats), Full Mutation (more than 200 CGG repeats), and Intermediate or Gray Zone Alleles (40-60 repeats). Normally, the FMR1 gene contains between 6 and 55 repeats of the CGG codon (trinucleotide repeats). In people with the Fragile X Syndrome, the FMR1 allele has over 230 repeats of this codon. Expansion of the CGG repeating codon to such a degree results in a methylation of that portion of the DNA, effectively silencing the expression of the FMR1 protein. This methylation of the FMR1 locus in chromosome band Xq27.3 is believed to result in constriction of the X chromosome which appears 'fragile' under the microscope at that point, a phenomenon that gave the syndrome its name. Mutation of the FMR1 gene leads to the transcriptional silencing of the fragile X-mental retardation protein, FMRP. In normal individuals, FMRP is believed to regulate a substantial population of mRNA: FMRP plays important roles in learning and memory, and also appears to be involved in development of axons, formation of synapses, and the wiring and development of neural circuits.

Amyotrophic lateral sclerosis (ALS), also called Lou Gehrig's disease, is a progressive, fatal neurological disease. ALS occurs when specific nerve cells in the brain and spinal cord that control voluntary movement gradually degenerate and causes the muscles under their control to weaken and waste away, leading to paralysis. Currently, there is no cure for ALS; nor is there a proven therapy that will prevent or reverse the course of the disorder.

The compounds described herein may be useful for treating spinal muscular atrophy (SMA). SMA is a neuromuscular disorder characterized by loss of motor neurons and progressive muscle wasting. SMA may be caused by a genetic defect in the SMN1 gene, which encodes SMN, a protein widely expressed in all eukaryotic cells and necessary for survival of motor neurons. Lower levels of SMN results in loss of function of neuronal cells in the anterior horn of the spinal cord and subsequent system-wide muscle wasting (atrophy). It has been reported that inhibition of GSK3 may result in the activation of its downstream constituents, such as β-catenin, c-Jun, and the cyclic AMP response element binding protein (CREB), which consequently upregulate Tcf/Lef gene transcription and CREB-induced gene transcription of neurotrophic factors, such as brain-derived neurotrophic factor (BDNF) (Gould et al., Neuropsychopharmacology, 2005, 30, 1223-1237; Tanis et al., *Ann. Med.*, 2007, 39, 531-544). BDNF may help support the survival of existing neurons and promote neurogenesis (Chuang et al., *Front. Mol. Neurosci.*, 2011, 4, 1-12). GSK3 inhibitor BIP-135

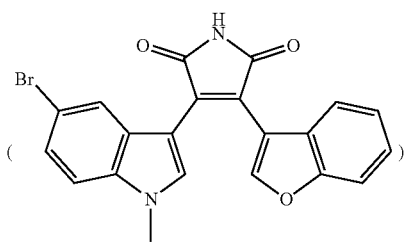 [SMILES: Cn1cc(C2=C(c3coc4ccccc34)C(=O)NC2=O)c2cc(Br)ccc21]

was tested in a transgenic Δ7 SMA KO mouse model of SMA and found to prolong the median survival of the mice (Chen et al., *ACS Chem. Neurosci.*, 2012, 3, 5-11). In addition, BIP-135 was shown to elevate the SMN protein level in SMA patient-derived fibroblast cells as determined by Western blot, and was neuroprotective in a cell-based, SMA-related model of oxidative stress-induced neurodegeneration (Chen et al., *ACS Chem. Neurosci.*, 2012, 3, 5-11).

Parkinson's disease is a disturbance of voluntary movement in which muscles become stiff and sluggish. Symptoms of the disease include difficult and uncontrollable rhythmic twitching of groups of muscles that produces shaking or tremors. The disease is caused by degeneration of pre-synaptic dopaminergic neurons in the brain and specifically in the brain stem. As a result of the degeneration, an inadequate release of the chemical transmitter dopamine occurs during neuronal activity. Currently, Parkinson's disease is treated with several different compounds and combinations. Levodopa (L-dopa), which is converted into dopamine in the brain, is often given to restore muscle control. Perindopril, an ACE inhibitor that crosses the blood-brain barrier, is used to improve patients' motor responses to L-dopa. Carbidopa is administered with L-dopa in order to delay the conversion of L-dopa to dopamine until it reaches the brain, and it also lessens the side effects of L-dopa. Other drugs used in Parkinson's disease treatment include dopamine mimickers Mirapex (pramipexole dihydrochloride) and Requip (ropinirole hydrochloride), and Tasmar (tolcapone), a COMT inhibitor that blocks a key enzyme responsible for breaking down levodopa before it reaches the brain.

The term "psychiatric disorder" refers to a condition or disorder relating to the functioning of the brain and the cognitive processes or behavior. Psychiatric disorders may be further classified based on the type of neurological disturbance affecting the mental faculties. Psychiatric disorders are expressed primarily in abnormalities of thought, feeling, emotion, and/or behavior producing either distress or impairment of function (for example, impairment of mental function such with dementia or senility). The term "psychiatric disorder" is, accordingly, sometimes used interchangeably with the term "mental disorder" or the term "mental illness".

A psychiatric disorder is often characterized by a psychological or behavioral pattern that occurs in an individual and is thought to cause distress or disability that is not expected as part of normal development or culture. Definitions, assessments, and classifications of mental disorders can vary, but guideline criteria listed in the International Classification of Diseases and Related Health Problems (ICD, published by the World Health Organization, WHO), or the Diagnostic and Statistical Manual of Mental Disorders (DSM, published by the American Psychiatric Association, APA) and other manuals are widely accepted by mental health professionals. Individuals may be evaluated for various psychiatric disorders using criteria set forth in these and other publications accepted by medical practitioners in the field and the manifestation and severity of a psychiatric disorder may be determined in an individual using these publications.

Categories of diagnoses in these schemes may include dissociative disorders, mood disorders, anxiety disorders, psychotic disorders, eating disorders, developmental disorders, personality disorders, and other categories. There are different categories of mental disorder, and many different facets of human behavior and personality that can become disordered.

One group of psychiatric disorders includes disorders of thinking and cognition, such as schizophrenia and delirium. A second group of psychiatric disorders includes disorders of mood, such as affective disorders and anxiety. A third group of psychiatric disorders includes disorders of social behavior, such as character defects and personality disorders. And a fourth group of psychiatric disorders includes disorders of learning, memory, and intelligence, such as mental retardation and dementia. Accordingly, psychiatric disorders encompass schizophrenia, delirium, attention deficit disorder (ADD), schizoaffective disorder, depression (e.g., lithium-resistant depression), mania, attention deficit disorders, drug addiction, dementia, agitation, apathy, anxiety, psychoses, personality disorders, bipolar disorders, unipolar affective disorder, obsessive-compulsive disorders, eating disorders, post-traumatic stress disorders, irritability, adolescent conduct disorder and disinhibition.

Some diseases classified as neurodegenerative diseases, for example Alzheimer's disease, also sometimes show aspects of psychiatric disorders as listed herein, for example disorders of memory or dementia. Some neurodegenerative diseases or manifestations thereof can, accordingly, also be referred to as psychiatric disorders. These terms are, therefore, not mutually exclusive.

The state of anxiety or fear can become disordered, so that it is unusually intense or generalized over a prolonged period of time. Commonly recognized categories of anxiety disorders include specific phobia, generalized anxiety disorder, social anxiety disorder, panic disorder, agoraphobia, obsessive-compulsive disorder, post-traumatic stress disorder.

Relatively long lasting affective states can also become disordered. Mood disorder involving unusually intense and sustained sadness, melancholia or despair is known as clinical depression (or major depression), and may more generally be described as emotional dysregulation. Milder but prolonged depression can be diagnosed as dysthymia. Bipolar disorder involves abnormally "high" or pressured mood states, known as mania or hypomania, alternating with normal or depressed mood.

Patterns of belief, language use and perception can become disordered. Psychotic disorders centrally involving this domain include schizophrenia and delusional disorder. Schizoaffective disorder is a category used for individuals showing aspects of both schizophrenia and affective disorders. Schizotypy is a category used for individuals showing some of the traits associated with schizophrenia but without meeting cut-off criteria.

The fundamental characteristics of a person that influence his or her cognitions, motivations, and behaviors across situations and time can be seen as disordered due to being abnormally rigid and maladaptive. Categorical schemes list a number of different personality disorders, such as those classed as eccentric (e.g., paranoid personality disorder, schizoid personality disorder, schizotypal personality disorder), those described as dramatic or emotional (antisocial personality disorder, borderline personality disorder, histrionic personality disorder, narcissistic personality disorder) or those seen as fear-related (avoidant personality disorder, dependent personality disorder, obsessive-compulsive personality disorder).

Other disorders may involve other attributes of human functioning. Eating practices can be disordered, with either compulsive over-eating or under-eating or binging. Categories of disorder in this area include anorexia nervosa, bulimia nervosa, exercise bulimia or binge eating disorder. Sleep disorders such as insomnia also exist and can disrupt normal sleep patterns. The other disorders may also include sexual disorders, such as dyspareunia and ego-dystonic sexuality. People who are abnormally unable to resist urges, or impulses, to perform acts that could be harmful to themselves or others, may be classed as having an impulse control disorder, including various kinds of tic disorders such as Tourette's Syndrome, and disorders such as kleptomania (stealing) or pyromania (fire-setting). Substance-use disorders include substance abuse disorder. Addictive gambling may be classed as a disorder. Inability to sufficiently adjust to life circumstances may be classed as an adjustment disorder. The category of adjustment disorder is usually reserved for problems beginning within three months of the event or situation and ending within six months after the stressor stops or is eliminated. People who suffer severe disturbances of their self-identity, memory and general awareness of themselves and their surroundings may be classed as having a dissociative identity disorder, such as depersonalization disorder (which has also been called multiple personality disorder, or "split personality"). Factitious disorders, such as Munchausen syndrome, also exist where symptoms are experienced and/or reported for personal gain.

Disorders appearing to originate in the body, but thought to be mental, are known as somatoform disorders, including somatization disorder. There are also disorders of the perception of the body, including body dysmorphic disorder. Neurasthenia is a category involving somatic complaints as well as fatigue and low spirits/depression, which is officially recognized by the ICD (version 10) but not by the DSM (versions IV and V). Memory or cognitive disorders, such as amnesia or Alzheimer's disease are also sometimes classified as psychiatric disorders.

Other proposed disorders include: self-defeating personality disorder, sadistic personality disorder, passive-aggressive personality disorder, premenstrual dysphoric disorder, video game addiction or internet addiction disorder.

Bipolar disorder is a psychiatric diagnosis that describes a category of mood disorders defined by the presence of one or more episodes of abnormally elevated mood clinically referred to as mania or, if milder, hypomania. Individuals who experience manic episodes also commonly experience depressive episodes or symptoms, or mixed episodes in which features of both mania and Depression are present at the same time. These episodes are usually separated by periods of "normal" mood, but in some individuals, Depression and mania may rapidly alternate, known as rapid cycling. Extreme manic episodes can sometimes lead to psychotic symptoms such as delusions and hallucinations. The disorder has been subdivided into bipolar I, bipolar II, cyclothymia, and other types, based on the nature and severity of mood episodes experienced; the range is often described as the bipolar spectrum.

Autism (also referred to as autism spectrum disorder, or ASD) is a disorder that seriously impairs the functioning of individuals. It is characterized by self-absorption, a reduced ability to communicate with or respond to the outside world, rituals and compulsive phenomena, and mental retardation. Autistic individuals are also at increased risk of developing seizure disorders, such as epilepsy. While the actual cause of Autism is unknown, it appears to include one or more genetic factors, as indicated by the fact that the concordance rate is higher in monozygotic twins than in dizygotic twins, and may also involve immune and environmental factors, such as diet, toxic chemicals and infections.

Schizophrenia is a disorder that affects about one percent of the world population. Three general symptoms of schizophrenia are often referred to as positive symptoms, negative symptoms, and cognitive symptoms. Positive symptoms can include delusions (abnormal beliefs), hallucinations (abnormal perceptions), and disorganized thinking. The hallucinations of schizophrenia can be auditory, visual, olfactory, or tactile. Disorganized thinking can manifest itself in schizophrenic patients by disjointed speech and the inability to maintain logical thought processes. Negative symptoms can represent the absence of normal behavior. Negative symptoms include emotional flatness or lack of expression and can be characterized by social withdrawal, reduced energy, reduced motivation, and reduced activity. Catatonia can also be associated with negative symptoms of schizophrenia. The symptoms of schizophrenia should continuously persist for a duration of about six months in order for the patient to be diagnosed as schizophrenic. Based on the types of symptoms a patient reveals, schizophrenia can be categorized into subtypes including catatonic schizophrenia, paranoid schizophrenia, and disorganized schizophrenia.

Examples of antipsychotic drugs that may be used to treat schizophrenic patients include phenothizines, such as chlorpromazine and trifluopromazine; thioxanthenes, such as chlorprothixene; fluphenazine; butyropenones, such as haloperidol; loxapine; mesoridazine; molindone; quetiapine; thiothixene; trifluoperazine; perphenazine; thioridazine; risperidone; dibenzodiazepines, such as clozapine; and olanzapine. Although these compounds may relieve the symptoms of schizophrenia, their administration can result in undesirable side effects including Parkinson's disease-like symptoms (tremor, muscle rigidity, loss of facial expression); dystonia; restlessness; tardive dyskinesia; weight gain; skin problems; dry mouth; constipation; blurred vision; drowsiness; slurred speech and agranulocytosis.

Mood disorders are typically characterized by pervasive, prolonged, and disabling exaggerations of mood and affect that are associated with behavioral, physiologic, cognitive, neurochemical and psychomotor dysfunctions. The major mood disorders include major depressive disorder (also known as unipolar disorder), bipolar disorder (also known as manic depressive illness or bipolar depression), dysthymic disorder.

The term "depression", sometimes used interchangeably with "depressive disorder" and refers to mood disorders manifesting in morbid sadness, dejection, or melancholy. Depressive disorders can involve serotonergic and noradrenergic neuronal systems based on current therapeutic regimes that target serotonin and noradrenalin receptors. Mania may result from an imbalance in certain chemical messengers within the brain. Administering phosphotidyl choline has been reported to alleviate the symptoms of mania. In certain embodiments, the depression described herein is lithium-resistant depression.

Mania is a sustained form of euphoria that affects millions of people in the United States who suffer from depression. Manic episodes can be characterized by an elevated, expansive, or irritable mood lasting several days, and is often accompanied by other symptoms, such as, over-activity, over-talkativeness, social intrusiveness, increased energy, pressure of ideas, grandiosity, distractibility, decreased need for sleep, and recklessness. Manic patients can also experience delusions and hallucinations.

Anxiety disorders are characterized by frequent occurrence of symptoms of fear including arousal, restlessness, heightened responsiveness, sweating, racing heart, increased blood pressure, dry mouth, a desire to run or escape, and avoidance behavior. Generalized anxiety persists for several months, and is associated with motor tension (trembling, twitching, muscle aches, restlessness); autonomic hyperactivity (shortness of breath, palpitations, increased heart rate, sweating, cold hands), and vigilance and scanning (feeling on edge, exaggerated startle response, difficult in concentrating). Benzodiazepines, which enhance the inhibitory effects of the gamma aminobutyric acid (GABA) type A receptor, are frequently used to treat anxiety. Buspirone is another effective anxiety treatment.

Schizoaffective disorder describes a condition where both the symptoms of a mood disorder and schizophrenia are present. A person may manifest impairments in the perception or expression of reality, most commonly in the form of auditory hallucinations, paranoid or bizarre delusions or disorganized speech and thinking, as well as discrete manic and/or depressive episodes in the context of significant social or occupational dysfunction.

In some embodiments, a provided compound is useful in treating attention deficit hyperactivity disorder (ADHD).

In certain embodiments, a provided compound stimulates neurogenesis. Accordingly, in some embodiments, a provided compound is useful in treating diseases that are related to neurogenesis. For example, a provided compound is useful for treating a neurological disorder in a subject comprising administering to the subject an effective amount of a provided compound or pharmaceutically acceptable salt thereof. In some embodiments, the neurological disorder is cognitive decline associated with normal aging, traumatic brain injury, Parkinson's disease, major depression, bipolar disorder, epilepsy, spinocerebellar ataxia, Huntington's disease, ALS, stroke, radiation therapy, post-traumatic stress disorder, Down syndrome, chronic stress, retinal degeneration, spinal cord injury, peripheral nerve injury, physiological weight loss associated with various conditions, abuse of a neuroactive drug, spinal cord injury, or cognitive decline associated with chemotherapy.

In some embodiments, a provided compound is useful in regulating circadian rhythms in a subject in need thereof.

In some embodiments, a provided compound is useful in treating alopecia.

In some embodiments, a provided compound is useful as an immunopotentiator.

In some embodiments, a provided compound is useful in treating cancer. The term "cancer" refers to a class of diseases characterized by the development of abnormal cells that proliferate uncontrollably and have the ability to infiltrate and destroy normal body tissues. See, e.g., *Stedman's Medical Dictionary*, 25th ed.; Hensyl ed.; Williams & Wilkins: Philadelphia, 1990. Exemplary cancers include acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma: ocular cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenström's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; and multiple myeloma (MM)), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendoctrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

The cancer that is treated by a provided compound may be GSK3α- and/or GSK3β-mediated. In some embodiments, a provided compound is useful in treating a cancer described herein. For example, in some embodiments, a provided compound is useful in treating leukemia. In certain embodiments, a provided compound is useful in treating acute myeloid leukemia (AML). In certain embodiments, a provided compound is useful in treating acute lymphocytic leukemia (ALL), chronic myelocytic leukemia (CML), and/or chronic lymphocytic leukemia (CLL). In some embodiments, treatment of leukemia (e.g., acute myeloid leukemia) is effected by inhibition of GSK3α. In some embodiments, a provided compound is useful in treating multiple myeloma. In some embodiments, a provided compound is useful in treating glioma or pancreatic cancer. In some embodiments, a provided compound is useful in treating breast cancer, non-small cell lung carcinoma, thyroid cancer, T-cell or B-cell leukemia, or a virus-induced tumor.

GSK3α and GSK3β are also implicated in metabolic disorders, such as diabetes (e.g., type II diabetes) (A. S. Wagman, K. W. Johnson and D. E. Bussiere, Curr. Pharm. Design, 2004, 10, 1105). The term "metabolic disorder" refers to any disorder that involves an alteration in the normal metabolism of carbohydrates, lipids, proteins, nucleic acids, or a combination thereof. A metabolic disorder is associated with either a deficiency or excess in a metabolic pathway resulting in an imbalance in metabolism of nucleic acids, proteins, lipids, and/or carbohydrates. Factors affecting metabolism include the endocrine (hormonal) control system (e.g., the insulin pathway, the enteroendocrine hormones including GLP-1, PYY or the like), the neural control system (e.g., GLP-1 in the brain), or the like. Examples of metabolic disorders include diabetes (e.g., type 1 diabetes, type 2 diabetes, gestational diabetes), hyperglycemia, hyperinsulinemia, insulin resistance, and obesity. In certain embodiments, the metabolic disorder is type II diabetes.

GSK3 activity is elevated in human and rodent models of diabetes, and various GSK3 inhibitors improve glucose tolerance and insulin sensitivity in rodent models of obesity and diabetes. Unlike GSK3 mutants, which die before birth, GSK3α knockout (GSK3α KO) animals are viable but display enhanced glucose and insulin sensitivity accompanied by reduced fat mass (Katrina et al., *Cell Metabolism* 6, 329-337, October 2007). Fasted and glucose-stimulated hepatic glycogen content was enhanced in GSK3α KO mice, whereas muscle glycogen was unaltered. Insulin-stimulated protein kinase B (PKB/Akt) and GSK3β phosphorylation was higher in GSK3α KO livers compared to wild-type littermates, and IRS-1 expression was markedly increased. It was concluded that GSK3 isoforms exhibit tissue-specific physiological functions and that GSK3α KO mice are insulin sensitive, reinforcing the potential of GSK3 as a therapeutic target for type II diabetes.

In some embodiments, a provided compound is useful in treating a metabolic disorder. In some embodiments, a provided compound is useful in treating diabetes (e.g., Type 1 diabetes, Type 2 diabetes, or gestational diabetes). In some embodiments, a provided compound is useful in treating type 2 diabetes. In some embodiments, a provided compound is useful in treating obesity.

β-catenin stabilization has been linked to neoplastic concerns for other GSK3 inhibitors (e.g., non-selective GSK3 inhibitors). In certain embodiments, the activity of a GSK3α inhibitor that is selective for GSK3α over GSK3β is independent of β-catenin stabilization and translocation to the nucleus.

It has been reported that GSK3 inhibitors may be useful in treating Fragile X syndrome. For example, Mines et al. (*PLoS One,* 2010, 5(3):e9706) discloses that These findings provide the first identification of links between GSK3 and social behaviors and suggest that dysregulated GSK3 may contribute to some of the social impairments associated with loss of [Fragile X mental retardation protein (FMRP)] and that these might be partially remedied by lithium administration, also supporting the utility of [Fragile X mental retardation 1 (Fmr1)] knockout as a means to identify mechanisms underlying social impairments common among [autism (ASD)] and [Fragile X syndrome (FXS)] patients and for exploration of therapeutic interventions that may enhance social interactions.

However, it was not known in the art that a GSK3α inhibitor that is selective for GSK3α over GSK3β (e.g., a GSK3 inhibitor that selectively inhibits the activity of GSK3α, as compared to GSK3β) may be more useful in treating Fragile X syndrome than does a GSK3β inhibitor that is selective for GSK3β over GSK3α (e.g., a GSK3 inhibitor that selectively inhibits the activity of GSK3β, as compared to GSK3α) and than does a non-selective GSK3 inhibitor. In another aspect, the present disclosure provides methods of treating Fragile X syndrome comprising administering to a subject suffering from Fragile X syndrome a therapeutically effective amount of a GSK3α inhibitor, wherein the GSK3α inhibitor selectively inhibits the activity of GSK3α, as compared to GSK3β. The methods of treating Fragile X syndrome described herein may have advantages over the known methods of treating Fragile X syndrome. One of such advantages may be lower dosages, less frequent dosages, higher subject compliance, easier administration, lower toxicity, less severe adverse effects, less frequent adverse effects, lower costs, or a combination thereof. In certain embodiments, the amount of the GSK3α inhibitor in a method of treating Fragile X syndrome is lower than (e.g., lower than 90% of, lower than 70% of, lower than 50% of, lower than 30% of, lower than 10% of, lower than 3% of, lower than 1% of, or lower than 0.1% of) a therapeutically effective amount of a GSK3β inhibitor or non-selective GSK3 inhibitor for treating Fragile X syndrome.

It has been reported that GSK3 is implicated in ADHD (Shim et al., *Prog. Neuropsychopharmacol. Biol. Psychiatry,* 2012, 39, 57-61; Del'Guidice et al., *Med. Sci. (Paris)*, 2010, 26, 647-651; and Mines et al., *Eur. J. Pharmacol.*, 2013, 698, 252-258). It has also been reported that GSK3 is implicated in seizures (e.g., childhood seizure) (Niceta et al., *Am. J. Hum. Genet.*, 2015, 96, 816-825). In another aspect, the present disclosure provides methods of treating ADHD comprising administering to a subject suffering from ADHD a therapeutically effective amount of a GSK3α inhibitor, wherein the GSK3α inhibitor selectively inhibits the activity of GSK3α, as compared to GSK3β. The methods of treating ADHD described herein may have advantages over the known methods of treating ADHD. One of such advantages may be lower dosages, less frequent dosages, higher subject compliance, easier administration, lower toxicity, less severe adverse effects, less frequent adverse effects, lower costs, or a combination thereof. In certain embodiments, the amount of the GSK3α inhibitor in a method of treating ADHD is lower than (e.g., lower than 90% of, lower than 70% of, lower than 50% of, lower than 30% of, lower than 10% of, lower than 3% of, lower than 1% of, or lower than 0.1% of) a therapeutically effective amount of a GSK3β inhibitor or non-selective GSK3 inhibitor for treating ADHD.

In another aspect, the present disclosure provides methods of treating childhood seizure comprising administering to a subject suffering from childhood seizure a therapeutically effective amount of a GSK3α inhibitor, wherein the GSK3α inhibitor selectively inhibits the activity of GSK3α, as compared to GSK3β. The methods of treating childhood seizure described herein may have advantages over the known methods of treating childhood seizure. One of such advantages may be lower dosages, less frequent dosages, higher subject compliance, easier administration, lower toxicity, less severe adverse effects, less frequent adverse effects, lower costs, or a combination thereof. In certain embodiments, the amount of the GSK3α inhibitor in a method of treating childhood seizure is lower than (e.g., lower than 90% of, lower than 70% of, lower than 50% of, lower than 30% of, lower than 10% of, lower than 3% of, lower than 1% of, or lower than 0.1% of) a therapeutically effective amount of a GSK3β inhibitor or non-selective GSK3 inhibitor for treating childhood seizure.

It has been reported that GSK3 inhibitors may be useful in treating a mood disorder. For example, Gould et al. (*Curr. Drug Targets*, 2006, (11): 1399-409) discloses that "regulating GSK-3 may represent a target for novel medications to treat mood disorders." Moreover, it was known that lithium is useful in treating mood disorders. Beaulieu et al. (*Pharmacol. Sci.*, 2007, 28(4): 166-72) discloses that "a direct or indirect inhibition of GSK-3 might contribute to the psychopharmacological actions of lithium, at least in part, by inhibiting dopamine responses."

However, it was not known in the art that a GSK3α inhibitor that is selective for GSK3α over GSK3β may be more useful in treating intellectual disability syndrome than does a GSK3β inhibitor that is selective for GSK3β over GSK3α. In another aspect, the present disclosure provides methods of treating intellectual disability syndrome comprising administering to a subject suffering from intellectual disability syndrome a therapeutically effective amount of a GSK3α inhibitor, wherein the GSK3α inhibitor selectively inhibits the activity of GSK3α, as compared to GSK3β. The methods of treating intellectual disability syndrome described herein may have advantages over the known methods of treating intellectual disability syndrome. One of such advantages may be lower dosages, less frequent dosages, higher subject compliance, easier administration, lower toxicity, less severe adverse effects, lower costs, or a combination thereof. In certain embodiments, the amount of the GSK3α inhibitor in a method of treating intellectual disability syndrome is lower than (e.g., lower than 90% of, lower than 70% of, lower than 50% of, lower than 30% of, lower than 10% of, lower than 3% of, lower than 1% of, or lower than 0.1% of) a therapeutically effective amount of a GSK3β inhibitor or non-selective GSK3 inhibitor for treating intellectual disability.

It has been reported that GSK3 inhibitors may be useful in treating diabetes. For example, Doble et al. (*Developmental Cell*, 2007, 12, 957-971) discloses that GSK-3α and GSK-3β are equally capable of maintaining low levels of β-catenin, and that only upon inactivation of three of the four alleles, or complete loss of all four, is there any discernable impact on Wnt signaling proteins and β-catenin levels. This is of clinical relevance in conditions in which elevated GSK-3 activity is deleterious, such as . . . Type 11 diabetes.

Moreover, Macaulay et al. (*Cell Metab.* 2007, 6(4):329-37) discloses that "various GSK-3 inhibitors improve glucose tolerance and insulin sensitivity in rodent models of obesity and diabetes . . . . GSK-3 isoforms exhibit tissue-specific physiological functions and that GSK-3a KO mice are insulin sensitive, reinforcing the potential of GSK-3 as a therapeutic target for type II diabetes."

However, it was not known in the art that a GSK3α inhibitor that is selective for GSK3α over GSK3β may be more useful in treating diabetes than does a GSK3β inhibitor that is selective for GSK3β over GSK3α. In another aspect, the present disclosure provides methods of treating diabetes comprising administering to a subject suffering from diabetes a therapeutically effective amount of a GSK3α inhibitor, wherein the GSK3α inhibitor selectively inhibits the activity of GSK3α, as compared to GSK3β. The methods of treating diabetes described herein may have advantages over the known methods of treating diabetes. One of such advantages may be lower dosages, less frequent dosages, higher subject compliance, easier administration, lower toxicity, less severe adverse effects, less frequent adverse effects, lower costs, or a combination thereof. In certain embodiments, the amount of the GSK3α inhibitor in a method of treating diabetes is lower than (e.g., lower than 90% of, lower than 70% of, lower than 50% of, lower than 30% of, lower than 10% of, lower than 3% of, lower than 1% of, or lower than 0.1% of) a therapeutically effective amount of a GSK3β inhibitor or non-selective GSK3 inhibitor for treating diabetes. In certain embodiments, the diabetes is Type I diabetes. In certain embodiments, the diabetes is Type II diabetes.

It has been reported that GSK3 inhibitors may be useful in treating AML. For example, Banerji et al. (*J. Clin. Invest.*, 2012, 122(3):935-47) discloses that "In summary, these studies suggest a role for GSK-3α in [acute myeloid leukemia (AML)] differentiation and support a potential role for GSK-3α-directed targeted therapy."

However, it was not known in the art that a GSK3α inhibitor that is selective for GSK3α over GSK3β may be more useful in treating AML than does a GSK3β inhibitor that is selective for GSK3β over GSK3α. In another aspect, the present disclosure provides methods of treating AML comprising administering to a subject suffering from AML a therapeutically effective amount of a GSK3α inhibitor, wherein the GSK3α inhibitor selectively inhibits the activity of GSK3α, as compared to GSK3β. The methods of treating AML described herein may have advantages over the known methods of treating AML. One of such advantages may be lower dosages, less frequent dosages, higher subject compliance, easier administration, lower toxicity, less severe adverse effects, less frequent adverse effects, lower costs, or a combination thereof. In certain embodiments, the amount of the GSK3α inhibitor in a method of treating AML is lower than (e.g., lower than 90% of, lower than 70% of, lower than 50% of, lower than 30% of, lower than 10% of, lower than 3% of, lower than 1% of, or lower than 0.1% of) a therapeutically effective amount of a GSK3β inhibitor or non-selective GSK3 inhibitor for treating AML. In certain embodiments, the AML is acute promyelocytic leukemia.

It has been reported that GSK3 inhibitors may be useful in treating autism. For example, Mines et al. discloses that Fragile X mental retardation 1 (Fmr1) knockout mice is an animal model for studying the molecular mechanism of autism (ASD) and for developing treatment of autism. Mines et al. also discloses that:

> These findings provide the first identification of links between GSK3 and social behaviors and suggest that dysregulated GSK3 may contribute to some of the social impairments associated with loss of [Fragile X mental retardation protein (FMRP)] and that these might be partially remedied by lithium administration, also supporting the utility of Fmr1 knockout as a means to identify mechanisms underlying social impairments common among ASD and [Fragile X syndrome (FXS)] patients and for exploration of therapeutic interventions that may enhance social interactions.

However, it was not known in the art that a GSK3α inhibitor that is selective for GSK3α over GSK3β may be more useful in treating autism than does a GSK3β inhibitor that is selective for GSK3β over GSK3α. In another aspect, the present disclosure provides methods of treating autism comprising administering to a subject suffering from autism a therapeutically effective amount of a GSK3α inhibitor, wherein the GSK3α inhibitor selectively inhibits the activity of GSK3α, as compared to GSK3β. The methods of treating autism described herein may have advantages over the known methods of treating autism. One of such advantages may be lower dosages, less frequent dosages, higher subject compliance, easier administration, lower toxicity, less severe adverse effects, less frequent adverse effects, lower costs, or a combination thereof. In certain embodiments, the amount of the GSK3α inhibitor in a method of treating autism is lower than (e.g., lower than 90% of, lower than 70% of, lower than 50%, of, lower than 30% of, lower than 10% of, lower than 3% of, lower than 1% of, or lower than 0.1% of) a therapeutically effective amount of a GSK3β inhibitor or non-selective GSK3 inhibitor for treating autism.

It has been reported that GSK3 inhibitors may be useful in treating a psychiatric disorder. See, e.g., Mukai et al. Neuron, 2015, 86(3):680-95. However, it was not known in the art that a GSK3α inhibitor that is selective for GSK3α over GSK3β may be more useful in treating a psychiatric disorder than does a GSK3β inhibitor that is selective for GSK3β over GSK3α. In another aspect, the present disclosure provides methods of treating a psychiatric disorder comprising administering to a subject suffering from the psychiatric disorder a therapeutically effective amount of a GSK3α inhibitor, wherein the GSK3α inhibitor selectively inhibits the activity of GSK3α, as compared to GSK3β. The methods of treating a psychiatric disorder described herein may have advantages over the known methods of treating the psychiatric disorder. One of such advantages may be lower dosages, less frequent dosages, higher subject compliance, easier administration, lower toxicity, less severe adverse effects, less frequent adverse effects, lower costs, or a combination thereof. In certain embodiments, the amount of the GSK3α inhibitor in a method of treating a psychiatric disorder is lower than (e.g., lower than 90% of, lower than 70% of, lower than 50% of, lower than 30% of, lower than 10% of, lower than 3% of, lower than 1% of, or lower than 0.1% of) a therapeutically effective amount of a GSK3β inhibitor or non-selective GSK3 inhibitor for treating the psychiatric disorder. In certain embodiments, the psychiatric disorder is schizophrenia.

In another aspect, provided herein are uses of the compounds described herein. In another aspect, provided herein are uses of the pharmaceutical compositions described herein. In certain embodiments, the uses are as described in the methods described herein.

EXAMPLES

In order that the invention described herein may be more fully understood, the following examples are set forth. The synthetic and biological examples described in this application are offered to illustrate the compounds, pharmaceutical compositions, and methods provided herein and are not to be construed in any way as limiting their scope. A compound described herein may be referred to by using two or more different compound numbers. A compound described herein may be tested two or more times under the same or different conditions for determining a property and, therefore, may show different values of the property.

Example 1. Synthesis of Exemplary Compounds

The compounds provided herein can be prepared from readily available starting materials using the following general methods and procedures. It will be appreciated that where typical or preferred process conditions (e.g., reaction temperatures, times, mole ratios of reactants, solvents, and pressures) are given, other process conditions can also be used unless otherwise stated. Optimum reaction conditions may vary with the particular reactants or solvents used, but such conditions can be determined by those skilled in the art by routine optimization procedures.

Additionally, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in Greene et al., *Protecting Groups in Organic Synthesis*, Second Edition, Wiley, New York, 1991, and references cited therein.

Exemplary compounds described herein were prepared according to the method depicted in Schemes 1 to 6.

Scheme 1

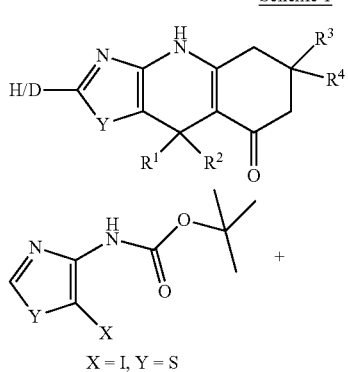

X = I, Y = S

-continued

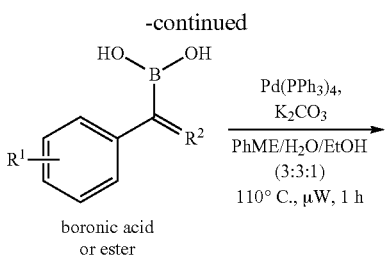

boronic acid
or ester

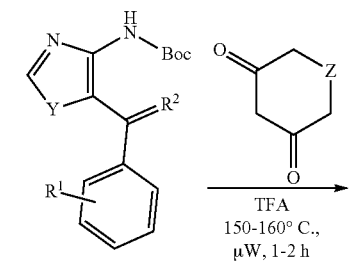

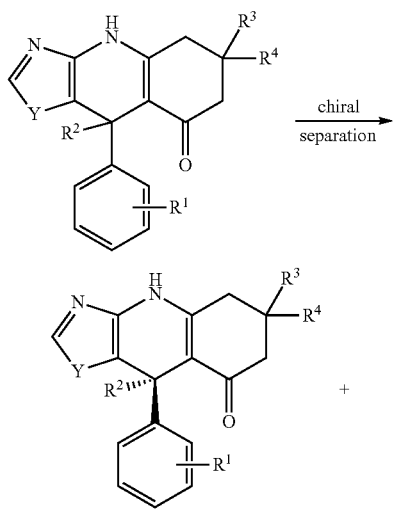

chiral separation

Scheme 2

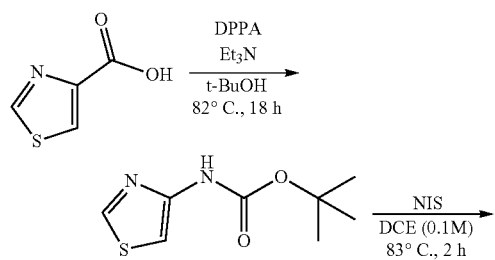

-continued

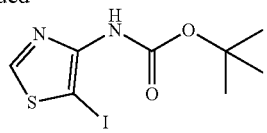

Tert-Butyl (5-iodothiazol-4-yl)carbamate

Prepared by slight modification to the published procedure (Koolman, H.; Heinrich, T.; Reggelin, M. *Synthesis*, 2010, 3152. DOI: 10.1055/s-0030-1258159).

To a suspension of thiazole-4-carboxylic acid (2.50 g, 19.3 mmol, 1.0 eq) in t-butanol (35 mL), triethylamine (3.00 mL, 21.4 mmol, 1.11 eq) and diphenylphosphoryl azide (4.50 mL, 20.8 mmol, 1.08 eq) were added. The resulting solution was heated at 82° C. for 18 h, then cooled to room temperature. The solvent was evaporated, and the residue was dissolved in EtOAc (100 mL). The organics were washed with 1 M NaOH, water, and brine, dried over MgSO$_4$, filtered, and evaporated. The crude material was purified via flash column chromatography (10-50% EtOAc/hexanes) to provide the thiazole carbamate (2.74 g, >99% purity, 71% yield) as a white solid.

$^1$H NMR (400 MHz, Chloroform-d) δ 8.58 (d, J=2.3 Hz, 1H), 8.24 (br s, 1H), 7.30 (br s, 1H), 1.54 (s, 9H).

To a solution of tert-butyl thiazol-4-ylcarbamate (2.50 g, 12.4 mmol, 1.0 eq) in 1,2-dichloroethane (120 mL), N-iodosuccinimide (3.00 g, 13.3 mmol, 1.07 eq) was added. The resulting suspension was heated at 83° C. until the starting material was consumed (TLC, 2 h), during which it became a red solution. After cooling to room temperature, saturated aqueous Na$_2$S$_2$O$_3$ and water were added and the layers were separated. The aqueous layer was extracted with CH$_2$Cl$_2$ and the combined organics were dried over MgSO$_4$, decolorized with activated charcoal, filtered through Celite®, and evaporated to provide tert-butyl (5-iodothiazol-4-yl)carbamate (3.67 g, 95% purity, 86% yield) as a pale yellow solid.

Reactions run at higher concentration resulted in lower yield and purity.

$^1$H NMR (400 MHz, Chloroform-d) δ 8.87 (s, 1H), 6.48 (s, 1H), 1.53 (s, 9H).

Scheme 3

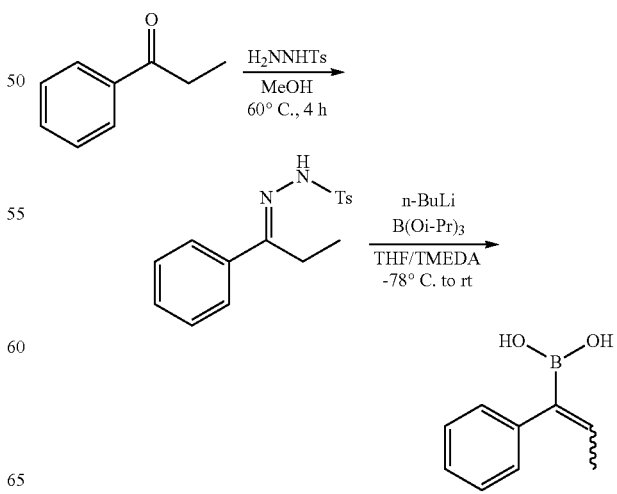

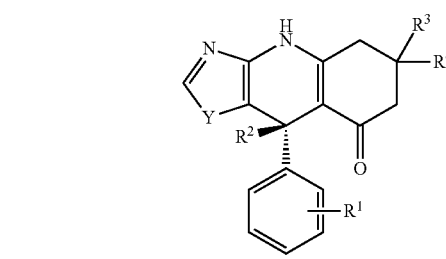

4-Methyl-N'-(1-phenylpropylidene)benzenesulfono-hydrazide

To a solution of p-toluenesulfonylhydrazide (1.40 g, 7.52 mmol, 1.0 eq) in methanol (7.5 mL) at 60° C., propiophenone (1.00 mL, 7.52 mmol, 1.0 eq) was slowly added. The mixture was stirred at 60° C. for 4 h, then cooled to room temperature. The solvent was evaporated, and the solids were washed with Et$_2$O and hexanes to provide the tosyl hydrazone (1.98 g, >99% purity, 87% yield) as a white solid.

(1-Phenylprop-1-en-1-yl)boronic Acid

To a partially frozen colorless solution of toluenesulfonohydrazide (1.00 g, 3.30 mmol, 1.0 eq) in 1:1 THF/TMEDA (20 mL) at −78° C., n-butyllithium (2.5 M in hexane, 5.30 mL, 13.2 mmol, 4.0 eq) was slowly added. The dark red mixture was allowed to stir at −78° C. for 30 min and then warmed to 25° C. and stirred 1 h. The reaction mixture was re-cooled to −78° C., triisopropyl borate (3.80 mL, 16.4 mmol, 5.0 eq) was added, and the solution was allowed to warm to room temperature and stirred 2 h. The resulting pale green-yellow suspension was quenched with 35 mL 4 M HCl and stirred 10 min. Diethyl ether was added, and the layers were separated. The aqueous layer was extracted with Et$_2$O (2×20 mL), and the combined organic layers were extracted with 1 M NaOH (3×25 mL). The pH of the basic aqueous layer was adjusted to ~4 with concentrated HCl, and was extracted with Et$_2$O (3×30 mL). The combined ether extracts were dried over MgSO$_4$, filtered, and evaporated to provide the crude boronic acid (482 mg, 90% yield) as a yellow semi-solid. The crude E/Z mixture was used directly in the Suzuki coupling.

Method A: Suzuki Coupling

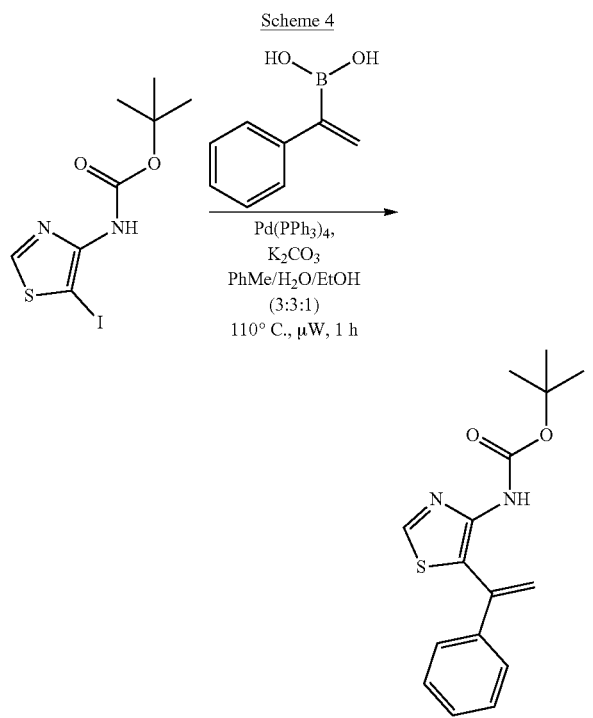

Tert-Butyl (5-(I-phenylvinyl)thiazol-4-yl)carbamate

To a microwave tube, tert-butyl (5-iodothiazol-4-yl)carbamate (100 mg, 0.307 mmol, 1.0 eq), (1-phenylvinyl)boronic acid (70 mg, 0.47 mmol, 1.5 eq), tetrakis(triphenylphosphine)palladium(0) (55 mg, 0.062 mmol, 0.2 eq), potassium carbonate (150 mg, 1.08 mmol, 3.5 eq), and 3:3:1 toluene:water:ethanol (1.75 mL) were added. The resulting biphasic mixture was heated at 100° C. for 1 h, then cooled to room temperature. The layers were separated, and the aqueous layer was extracted with EtOAc. The combined organics were dried over MgSO$_4$, filtered, and evaporated, and the residue was purified by flash column chromatography (0-100% EtOAc/hexanes) to provide the phenylvinyl thiazole (82.7 mg, >99% purity, 89% yield) as a yellow solid.

$^1$H NMR (400 MHz, Chloroform-d) δ 8.64 (s, 1H), 7.34 (s, 5H), 6.21 (br s, 1H), 5.63 (s, 1H), 5.54 (s, 1H), 1.35 (s, 9H).

Method B: Direct Coupling with Tosylhydrazones

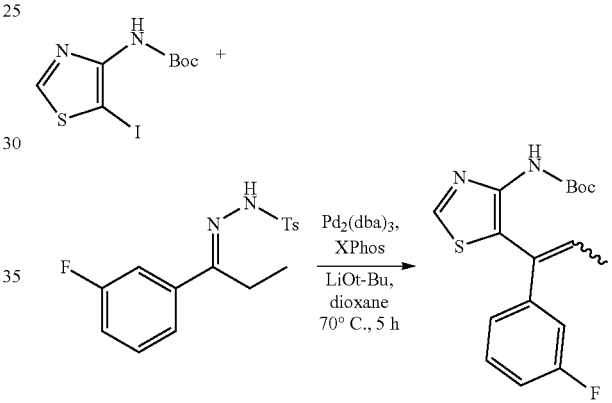

Tert-Butyl (5-(1-(3-fluorophenyl)prop-1-en-1-yl)thiazol-4-yl)carbamate

To a mixture of the tosyl hydrazone (73.3 mg, 0.229 mmol, 1.5 eq), XPhos (7.3 mg, 0.015 mmol, 0.1 eq), Pd$_2$(dba)$_3$ (7.0 mg, 0.0077 mmol, 0.05 eq), and lithium t-butoxide (36.7 mg, 0.459 mmol, 3.0 eq) under argon, a solution of the iodothiazole (50 mg, 0.15 mmol, 1.0 eq) in degassed 1,4-dioxane (0.8 mL) was added. The mixture was heated at 70° C. for 5 h, then diluted with CH$_2$Cl$_2$ and filtered through Celite®. The solvent was evaporated, and the residue was purified by flash column chromatography (0-100% EtOAc/hexanes) to provide the alkenyl thiazole

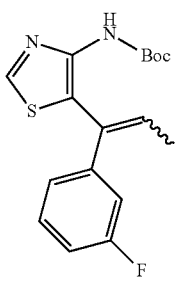

(30 mg, 59% yield) as an inconsequential mixture of E/Z isomers.

General Procedure for Formation of Tricyclic Compounds

Scheme 6

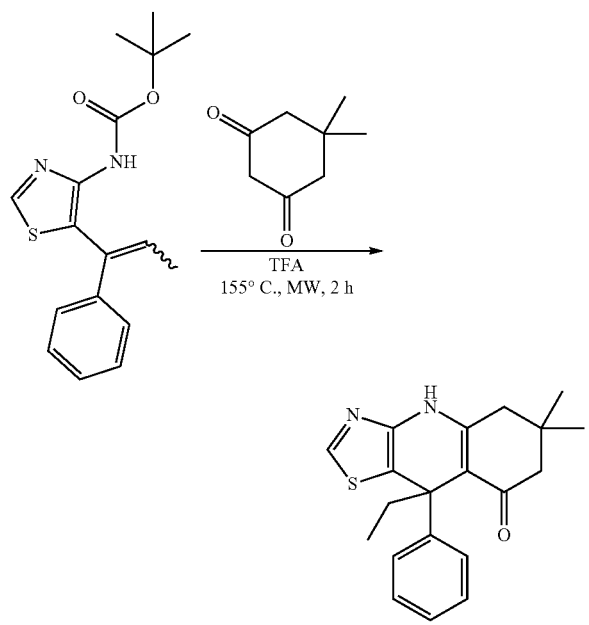

9-Ethyl-6,6-dimethyl-9-phenyl-5,6,7,9-tetrahydrothiazolo[4,5-b]quinolin-8(4H)-one A solution of the Boc-amino thiazole

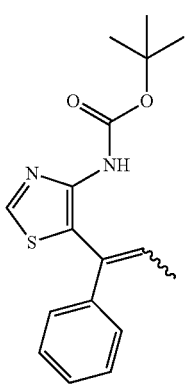

(200 mg, 0.632 mmol, 1.0 eq, prepared using method A in 52% yield) and dimedone (110 mg, 0.785 mmol, 1.24 eq) in trifluoroacetic acid (3.0 mL) was heated in a microwave at 155° C. for 2 h. The solvent was evaporated, and the residue was dissolved in $CH_2Cl_2$. Saturated aqueous $NaHCO_3$ was added, and the layers were separated. The aqueous layer was extracted with $CH_2Cl_2$, and the combined organics were dried over $MgSO_4$, filtered, and evaporated. The residue was purified by flash column chromatography (5-60% EtOAc/hexanes) to provide the tricyclic compound

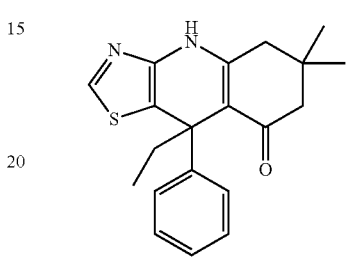

(110 mg, >99% purity, 51% yield) as pale yellow solid. Alternatively, the material may be recrystallized from EtOH/$H_2O$.

The enantiomers were separated by chiral HPLC: Chiralpak IC, 80:20 A/B (A: 0.1% diethylamine/n-hexane, B: 1:1 dichloromethane/methanol).

$^1$H NMR (400 MHz, DMSO-$d_6$) δ 10.09 (s, 1H), 8.77 (s, 1H), 7.33 (d, J=7.5 Hz, 2H), 7.21 (t, J=7.7 Hz, 2H), 7.05 (t, J=7.2 Hz, 1H), 2.99 (dq, J=14.9, 7.4 Hz, 1H), 2.49-2.43 (m, 2H), 2.10-2.00 (m, 2H), 1.98 (dd, J=7.6, 5.5 Hz, 1H), 1.04 (s, 3H), 1.02 (s, 3H), 0.75 (t, J=7.3 Hz, 3H). MS (ESI) 339.1 [M+H]$^+$

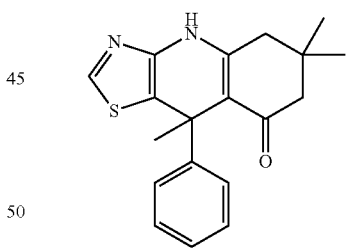

6,6,9-Trimethyl-9-phenyl-5,6,7,9-tetrahydrothiazolo[4,5-b]quinolin-8(4H)-one

Cross coupling: method A, 89% yield. Cyclization: 39% yield. Chiral HPLC: Chiralpak IC, 85:15 A/B (A: 0.1% diethylamine/n-hexane, B: 1:1 dichloromethane/methanol).

$^1$H NMR (400 MHz, Chloroform-d) δ 8.41 (s, 1H), 7.89 (s, 1H), 7.43 (d, J=7.6 Hz, 2H), 7.26 (t, J=7.7 Hz, 2H), 7.12 (t, J=7.3 Hz, 1H), 2.43 (s, 2H), 2.21 (d, J=16.1 Hz, 1H), 2.15 (s, 3H), 2.13 (d, J=16.1 Hz, 1H), 1.11 (s, 3H), 1.08 (s, 3H). MS (ESI): 324.9 [M+H]$^+$.

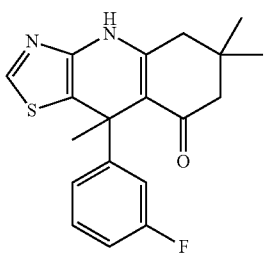 [SMILES: CC1(C)CC(=O)C2=C(C1)Nc1ncsc1C2(C)c1cccc(F)c1]

9-(3-Fluorophenyl)-6,6,9-trimethyl-5,6,7,9-tetrahydrothiazolo[4,5-b]quinolin-8(4H)-one Cross coupling: method A using the commercially available pinacol ester, 52% yield. Cyclization: 48% yield. Chiral HPLC: Chiralpak IC, 85:15 A/B (A: 0.1% diethylamine/n-hexane, B: 1:1 dichloromethane/methanol).
$^1$H NMR (400 MHz, Methanol-d$_4$) δ 8.60 (s, 1H), 7.23-7.20 (m, 1H), 7.14-7.02 (m, 2H), 6.85-6.77 (m, 1H), 2.15 (d, J=6.1 Hz, 2H), 2.08 (s, 3H), 1.82-1.72 (m, 2H), 1.09 (d, J=9.6 Hz, 6H). MS (ESI): 343.3 [M+H]$^+$.

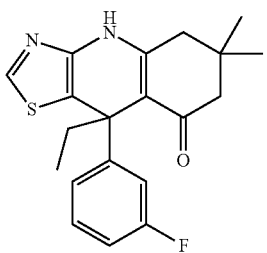 [SMILES: CCC1(c2cccc(F)c2)C2=C(CC(C)(C)CC2=O)Nc2ncsc21]

9-Ethyl-9-(3-fluorophenyl)-6,6-dimethyl-5,6,7,9-tetrahydrothiazolo[4,5-b]quinolin-8(4H)-one Cyclization: 26% yield. Chiral HPLC: Chiralpak IC, 95:5 A/B (A: 0.1% diethylamine/n-hexane, B: ethanol).
$^1$H NMR (400 MHz, Chloroform-d) δ 8.45 (s, 1H), 7.25-719 (m, 2H), 7.13-7.08 (m, 1H), 6.85-6.75 (m, 1H), 3.20-3.08 (m, 1H), 2.52-2.42 (m, 2H), 2.25-2.10 (m, 2H), 2.06-1.95 (m, 1H), 1.14 (s, 3H), 1.10 (s, 3H), 0.84 (t, J=7.4 Hz, 3H). MS (ESI): 357.2 [M+H]$^+$.

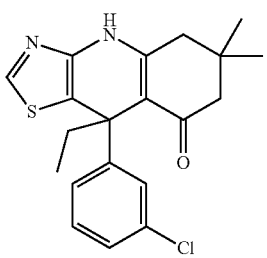 [SMILES: CCC1(c2cccc(Cl)c2)C2=C(CC(C)(C)CC2=O)Nc2ncsc21]

9-(3-Chlorophenyl)-9-ethyl-6,6-dimethyl-5,6,7,9-tetrahydrothiazolo[4,5-b]quinolin-8(4H)-one Cross coupling: method B, 44% yield. Cyclization: 11% yield. Chiral HPLC: Chiralpak IC, 80:20 A/B (A: 0.1% diethylamine/n-hexane, B: 1:1 dichloromethane/methanol).
$^1$H NMR (400 MHz, Chloroform-d) δ 8.46 (s, 1H), 8.10 (s, 1H), 7.45-7.30 (m, 2H), 7.18 (t, J=7.8 Hz, 1H), 7.12-7.05 (m, 1H), 3.21-3.06 (m, 1H), 2.55-2.40 (m, 2H), 2.27-2.10 (m, 2H), 2.08-1.95 (m, 1H), 1.14 (s, 3H), 1.10 (s, 3H), 0.85 (t, J=7.4 Hz, 3H). MS (ESI): 373.2 [M+H]$^+$.

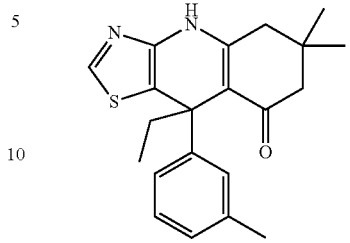

9-Ethyl-6,6-dimethyl-9-(m-tolyl)-5,6,7,9-tetrahydrothiazolo[4,5-b]quinolin-8(4H)-one Cross coupling: method A, 36% yield. Cyclization: 44% yield. Chiral HPLC: Chiralpak IC, 85:15 A/B (A: 0.1% diethylamine/n-hexane, B: 1:1 dichloromethane/methanol).
$^1$H NMR (400 MHz, Chloroform-d) δ 8.42 (s, 1H), 7.20 (d. J=5.9 Hz, 2H), 7.13 (t, J=7.9 Hz, 1H), 6.93 (s, 1H), 6.91 (s, 1H), 3.16 (dq, J=13.3, 7.4 Hz, 1H), 2.45 (d, J=1.4 Hz, 2H), 2.29 (s, 3H), 2.18 (dd, J=29.7, 16.0 Hz, 2H), 2.05 (dq, J=13.2, 7.4 Hz, 1H), 1.14 (s, 3H), 1.10 (s, 3H), 0.84 (t, J=7.3 Hz, 3H). MS (ESI): 353.7 [M+H]f.

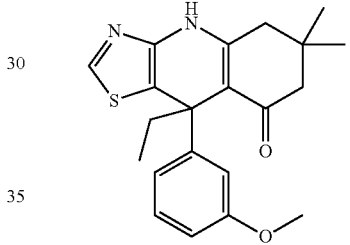

9-Ethyl-9-(3-methoxyphenyl)-6,6-dimethyl-5,6,7,9-tetrahydrothiazolo[4,5-b]quinolin-8(4H)-one Cross coupling: method A, 57% yield. Cyclization: 24% yield. Chiral HPLC: Chiralpak IC, 85:15 A/B (A: 0.1% diethylamine/n-hexane, B: 1:1 dichloromethane/methanol).
$^1$H NMR (400 MHz, Chloroform-d) δ 8.42 (s, 1H), 7.21-7.15 (m, 2H), 7.03 (d, J=7.9 Hz, 1H), 6.99-6.96 (m, 1H), 6.66 (dd, J=8.1, 1.9 Hz, 1H), 3.75 (s, 3H), 3.14 (dq, J=14.8, 7.4 Hz, 1H), 2.51-2.40 (m, 2H), 2.26-2.13 (m, 2H), 2.04 (dq, J=14.5, 7.3 Hz, 1H), 1.14 (s, 3H), 1.11 (s, 3H), 0.84 (t, J=7.3 Hz, 3H). MS (ESI): 369.0 [M+H]$^+$.

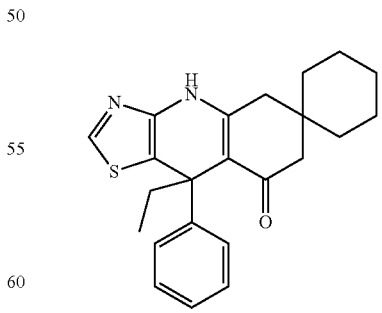

9'-Ethyl-9'-phenyl-5',9'-dihydro-4'H-spiro[cyclohexane-1,6'-thiazolo[4,5-b]quinolin]-8'(7'H)-one Cross coupling: method A, 52% yield. Cyclization: 29% yield using spiro[5.5]undecane-2,4-dione. Chiral HPLC:

Chiralpak IC, 85:15 A/B (A: 0.1% diethylamine/n-hexane, B: 1:1 dichloromethane/methanol).

$^1$H NMR (400 MHz, Chloroform-d) δ 8.42 (s, 1H), 7.43-7.39 (m, 2H), 7.24 (d, J=8.2 Hz, 2H), 7.11 (t, J=7.3 Hz, 1H), 6.84 (s, 1H), 3.17 (dq, J=14.7, 7.4 Hz, 1H), 2.50 (d, J=3.6 Hz, 2H), 2.28 (d, J=16.3 Hz, 1H), 2.18 (d, J=16.3 Hz, 1H), 2.04 (dq, J=14.6, 7.3 Hz, 1H), 1.48 (d, J=17.1 Hz, 10H), 0.84 (t, J=7.4 Hz, 3H). MS (ESI): 379.4 [M+H]$^+$.

Example 2. Additional Synthesis of Exemplary Compounds

The term "E1", "E2", "E3" or "E4" included in the compound number of an compound refers to the order of elution (from the first to the last) of the compound from a column described herein (e.g., an SFC column described herein) compared to the compound's stereoisomers (e.g., enantiomers and diastereomers). For example, each of compounds 2-E1, 2-E2, 2-E3, and 2-E4 is a single stereoisomer of compound 2 and eluted in the order of 2-E1 (the first), 2-E2 (the second), 2-E3 (the third), and 2-E4 (the fourth) from the SFC column described herein.

Additional General Procedure for the Synthesis of Exemplary Compounds

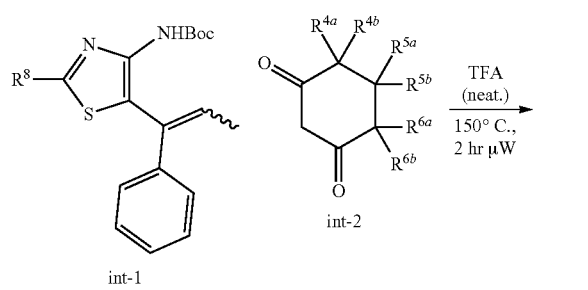

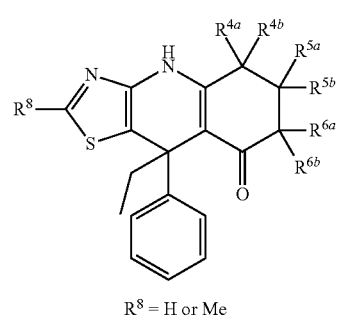

A solution of the int-1 (1.0 equiv.) and int-2 (1.3 equiv.) in TFA (0.3 M) was heated in microwave (μW) at 150° C. for 2 hours. Analysis by LCMS revealed int-1 consumed completely and new peak with a mass consistent with desired product. DCM was added into the reaction mixture, and saturated aqueous NaHCO$_3$ was slowly added. The aqueous layer was extracted with DCM (3 times), and the combined organic phases were dried over MgSO$_4$ and filtered, and evaporated. The crude reaction mixture was dried under vacuo and purified by column chromatography (eluent: 0-50% EtOAc in heptane) to provide the exemplary compound.

Preparation of Int-1

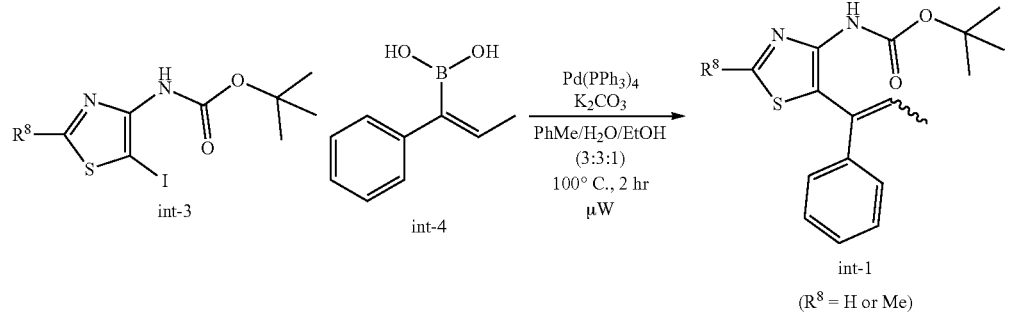

To a microwave tube, int-3 (1.0 equiv.), int-4 (1.5 equiv.), tetrakis(triphenylphosphine) palladium (0) (0.2 equiv.), K$_2$CO$_3$ (3.5 equiv.), and a mixture of toluene/water/ethanol (3:3:1, 0.17 M) was added. The resulting biphasic mixture was heated in microwave at 100° C. for 2 hours. The layers were separated, and the aqueous layer was extracted with EtOAc (3 times). The combined organic phases were dried over MgSO$_4$ and filtered. The solvent was removed in vacuo and the residue was purified by flash column chromatography (eluent: 0-20% EtOAc in heptane) to provide int-1 (R$^8$=H, 76.7% yield; R$^8$=Me, 54.8% yield) as a mixture of E/Z isomers.

$^1$H NMR (400 MHz, chloroform-d, R$^8$=H) for major regioisomer: δ 8.77 (s, 1H), 7.39-7.21 (m, 5H), 6.37 (q, J=7.0 Hz, 1H),), 6.22 (br s, 1H), 1.82 (d, J=7.3 Hz, 3H), 1.42 (s, 9H).

$^1$H NMR (500 MHz, chloroform-d, R$^8$=Me) for major regioisomer: δ 7.38-7.21 (m, 5H), 6.31 (q, J=7.3 Hz, 1H), 6.09 (br s, 1H), 2.71 (s, 3H), 1.83 (d, J=7.3 Hz, 3H), 1.41 (s, 9H).

Preparation of Int-3

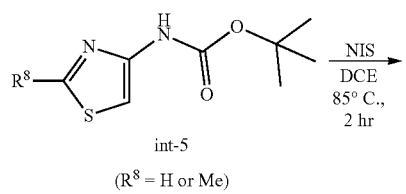
(R⁸ = H or Me)

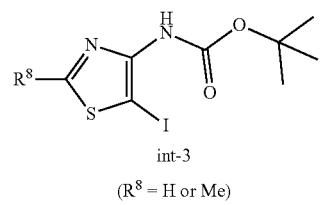
(R⁸ = H or Me)

N-Iodosuccinimide (1.2 equiv.) was introduced into a solution of int-5 (1.0 equiv.) in DCE (0.1 M), and the reaction mixture was heated under reflux (90° C.) for 2 hours. After cooling, the mixture was washed twice with water and with saturated sodium thiosulfate solution. The combined organic phases are dried over sodium sulfate and filtered. The solvent was removed in vacuo and the residue was purified by flash chromatography to give int-3 as a white solid (R⁸=H, 62% yield; R⁸=Me, 47% yield).

$^1$H NMR (500 MHz, chloroform-d, R⁸=H) δ 8.86 (s, 1H), 6.55 (br s, 1H), 1.52 (s, 9H).

$^1$H NMR (500 MHz, methanol-d$_4$, R⁸=Me) δ 2.67 (s, 3H), 1.53 (s, 9H).

Preparation of Int-4

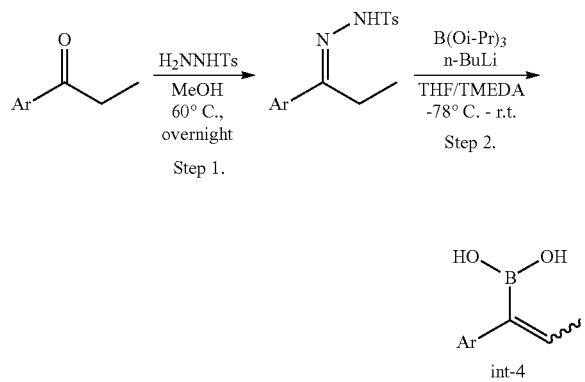

Step 1

A mixture of 1-arylpropan-1-one (1.0 equiv.) and 4-methylbenzenesulfonohydrazide (1.0 equiv.) in MeOH (0.5 M) was heated under 60° C. for 16 hours. After cooling to room temperature, the crude reaction mixture was dried under vacuo and taken forward for next step without further purification.

Step 2

To a solution of 4-methyl-N-1-arylpropylideneaminobenzenesulfonamide (1.0 equiv.) in THF/TMEDA (1:1 mixture, 0.17 M) at −78° C., n-BuLi (4.0 equiv.) was slowly added. The dark red mixture was stirred at −78° C. for 30 min, and then slowly warmed up to room temperature and stirred for 1 hour. The reaction mixture was re-cooled to −78° C., triisopropyl borate (5.0 equiv.) was added dropwise, and the solution was slowly warmed up to room temperature and stirred for 2 hours. The resulting dark brown suspension was quenched with 4.0 M HCl and stirred for 10 min. Diethyl ether was added, and the layers were separated. The aqueous layer was extracted with diethyl ether (3 times), and the combined organic phases were extracted with 1.0 M NaOH solution (3 times). The pH of the basic aqueous layer was adjusted to ~4 by adding concentrated HCl, and aqueous phase was extracted with diethyl ether (3 times). The combined organic phases were dried over MgSO$_4$ and filtered. The crude reaction mixture was dried under vacuo to provide int-4 as a yellow semi-solid. The crude E/Z mixture was taken forward for Suzuki coupling without further purification.

Preparation of Int-6

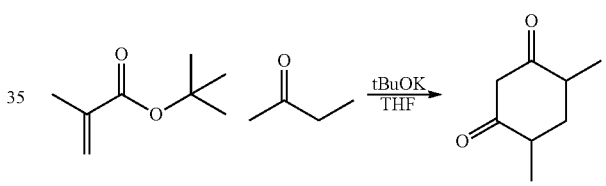

To a solution of butan-2-one (1.06 g, 14.76 mmol, 1.31 mL, 1.2 equiv.) in THF (120.00 mL, 0.12 M) was added potassium tert-butoxide (1.66 g, 14.76 mmol, 1.2 equiv.) at 0° C. After 5 mins, tert-butyl 2-methylprop-2-enoate (1.75 g, 12.30 mmol, 1.99 mL, 1.0 equiv.) was added dropwise. The reaction mixture was warm to room temperature and stirred for 24 hours. The reaction mixture was quenched by the addition of 1.0 M aqueous HCl to pH=4. The resulting biphasic mixture was separated. The organic layers were washed with 10 mL of saturated NaHCO$_3$ solution, followed by 10 mL of brine. The combined aqueous phases were extracted with a mixture of chloroform/2-propanol (ratio=9:1, 5 times). The combined organic phases were dried over Na$_2$SO$_4$, filtered and dried. The crude material was purified by column chromatography (eluent: 0-20% EtOAc in heptane) to provide int-6 (1.35 g, 9.63 mmol, 78.30% yield) as a pale yellow solid. Int-6 was a cis-enriched isomer according to the reference (JOC 2001, 66, 8000).

$^1$H NMR (500 MHz, methanol-d$_4$) δ ppm 3.38-3.51 (m, 2H), 2.65-2.73 (m, 2H), 2.16 (dt, J=14.0, 5.5 Hz, 1H), 1.17 (d, J=6.7 Hz, 6H).

Preparation of Compounds 2-E1, 2-E2, 2-E3, and 2-E4

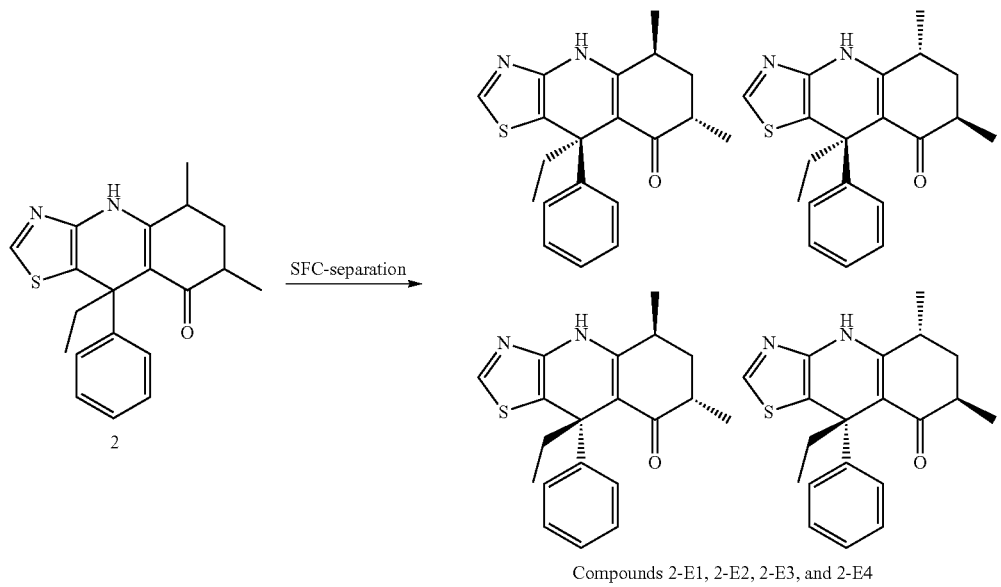

Compounds 2-E1, 2-E2, 2-E3, and 2-E4

Compound 2 (150 mg, 8.2% yield from cyclization) was separated by SFC (Column: WHELK-O1 250×30 mm, 5 µm; Condition: 20% Ethanol w/ 0.1% $NH_3H_2O$; Flow Rate: 60 mL/min) to give 2-E1 (20.0 mg, Rt=5.757 min), 2-E2 (26.0 mg, Rt=4.988 min), 2-E3 (20.0 mg, Rt=4.175 min) and 2-E4 (24.0 mg, Rt=3.886 min). The absolute stereochemistry of 2-E1, 2-E2, 2-E3, and 2-E4 was not determined. Note: The order of elution of 4 isomers via SFC separation is different from the order of elution from analytical method.

Data for 2-E1

SFC: Column: (R,R)WHELK-O1 100×4.6 mm I.D., 5.0 µm; Mobile phase: A: $CO_2$: B: Ethanol (0.05% DEA); Gradient: from 5% to 40% of B in 5.5 min and hold 40%, for 3 min, then 5% of B for 1.5 min; Flow rate: 2.5 mL/min; Column temperature: 40° C., Rt=5.757 min.

HPLC: (Purity: 95.7%).
LCMS: (M+H: 338.9).
SFC: (ee: 100%).

$^1$H NMR (500 MHz, methanol-$d_4$) δ ppm 8.47 (s, 1H), 7.28 (dd, J=1.2, 8.4 Hz, 2H), 7.06-7.16 (m, 2H), 6.92-6.99 (m, 1H), 2.83-2.94 (m, 1H), 2.63-2.72 (m, 1H), 2.24-2.35 (m, 1H), 1.93-2.05 (m, 1H), 1.75-1.88 (m, 2H), 1.40 (d, J=7.2 Hz, 3H), 0.91 (d, J=6.8 Hz, 3H), 0.72 (t, J=7.2 Hz, 3H).

Data for 2-E2

SFC: Column: (R,R)WHELK-01 100×4.6 mm I.D., 5.0 µm; Mobile phase: A: $CO_2$; B: Ethanol (0.05% DEA); Gradient: from 5% to 40% of B in 5.5 min and hold 40%, for 3 min, then 5% of B for 1.5 min; Flow rate: 2.5 mL/min; Column temperature: 40° C., Rt=4.988 min.

HPLC: (Purity: 96.6%).
LCMS: (M+H: 338.9).
SFC: (ee: 100%).

$^1$H NMR (500 MHz, methanol-$d_4$) δ ppm 8.47 (s, 1H), 7.31 (dd, J=1.2, 8.4 Hz, 2H), 7.07-7.15 (m, 2H), 6.92-7.01 (m, 1H), 2.87-3.02 (m, 1H), 2.63-2.73 (m, 1H), 2.35-2.46 (m, 1H), 1.93-2.03 (m, 1H), 1.82-1.89 (m, 1H), 1.76-1.82 (m, 1H), 1.37 (d, J=7.2 Hz, 3H), 0.84 (d, J=6.8 Hz, 3H), 0.69-0.75 (m, 3H).

Data for 2-E3

SFC: Column: (R,R)WHELK-01 100×4.6 mm I.D., 5.0 µm; Mobile phase: A: $CO_2$; B: Ethanol (0.05% DEA); Gradient: from 5% to 40% of B in 5.5 min and hold 40%, for 3 min, then 5% of B for 1.5 min; Flow rate: 2.5 mL/min Column temperature: 40° C., Rt=4.175 min.

HPLC: (Purity: 97.6%).
LCMS: (M+H: 338.9).
SFC: (ee: 100%).

$^1$H NMR (500 MHz, methanol-$d_4$) δ ppm 8.47 (s, 1H), 7.31 (dd, J=1.2, 8.4 Hz, 2H), 7.07-7.15 (m, 2H), 6.92-7.01 (m, 1H), 2.87-3.02 (m, 1H), 2.63-2.73 (m, 1H), 2.35-2.46 (m, 1H), 1.93-2.03 (m, 1H), 1.82-1.89 (m, 1H), 1.76-1.82 (m, 1H), 1.37 (d, J=7.2 Hz, 3H), 0.84 (d, J=6.8 Hz, 3H), 0.69-0.75 (m, 3H).

Data for 2-E4

SFC: Column: (R,R)WHELK-01 100×4.6 mm I.D., 5.0 µm; Mobile phase: A: $CO_2$; B: Ethanol (0.05% DEA); Gradient: from 5% to 40% of B in 5.5 min and hold 40%, for 3 min, then 5% of B for 1.5 min; Flow rate: 2.5 mL/min; Column temperature: 40° C., Rt=3.886 min.

HPLC: (Purity: 93.6%).
LCMS: (M+H: 338.9).
SFC: (ee: 100%).

$^1$H NMR (500 MHz, methanol-$d_4$) δ ppm 8.47 (s, 1H), 7.28 (dd, J=1.2, 8.4 Hz, 2H), 7.06-7.16 (m, 2H), 6.92-6.99 (m, 1H), 2.83-2.94 (m, 1H), 2.63-2.72 (m, 1H), 2.24-2.35 (m, 1H), 1.93-2.05 (m, 1H), 1.75-1.88 (m, 2H), 1.40 (d, J=7.2 Hz, 3H), 0.91 (d, J=6.8 Hz, 3H), 0.72 (t, J=7.2 Hz, 3H).

Preparation of Compounds 3-E1 & 3-E2

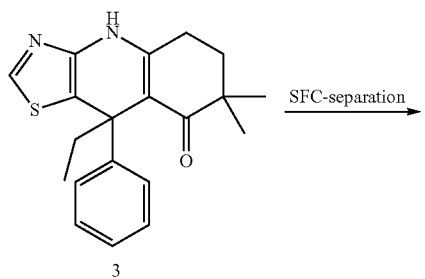

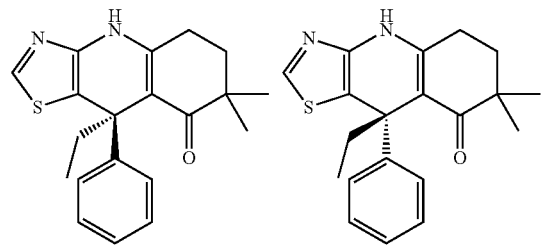

Compounds 3-E1 and 3-E2

Compound 3 (27 mg, 29.9% yield from cyclization) was separated by SFC (Column: CHIRALPAK IG 30×250 mm, 5 μm Condition: 40% Methanol w/ 0.1% DEA in $CO_2$; Flow Rate: 100 mL/min; ABPR 120 bar, MBPR 40 psi) to give 3-E1 (11.7 mg, Rt=1.925 min) and 3-E2 (12.8 mg, Rt=2.453 min). The absolute stereochemistry of 3-E1 & 3-E2 was not determined.

Data for 3-E1

HPLC: (Purity: 98.8%).

LCMS: (M+H: 339.0).

SFC: (ee: 100%).

$^1$H NMR (500 MHz, chloroform-d) δ ppm 8.41 (s, 1H), 7.40-7.42 (m, 2H), 7.23-7.27 (m, 2H), 7.09-7.12 (m, 1H), 3.06-3.13 (m, 1H), 2.58-2.71 (m, 2H), 2.01-2.09 (m, 1H), 1.84-1.93 (m, 2H), 1.08 (s, 3H), 0.99 (s, 3H), 0.83 (t, J=7.3 Hz, 3H).

Data for 3-E2

HPLC: (Purity: 94.7%).

LCMS: (M+H: 339.0).

SFC: (ee: 100%).

$^1$H NMR (500 MHz, chloroform-d) δ ppm 8.42 (s, 1H), 7.40-7.44 (m, 2H), 7.23-7.27 (m, 2H), 7.05-7.15 (m, 1H), 3.06-3.13 (m, 1H), 2.59-2.71 (m, 2H), 2.00-2.11 (m, 1H), 1.82-1.94 (m, 2H), 1.10 (s, 3H), 1.00 (s, 3H), 0.84 (t, J=7.3 Hz, 3H).

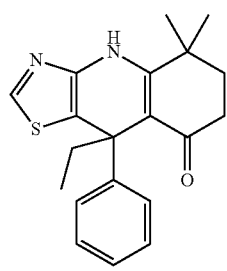

4

Preparation of Compound 4

Compound 4 (6.8 mg, 3.1% yield from cyclization).

Data for Compound 4

HPLC: (Purity: 98.0%).

LCMS: (M+H: 339.0).

$^1$H NMR (500 MHz, chloroform-d) δ ppm 8.44 (s, 1H), 7.42 (d, J=7.2 Hz, 2H), 7.25-7.29 (m, 2H), 7.13 (t, J=7.1 Hz, 1H), 7.07 (br s, 1H), 3.13 (dd, J=13.4, 7.3 Hz, 1H), 2.31-2.44 (m, 2H), 2.02-2.09 (m, 1H), 1.92 (t, J=6.7 Hz, 2H), 1.44 (s, 3H), 1.42 (s, 3H), 0.84 (t, J=7.3 Hz, 3H).

Preparation of Compounds 5-E1 & 5-E2

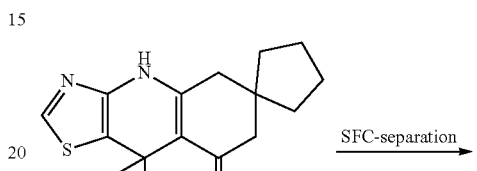

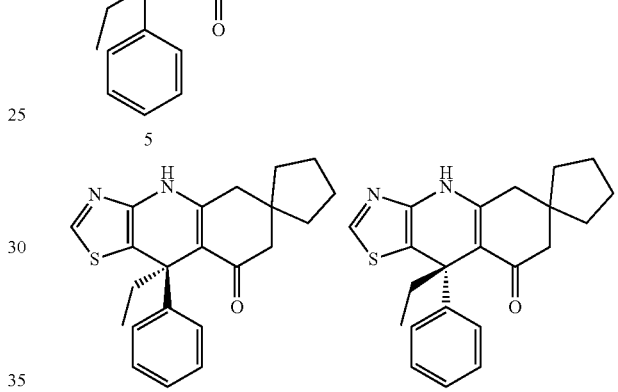

Compounds 5-E1 & 5-E2

Compound 5 (27.0 mg, 38.4% yield from cyclization) was separated by SFC (Column: CHIRALPAK IC 30×250 mm, 5 μm; Condition: 40% Ethanol w/ 0.1% DEA in $CO_2$; Flow Rate: 100 mL/min; ABPR 120 bar; MBPR 40 psi) to give 5-E1 (8.5 mg, Rt=1.650 min) and 5-E2 (7.5 mg, Rt=2.164 min). The absolute stereochemistry of 5-E1 & 5-E2 was not determined.

Data for 5-E1

HPLC: (Purity: 100%).

LCMS: (M+H: 365.2).

SFC: (ee: 100%).

$^1$H NMR (500 MHz, chloroform-d) δ ppm 8.42 (s, 1H), 7.57 (br s, 1H), 7.39-7.43 (m, 2H), 7.23-7.28 (m, 2H), 7.10-7.13 (m, 1H), 3.11-3.22 (m, 1H), 2.49-2.61 (m, 2H), 2.24-2.33 (m, 2H), 1.99-2.10 (m, 1H), 1.63-1.72 (m, 4H), 1.47-1.63 (m, 4H), 0.82-0.88 (m, 3H).

Data for 5-E2

HPLC: (Purity: 100%).

LCMS: (M+H: 365.2).

SFC: (ee: 100%).

$^1$H NMR (500 MHz, chloroform-d) δ ppm 8.43 (s, 1H), 7.39-7.43 (m, 2H), 7.24-7.28 (m, 2H), 7.09-7.13 (m, 1H), 3.10-3.20 (m, 1H), 2.48-2.63 (m, 2H), 2.22-2.33 (m, 2H), 2.00-2.11 (m, 1H), 1.63-1.70 (m, 4H), 1.45-1.63 (m, 4H), 0.81-0.88 (m, 3H).

Preparation of Compounds 6-E1, 6-E2, 6-E3 & 6-E4

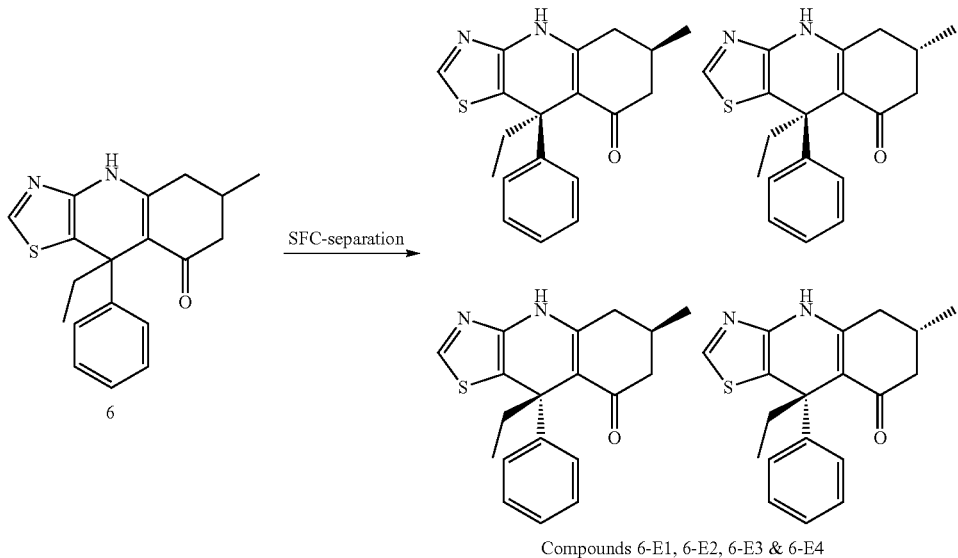

Compounds 6-E1, 6-E2, 6-E3 & 6-E4

Compound 6 (131.0 mg, 36.8% yield from cyclization) was separated by SFC (Column: CHIRALPAK IG 30×250 mm, 5 μm; Condition: 30% Ethanol w/ 0.1% DEA in CO$_2$; Flow Rate: 100 mL/min; ABPR 120 bar; MBPR 40 psi) to give 6-E1 (19.2 mg, Rt=4.023 min), 6-E4 (17.8 mg, Rt=5.672 min) and a mixture of 6-E2 and 6-E3. The mixture of 6-E2 and 6-E3 were separated by SFC (Column: CHIRALPAK IG 30×250 mm, 5 μm; Condition: 35% Ethanol w/ 0.1% DEA in CO$_2$; Flow Rate: 100 mL/min; ABPR 120 bar; MBPR 40 psi) to give 6-E2 (12.4 mg, Rt=4.439 min), 6-E3 (9.5 mg, Rt=4.883 min). The absolute stereochemistry of 6-E1, 6-E2, 6-E3 & 6-E4 was not determined.

Data for 6-E1

HPLC: (Purity: 97.2%).

LCMS: (M+H: 325.0).

SFC: (ee: 100%).

$^1$H NMR (400 MHz, chloroform-d) δ ppm 8.42 (s, 1H), 7.37-7.45 (m, 2H), 7.22-7.25 (m, 2H), 7.07-7.15 (m, 1H), 7.03 (br s, 1H), 3.02-3.16 (m, 1H), 2.25-2.52 (m, 4H), 1.95-2.12 (m, 2H), 1.09 (d, J=6.5 Hz 3H), 0.84 (t, J=7.3 Hz, 3H).

Data for 6-E2

HPLC: (Purity: 95.0%).

LCMS: (M+H: 325.0).

SFC: (ee: 100%).

$^1$H NMR (400 MHz, chloroform-d) δ ppm 8.42 (s, 1H), 7.40-7.47 (m, 2H), 7.23-7.28 (m, 2H), 7.08-7.16 (m, 1H), 6.92 (br s, 1H), 3.09-3.26 (m, 1H), 2.21-2.59 (m, 4H), 1.98-2.13 (m, 2H), 1.10 (d, J=6.5 Hz, 3H), 0.82 (t, J=7.4 Hz 3H).

Data for 6-E3

HPLC: (Purity: 98.3%).

LCMS: (M+H: 325.0).

SFC: (ee: 92.7%).

$^1$H NMR (400 MHz, chloroform-d) δ ppm 8.42 (s, 1H), 7.39-7.46 (m, 2H), 7.23-7.26 (m, 2H), 7.08-7.16 (m, 1H), 7.00 (br s, 1H), 3.09-3.29 (m, 1H), 2.23-2.57 (m, 4H), 1.97-2.15 (m, 2H), 1.10 (d, J=6.5 Hz, 3H), 0.83 (t, J=7.4 Hz, 3H).

Data for 6-E4

HPLC: (Purity: 97.8%).

LCMS: (M+H: 325.0).

SFC: (ee: 100%).

$^1$H NMR (400 MHz, chloroform-d) δ ppm 8.42 (s, 1H), 7.37-7.44 (m, 2H), 7.22-7.25 (m, 2H), 7.08-7.16 (m, 1H), 3.09 (dd, J=13.0, 7.5 Hz, 1H), 2.23-2.59 (m, 4H), 1.94-2.13 (m, 2H), 1.09 (d, J=6.3 Hz, 3H), 0.84 (t, J=7.4 Hz, 3H).

Preparation of Compounds 7-E1, 7-E2, 7-E3 & 7-E4

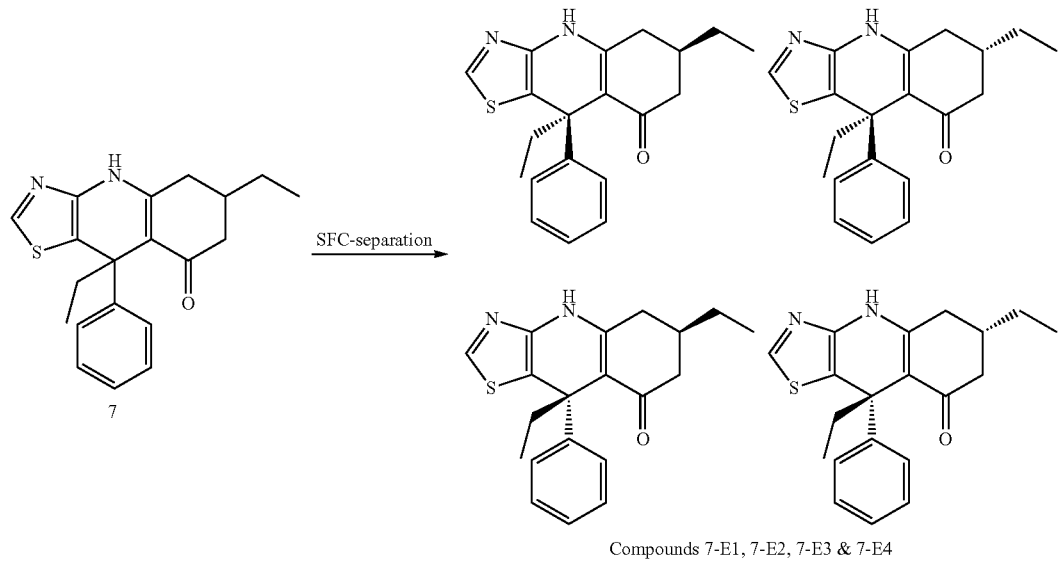

Compounds 7-E1, 7-E2, 7-E3 & 7-E4

Compound 7 (131.0 mg, 49.9% yield from cyclization) was separated by SFC (Column: CHIRALPAK IC 30×250 mm, 5 μm; Condition: 40% Methanol w/ 0.1% DEA in $CO_2$; Flow Rate: 100 mL/min; ABPR 120 bar; MBPR 40 psi) to give P1 (a mixture of 7-E1 and 7-E2) and P2 (a mixture of 7-E3 and 7-E4).

P1 was then separated by SFC (Column: CHIRALPAK IG 30×250 mm, 5 μm; Condition: 40% Ethanol w/ 0.1% DEA in $CO_2$; Flow Rate: 100 mL/min; ABPR 120 bar; MBPR 40 psi) to give 7-E1 (5.3 mg, Rt=3.201 min), 7-E2 (8.5 mg, Rt=4.039 min). P2 was then separated by SFC (Column: CHIRALPAK IA 30×250 mm, 5 μm; Condition: 30% Isopropanol w/ 0.1% DEA in $CO_2$; Flow Rate: 100 mL/min; ABPR 120 bar; MBPR 60 psi) to give 7-E3 (4.9 mg, Rt=3.653 min), 7-E4 (7.1 mg, Rt=4.125 min). The absolute stereochemistry of 7-E1, 7-E2, 7-E3 & 7-E4 was not determined.

Data for 7-E1
HPLC: (Purity: 100%).
LCMS: (M+H: 339.0).
SFC: (ee: 100%).
$^1$H NMR (500 MHz, methanol-$d_4$) δ ppm 8.62 (s, 1H), 7.44 (d, J=7.3 Hz, 2H), 7.25 (t, J=7.3 Hz, 2H), 7.10 (t, J=7.4 Hz, 1H), 3.13 (dq, J=13.1, 7.4 Hz, 1H), 2.72-2.79 (m, 1H), 2.47 (dd, J=16.5, 10.4 Hz, 1H), 2.27-2.35 (m, 1H), 2.02-2.14 (m, 3H), 1.49 (tq, J=14.3, 6.8 Hz, 2H), 0.99-1.03 (m, 3H), 0.85 (t, J=7.6 Hz, 3H).

Data for 7-E2
HPLC: (Purity: 98.1%).
LCMS: (M+H: 339.0).
SFC: (ee: 100%).
$^1$H NMR (500 MHz, methanol-$d_4$) δ ppm 8.62 (s, 1H), 7.41 (d, J=7.3 Hz, 2H), 7.24 (t, J=7.4 Hz, 2H), 7.07-7.11 (m, 1H), 3.03 (dd, J=12.8, 7.3 Hz, 1H), 2.71-2.80 (m, 1H), 2.50 (dd, J=16.5, 10.4 Hz, 1H), 2.33-2.41 (m, 1H), 2.08-2.15 (m, 1H), 1.98-2.08 (m, 2H), 1.48 (dd, J=14.0, 7.3 Hz, 2H), 1.01 (t, J=7.6 Hz, 3H), 0.87 (t, J=7.3 Hz, 3H).

Data for 7-E3
HPLC: (Purity: 95.8%).
LCMS: (M+H: 339.0).
SFC: (ee: 100%).
$^1$H NMR (500 MHz, methanol-$d_4$) δ ppm 8.62 (s, 1H), 7.44 (d, J=7.5 Hz, 2H), 7.25 (t, J=7.5 Hz, 2H), 7.10 (t, J=7.3 Hz, 1H), 3.13 (dd, J=13.1, 7.6 Hz, 1H), 2.75 (ddd, J=16.0, 4.1, 1.8 Hz, 1H), 2.47 (dd, J=16.2, 10.1 Hz, 1H), 2.29-2.34 (m, 1H), 2.02-2.16 (m, 3H), 1.42-1.57 (m, 2H), 1.01 (t, J=7.3 Hz, 3H), 0.85 (t, J=7.6 Hz, 3H).

Data for 7-E4
HPLC: (Purity: 97.4%).
LCMS: (M+H: 339.0).
SFC: (ee: 100%).
$^1$H NMR (500 MHz, methanol-$d_4$) δ ppm 8.62 (s, 1H), 7.41 (d, J=7.3 Hz, 2H), 7.22-7.26 (m, 2H), 7.09 (t, J=7.2 Hz, 1H), 3.00-3.07 (m, 1H), 2.71-2.77 (m, 1H), 2.50 (dd, J=16.5, 11.0 Hz, 1H), 2.33-2.41 (m, 1H), 1.98-2.15 (m, 3H), 1.48 (dq, J=14.2, 7.3 Hz, 2H), 0.99-1.03 (m, 3H), 0.87 (t, J=7.3 Hz, 3H).

Preparation of Compounds 8-E1, 8-E2, 8-E3 & 8-E4

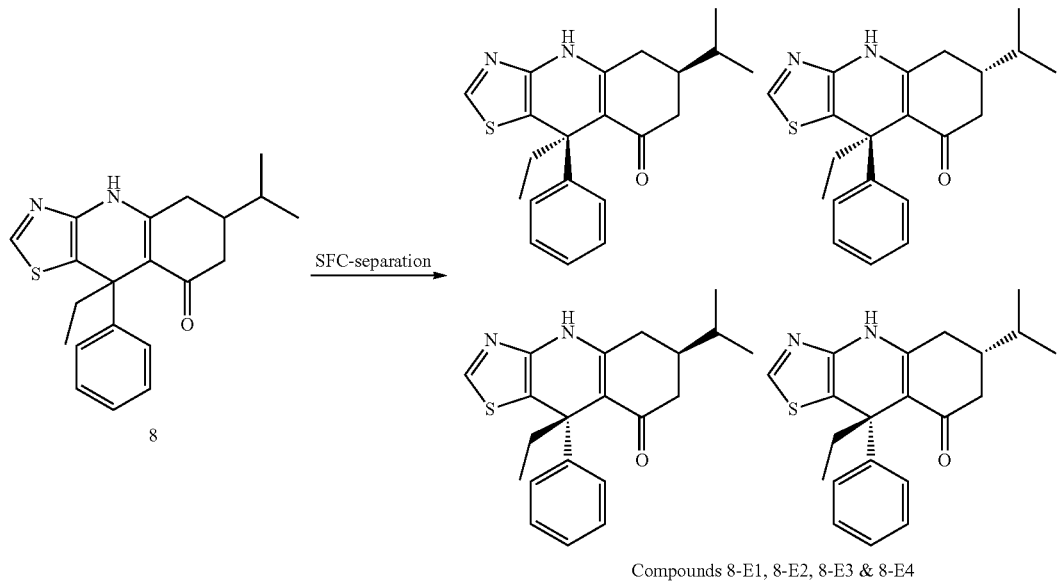

Compounds 8-E1, 8-E2, 8-E3 & 8-E4

Compound 8 (160.0 mg, 25.2% yield from cyclization) was separated by SFC (Column: REGIS (s,s) WHELK-O1 250×30 mm, 5 µm; Mobile phase: A: $CO_2$ B: Ethanol (0.05% $NH_3.H_2O$), Gradient: 35% of B and hold 35%; Flow Rate: 60 mL/min) to give 8-E1 (30.0 mg, Rt=4.961 min), 8-E2 (17.0 mg, Rt=5.625 min), 8-E3 (32.0 mg, Rt=5.952 min) and 8-E4 (50.0 mg, Rt=6.362 min). The absolute stereochemistry of -E1, 8-E2, 8-E3 & 8-E4 was not determined.

Data for 8-E1
HPLC: (Purity: 96.2%).
LCMS: (M+H: 353.0).
SFC: (ee: 100%).
$^1$H NMR (500 MHz, methanol-$d_4$) δ ppm 8.47 (s, 1H), 7.28-7.31 (m, 2H), 7.08-7.16 (m, 2H), 6.94-7.03 (m, 1H), 2.96-3.06 (m, 1H), 2.55-2.63 (m, 1H), 2.41-2.43 (m, 1H), 2.12-2.21 (m, 1H), 2.01-2.09 (m, 1H), 1.91-2.00 (m, 1H), 1.72-1.82 (m, 1H), 1.51-15.4 (m, 1H), 0.90 (d, J=6.8 Hz, 3H), 0.86 (d, J=6.8 Hz, 3H), 0.71 (t, J=7.4 Hz, 3H).

Data for 8-E2
HPLC: (Purity: 100.0%).
LCMS: (M+H: 353.1).
SFC: (ee: 100%).
$^1$H NMR (500 MHz, methanol-$d_4$) δ ppm 8.47 (s, 1H), 7.28-7.31 (m, 2H), 7.08-7.16 (m, 2H), 6.94-7.03 (m, 1H), 2.96-3.06 (m, 1H), 2.55-2.63 (m, 1H), 2.41-2.43 (m, 1H), 2.12-2.21 (m, 1H), 2.01-2.09 (m, 1H), 1.91-2.00 (m, 1H), 1.72-1.82 (m, 1H), 1.51-15.4 (m, 1H), 0.90 (d, J=6.8 Hz, 3H), 0.86 (d, J=6.8 Hz, 3H), 0.71 (t, J=7.4 Hz, 3H).

Data for 8-E3
HPLC: (Purity: 100.0%).
LCMS: (M+H: 353.0).
SFC: (ee: 100%).
$^1$H NMR (500 MHz, methanol-$d_4$) δ ppm 8.62 (s, 1H), 7.40-7.42 (m, 2H), 7.18-7.27 (m, 2H), 7.04-7.14 (m, 1H), 2.96-3.07 (m, 1H), 2.67-2.75 (m, 1H), 2.50-2.62 (m, 1H), 2.28-2.38 (m, 1H), 2.03-2.18 (m, 2H), 1.85-1.96 (m, 1H), 1.59-1.68 (m, 1H), 1.03 (d, J=6.8 Hz, 3H), 0.98 (d, J=6.8 Hz, 3H), 0.87 (t, J=7.4 Hz, 3H).

Data for 8-E4
HPLC: (Purity: 99.2%).
LCMS: (M+H: 339.0).
SFC: (ee: 100%).
$^1$H NMR (500 MHz, methanol-$d_4$) δ ppm 8.62 (s, 1H), 7.40-7.42 (m, 2H), 7.18-7.27 (m, 2H), 7.04-7.14 (m, 1H), 2.96-3.07 (m, 1H), 2.67-2.75 (m, 1H), 2.50-2.62 (m, 1H), 2.28-2.38 (m, 1H), 2.03-2.18 (m, 2H), 1.85-1.96 (m, 1H), 1.59-1.68 (m, 1H), 1.03 (d, J=6.8 Hz, 3H), 0.98 (d, J=6.8 Hz, 3H), 0.87 (t, J=7.4 Hz, 3H).

Preparation of Compound 9

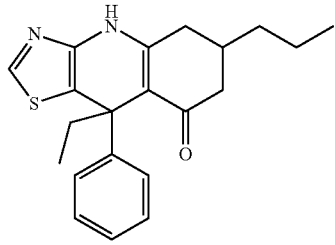

Compound 9 (73.7 mg, 27.4% yield from cyclization).

Data for Compound 9
HPLC: (Purity: 99.0%).
LCMS: (M+H: 353.0).
$^1$H NMR (400 MHz, chloroform-d) δ ppm 8.48 (d, J=1.5 Hz, 1H), 8.19 (br s, 1H), 7.37-7.44 (m, 2H), 7.21-7.29 (m, 2H), 7.03-7.18 (m, 1H), 3.05-3.24 (m, 1H), 2.37-2.58 (m, 3H), 1.96-2.21 (m, 3H), 1.22-1.43 (m, 4H), 0.89-0.97 (m, 3H), 0.80-0.88 (m, 3H).

Preparation of Compound 10

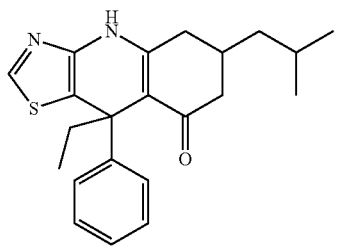

Compound 10 (58.2 mg, 19.2% yield from cyclization).
Data for Compound 10
  HPLC: (Purity: 99.4%).
  LCMS: (M+H: 367.0).
  ¹H NMR (400 MHz, chloroform-d) δ ppm 8.40-8.44 (m, 1H), 7.39-7.47 (m, 2H), 7.19-7.28 (m, 2H), 7.09-7.16 (m, 1H), 3.05-3.23 (m, 1H), 2.34-2.53 (m, 3H), 2.18-2.30 (m, 1H), 1.92-2.12 (m, 2H), 1.61-1.73 (m, 2H), 1.21-1.32 (m, 2H), 0.78-0.94 (m, 9H).

Preparation of Compounds 11-E1 & 11-E2

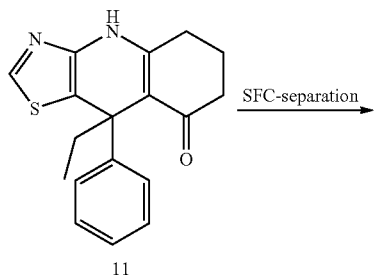

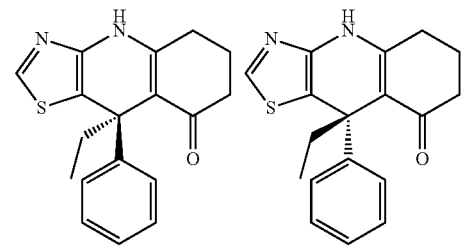

Compounds 11-E1 & 11-E2

Compound 11 (15 mg, 22.8% yield from cyclization) was separated by SFC (Column: CHIRALPAK IC 30×250 mm, 5 µm; Condition: 40% Ethanol w/ 0.1% DEA in CO₂; Flow Rate: 100 mL/min; ABPR 120 bar; MBPR 40 psi) to give II-E1 (6.6 mg, Rt=1.861 min) and 11-E2 (6.2 mg, Rt=2.574 min). The absolute stereochemistry of 11-E1 & 11-E2 was not determined.
Data for 11-E1
  HPLC: (Purity: 97.1%).
  LCMS: (M+H: 311.0).
  SFC: (ee: 100%).
  ¹H NMR (500 MHz, chloroform-d) δ ppm 8.42 (s, 1H), 7.40-7.47 (m, 2H), 7.37 (br s, 1H), 7.24-7.28 (m, 2H), 7.10-7.14 (m, 1H), 3.13 (dd, J=13.4, 7.3 Hz, 1H), 2.62 (td, J=6.3, 2.8 Hz, 2H), 2.25-2.39 (m, 2H), 2.00-2.09 (m, 3H), 0.84 (t, J=7.3 Hz, 3H).

Data for 11-E2
  HPLC: (Purity: 96.2%).
  LCMS: (M+H: 311.0).
  SFC: (ee: 100%).
  ¹H NMR (500 MHz, chloroform-d) δ ppm 8.42 (s, 1H), 7.43 (d, J=7.6 Hz, 2H), 7.23-7.30 (m, 2H), 7.10-7.14 (m, 1H), 3.10-3.17 (m, 1H), 2.62 (td, J=6.3, 3.4 Hz, 2H), 2.25-2.39 (m, 2H), 1.98-2.11 (m, 3H), 0.84 (t, J=7.3 Hz, 3H).

Preparation of Compound 13

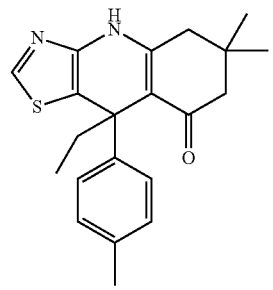

Compound 13 (6.6 mg, 9.0% yield from cyclization).
Data for Compound 13
  HPLC: (Purity: 97.9%).
  LCMS: (M+H: 353.2).
  ¹H NMR (500 MHz, chloroform-d) δ ppm 8.44 (s, 1H), 7.27-7.33 (m, 2H), 7.09 (br s, 1H), 7.04-7.10 (m, 2H), 3.14-3.21 (m, 1H), 2.41-2.48 (m, 2H), 2.27 (s, 3H), 2.12-2.25 (m, 2H), 1.92-2.08 (m, 1H), 1.13 (s, 3H), 1.09 (s, 3H), 0.84 (t, J=7.3 Hz, 3H).

Preparation of Compound 14

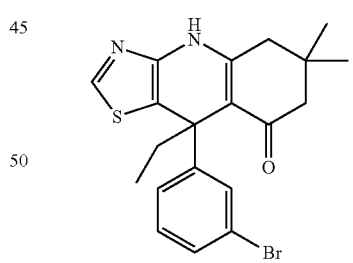

Compound 14 (1.0 mg, 0.5% yield from cyclization).
Data for Compound 14
  HPLC: (Purity: 80.3%).
  LCMS: (M: 416.1).
  ¹H NMR (500 MHz, methanol-d₄) δ ppm 8.67 (s, 1H), 7.55 (t, J=1.8 Hz, 1H), 7.40 (d, J=7.8 Hz, 1H), 7.26 (dt, J=7.9, 1.5 Hz, 1H), 7.17 (t, J=7.9 Hz, 1H), 3.01-3.10 (m, 1H), 2.58 (s, 2H), 2.10-2.24 (m, 2H), 2.01-2.10 (m, 1H), 1.15 (s, 3H), 1.12 (s, 3H), 0.86 (t, J=7.3 Hz, 3H).

Preparation of Compound 15

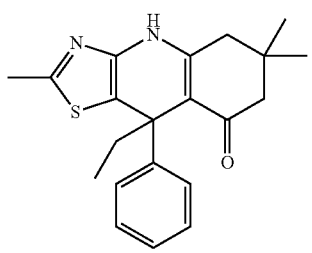

Compound 15 (79.9 mg, 34.0% yield from cyclization).
Data for Compound 15
 HPLC: (Purity: 97.8%).
 LCMS: (M+H: 353.0).
 $^1$H NMR (500 MHz, chloroform-d) δ ppm 7.42 (d, J=7.4 Hz, 2H), 7.23-7.27 (m, 2H), 7.16 (br s, 1H), 7.10-7.14 (m, 1H), 3.14 (dq, J=13.1, 7.4 Hz, 1H), 2.54 (s, 3H), 2.38-2.47 (m, 2H), 2.11-2.22 (m, 2H), 1.96-2.03 (m, 1H), 1.12 (s, 3H), 1.08 (s, 3H), 0.87 (t, J=7.3 Hz, 3H).

Preparation of Compound 16

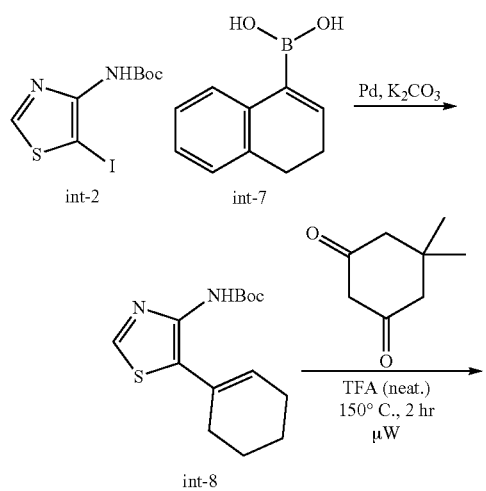

Compound 16 (150.0 mg, 29.4% yield from cyclization).
Data for Compound 16
 HPLC: (Purity: 94.5%).
 LCMS: (M+H: 351.1).
 $^1$H NMR (500 MHz, chloroform-d) δ ppm 9.33 (s, 1H), 7.27-7.32 (m, 2H), 7.18-7.25 (m, 2H), 3.35-3.40 (m, 2H), 3.22 (s, 2H), 2.82 (t, J=7.6 Hz, 2H), 2.63 (s, 2H), 1.98-2.05 (m, 2H), 1.13 (s, 6H).

Preparation of Compound 17

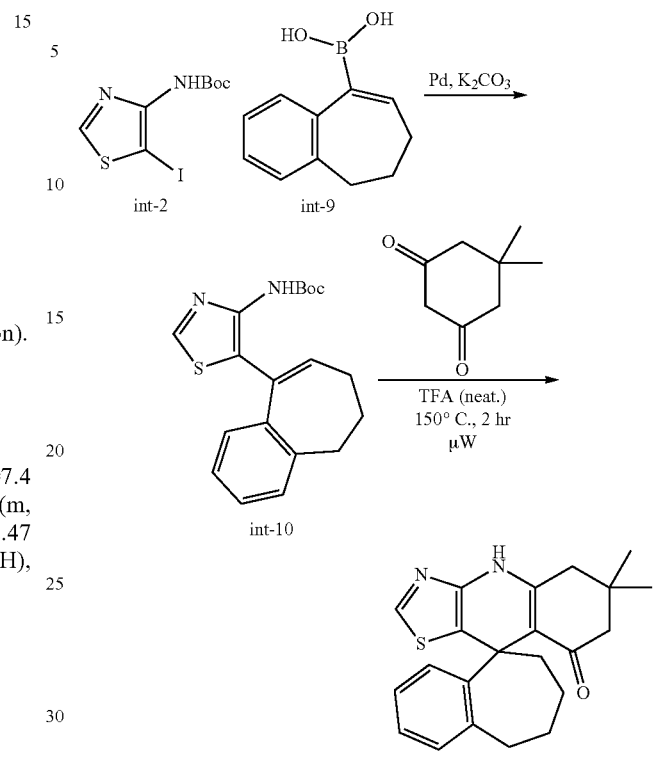

Compound 17 (8.0 mg, 3.0% yield from cyclization).
Data for Compound 17
 HPLC: (Purity: 97.3%).
 LCMS: (M+H: 365.2).
 $^1$H NMR (500 MHz, chloroform-d) δ ppm 9.35 (s, 1H), 7.25-7.31 (m, 2H), 7.16-7.21 (m, 2H), 3.37-3.42 (m, 2H), 3.23 (s, 2H), 2.66-2.70 (m, 2H), 2.62 (s, 2H), 1.70-1.84 (m, 4H), 1.13 (s, 6H).

Preparation of Compounds 18-E1 & 18-E2

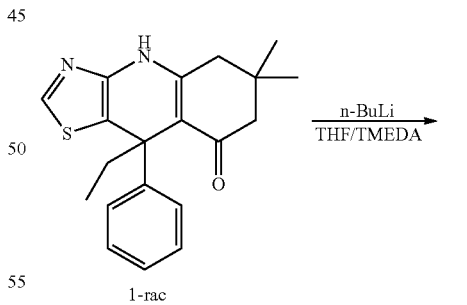

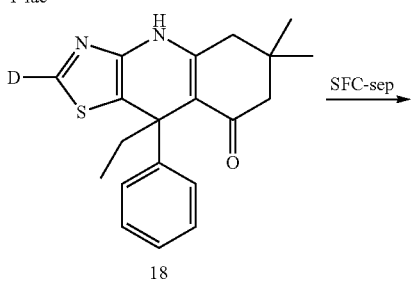

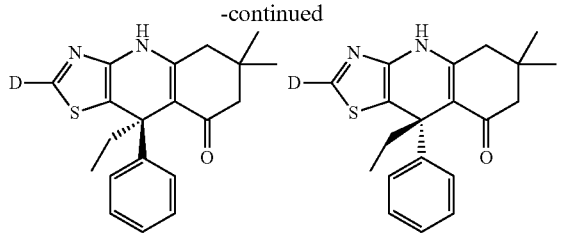
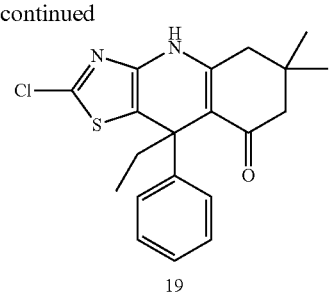

Compounds 18-E1 & 18-E2

19 n-Butyl lithium (0.83 mmol, 2.5 M, 330.90 μL, 4.0 equiv.) was added slowly under nitrogen to a stirred solution of compound 1-rac (0.21 mmol, 70.00 mg, 1.0 equiv.) and 4 Å MS (350 mg) in THF (1.40 mL) and TMEDA (0.7 mL) at −78° C., and the reaction mixture was stirred under −78° C. for 1 hour. Methanol-$d_4$ (1.0 mL) was slowly add to the reaction mixture under −78° C., and the reaction mixture was slowly warmed up to room temperature and stirred for 10 mins. The solvent was removed under vacuo and diluted with EtOAc and then washed with water. The aqueous phase was extracted with EtOAc (5 mL, 3 times). The combined organic phases were dried over $MgSO_4$ and dried in vacuo. The crude material was purified by column chromatography (eluent: 0-40% EtOAc in heptane) to provide compound 18 (70.00 mg, 0.21 mmol, 99.7% yield).

Compound 18 (70 mg, 99.7% yield from cyclization) was separated by SFC (Column: CHIRALPAK IC 30×250 mm, 5 μm; Condition: 30% Methanol in $CO_2$; Flow Rate: 100 mL/min; ABPR 120 bar; MBPR 40 psi) to give 18-E1 (34.6 mg, Rt=2.014 min) and 18-E2 (34.1 mg, Rt=2.674 min). The absolute stereochemistry of 18-E1 & 18-E2 was not determined.

Data for 18-E1
HPLC: (Purity: 99.6%).
LCMS: (M: 340.0).
SFC: (ee: 100%).
$^1$H NMR (500 MHz, chloroform-d) δ ppm 7.40-7.44 (m, 2H), 7.23-7.28 (m, 2H), 7.16 (br s, 1H), 7.09-7.15 (m, 1H), 3.14-3.25 (m, 1H), 2.40-2.51 (m, 2H), 2.10-2.24 (m, 2H), 2.05 (dd, J=12.8, 7.3 Hz, 1H), 1.14 (s, 3H), 1.09 (s, 3H), 0.85 (t, J=7.3 Hz, 3H).

Data for 18-E2
HPLC: (Purity: 100%).
LCMS: (M: 340.0).
SFC: (ee: 100%).
$^1$H NMR (500 MHz, chloroform-d) δ ppm 7.42 (d, J=7.5 Hz, 2H), 7.23-7.28 (m, 2H), 7.09-7.14 (m, 1H), 3.16-3.23 (m, 1H), 2.41-2.46 (m, 2H), 2.11-2.26 (m, 2H), 2.02-2.08 (m, 1H), 1.14 (s, 3H), 1.09 (s, 3H), 0.85 (t, J=7.6 Hz, 3H).

Preparation of Compound 19

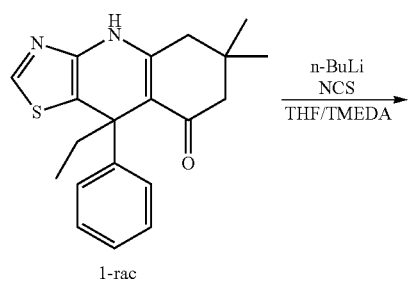

n-Butyl lithium (0.62 mmol, 2.5 M, 0.25 mL, 3.0 equiv.) was added slowly under nitrogen to a stirred solution of racemic compound 1-rac (0.21 mmol, 70.00 mg, 1.0 equiv.) and 4 Å MS (350 mg) in THF (1.40 mL) and TMEDA (0.7 mL) at −78° C., and the reaction mixture was stirred under −78° C. for 1 hour. N-chlorosuccinimide (0.31 mmol, 41.4 mg, 1.5 equiv.) in THF (0.5 mL) was slowly add to the reaction mixture under −78° C., and the reaction mixture was slowly warmed up to room temperature and stirred for 1 hour. The solvent was removed under vacuo and diluted with EtOAc and then washed with water. The aqueous phase was extracted with EtOAc (5 mL, 3 times). The combined organic phases were dried over $MgSO_4$ and dried in vacuo. The crude material was purified by column chromatography (eluent: 0-30% EtOAc in heptane) to provide compound 19 (53.0 mg, 0.14 mmol, 65.3% yield).

Data for Compound 19
HPLC: (Purity: 95.3%).
LCMS: (M+H: 373.0).
$^1$H NMR (400 MHz, chloroform-d) δ ppm 7.38-7.43 (m, 2H), 7.23-7.29 (m, 2H), 7.09-7.18 (m, 1H), 6.71 (br s, 1H), 3.09-3.19 (m, 1H), 2.37-2.49 (m, 2H), 2.10-2.24 (m, 2H), 1.91-2.05 (m, 1H), 1.13 (s, 3H), 1.09 (s, 3H), 0.88-0.94 (m, 3H).

Example 3. Co-Crystal Structure of GSK3β, Axin, and Compound 1-E2

Figure 2:
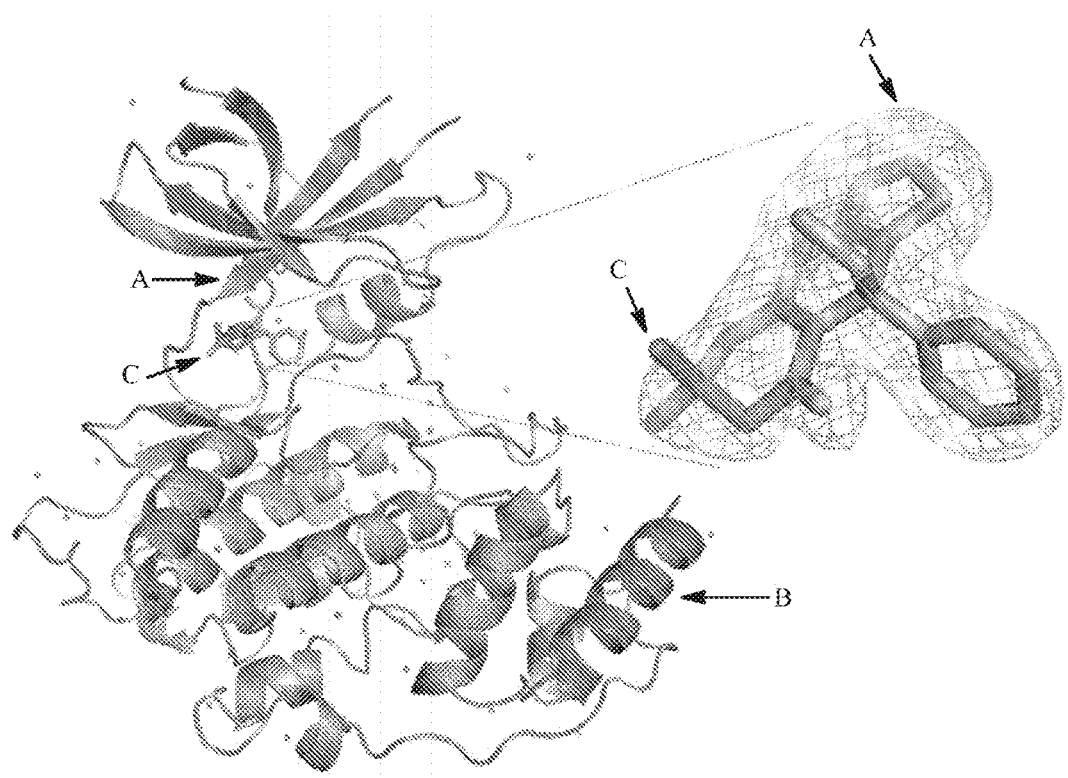
FIG. 2 shows an overall co-crystal structure of GSK3β (A), Axin (B), and compound 1-E2 (C). Difference density used to build and refine compound 1-E2 at 2.0 σ.
Figure 3:
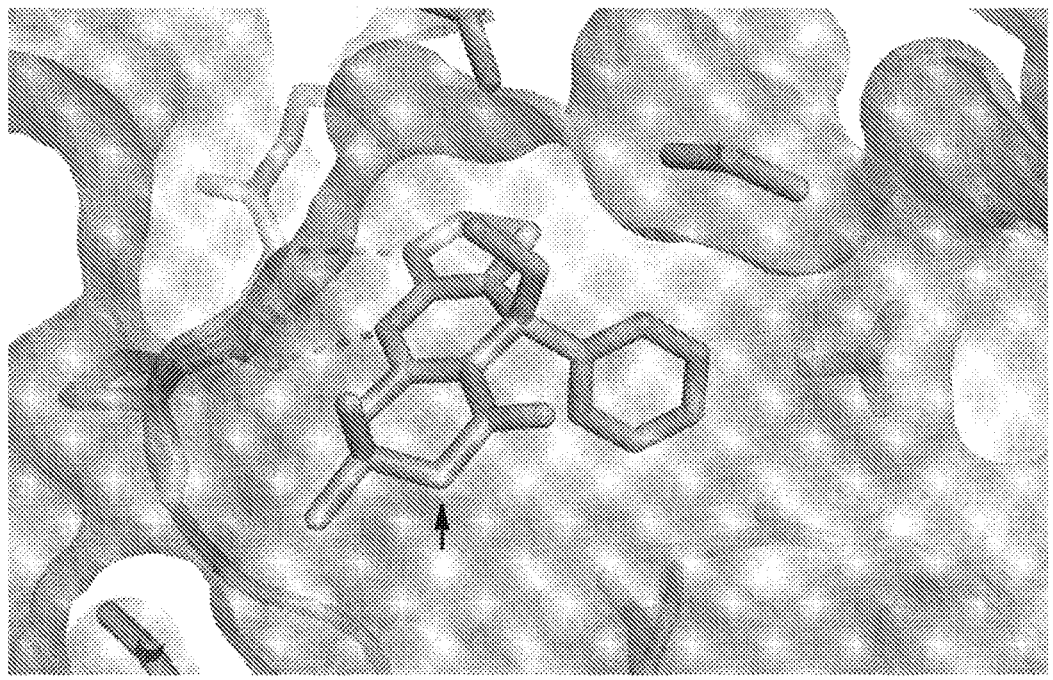
FIG. 3 shows a binding mode of compound 1-E2 (arrow) in the ATP site of GSK3β.
Figure 5A:
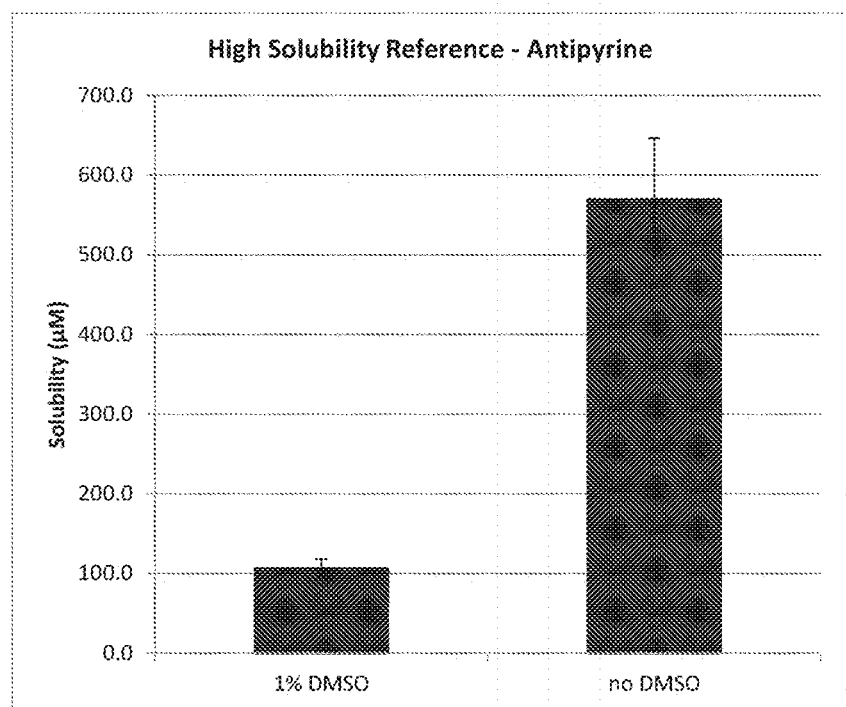
FIG. 5A shows the high solubility reference for the solubility assay.
Figure 5B:
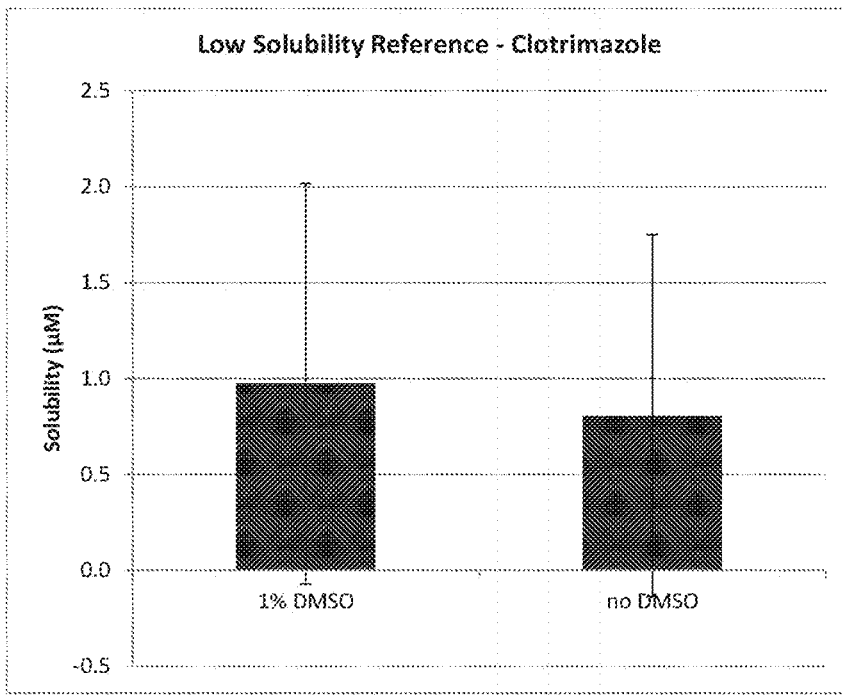
FIG. 5B shows the low solubility reference for the solubility assay.
Figure 6A:
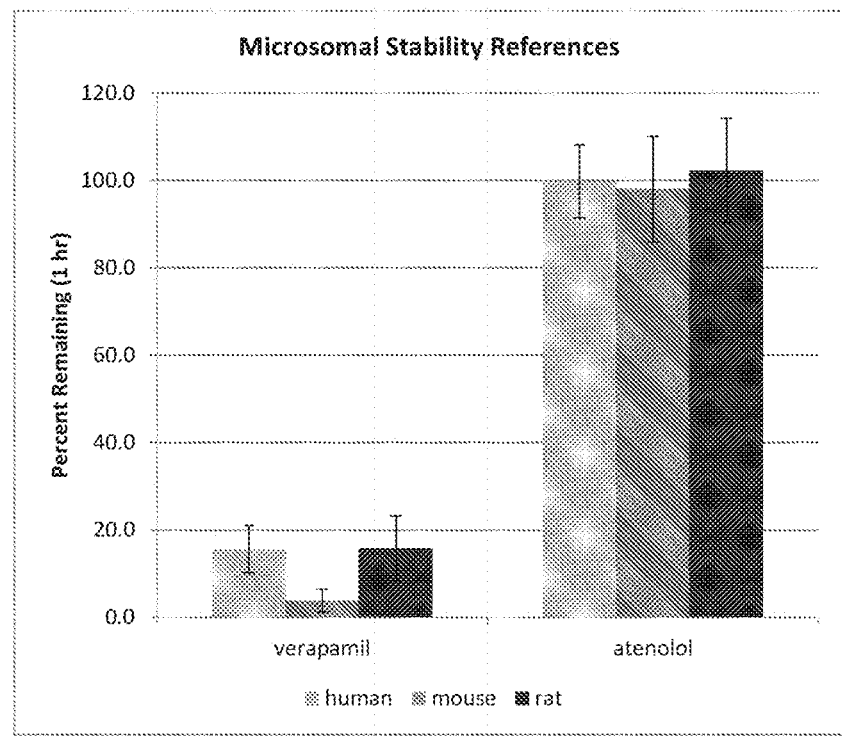
FIG. 6A shows the microsomal stability references for the microsomal stability assay.
Figure 6B:
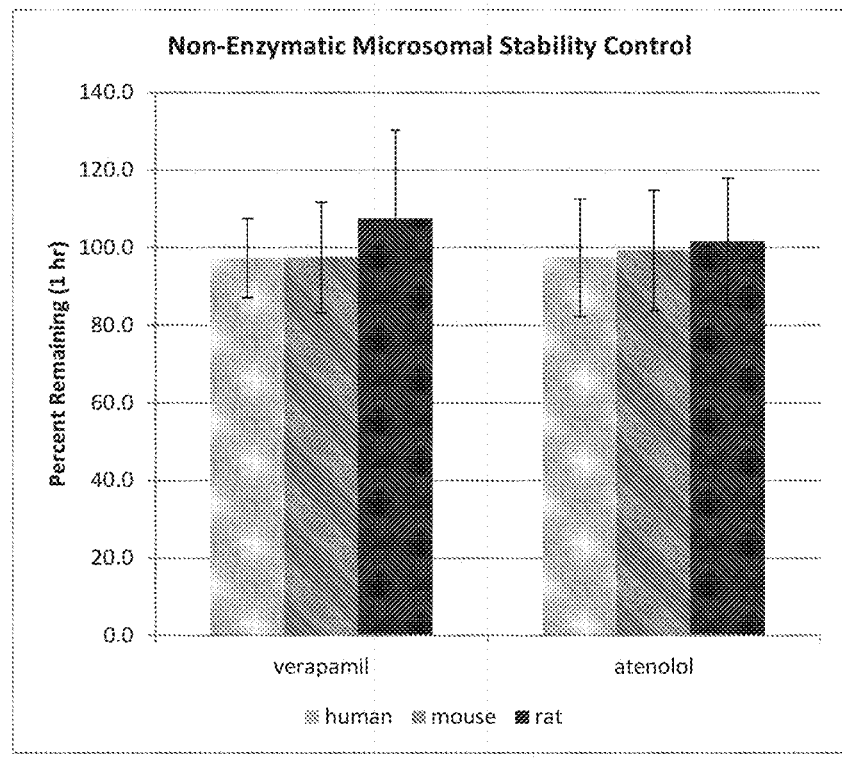
FIG. 6B shows the non-enzymatic microsomal stability control for the microsomal stability assay.
Figure 7A:
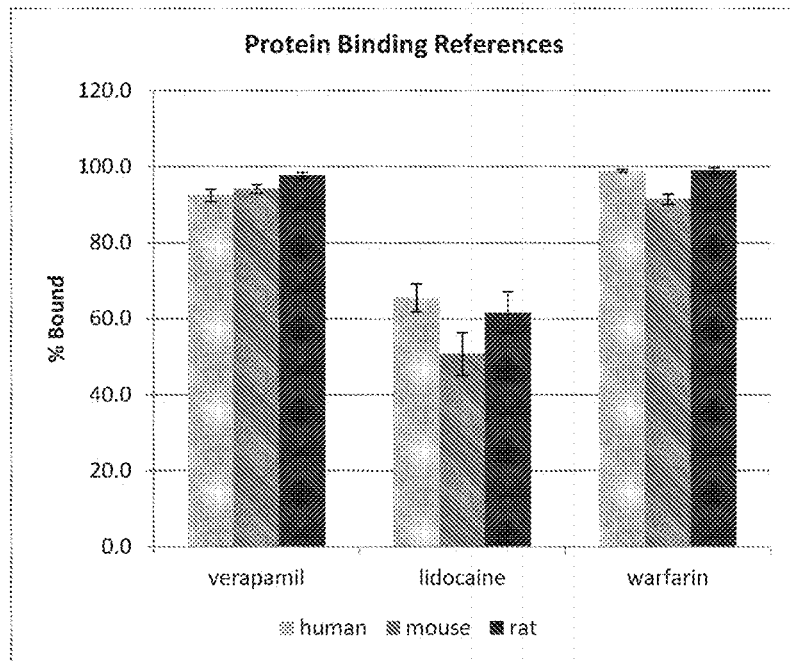
FIG. 7A shows the protein binding references for the plasma protein binding assay.
Figure 7B:
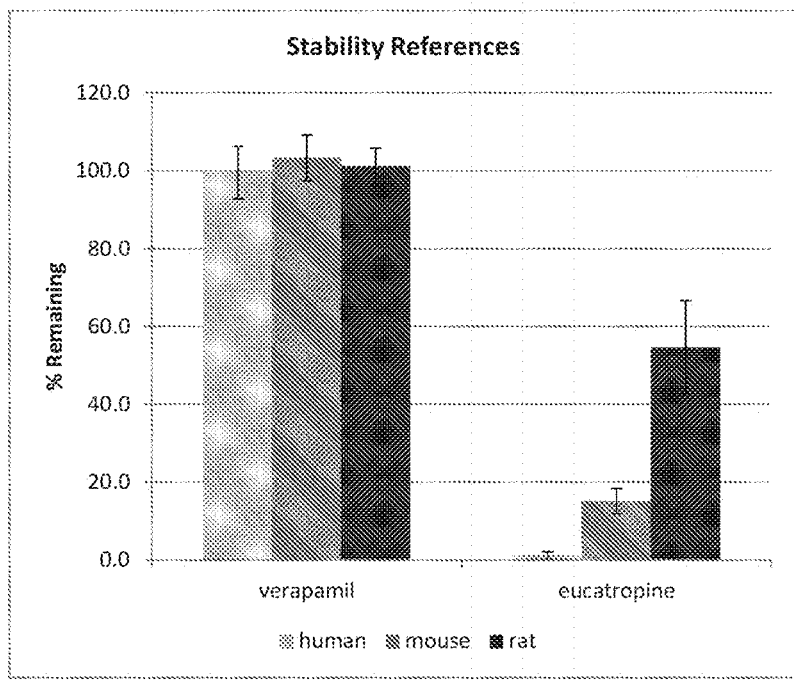
FIG. 7B shows the stability references for the plasma stability assay.

Human GSK3β 34-420 at 5 mg/ml was co-crystallized with an 0.25 mM Axin peptide (VEPQKFAEELIHR-LEAVQ) and 0.5 mM I-E2 in 0.1 M TRIS at pH 8.5, 0.05 mM Na citrate, and 24% PEG3350. The crystals were cryo-protected in 0.1 M TRIS at pH 8.5, 0.05 mM Na citrate, 30% PEG3350, and 15% glycerol and sent for data collection at APS. The structure was solved using phaser with the model 1O9U for molecular replacement and refined using Phenix to 2.29 Å R/Rfree of 20.1/25.8. Exemplary results are shown in FIGS. 2 and 3.

Example 4. Physical, Chemical, Biochemical, and Biological Assays of Exemplary Compounds Dose Response $IC_{50}$ Determination of Selected Compounds against Selected Kinases (Caliper Assay)

A selection of compounds was screened against a selected panel of kinases based on single point inhibitory ability to determine absolute inhibitory activity, leading to selectivity measurements. The assay utilized was identical to that of the single point inhibitory activity determination (MSA) but run in dose response. A solution of 4× inhibitor (5 μL), 4× substrate/ATP Metal solution (5 μL), and 2× Kinase solution (10 μL) was prepared with assay buffer (20 mM HEPES, 0.01% Triton X-100, 2 mM DTT, pH 7.5) and mixed/incubated in 384 well plates for 1 or 5 hours depending on the kinase, at room temperature. A solution of termination buffer (QuickScout Screening assist MSA; Carna Biosciences) (60 µL) was added to each well. The entire reaction mixture was then applied to a LabChip3000 system (Caliper Life Science) and the product and substrate peptide peaks were separated and quantified. Evaluation of kinase activity was then determined based on ratio of calculated peak heights of product (P) and substrate (S) peptides (P/(P+S)).

Mobility Shift Microfluidics Assay Protocol

Purified GSK3β or GSK3α was incubated with tested compounds in the presence of 4.3 µM of ATP (at or just below Km to study competitive inhibitors) and 1.5 µM peptide substrate (Peptide 15, Caliper) for 60 minutes at room temperature in 384-well plates (Seahorse Bioscience) in assay buffer that contained 100 mM HEPES (pH 7.5), 10 mM MgCl2, 2.5 mM DTT, 0.004% Tween-20, and 0.003% Briji-35. Reactions were terminated by the addition of 10 mM ethylenediaminetetraacetic acid (EDTA). Substrate and product were separated electrophoretically, and fluorescence intensity of the substrate and product was determined by Labchip EZ Reader II (Caliper Life Sciences). The kinase activity was measured as percent conversion. The reactions were performed in duplicate for each sample. The positive control, CHIR99021, was included in each plate and used to scale the data in conjunction with in-plate DMSO controls. The results were analyzed by Genedata Assay Analyzer. The percent inhibition was plotted against the compound concentration, and the IC50 value was determined from the logistic dose-response curve fitting. Values are the average of at least three experiments. Compounds were tested using a 12-point dose curve with 3-fold serial dilution starting from 33 µM. Exemplary results are shown in Table 1.

Functional Profiling

Briefly, a selection of compounds was screened against a panel of kinases at a single concentration of 10 µM. The kinases were selected from all families of the kinome and in all represented 60% of the entire kinome for a total of 311 kinases screened. This was completed using one of two assays, depending on the kinase being examined: 1) IMAP Assay. A solution of 4× inhibitor, 4× substrate/ATP/metal solution and 2× kinase solution was prepared with assay buffer (20 mM HEPES, 0.01% Tween-20, 2 mM DTT, pH 7.4) and mixed, then incubated in 384-well black plates for 1 hour at room temperature. The IMAP binding reagent (IMAP Screening Express kit; Molecular Devices) was added to each well and incubated for 30 minutes. Kinase activity was then evaluated by fluorescence polarization at 485 nM (excitation) and 530 nM (emission) of each well. 2) Off-Chip Mobility Shift Assay (MSA). A solution of 4× inhibitor, 4× substrate/ATP/metal solution and 2× kinase solution was prepared with assay buffer (20 mM HEPES, 0.01% Triton X-100, 2 mM DTT, pH 7.5) and mixed, then incubated in 384-well plates for 1 or 5 hours depending on the kinase, at room temperature. Termination buffer (QuickScout Screening assist MSA; Carna Biosciences) was added to each well. The entire reaction mixture was then applied to a LabChip3000 system (Caliper Life Science), and the product and substrate peptide peaks were separated and quantified. Kinase activity was then determined based on the ratio of calculated peak heights of product (P) and substrate (S) peptides (P/(P+S)). For dose response IC50 determination: A solution of 4× inhibitor, 4× substrate/ATP/metal solution and 2× kinase solution was prepared with assay buffer (20 mM HEPES, 0.01% Triton X-100, 2 mM DTT, pH 7.5) and mixed, then incubated in 384-well plates for 1 or 5 hours, depending on the kinase, at room temperature. Termination buffer (QuickScout Screening assist MSA: Carna Biosciences) was added to each well. The entire reaction mixture was then applied to a LabChip3000 system (Caliper Life Science), and the product and substrate peptide peaks were separated and quantified. Kinase activity was then determined based on ratio of calculated peak heights of product (P) and substrate (S) peptides (P/(P+S)). Exemplary results are shown in Table 4.

MDR1/MDCK Assay

The MDR1/MDCK assay is run at Absorption Systems. This assay is used to determine the blood-brain barrier (BBB) penetration potential of a test compound using MDR1-MDCK cell monolayers. Catalog number EA203. Exemplary results are shown in Table 3.

Deliverables

The percent recovery of the test compound from the Transwell® wells containing MDR1-MDCK cell monolayers The apparent permeability ($P_{app}$) in both directions The efflux ratio ($P_{app}$ B to A)/($P_{app}$ A to B)

The blood-brain barrier penetration potential classification:

High when
$P_{app}$ A to B≤3.0×10$^{-6}$ cm/s, and efflux <3.0

Moderate when
$P_{app}$ A to B≥3.0×10$^{-6}$ cm/s, and 10>efflux ≥3.0

Low when either
$P_{app}$ A to B≥3.0×10$^{-6}$ cm/s, and efflux ≥10, or when
$P_{app}$ A to B<3.0×10$^{-6}$ cm/s.

Substrate

Test compound at 5 µM in HBSSg with maximum DMSO concentration not greater than 1%.

Assay System

Confluent monolayers of MDR1-MDCK cells, 7 to 11 days old.

Assay Conditions

Receiver well with 1% BSA in modified Hanks buffer (HBSSg)

Apical and basolateral side at pH 7.4

Dose two monolayers in each direction (N=2)

Dose apical side for (A to B) assessment

Dose basolateral side for (B to A) assessment

Sample both apical and basolateral sides at 120 minutes

Determine the concentrations of test compound using a generic LC-MS/MS method with a minimum 4 point calibration curve.

Assay QC

The quality of the cell monolayer batch is verified using control compounds before monolayers are released for use The quality of each monolayer used in the assay is verified by a TEER measurement and by calculating the $P_{app}$ for a control compound.

Solubility (SOL)

1% DMSO in PBS

Solubility of compound was tested in triplicate by diluting a 10 mM DMSO solution with PBS. Maximum concentration of compound in solution was 100 µM. Order by selecting Solubility (MLPCN Default) in Prometheus.

PBS-Only

Solubility of compound was tested in triplicate by drying down a 10 mM DMSO solution and then attempting to reconstitute in 100% PBS. Maximum concentration of compound in solution was 500 µM. Order by selecting Solubility, no DMSO co-solvent in Prometheus.

Assay Parameters

Compound requirements (1% DMSO in PBS): 30 µL of a 10 mM DMSO solution. Compound requirements (PBS-only): 60 µL of a 10 mM DMSO solution. Equilibration time: 18 hours at room temperature.

Microsomal Stability (MIC)

Stability of compound in liver microsomes was tested in duplicate by incubating compound at 1 µM for 60 minutes at 37° C. Compound level at 60 minutes was compared to level at 0 minutes, and percent remaining was calculated. Order by selecting Microsomal Stability in Prometheus, checking boxes for desired species.

Assay Parameters

Available species: human, mouse (CD-1), and rat (Sprague-Dawley). Compound requirements: 5 µL of a 10 mM DMSO solution. Incubation time: 60 minutes at 37° C. Test Concentration: 1 µM.

Assay Controls

Microsomes with NADPH without compound-matrix interference. Microsomes plus compound without NADPH-non-enzymatic instability.

Plasma Stability and Plasma Protein Binding (PBP)

Stability of compound in plasma was tested in duplicate by incubating compound at 5 µM for 5 hours at 37° C. Compound level at 5 hours was compared to level at 0 hours, and percent remaining was calculated. Binding to plasma proteins was tested in duplicate by incubating compound in plasma at 5 µM for 5 hours at 37° C. in the Rapid Equilibrium Dialysis (RED) Device. Compound level in plasma compartment was compared to compound level in buffer compartment to calculate percent bound. Order by selecting Plasma Stability and Plasma Protein Binding in Prometheus, checking boxes for desired species.

Assay Parameters

Available species: human, mouse (CD-1), and rat (Sprague-Dawley). Compound requirements: 15 µL of a 10 mM DMSO solution. Incubation time: 5 hours at 37° C. Test Concentration: 5 µM.

Other experimental conditions were standard in the art.

Exemplary results are shown in Tables 1 to 4.

TABLE 1

Activity of exemplary compounds in inhibiting GSK3α and GSK3β

| Compound | GSK3α IC$_{50}$ (µM) | GSK3β IC$_{50}$ (µM) |
|---|---|---|
| [structure] | 0.238 | 0.384 |
| [structure] | 18.5 | 28.6 |
| [structure] | 0.203 | 0.455 |
| [structure] | 6.23 | 12.5 |

TABLE 1-continued

Activity of exemplary compounds in inhibiting GSK3α and GSK3β

| Compound | GSK3α IC$_{50}$ (μM) | GSK3β IC$_{50}$ (μM) |
|---|---|---|
| 1 or 1-E2 | 0.014 | 0.065 |
| 1-E1 | >30 | >30 |
| (3-F phenyl analog) | 0.599 | 2.27 |
| (3-F phenyl analog, other enantiomer) | >30 | >30 |
| (3-Cl phenyl analog) | 0.293 | 1.18 |

TABLE 1-continued

Activity of exemplary compounds in inhibiting GSK3α and GSK3β

| Compound | GSK3α IC$_{50}$ (μM) | GSK3β IC$_{50}$ (μM) |
| --- | --- | --- |
| (thiazolo-tetrahydroquinolinone with ethyl and 3-chlorophenyl substituents) | >30 | >30 |
| (thiazolo-tetrahydroquinolinone with ethyl and 3-methylphenyl substituents, wedge bond) | 0.069 | 0.245 |
| (thiazolo-tetrahydroquinolinone with ethyl and 3-methylphenyl substituents, hashed bond) | 4.36 | 11.7 |
| (thiazolo-tetrahydroquinolinone with ethyl and 3-methoxyphenyl substituents, wedge bond) | 0.024 | 0.110 |
| (thiazolo-tetrahydroquinolinone with ethyl and 3-methoxyphenyl substituents, hashed bond) | 10.6 | 10.5 |

TABLE 1-continued
Activity of exemplary compounds in inhibiting GSK3α and GSK3β
| Compound | GSK3α IC$_{50}$ (μM) | GSK3β IC$_{50}$ (μM) |
| --- | --- | --- |
| 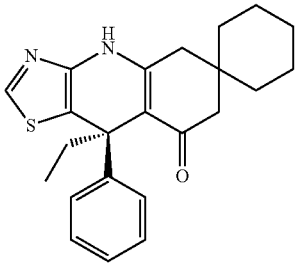 [SMILES: CC[C@@]1(c2ccccc2)C2=C(CC3(CCCCC3)CC2=O)Nc2ncsc21] | 0.155 | 0.447 |
| 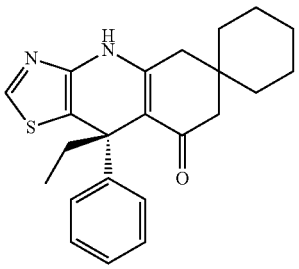 [SMILES: CC[C@]1(c2ccccc2)C2=C(CC3(CCCCC3)CC2=O)Nc2ncsc21] | 3.66 | 1.89 |
| 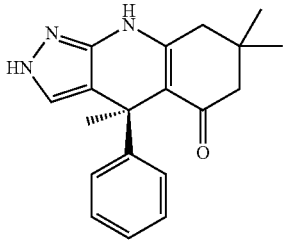 [SMILES: CC1(C)CC(=O)C2=C(C1)Nc1n[nH]cc1[C@]2(C)c1ccccc1] | 0.042 | 0.225 |
| 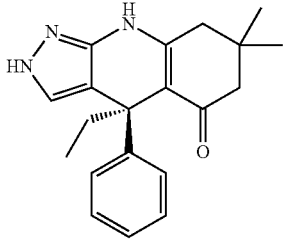 [SMILES: CC[C@@]1(c2ccccc2)C2=C(CC(C)(C)CC2=O)Nc2n[nH]cc21] | 0.066 | 0.507 |
| 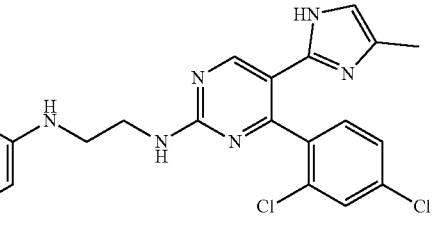<br>CHIR-99021 | 0.002 | 0.002 |

TABLE 2

Solubility, stability, and plasma protein binding assay results for exemplary compounds

| Compound | Thermodynamic Solubility in PBS at about 23° C. (μM) | Plasma Stability (Mouse, % remaining) | Plasma Stability (Human, % remaining) | Plasma Protein Binding (Mouse, % bound) | Plasma Protein Binding (Human, % bound) | Mouse Liver Microsomal Stability, % remaining | Human Liver Microsomal Stability, % remaining |
|---|---|---|---|---|---|---|---|
| (structure) | 34 | 100% | 100% | 99.6% | 99.5% | 0.7% | 17.7% |
| (structure) | 17 | 100% | 100% | 92.6% | 95.1% | 5.6% | 6.6% |
| (structure) | 100 | 96.0% | 99.2% | 95.7% | 97.1% | 3.9% | 2.4% |
| (structure) | 37 | 98.1% | 98.7% | 97.7% | 98.2% | 11.1% | 0.0% |
| (structure) | 75 | 97.8% | 98.9% | 95.5% | 98.1% | 8.2% | 0.7% |

TABLE 2-continued

Solubility, stability, and plasma protein binding assay results for exemplary compounds

| Compound | Thermodynamic Solubility in PBS at about 23° C. (µM) | Plasma Stability (Mouse, % remaining) | Plasma Stability (Human, % remaining) | Plasma Protein Binding (Mouse, % bound) | Plasma Protein Binding (Human, % bound) | Mouse Liver Microsomal Stability, % remaining | Human Liver Microsomal Stability, % remaining |
|---|---|---|---|---|---|---|---|
| 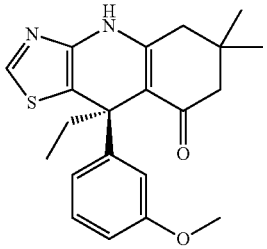 [SMILES: CC[C@@]1(c2cccc(OC)c2)C2=C(CC(C)(C)CC2=O)Nc2ncsc21] | 153 | 97.0% | 98.3% | 92.3% | 97.5% | 10.8% | 1.6% |
| 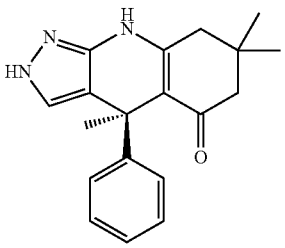 [SMILES: CC1(C)CC(=O)C2=C(C1)Nc1n[nH]cc1[C@]2(C)c1ccccc1] | >500 | 96.6% | 100% | 79.4% | | 100% | 100% |
| 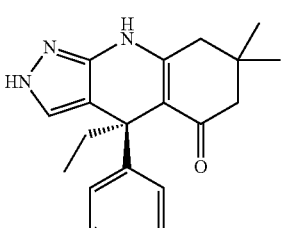 | 480 | 95.3% | | 78.8% | | 93% | 95% |
| 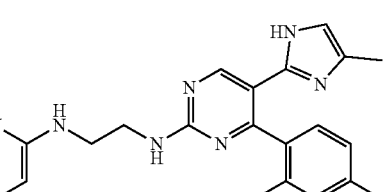 CHIR-99021 | 116 | 97.0% | 100% | 95.7% | 96.1% | 4.0% | 3.0% |

TABLE 3

MDR1 MDCK permeability assay results for exemplary compounds

| Compound | MDR1 MDCK A to B ($10^{-6}$ cm/s) | MDR1 MDCK B to A ($10^{-6}$ cm/s) | Efflux Ratio |
|---|---|---|---|
| (thiazolo-quinolinone with methyl and phenyl substituents) | 28.4 | 62.8 | 2.2 |
| (thiazolo-quinolinone with ethyl and phenyl substituents) — 1 or 1-E2 | 24.2 | 62.1 | 2.6 |
| (pyrazolo-quinolinone with methyl and phenyl substituents) | 1.82 | 66.1 | 36 |
| (pyrazolo-quinolinone with ethyl and phenyl substituents) | 1.26 | 57.7 | 46 |
| (pyridine-pyrimidine-imidazole with 2,4-dichlorophenyl and nitrile) | 6.50 | 64.2 | 9.9 |

Table 4 includes exemplary results from a Carna kinome panel of compound 1, demonstrating the selectivity of the test compound across 313 kinases. Specifically, Table 4 shows percent inhibition at 10 μM of the test compound, and $IC_{50}$ values were determined for kinases with >50% inhibition at 10 μM of the test compound. In Table 4, "nd" denotes "not determined."

TABLE 4

Percent inhibition and $IC_{50}$ for compound 1 against select kinases

| Kinase | % Inhibition at 10 μM of the test compound | $IC_{50}$ (μM) |
| --- | --- | --- |
| GSK3α | 98.0 | 0.0313 |
| GSK3β | 97.7 | 0.137 |
| PIK3CA/PIK3R1 | 65.1 | >10 |
| CDK9/CycT1 | 60.5 | 6.48 |
| CDK2/CycA2 | 58.8 | 6.91 |
| CDK3/CycE1 | 55.5 | 6.22 |
| CDK2/CycE1 | 53.4 | 8.52 |
| CDK5/p25 | 41.2 | nd |
| EPHA7 | 33.9 | nd |
| CDC2/CycB1 | 22.7 | nd |
| CDK7/CycH/MAT1 | 22.6 | nd |
| EPHA3 | 22.5 | nd |
| EGFR(L858R) | 22.2 | nd |
| EPHA6 | 21.3 | nd |
| EGFR | 21.2 | nd |
| NEK6 | 20.9 | nd |
| CDK4/CycD3 | 18.1 | nd |
| p38δ | 18.0 | nd |
| PAK4 | 17.0 | nd |
| MLK2_Cascade | 16.1 | nd |
| TRKB | 16.0 | nd |
| EPHB2 | 14.5 | nd |
| YES(T348I) | 13.5 | nd |
| MOS_Cascade | 12.4 | nd |
| TNK1 | 11.7 | nd |
| MAP3K3_Cascade | 11.1 | nd |
| TIE2 | 11.1 | nd |
| FGR | 10.6 | nd |
| MAP3K4_Cascade | 10.1 | nd |
| skMLCK | 9.7 | nd |
| EPHA5 | 9.3 | nd |
| PKCη | 9.3 | nd |
| MET | 8.9 | nd |
| PKN1 | 8.9 | nd |
| p38γ | 8.9 | nd |
| TNIK | 8.6 | nd |
| AurC | 8.5 | nd |
| FRK | 8.4 | nd |
| PDHK4 | 8.3 | nd |
| CK1δ | 8.2 | nd |
| TAK1-TAB1_Cascade | 8.0 | nd |
| AMPKα1/β1/γ1 | 7.6 | nd |
| MLK1_Cascade | 7.5 | nd |
| NEK1 | 7.5 | nd |
| MLK3_Cascade | 7.3 | nd |
| KIT | 7.1 | nd |
| ROCK1 | 7.0 | nd |
| CHK1 | 7.0 | nd |
| JAK3 | 6.9 | nd |
| QIK | 6.9 | nd |
| IRR | 6.6 | nd |
| AXL | 6.5 | nd |
| MAP2K2_Cascade | 6.4 | nd |
| FLT1 | 6.2 | nd |
| BRAF_Cascade | 6.2 | nd |
| CSK | 6.1 | nd |
| BRAF(V600E)_Cascade | 6.1 | nd |
| LYNa | 6.0 | nd |
| PHKG1 | 5.9 | nd |
| SIK | 5.6 | nd |
| Erk1 | 5.6 | nd |
| MAP2K6_Cascade | 5.6 | nd |
| CDK6/CycD3 | 5.5 | nd |
| LATS2 | 5.4 | nd |
| MAP3K5_Cascade | 5.4 | nd |
| TRKA | 5.4 | nd |
| EPHB4 | 5.3 | nd |
| BLK | 5.0 | nd |
| CK1α | 4.3 | nd |
| MAP2K5_Cascade | 4.3 | nd |
| MGC42105 | 4.3 | nd |
| PRKX | 4.2 | nd |
| MST2 | 4.2 | nd |
| IKKε | 4.2 | nd |
| INSR | 4.1 | nd |
| FGFR4(V550E) | 4.0 | nd |
| DYRK2 | 4.0 | nd |
| CLK3 | 3.9 | nd |
| PAK6 | 3.9 | nd |
| MER | 3.8 | nd |
| p38β | 3.8 | nd |
| TYRO3 | 3.8 | nd |
| MAP2K4_Cascade | 3.7 | nd |
| PLK3 | 3.4 | nd |
| MAP3K2_Cascade | 3.4 | nd |
| CHK2 | 3.3 | nd |
| FGFR4(V550L) | 3.3 | nd |
| MRCKα | 3.3 | nd |
| YES | 3.3 | nd |
| CK1ε | 3.1 | nd |
| TSSK2 | 3.1 | nd |
| JNK3 | 3.1 | nd |
| CK1γ2 | 3.1 | nd |
| LTK | 3.1 | nd |
| SRPK2 | 3.1 | nd |
| EPHA8 | 3.0 | nd |
| EML4-ALK | 2.9 | nd |
| MAP2K3_Cascade | 2.9 | nd |
| FLT3 | 2.9 | nd |
| PAK5 | 2.9 | nd |
| p70S6K | 2.9 | nd |
| RET(G691S) | 2.8 | nd |
| PDGFRα(V561D) | 2.8 | nd |
| FGFR4 | 2.8 | nd |
| MAP2K7_Cascade | 2.8 | nd |
| CaMK2β | 2.8 | nd |
| PKD3 | 2.7 | nd |
| FGFR1(V561M) | 2.6 | nd |
| DLK_Cascade | 2.5 | nd |
| PDGFRβ | 2.5 | nd |
| FYN(isoform b) | 2.4 | nd |
| PKCδ | 2.4 | nd |
| IKKβ | 2.3 | nd |
| MRCKβ | 2.0 | nd |
| EPHA1 | 2.0 | nd |
| IGF1R | 2.0 | nd |
| FYN(isoform a) | 1.8 | nd |
| ALK(F1174L) | 1.8 | nd |
| PLK2 | 1.7 | nd |
| LCK | 1.7 | nd |
| EEF2K | 1.6 | nd |
| FGFR3 | 1.6 | nd |
| CRIK | 1.6 | nd |
| MELK | 1.6 | nd |
| MINK | 1.5 | nd |
| Haspin | 1.5 | nd |
| NuaK2 | 1.5 | nd |
| CK1γ3 | 1.5 | nd |
| MST3 | 1.4 | nd |
| DDR1 | 1.4 | nd |
| RSK2 | 1.4 | nd |
| FGFR2 | 1.4 | nd |
| RET(S891A) | 1.4 | nd |
| CaMK1δ | 1.3 | nd |
| CK1γ1 | 1.2 | nd |
| MSSK1 | 1.2 | nd |
| MAP4K2 | 1.1 | nd |
| PIM3 | 1.1 | nd |

TABLE 4-continued

Percent inhibition and IC$_{50}$ for compound 1 against select kinases

| Kinase | % Inhibition at 10 μM of the test compound | IC$_{50}$ (μM) |
| --- | --- | --- |
| p38α | 1.1 | nd |
| PKD1 | 1.0 | nd |
| AKT2 | 1.0 | nd |
| PGK | 0.9 | nd |
| CLK2 | 0.9 | nd |
| NEK2 | 0.9 | nd |
| PBK | 0.8 | nd |
| LYNb | 0.8 | nd |
| MSK2 | 0.7 | nd |
| AKT1 | 0.7 | nd |
| DDR2 | 0.6 | nd |
| RET(M918T) | 0.6 | nd |
| p70S6Kβ | 0.5 | nd |
| WNK2 | 0.5 | nd |
| PKCζ | 0.5 | nd |
| Erk2 | 0.5 | nd |
| MARK2 | 0.4 | nd |
| AurA | 0.4 | nd |
| ABL(T315I) | 0.4 | nd |
| TRKC | 0.4 | nd |
| HGK | 0.4 | nd |
| WNK3 | 0.3 | nd |
| PIM2 | 0.3 | nd |
| BRK | 0.3 | nd |
| DYRK3 | 0.3 | nd |
| HIPK1 | 0.3 | nd |
| PDGFRα(T674I) | 0.3 | nd |
| FMS | 0.3 | nd |
| PAK1 | 0.3 | nd |
| NEK9 | 0.3 | nd |
| KDR | 0.2 | nd |
| NDR1 | 0.2 | nd |
| PDHK2 | 0.1 | nd |
| PIM1 | 0.0 | nd |
| MUSK | 0.0 | nd |
| EPHA4 | 0.0 | nd |
| ITK | 0.0 | nd |
| KIT(D816E) | −0.2 | nd |
| ROS | −0.2 | nd |
| FLT4 | −0.2 | nd |
| EPHA2 | −0.3 | nd |
| SRPK1 | −0.3 | nd |
| AurB | −0.4 | nd |
| EPHB1 | −0.4 | nd |
| PKACα | −0.6 | nd |
| SLK | −0.6 | nd |
| Erk5 | −0.6 | nd |
| ARG | −0.6 | nd |
| PKCε | −0.7 | nd |
| PKACβ | −0.8 | nd |
| SPHK2 | −0.8 | nd |
| JAK2 | −0.9 | nd |
| HER2 | −1.0 | nd |
| MAP3K1_Cascade | −1.0 | nd |
| MSK1 | −1.0 | nd |
| IRAK4 | −1.2 | nd |
| NDR2 | −1.2 | nd |
| TXK | −1.3 | nd |
| ABL(E255K) | −1.4 | nd |
| COT_Cascade | −1.5 | nd |
| JNK2 | −1.5 | nd |
| RET(Y791F) | −1.6 | nd |
| IKKα | −1.6 | nd |
| CGK2 | −1.6 | nd |
| CaMK2α | −1.6 | nd |
| BTK | −1.6 | nd |
| MARK1 | −1.7 | nd |
| SGK | −1.7 | nd |
| RET | −1.9 | nd |
| HIPK3 | −1.9 | nd |
| FAK | −2.0 | nd |
| RSK1 | −2.0 | nd |
| WNK1 | −2.1 | nd |
| SRC | −2.2 | nd |
| SGK3 | −2.3 | nd |
| ALK(L1152insT) | −2.3 | nd |
| NEK4 | −2.5 | nd |
| HIPK2 | −2.5 | nd |
| CAMK1α | −2.6 | nd |
| ABL | −2.7 | nd |
| PKCι | −2.7 | nd |
| AurA/TPX2 | −2.7 | nd |
| MNK2 | −2.8 | nd |
| BRSK2 | −2.9 | nd |
| HCK | −3.0 | nd |
| FGFR3(K650E) | −3.0 | nd |
| PYK2 | −3.1 | nd |
| ALK | −3.1 | nd |
| ROCK2 | −3.1 | nd |
| MAP2K1_Cascade | −3.2 | nd |
| MST4 | −3.3 | nd |
| MARK3 | −3.3 | nd |
| MNK1 | −3.4 | nd |
| PDGFRα(D842V) | −3.4 | nd |
| KIT(V654A) | −3.5 | nd |
| ALK(C1156Y) | −3.7 | nd |
| CK2α1/β | −3.7 | nd |
| NEK7 | −3.9 | nd |
| RON | −3.9 | nd |
| HER4 | −4.0 | nd |
| PDK1 | −4.0 | nd |
| FGFR3(K650M) | −4.0 | nd |
| AMPKα2/β1/γ1 | −4.1 | nd |
| ACK | −4.1 | nd |
| KIT(T670I) | −4.2 | nd |
| MET(M1250T) | −4.2 | nd |
| AKT3 | −4.5 | nd |
| RSK4 | −4.6 | nd |
| LOK | −4.7 | nd |
| KIT(D816Y) | −4.7 | nd |
| KIT(D816V) | −4.8 | nd |
| EPHB3 | −4.8 | nd |
| RSK3 | −4.9 | nd |
| ALK(G1202R) | −5.0 | nd |
| PHKG2 | −5.0 | nd |
| FGFR1 | −5.0 | nd |
| TSSK1 | −5.0 | nd |
| TSSK3 | −5.1 | nd |
| PASK | −5.2 | nd |
| ALK(L1196M) | −5.2 | nd |
| CaMK2γ | −5.2 | nd |
| TBK1 | −5.3 | nd |
| PLK1 | −5.3 | nd |
| CaMK4 | −5.4 | nd |
| PKACγ | −5.6 | nd |
| EGFR(d746-750/T790M) | −5.6 | nd |
| DYRK1A | −5.8 | nd |
| KIT(V560G) | −5.8 | nd |
| SYK | −5.8 | nd |
| TAOK2 | −5.9 | nd |
| PEK | −6.0 | nd |
| EGFR(d746-750) | −6.1 | nd |
| EGFR(L861Q) | −6.1 | nd |
| FES | −6.2 | nd |
| JAK1 | −6.4 | nd |
| SPHK1 | −6.5 | nd |
| MST1 | −6.6 | nd |
| RAF1_Cascade | −6.7 | nd |
| CLK1 | −7.2 | nd |
| JNK1 | −7.3 | nd |
| PKCβ1 | −7.4 | nd |
| NPM1-ALK | −7.5 | nd |
| FER | −7.5 | nd |
| DCAMKL2 | −7.6 | nd |
| PKCγ | −7.7 | nd |
| MET(D1228H) | −7.7 | nd |
| ALK(R1275Q) | −8.0 | nd |

TABLE 4-continued

Percent inhibition and IC$_{50}$ for compound 1 against select kinases

| Kinase | % Inhibition at 10 μM of the test compound | IC$_{50}$ (μM) |
|---|---|---|
| MAPKAPK 5 | −8.5 | nd |
| CaMK2δ | −8.6 | nd |
| SGK2 | −8.7 | nd |
| DAPK1 | −8.7 | nd |
| IRAK1 | −8.9 | nd |
| PKR | −8.9 | nd |
| TEC | −9.1 | nd |
| CDC7/ASK | −9.1 | nd |
| NuaK1 | −9.2 | nd |
| PDGFRα | −10.1 | nd |
| BMX | −10.6 | nd |
| PKCβ2 | −10.7 | nd |
| PKCα | −11.0 | nd |
| PKCθ | −11.2 | nd |
| CK2α2/β | −11.4 | nd |
| MET(Y1235D) | −12.2 | nd |
| HIPK4 | −12.5 | nd |
| BRSK1 | −12.9 | nd |
| MAPKAPK2 | −13.4 | nd |
| PKD2 | −13.8 | nd |
| EGFR(T790M) | −13.8 | nd |
| SRM | −15.1 | nd |
| EGFR(T790M/L858R) | −15.5 | nd |
| MAPKAPK3 | −15.5 | nd |
| MARK4 | −15.7 | nd |
| PAK2 | −15.7 | nd |
| DYRK1B | −18.1 | nd |
| TYK2 | −18.9 | nd |

Example 5. Additional GSK3 Alpha and GSK3 Beta Biochemical Assay (TR-FRET Assay)

Materials

| Assay buffer | Brand&Catalog No | Comments |
|---|---|---|
| Tris Base | Sigma 10708976001 | |
| Tris HCl | Sigma RES3098T-B701X | |
| MgCl$_2$ | FLUKA-63020 | |
| BSA | Amresco-0332 | |
| DTT | Sigma-43815 | |
| GSK3 alpha recombinant enzyme | SignalChem Cat # G08-10G, Lot # G1332-7 | 0.1 mg/ml; 1.23 uM stock |
| GSK3 beta recombinant enzyme | SignalChem Cat # G09-10G, Lot # P1578-8 | 0.1 mg/ml; 1.37 uM stock |
| Biotinylated-peptide substrate | Anaspec | dissolved in water at 2 mM (Optional: dilute to 20 uM working stocks) |
| ATP | Invitrogen PV3227 | 10 mM stock |
| TR-FRET detection buffer | Invitrogen PV3574 (100 mL) | Dilute detection reagents in this buffer |
| Strepavidin-d$_2$ | Cisbio Cat # 610SADLB | Reconstitute in 1 mL water for 16.67 uM stock |
| Tb2+-labeled pSer641 antibody | Cisbio | 4.5 uM stock |
| EDTA | Sigma-E6758 | 250 mM EDTA, pH 8 |
| Greiner 384-well, F-Bottom, Small Volume, White plate | Greiner Bio-One # 784075 | |

Equipment

Labcyte ECHO 550 acoustic dispenser (or Labcyte POD automation platform) for dispensing of defined compound volumes (in 2.5 nL increments)

PerkinElmer Envision Reader (model 2104-0020) equipped with TRF Laser option (for excitation at 337 nm)

Mirror: LANCE/Delfia Dual/Bias D400/D630 PE Barcode 446

Emission Filter: XL-665 (PE Barcode 205) (665 nm; 7.5 nm bandwidth)

Emission Filter 2: Europium 615 (PE Barcode 203) (615 nm; 8.5 nm bandwidth)

Multidrop Combi Reagent Dispenser (Thermo Scientific 5840300) with small-metal plastic tip-dispensing cassette (Thermo Scientific 24073296).

Assay Details

Assay Buffer 50 mM Tris 7.5

20 mM MgCl$_2$

50 μM DTT (Add fresh from 1 M frozen stock)

0.01% BSA (Add fresh from 1% stock).

Quench Solution 250 mM EDTA, pH 8.

Assay Condition (Final Concentrations after all Additions)

1 nM enzyme, 200 nM biotinylated peptide

4 μM ATP (GSK3 alpha) or 2 μM ATP (GSK3 beta)

42 mM (2 μl 250 mM EDTA)

20 nM Strepavidin-d2

1 nM Tb2+-pSer641 antibody.

Procedure

Preparation of Compound Plate

The reaction volume is 10 μL, and the final percent DMSO is 1%. The total volume of DMSO is therefore 100 nL. It is critical that the percentage of DMSO be controlled and consistent across the plate. The top concentration of test compounds is typically 5 μM. The High control is with all assay components but no inhibitor, the low control is with all assay components but no enzyme.

Compounds are transferred to the assay plate using the ECHO in 2.5 nL increments. Intermediate stock concentrations of compounds are used for dispensing the smaller amounts of compounds which is needed for the lower concentration portions of the titration series. The details of these intermediate stocks preparation are included in Appendix 1. Compound titration series are prepared from the working stocks by dispensing the appropriate volumes into the appropriate wells. DMSO is then backfilled to a final volume of 100 nL. The volumes for each concentration are included in Appendix 1.

Figure 4:
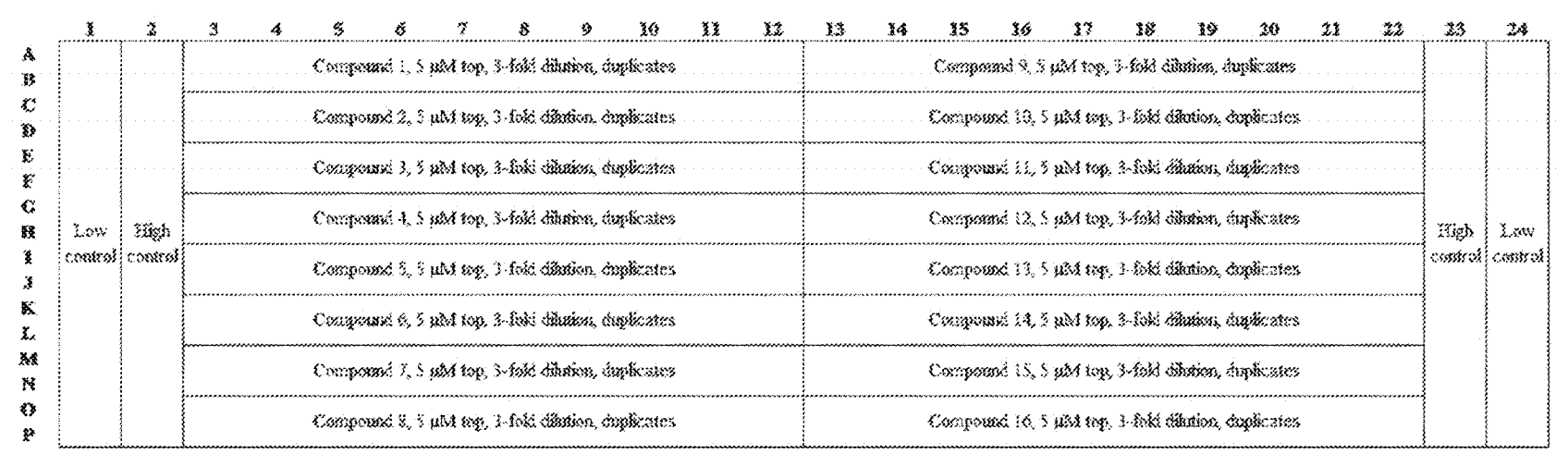

Each compound is assayed in duplicates. The plate map is shown in FIG. 4.

Test Procedure

10 μl kinase reaction: 1 nM GSK3alpha or beta, 200 nM biotin-peptide substrate, ATP=K$_m$ (4 μM for alpha, 2 μM for beta), 100 min reaction at room temperature. Quench with 2 μl 250 mM EDTA (final after quench=42 mM).

Detection

Add 10 μl 2× detection to 12 μl quenched reaction.

Make 2× detection reagents in Invitrogen TR-FRET detection buffer for final 20 nM Strepavidin-d2, 1 nM $Tb^{2+}$-pSer641 antibody (using 20 μl as final volume). 2× detection=40 nM Strepavidin-d2, 2 nM $Tb^{2+}$-pSer641 antibody.

Incubate with detection reagents for 60 min at room temperature and read plate on Envision plate reader using Ex: 340 nm, Ex: 615 nM and 665 nM. Take TR-FRET ratio 665/615.2.10 Use HTRF ratio to analyze data.

Sample Assay Set Up with Volumes:
10 μl reaction:
100 nL compound
5 μl 2× enzyme
5 μl 2× substrates to initiate reaction.

Incubate at room temperature for 100 min and quench with 2 μl 250 mM EDTA.

Add 10 μl 2× detection reagents and incubate for 60 min at room temperature.

Read on Envision plate reader.

Data Analysis Using XLFit

XLFit is used for results which are archived into a database. The data is normalized as a percentage of uninhibited control minus max inhibited controls.

An entire plate is failed or invalidated within XLFit if it fails to meet the following criteria: Z' greater than 0.5.

A control compound is included on every dose titration plate as an indication of assay consistency. If the control compound IC50 is not within 3 fold of previously determined values, the plate will be retested.

APPENDIX 1. PREPARATION OF COMPOUND PLATES USING ECHO

GSK3 Test compounds
Plate type Greiner 384-well, F-Bottom, Small Volume, White plate
Kinase reaction volume 10 μL
Top concentration 5 μM
Final volume DMSO 100 nL (1% DMSO).

| Data Point | intermediate | source (mM) | Transfer (nL) | Backfill (nL) | concentration (uM) | DMSO (%) |
|---|---|---|---|---|---|---|
| 1 | 0 | 5 | 10 | 90 | 5 | 1 |
| 2 | 1* | 0.185185185 | 90 | 10 | 1.666666667 | 1 |
| 3 | 1 | 0.185185185 | 30 | 70 | 0.555555556 | 1 |
| 4 | 1 | 0.185185185 | 10 | 90 | 0.185185185 | 1 |
| 5 | 2** | 0.006858711 | 90 | 10 | 0.061728395 | 1 |
| 6 | 2 | 0.006858711 | 30 | 70 | 0.020576132 | 1 |
| 7 | 2 | 0.006858711 | 10 | 90 | 0.006858711 | 1 |
| 8 | 3*** | 0.001016105 | 22.5 | 77.5 | 0.002286237 | 1 |
| 9 | 3 | 0.001016105 | 7.5 | 92.5 | 0.000762079 | 1 |
| 10 | 3 | 0.001016105 | 2.5 | 97.5 | 0.000254026 | 1 |

*Intermediate 1 is prepared by transfer of 1350 nL 5 mM stock and backfilling with DMSO to a total volume of 36.45 μL. The resulting source plate should be vortexed briefly to ensure full mixing of the intermediate stock solution.
**Intermediate 2 is prepared by transfer of 50 nL 5 mM stock and backfilling with DMSO to a total volume of 36.45 μL. The resulting source plate should be vortexed briefly to ensure full mixing of the intermediate stock solution.
***Intermediate 3 is prepared by transfer of 7.5 nL 5 mM stock and backfilling with DMSO to a total volume of 36.90 μL. The resulting source plate should be vortexed briefly to ensure full mixing of the intermediate stock solution.

Exemplary results are shown in Table 5.

Example 6. Additional MDCK Permeability (MDR1-MDCK) Assay

The conditions of this assay were essentially the same as the conditions of the MDR1/MDCK assay of Example 4. Exemplary results are shown in Table 5.

TABLE 5

Additional assay results for exemplary compounds

| Compound Number | GSK3α TR-FRET BIOCHEMICAL (TR-FRET) GMean $IC_{50}$ (μM) | GSK3β TR-FRET BIOCHEMICAL (TR-FRET) GMean $IC_{50}$ (μM) | GSK3α over GSK3 β selectivity @ Km* | MDCK PERMEABILITY (MDR1-MDCK) Mean Papp(A-B) ($10^{-6}$ cm/s) | MDCK PERMEABILITY (MDR1-MDCK) Mean Papp(B-A) ($10^{-6}$ cm/s) | MDCK PERMEABILITY (MDR1-MDCK) Mean P. Ratio(B-A/A-B) |
|---|---|---|---|---|---|---|
| 1-E1 | >5.000 | >5.000 | 1.000 | | | |
| 1-E2 | 0.037 | 0.190 | 5.163 | 7.667 | 24.422 | 3.200 |
| 2 | 0.130 | 0.353 | 2.724 | | | |
| 2-E1 | 0.045 | 0.172 | 3.831 | 11.118 | 57.121 | 5.137 |
| 2-E2 | 0.355 | 0.931 | 2.626 | 5.095 | 26.063 | 5.115 |
| 2-E3 | >5.000 | >5.000 | 1.000 | 3.650 | 29.126 | 7.980 |
| 2-E4 | >5.000 | >5.000 | 1.000 | 2.340 | 21.860 | 9.341 |
| 3 | 0.254 | 0.951 | 3.741 | | | |
| 3-E1 | 0.204 | 0.645 | 3.155 | | | |
| 3-E2 | >5.000 | >5.000 | 1.000 | | | |
| 4 | 0.174 | 0.627 | 3.605 | | | |
| 5 | 0.080 | 0.366 | 4.579 | | | |

TABLE 5-continued

Additional assay results for exemplary compounds

| Compound Number | GSK3α TR-FRET BIOCHEMICAL (TR-FRET) GMean IC$_{50}$ (μM) | GSK3β TR-FRET BIOCHEMICAL (TR-FRET) GMean IC$_{50}$ (μM) | GSK3α over GSK3 β selectivity @ Km* | MDCK PERMEABILITY (MDR1-MDCK) Mean Papp(A-B) ($10^{-6}$ cm/s) | MDCK PERMEABILITY (MDR1-MDCK) Mean Papp(B-A) ($10^{-6}$ cm/s) | MDCK PERMEABILITY (MDR1-MDCK) Mean P. Ratio(B-A/A-B) |
|---|---|---|---|---|---|---|
| 5-E1 | 0.024 | 0.126 | 5.179 | 16.321 | 24.318 | 1.490 |
| 5-E2 | >5.000 | >5.000 | 1.000 | | | |
| 6 | 0.194 | 0.684 | 3.521 | | | |
| 6-E1 | >5.000 | >5.000 | 1.000 | | | |
| 6-E2 | >5.000 | >5.000 | 1.000 | | | |
| 6-E3 | 0.078 | 0.241 | 3.112 | 6.735 | 26.636 | 3.955 |
| 6-E4 | 0.047 | 0.147 | 3.134 | 8.901 | 20.499 | 2.303 |
| 7 | 0.171 | 0.592 | 3.468 | | | |
| 7-E1 | 0.084 | 0.265 | 3.164 | 7.709 | 26.662 | 3.459 |
| 7-E2 | 0.084 | 0.217 | 2.591 | 7.679 | 28.195 | 3.672 |
| 7-E3 | >5.000 | >5.000 | 1.000 | 5.454 | 25.153 | 4.612 |
| 7-E4 | >5.000 | >5.000 | 1.000 | 4.754 | 26.980 | 5.675 |
| 8 | 0.365 | 0.927 | 2.541 | | | |
| 8-E1 | 0.138 | 0.347 | 2.515 | 3.905 | 11.560 | 2.960 |
| 8-E2 | >5.000 | >5.000 | 1.000 | 4.812 | 16.015 | 3.328 |
| 8-E3 | 0.063 | 0.225 | 3.582 | 5.916 | 14.716 | 2.488 |
| 8-E4 | >5.000 | >5.000 | 1.000 | 4.400 | 11.811 | 2.684 |
| 9 | 0.184 | 0.418 | 2.274 | | | |
| 10 | 0.189 | 0.644 | 3.404 | | | |
| 11 | 0.419 | >1.670 | 3.981 | | | |
| 11-E1 | 0.515 | 1.524 | 2.959 | | | |
| 11-E2 | >5.000 | >5.000 | 1.000 | | | |
| 13 | 0.187 | 0.619 | 3.318 | | | |
| 14 | 0.041 | 0.234 | 5.757 | | | |
| 15 | >5.000 | >5.000 | 1.000 | | | |
| 16 | >5.000 | >5.000 | 1.000 | | | |
| 17 | >5.000 | >5.000 | 1.000 | | | |
| 18 | 0.118 | 0.500 | 4.219 | | | |
| 18-E1 | 0.044 | 0.187 | 4.228 | 13.396 | 32.627 | 2.436 |
| 18-E2 | >5.000 | >5.000 | 1.000 | | | |
| 19 | 1.990 | 4.349 | 2.185 | | | |

*As calculated by dividing GSK3β TR-FRET BIOCHEMICAL (TR-FRET) GMean IC$_{50}$ (μM) by GSK3α TR-FRET BIOCHEMICAL (TR-FRET) GMean IC$_{50}$ (μM).

Other Embodiments

The foregoing has been a description of certain non-limiting embodiments of the invention. Those of ordinary skill in the art will appreciate that various changes and modifications to this description may be made without departing from the spirit or scope of the present invention, as defined in the following claims.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising," "including," and "containing," and all other tenses thereof, are intended to be open and permits the inclusion of additional possibilities (e.g., elements or steps). Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A compound of Formula (I):

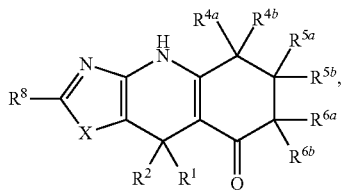
(I)

or a pharmaceutically acceptable salt, solvate, hydrate, polymorph, co-crystal, tautomer, stereoisomer, or isotopically labeled compound thereof, wherein:

X is —O— or —S—;

$R^1$ is substituted or unsubstituted $C_{1-12}$ alkyl, substituted or unsubstituted $C_{2-12}$ alkenyl, substituted or unsubstituted $C_{2-12}$ alkynyl, substituted or unsubstituted, 3- to 13-membered, monocyclic or bicyclic carbocyclyl, substituted or unsubstituted, 3- to 13-membered, monocyclic or bicyclic heterocyclyl, substituted or unsubstituted, 6- to 11-membered, monocyclic or bicyclic aryl, or substituted or unsubstituted, 5- to 11-membered, monocyclic or bicyclic heteroaryl;

$R^2$ is substituted or unsubstituted $C_{1-6}$ alkyl, substituted or unsubstituted $C_{2-6}$ alkenyl, substituted or unsubstituted $C_{2-6}$ alkynyl, substituted or unsubstituted, 3- to 7-membered, monocyclic carbocyclyl, or substituted or unsubstituted phenyl;

or $R^1$ and $R^2$ are joined to form substituted or unsubstituted, 3- to 13-membered, monocyclic or bicyclic carbocyclyl, or substituted or unsubstituted, 3- to 13-membered, monocyclic or bicyclic heterocyclyl;

each one of $R^{4a}$ and $R^{4b}$ is independently hydrogen, halogen, —CN, —$OR^A$, —$SR^A$, —$N(R^A)_2$, substituted or unsubstituted $C_{1-6}$ alkyl, substituted or unsubstituted $C_{2-6}$ alkenyl, or substituted or unsubstituted $C_{2-6}$ alkynyl; or $R^{4a}$ and $R^{4b}$ are joined to form substituted or unsubstituted $C_{1-6}$ alkenyl, substituted or unsubstituted, 3- to 7-membered, monocyclic carbocyclyl, or substituted or unsubstituted, 3- to 7-membered, monocyclic heterocyclyl;

each one of $R^{5a}$ and $R^{5b}$ is independently hydrogen, halogen, —CN, —$OR^A$, —$SR^A$, —$N(R^A)_2$, substituted or unsubstituted $C_{1-6}$ alkyl, substituted or unsubstituted $C_{2-6}$ alkenyl, or substituted or unsubstituted $C_{2-6}$ alkynyl; or $R^{5a}$ and $R^{5b}$ are joined to form substituted or unsubstituted $C_{1-6}$ alkenyl, substituted or unsubstituted, 3- to 7-membered, monocyclic carbocyclyl, or substituted or unsubstituted, 3- to 7-membered, monocyclic heterocyclyl;

each one of $R^{6a}$ and $R^{6b}$ is independently hydrogen, halogen, —CN, —$OR^A$, —$SR^A$, —$N(R^A)_2$, substituted or unsubstituted $C_{1-6}$ alkyl, substituted or unsubstituted $C_{2-6}$ alkenyl, or substituted or unsubstituted $C_{2-6}$ alkynyl; or $R^{6a}$ and $R^{6b}$ are joined to form substituted or unsubstituted $C_{1-6}$ alkenyl, substituted or unsubstituted, 3- to 7-membered, monocyclic carbocyclyl, or substituted or unsubstituted, 3- to 7-membered, monocyclic heterocyclyl;

$R^8$ is hydrogen, halogen, —CN, —$OR^A$, —$SR^A$, —$N(R^A)_2$, substituted or unsubstituted $C_{1-4}$ alkyl, substituted or unsubstituted alkenyl, substituted or unsubstituted $C_{2-6}$ alkynyl, or substituted or unsubstituted, 3- to 5-membered, monocyclic carbocyclyl;

each $R^A$ is independently hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted, 3- to 7-membered, monocyclic carbocyclyl, substituted or unsubstituted, 3- to 7-membered, monocyclic heterocyclyl, substituted or unsubstituted phenyl, substituted or unsubstituted, 5- or 6-membered, monocyclic heteroaryl, an oxygen protecting group when attached to an oxygen atom, a sulfur protecting group when attached to a sulfur atom, or a nitrogen protecting group when attached to a nitrogen atom; or two $R^A$ attached to the same nitrogen atom are joined to form substituted or unsubstituted, 3- to 7-membered, monocyclic heterocyclyl, or substituted or unsubstituted, 5- or 6-membered, monocyclic heteroaryl;

each instance of the heterocyclyl comprises in the heterocyclic ring system one, two, three, or four heteroatoms independently selected from the group consisting of oxygen, nitrogen, and sulfur, as valency permits; and each instance of the heteroaryl comprises in the heteroaryl ring system one, two, three, or four heteroatoms independently selected from the group consisting of oxygen, nitrogen, and sulfur, as valency permits.

2. The compound of claim 1, or a pharmaceutically acceptable salt, solvate, hydrate, polymorph, co-crystal, tautomer, stereoisomer, or isotopically labeled compound thereof, wherein $R^1$ is substituted or unsubstituted phenyl.

3. The compound of claim 1, or a pharmaceutically acceptable salt, solvate, hydrate, polymorph, co-crystal, tautomer, stereoisomer, or isotopically labeled compound thereof, wherein $R^2$ is —$CH_3$ or —$C_2H_5$.

4. The compound of claim 1, or a pharmaceutically acceptable salt, solvate, hydrate, polymorph, co-crystal, tautomer, stereoisomer, or isotopically labeled compound thereof, wherein the compound is of the formula:

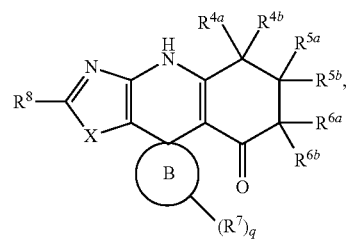

wherein:
Ring B is substituted or unsubstituted, 3- to 7-membered, monocyclic carbocyclyl, or substituted or unsubstituted, 3- to 7-membered, monocyclic heterocyclyl;
each instance of $R^7$ is independently hydrogen, halogen, substituted or unsubstituted $C_{1-12}$ alkyl, substituted or unsubstituted $C_{2-12}$ alkenyl, substituted or unsubstituted $C_{2-12}$ alkynyl, substituted or unsubstituted, 3- to 13-membered, monocyclic or bicyclic carbocyclyl, substituted or unsubstituted, 3- to 13-membered, monocyclic or bicyclic heterocyclyl, substituted or unsubstituted, 6- to 11-membered, monocyclic or bicyclic aryl, substituted or unsubstituted, 5- to 11-membered, monocyclic or bicyclic heteroaryl, —$OR^A$, —$N(R^A)_2$, —$SR^A$, —CN, —SCN, —C(=O)$R^A$, —C(=O)$OR^A$, —C(=O)N($R^A$)$_2$, —C(=N$R^A$)$R^A$, —C(=N$R^A$)$OR^A$, —C(=N$R^A$)N($R^A$)$_2$, —NO$_2$, —N$_3$, —N$R^A$C(=O)$R^A$, —N$R^A$C(=O)$OR^A$, —N$R^A$C(=O)N($R^A$)$_2$, —N$R^A$C(=N$R^A$)$R^A$, —N$R^A$C(=N$R^A$)$OR^A$, —N$R^A$C(=N$R^A$)N($R^A$)$_2$, —OC(=O)$R^A$, —OC(=O)$OR^A$, —OC(=O)N($R^A$)$_2$, —OC(=N$R^A$)$R^A$, —OC(=N$R^A$)$OR^A$, —OC(=N$R^A$)N($R^A$)$_2$, —N$R^A$S(=O)$_2R^A$, —N$R^A$S(=O)$_2OR^A$, —N$R^A$S(=O)$_2$N($R^A$)$_2$, —OS(=O)$_2R^A$, —OS(=O)$_2OR^A$, —OS(=O)$_2$N($R^A$)$_2$, —S(=O)$_2R^A$, —S(=O)$_2OR^A$, or —S(=O)$_2$N($R^A$)$_2$; or two $R^7$ groups are joined to form substituted or unsubstituted, 3- to 7-membered, monocyclic carbocyclyl, substituted or unsubstituted, 3- to 7-membered, monocyclic heterocyclyl, substituted or unsubstituted phenyl, or substituted or unsubstituted, 5- or 6-membered, monocyclic heteroaryl; and
q is 0, 1, 2, 3, 4, 5, 6, 7, 8, 9, 10, 11, or 12, as valency permits.

5. The compound of claim 1, or a pharmaceutically acceptable salt, solvate, hydrate, polymorph, co-crystal, tautomer, stereoisomer, or isotopically labeled compound thereof, wherein the compound is of the formula:

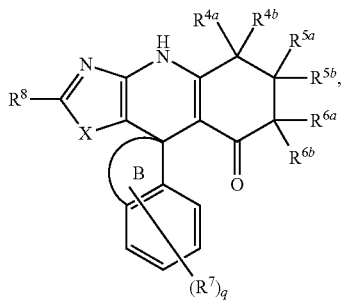

wherein:
Ring B is substituted or unsubstituted, 3- to 7-membered, monocyclic carbocyclyl, or substituted or unsubstituted, 3- to 7-membered, monocyclic heterocyclyl;
each instance of $R^7$ is independently hydrogen, halogen, substituted or unsubstituted $C_{1-12}$ alkyl, substituted or unsubstituted $C_{2-12}$ alkenyl, substituted or unsubstituted $C_{2-12}$ alkynyl, substituted or unsubstituted, 3- to 13-membered, monocyclic or bicyclic carbocyclyl, substituted or unsubstituted, 3- to 13-membered, monocyclic or bicyclic heterocyclyl, substituted or unsubstituted, 6- to 11-membered, monocyclic or bicyclic aryl, substituted or unsubstituted, 5- to 11-membered, monocyclic or bicyclic heteroaryl, —$OR^A$, —$N(R^A)_2$, —$SR^A$, —CN, —SCN, —C(=O)$R^A$, —C(=O)$OR^A$, —C(=O)N($R^A$)$_2$, —C(=N$R^A$)$R^A$, —C(=N$R^A$)$OR^A$, —C(=N$R^A$)N($R^A$)$_2$, —NO$_2$, —N$_3$, —N$R^A$C(=O)$R^A$, —N$R^A$C(=O)$OR^A$, —N$R^A$C(=O)N($R^A$)$_2$, —N$R^A$C(=N$R^A$)$R^A$, —N$R^A$C(=N$R^A$)$OR^A$, —N$R^A$C(=N$R^A$)N($R^A$)$_2$, —OC(=O)$R^A$, —OC(=O)$OR^A$, —OC(=O)N($R^A$)$_2$, —OC(=N$R^A$)$R^A$, —OC(=N$R^A$)$OR^A$, —OC(=N$R^A$)N($R^A$)$_2$, —N$R^A$S(=O)$_2R^A$, —N$R^A$S(=O)$_2OR^A$, —N$R^A$S(=O)$_2$N($R^A$)$_2$, —OS(=O)$_2R^A$, —OS(=O)$_2OR^A$, —OS(=O)$_2$N($R^A$)$_2$, —S(=O)$_2R^A$, —S(=O)$_2OR^A$, or —S(=O)$_2$N($R^A$)$_2$; or two $R^7$ groups on the same carbon atom are joined to form substituted or unsubstituted $C_{1-6}$ alkenyl; and
q is 0, 1, 2, 3, 4, 5, 6, 7, 8, 9, 10, 11, or 12, as valency permits.

6. The compound of claim 1, or a pharmaceutically acceptable salt, solvate, hydrate, polymorph, co-crystal, tautomer, stereoisomer, or isotopically labeled compound thereof, wherein the compound is of the formula:

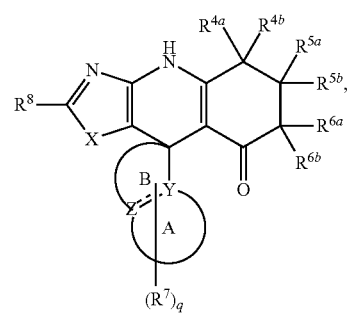

wherein:
Ring A is substituted or unsubstituted, 5- to 6-membered, monocyclic heteroaryl,
Ring B is substituted or unsubstituted, 3- to 7-membered, monocyclic carbocyclyl, or substituted or unsubstituted, 3- to 7-membered, monocyclic heterocyclyl;
Y is C or N;
Z is C or N;
===== is a single or double bond, as valency permits;
each instance of $R^7$ is independently hydrogen, halogen, substituted or unsubstituted $C_{1-12}$ alkyl, substituted or unsubstituted $C_{2-12}$ alkenyl, substituted or unsubstituted $C_{2-12}$ alkynyl, substituted or unsubstituted, 3- to 13-membered, monocyclic or bicyclic carbocyclyl, substituted or unsubstituted, 3- to 13-membered, monocyclic or bicyclic heterocyclyl, substituted or unsubstituted, 6- to 11-membered, monocyclic or bicyclic aryl, substituted or unsubstituted, 5- to 11-membered, monocyclic or bicyclic heteroaryl, —$OR^A$, —$N(R^A)_2$, —$SR^A$, —CN, —SCN, —C(=O)$R^A$, —C(=O)$OR^A$, —C(=O)N($R^A$)$_2$, —C(=N$R^A$)$R^A$, —C(=N$R^A$)$OR^A$, —C(=N$R^A$)N($R^A$)$_2$, —NO$_2$, —N$_3$, —N$R^A$C(=O)$R^A$, —N$R^A$C(=O)$OR^A$, —N$R^A$C(=O)N($R^A$)$_2$, —N$R^A$C(=N$R^A$)$R^A$, —N$R^A$C(=N$R^A$)$OR^A$, —N$R^A$C(=N$R^A$)N($R^A$)$_2$, —OC(=O)$R^A$, —OC(=O)$OR^A$, —OC(=O)N($R^A$)$_2$, —OC(=N$R^A$)$R^A$, —OC(=N$R^A$)$OR^A$, —OC(=N$R^A$)N($R^A$)$_2$, —N$R^A$S(=O)$_2R^A$, —N$R^A$S(=O)$_2OR^A$, —N$R^A$S(=O)$_2$N($R^A$)$_2$, —OS(=O)$_2R^A$, —OS(=O)$_2OR^A$, —OS(=O)$_2$N($R^A$)$_2$, —S(=O)$_2R^A$, —S(=O)$_2OR^A$, or —S(=O)$_2$N($R^A$)$_2$; or two $R^7$ groups on the same carbon atom are joined to form substituted or unsubstituted $C_{1-6}$ alkenyl; and
q is 0, 1, 2, 3, 4, 5, 6, 7, 8, 9, 10, 11, or 12, as valency permits.

7. The compound of claim 1, or a pharmaceutically acceptable salt, solvate, hydrate, polymorph, co-crystal, tautomer, stereoisomer, or isotopically labeled compound thereof, wherein each one of $R^{4a}$ and $R^{4b}$ is hydrogen.

8. The compound of claim 1, or a pharmaceutically acceptable salt, solvate, hydrate, polymorph, co-crystal, tautomer, stereoisomer, or isotopically labeled compound thereof, wherein each one of $R^{5a}$ and $R^{5b}$ is substituted or unsubstituted $C_{1-6}$ alkyl.

9. The compound of claim 1, or a pharmaceutically acceptable salt, solvate, hydrate, polymorph, co-crystal, tautomer, stereoisomer, or isotopically labeled compound thereof, wherein each one of $R^{6a}$ and $R^{6b}$ is hydrogen.

10. The compound of claim 1, or a pharmaceutically acceptable salt, solvate, hydrate, polymorph, co-crystal, tautomer, stereoisomer, or isotopically labeled compound thereof, wherein $R^8$ is hydrogen.

11. The compound of claim 1, or a pharmaceutically acceptable salt, solvate, hydrate, polymorph, co-crystal, tautomer, stereoisomer, or isotopically labeled compound thereof, wherein the compound is of the formula:

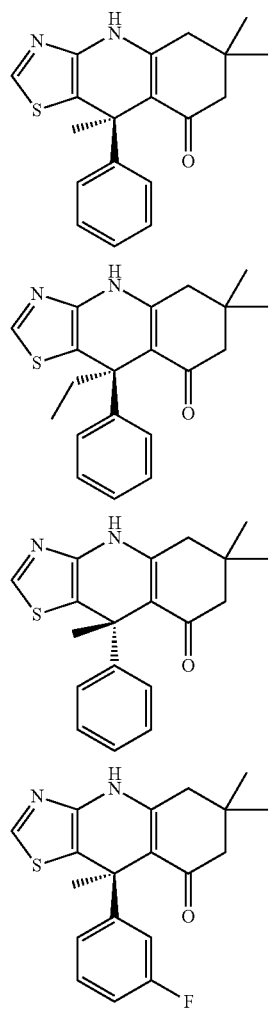

-continued

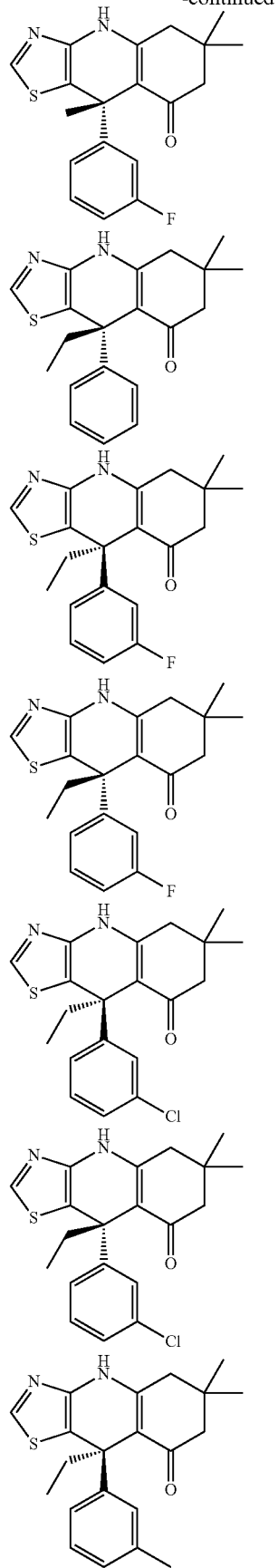

189
-continued
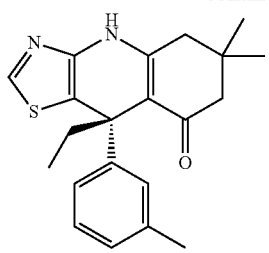
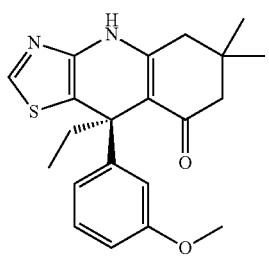
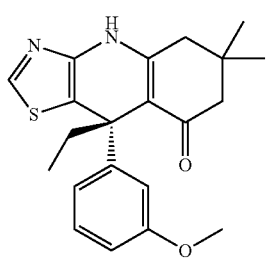
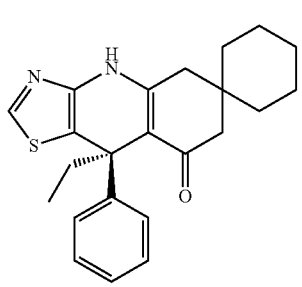
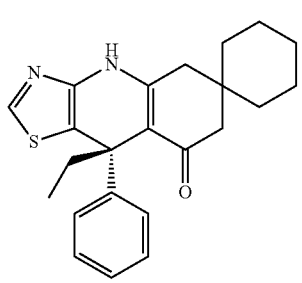
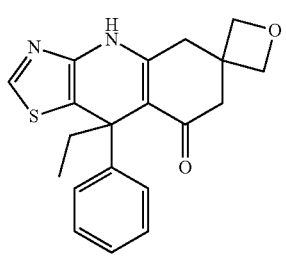
190
-continued
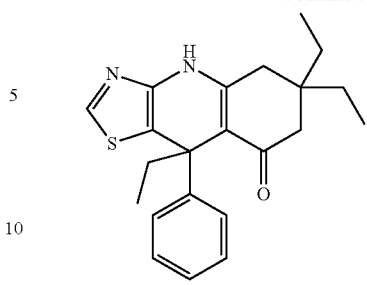
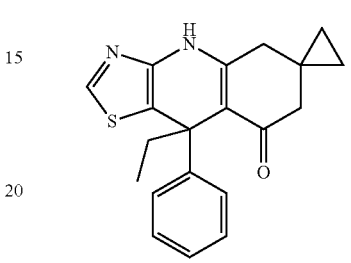
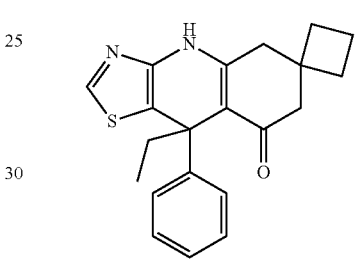
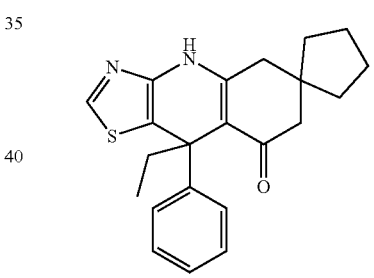
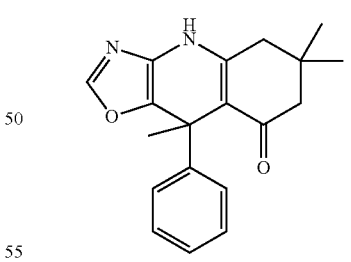
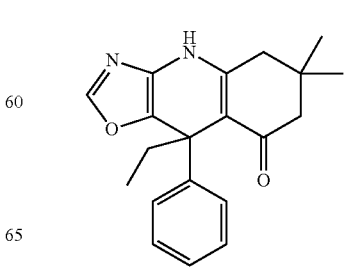

191
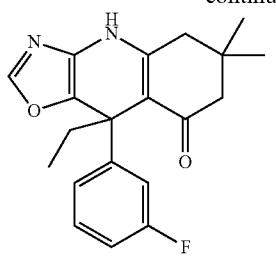
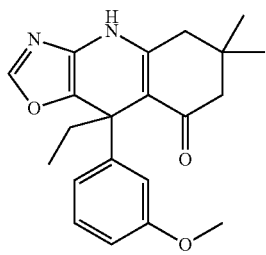
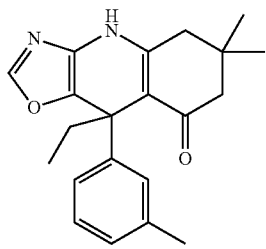
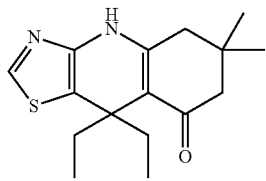
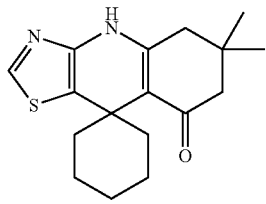
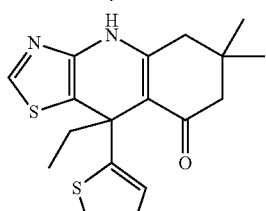
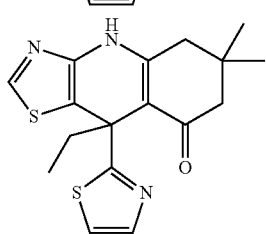
192
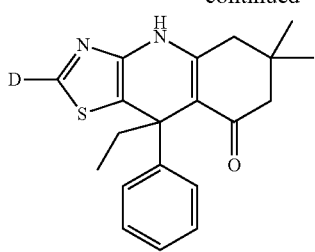
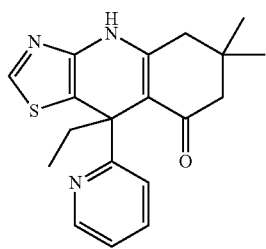
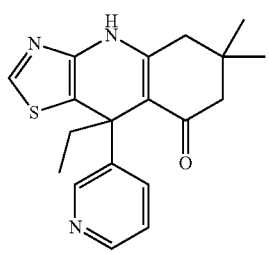
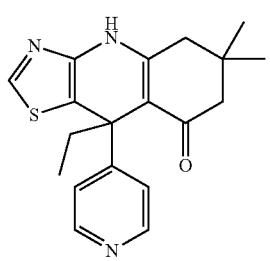
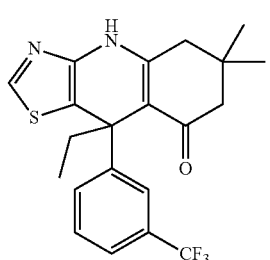
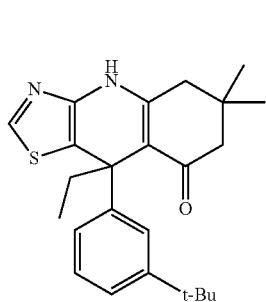

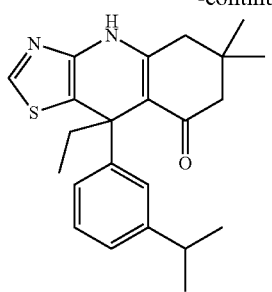
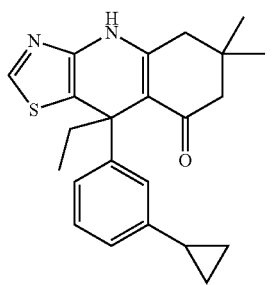
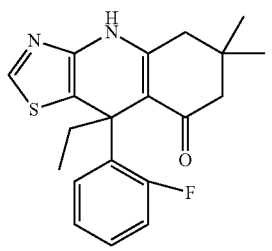
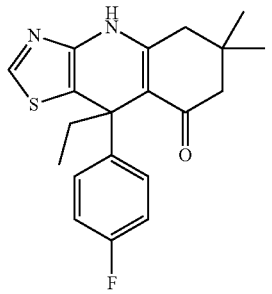
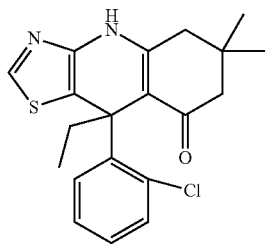
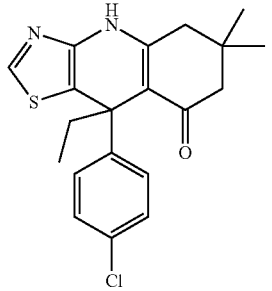
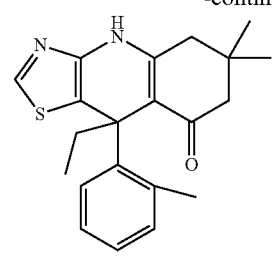
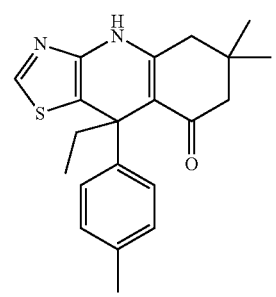
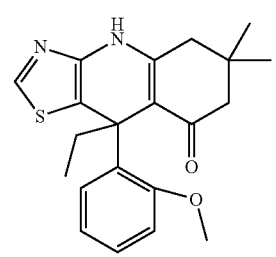
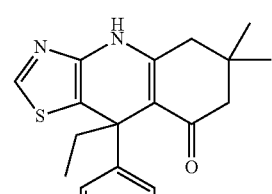
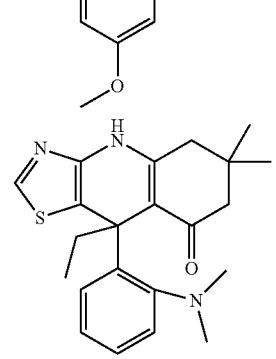
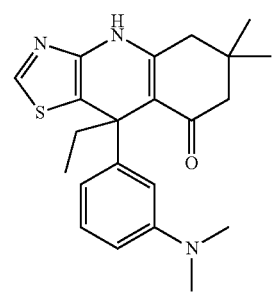

195
-continued
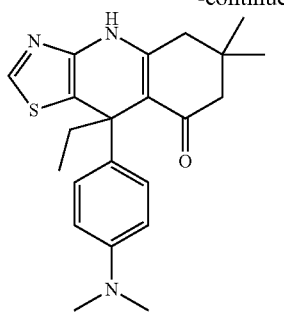
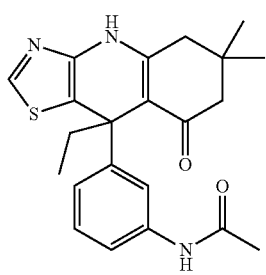
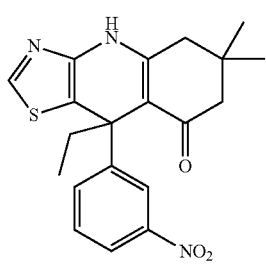
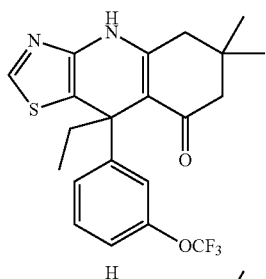
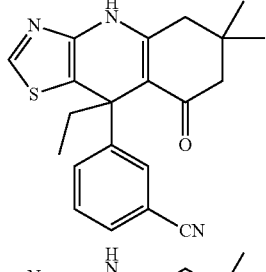
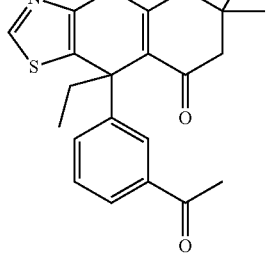
196
-continued
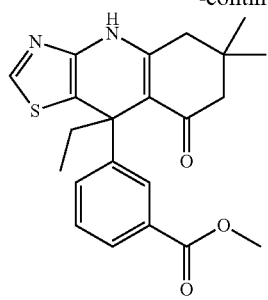
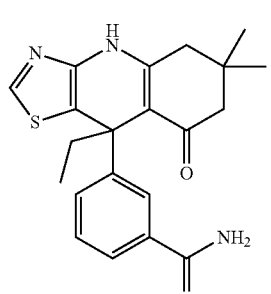
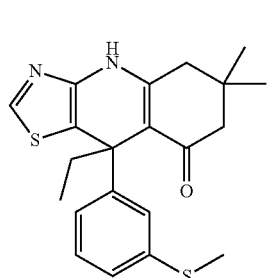
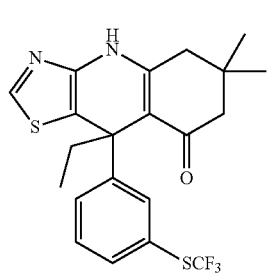
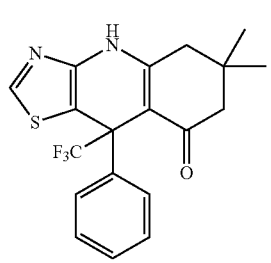
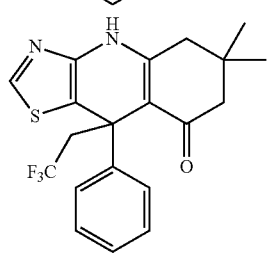

197
-continued
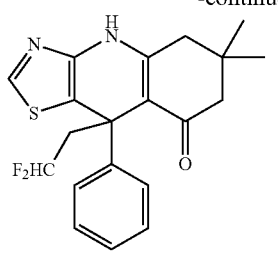
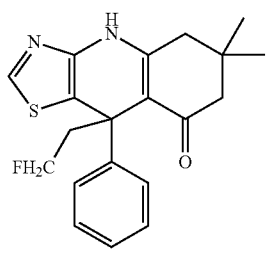
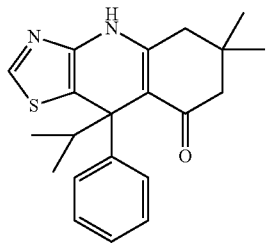
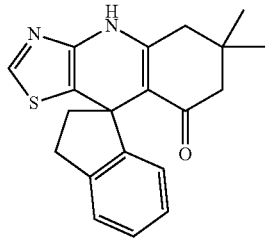
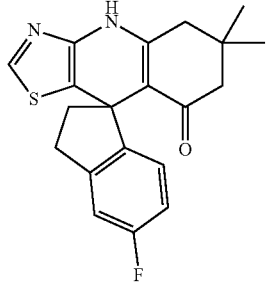
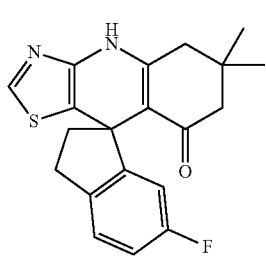
198
-continued
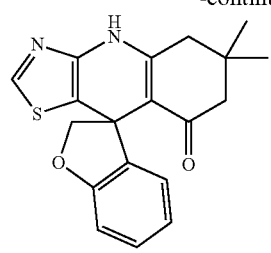
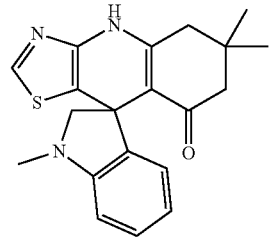
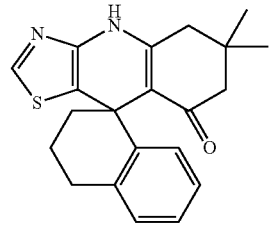
or
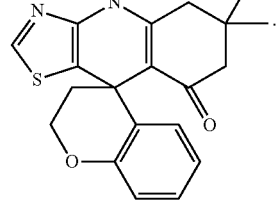
12. The compound of claim 1, or a pharmaceutically acceptable salt, solvate, hydrate, polymorph, co-crystal, tautomer, stereoisomer, or isotopically labeled compound thereof, wherein the compound is of the formula:
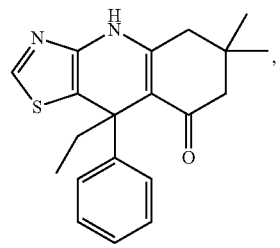
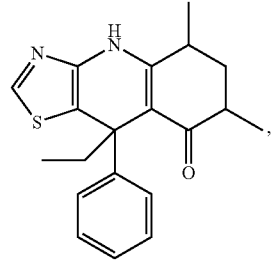

199
-continued
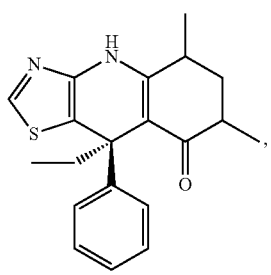
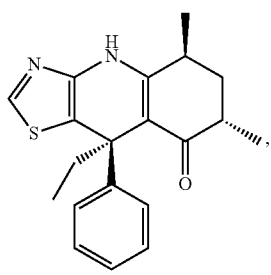
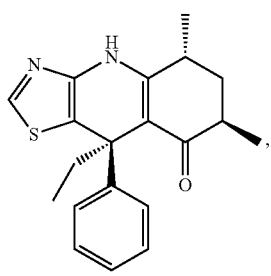
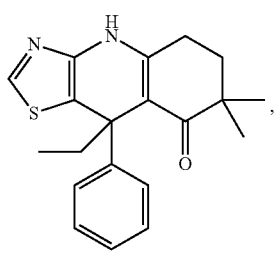
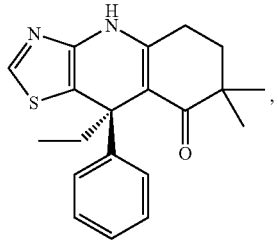
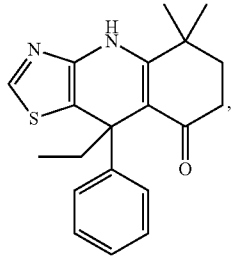
200
-continued
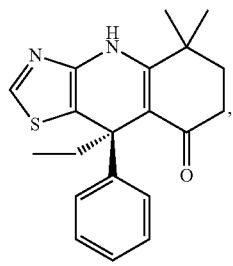
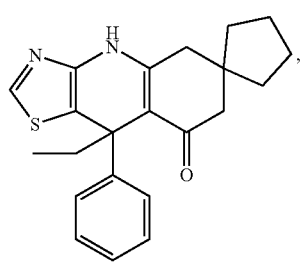
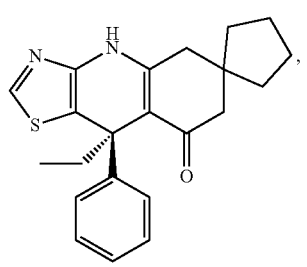
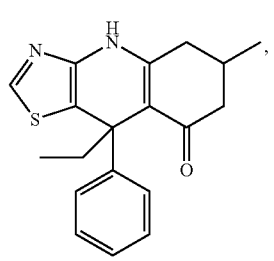
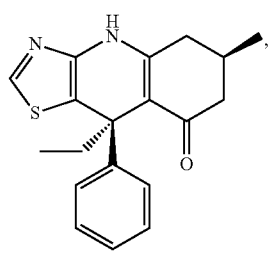
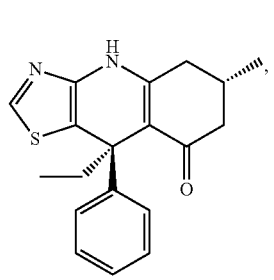

201
-continued
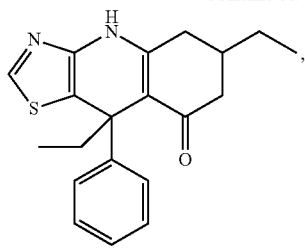
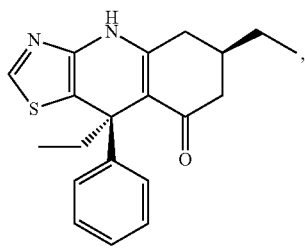
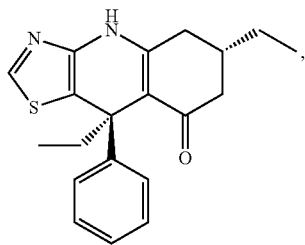
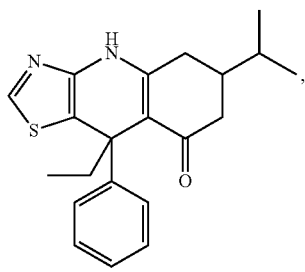
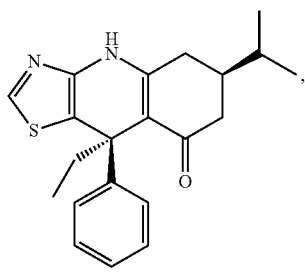
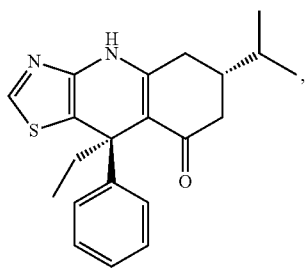
202
-continued
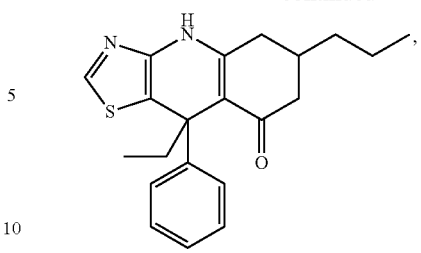
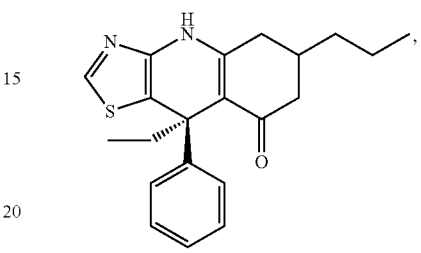
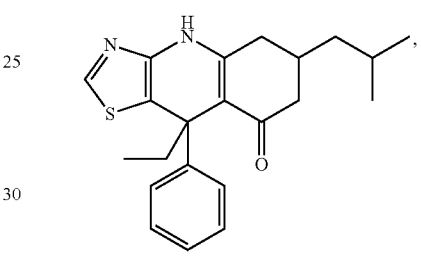
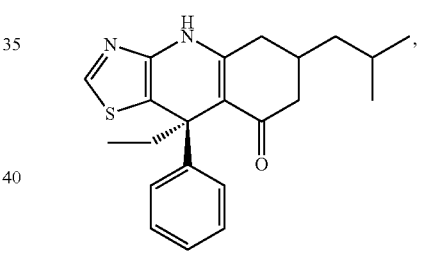
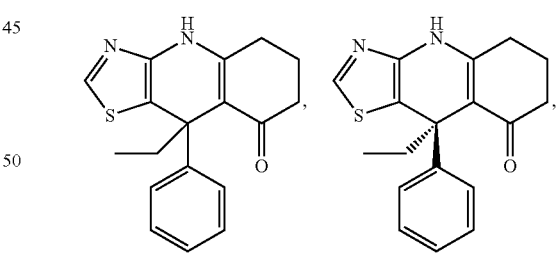
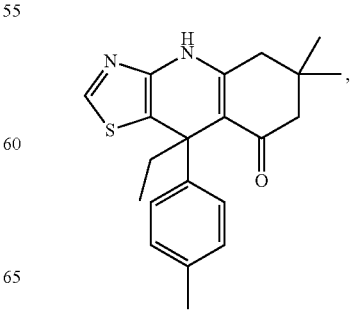

203
-continued
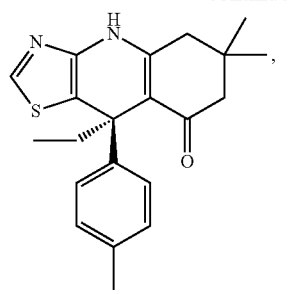
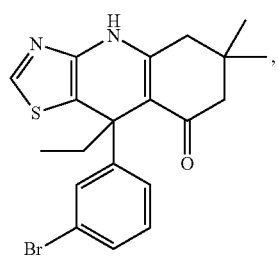
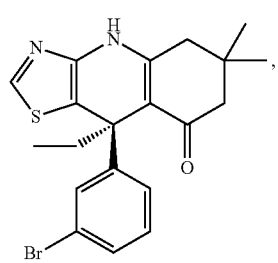
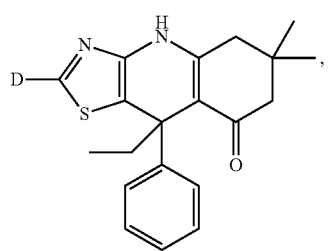
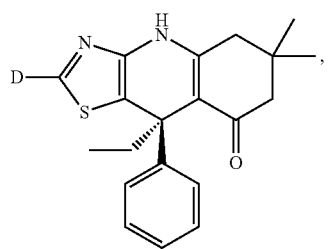
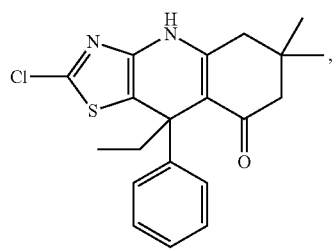
204
-continued
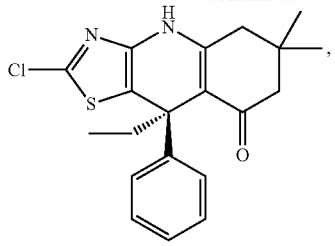
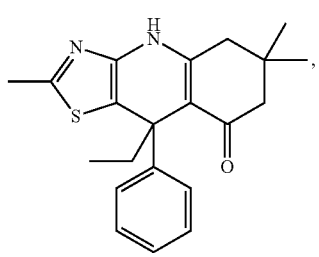
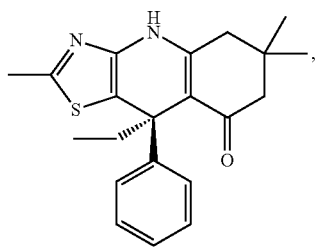
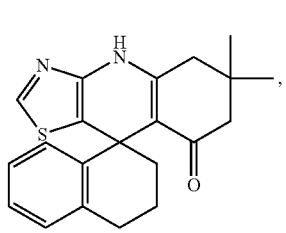
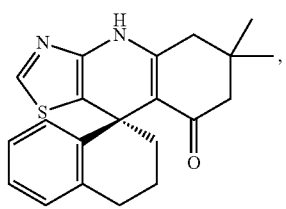
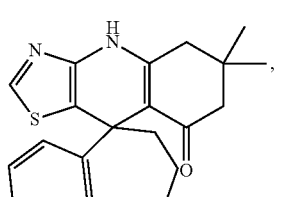
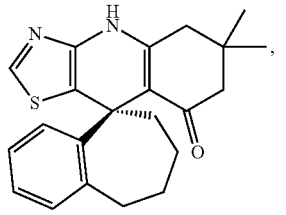

205
-continued
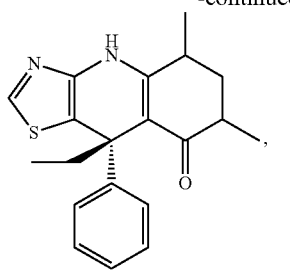
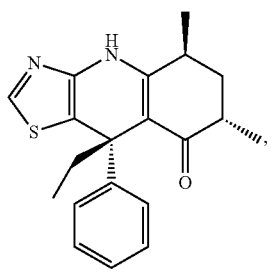
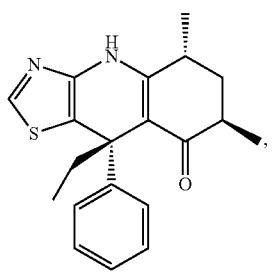
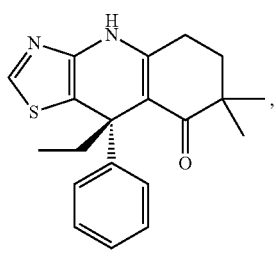
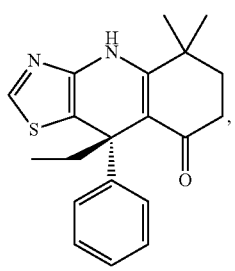
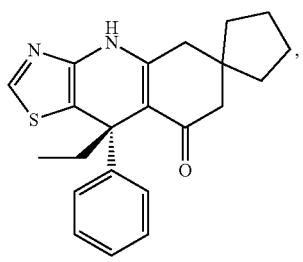
206
-continued
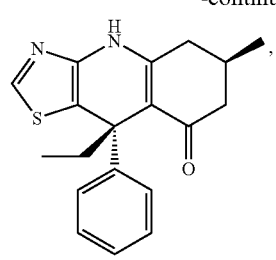
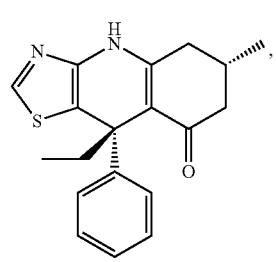
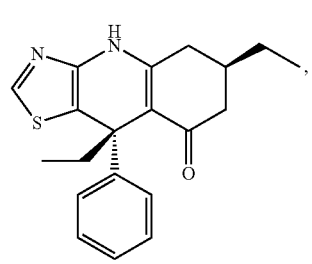
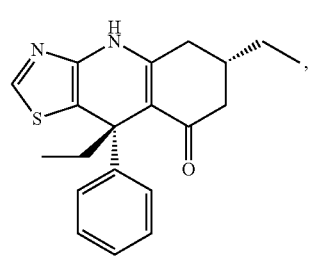
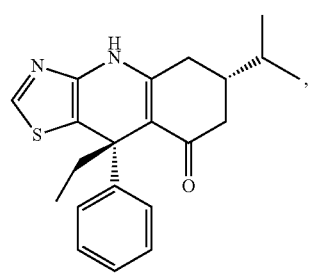
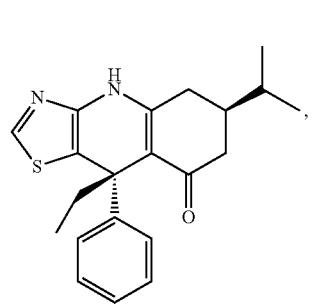

207
-continued

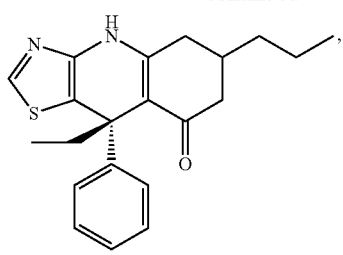

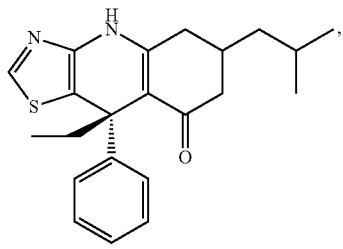

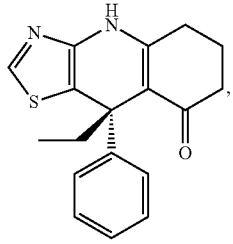

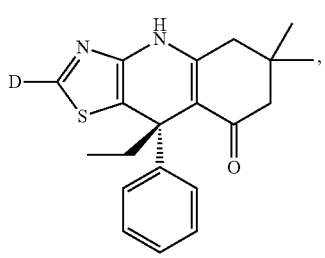

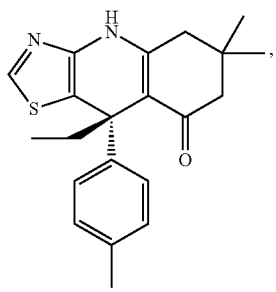

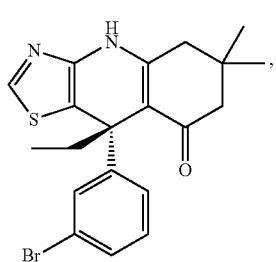

208
-continued

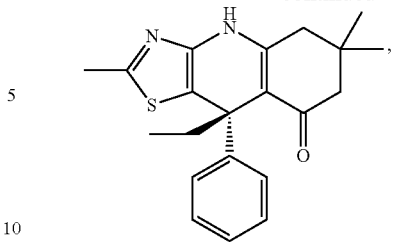

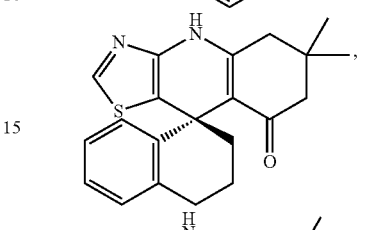

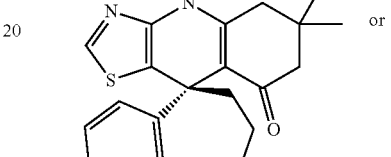

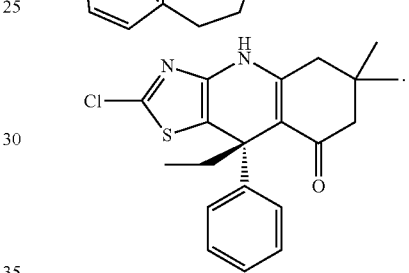

13. A pharmaceutical composition comprising:
a compound of claim 1, or a pharmaceutically acceptable salt, solvate, hydrate, polymorph, co-crystal, tautomer, stereoisomer, or isotopically labeled compound thereof; and
optionally a pharmaceutically acceptable excipient.

14. A method of treating a disease in a subject in need thereof, the method comprising administering to the subject an effective amount of a compound of claim 1, or a pharmaceutically acceptable salt, solvate, hydrate, polymorph, co-crystal, tautomer, stereoisomer, or isotopically labeled compound thereof, wherein the effective amount is effective for treating the disease, and the disease is fragile X syndrome, autism, attention deficit hyperactivity disorder, schizophrenia, a mood disorder, epilepsy, Type II diabetes, obesity, Alzheimer's disease, Parkinson's disease, seizure, amyotrophic lateral sclerosis, a prion disease, colon cancer, acute myeloid leukemia, acute lymphocytic leukemia, or pancreatic cancer.

15. A method of inhibiting the activity of a glycogen synthase kinase 3 (GSK3) in a subject in need thereof, the method comprising administering to the subject an effective amount of a compound of claim 1, or a pharmaceutically acceptable salt, solvate, hydrate, polymorph, co-crystal, tautomer, stereoisomer, or isotopically labeled compound thereof, wherein the effective amount is effective for inhibiting the activity of the GSK.3.

16. A method of inhibiting the activity of a glycogen synthase kinase 3 (GSK3) in a cell or tissue, the method comprising contacting the cell or tissue with an effective amount of a compound of claim 1, or a pharmaceutically acceptable salt, solvate, hydrate, polymorph, co-crystal, tautomer, stereoisomer, or isotopically labeled compound thereof, wherein the effective amount is effective for inhibiting the activity of the GSK3.

17. A method of preparing a compound of claim 1, or a salt thereof, the method comprising (a) reacting a compound of Formula (A):

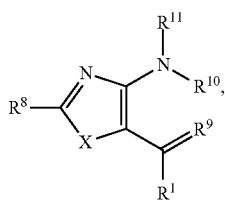

(A)

or a salt thereof, with a compound of Formula (B):

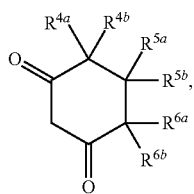

(B)

or a salt thereof, wherein:
$R^9$ is substituted or unsubstituted $C_{1-6}$ alkyl;
$R^{10}$ is hydrogen or a nitrogen protecting group; and
$R^{11}$ is hydrogen or a nitrogen protecting group;
wherein when at least one of $R^{10}$ and $R^{11}$ is a nitrogen protecting group, the step of reacting is performed under a condition that deprotects all the nitrogen protecting groups.

18. A kit comprising:
a compound of claim 1, or a pharmaceutically acceptable salt, solvate, hydrate, polymorph, co-crystal, tautomer, stereoisomer, or isotopically labeled compound thereof.

19. The compound of claim 1, or a pharmaceutically acceptable salt, solvate, hydrate, polymorph, co-crystal, tautomer, stereoisomer, or isotopically labeled compound thereof, wherein X is —S—.

20. The compound of claim 1, or a pharmaceutically acceptable salt, solvate, hydrate, polymorph, co-crystal, tautomer, stereoisomer, or isotopically labeled compound thereof, wherein $R^2$ is substituted or unsubstituted $C_{1-6}$ alkyl.

21. The compound of claim 1, or a pharmaceutically acceptable salt, solvate, hydrate, polymorph, co-crystal, tautomer, stereoisomer, or isotopically labeled compound thereof, wherein $R^{4a}$ is substituted or unsubstituted $C_{1-6}$ alkyl, and $R^{4b}$ is hydrogen, or each one of $R^{4a}$ and $R^{4b}$ is substituted or unsubstituted $C_{1-6}$ alkyl.

22. The compound of claim 1, or a pharmaceutically acceptable salt, solvate, hydrate, polymorph, co-crystal, tautomer, stereoisomer, or isotopically labeled compound thereof, wherein each one of $R^{5a}$ and $R^{5b}$ is hydrogen; or $R^{5a}$ is substituted or unsubstituted $C_{1-6}$ alkyl, and $R^{5b}$ is hydrogen.

23. The compound of claim 1, or a pharmaceutically acceptable salt, solvate, hydrate, polymorph, co-crystal, tautomer, stereoisomer, or isotopically labeled compound thereof, wherein each one of $R^{5a}$ and $R^{5b}$ is —$CH_3$.

24. The compound of claim 1, or a pharmaceutically acceptable salt, solvate, hydrate, polymorph, co-crystal, tautomer, stereoisomer, or isotopically labeled compound thereof, wherein $R^{6a}$ is substituted or unsubstituted $C_{1-6}$ alkyl, and $R^{6b}$ is hydrogen, or each one of $R^{6a}$ and $R^{6b}$ is substituted or unsubstituted $C_{1-6}$ alkyl.

25. The compound of claim 1, or a pharmaceutically acceptable salt, tautomer, or isotopically labeled compound thereof.

26. The method of claim 14, wherein the disease is fragile X syndrome.

27. The method of claim 14, wherein the disease is autism.

28. The method of claim 14, wherein the disease is attention deficit hyperactivity disorder.

29. The method of claim 14, wherein the disease is schizophrenia.

30. The method of claim 14, wherein the disease is a mood disorder.

31. The method of claim 30, wherein the mood disorder is bipolar disorder.

32. The method of claim 14, wherein the disease is childhood seizure.

33. The method of claim 14, wherein the disease is Type II diabetes.

34. The method of claim 14, wherein the disease is acute myeloid I leukemia.

35. The method of claim 14, wherein the disease is acute lymphocytic leukemia.

36. The method of claim 14, wherein the disease is colon cancer.

37. The method of claim 14, wherein the disease is pancreatic cancer.

38. The method of claim 14, wherein the disease is obesity.

39. The method of claim 14, wherein the disease is Alzheimer's disease.

40. The method of claim 14, wherein the disease is Parkinson's disease.

41. The method of claim 14, wherein the disease is amyotrophic lateral sclerosis.

* * * * *